US008076337B2

(12) United States Patent
Martinez et al.

(10) Patent No.: US 8,076,337 B2

(45) Date of Patent: Dec. 13, 2011

(54) ANTITUMORAL DERIVATIVES OF ET-743

(75) Inventors: Valentin Martinez, Madrid (ES); Maria Flores, Sevilla (ES); Pilar Gallego, Madrid (ES); Carmen Cuevas, Madrid (ES); Simon Munt, Madrid (ES); Ignacio Manzanares, Madrid (ES)

(73) Assignee: Pharma Mar, S.A. (ES)

( * ) Notice: Subject to any disclaimer, the term of this patent is extended or adjusted under 35 U.S.C. 154(b) by 0 days.

(21) Appl. No.: 12/755,218

(22) Filed: Apr. 6, 2010 (Under 37 CFR 1.47)

(65) Prior Publication Data

US 2010/0197695 A1 Aug. 5, 2010

Related U.S. Application Data

(63) Continuation of application No. 10/484,060, filed as application No. PCT/GB02/03288 on Jul. 17, 2002, now Pat. No. 7,759,345.

(30) Foreign Application Priority Data

Jul. 17, 2001 (GB) .................................. 0117402.8

(51) Int. Cl.

*A01N 43/58* (2006.01)
*A01N 43/60* (2006.01)
*A61K 31/50* (2006.01)
*A61K 31/495* (2006.01)
*C07D 241/36* (2006.01)

(52) U.S. Cl. ....................................... 514/250; 544/342

(58) Field of Classification Search ........................ None
See application file for complete search history.

(56) References Cited

U.S. PATENT DOCUMENTS

| | | | |
|---|---|---|---|
| 5,089,273 | A | 2/1992 | Rinehart et al. |
| 5,149,804 | A | 9/1992 | Rinehart et al. |
| 5,256,663 | A | 10/1993 | Rinehart et al. |
| 5,478,932 | A | 12/1995 | Rinehart et al. |
| 5,654,426 | A | 8/1997 | Rinehart et al. |
| 5,721,362 | A | 2/1998 | Corey et al. |
| 5,985,876 | A | 11/1999 | Rinehart et al. |
| 6,124,292 | A | 9/2000 | Corey |
| 6,124,293 | A | 9/2000 | Rinehart et al. |
| 6,316,214 | B1 | 11/2001 | Rinehart et al. |
| 6,348,467 | B1 | 2/2002 | Corey |
| 6,544,560 | B1 | 4/2003 | Bullent et al. |
| 6,569,859 | B1 | 5/2003 | Corey |
| 6,686,470 | B2 | 2/2004 | Danishefsky et al. |
| 6,712,023 | B2 | 3/2004 | Targotay et al. |
| 6,815,544 | B2 | 11/2004 | Corey |
| 6,867,334 | B2 | 3/2005 | Rinehart et al. |
| 7,115,743 | B2 | 10/2006 | Rinehart et al. |
| 7,202,361 | B2 | 4/2007 | Flores et al. |
| 7,241,892 | B1 | 7/2007 | Cuevas et al. |
| 7,247,629 | B2 | 7/2007 | Manzanares et al. |
| 7,309,601 | B2 | 12/2007 | Pérez Esteban et al. |
| 7,410,969 | B2 | 8/2008 | Manzanares et al. |
| 7,420,051 | B2 | 9/2008 | Francesh et al. |
| 7,524,956 | B2 | 4/2009 | Cuevas et al. |
| 7,622,458 | B2 | 11/2009 | Rybak |
| 7,723,068 | B2 | 5/2010 | Iglesias et al. |
| RE41,614 | E | 8/2010 | Corey |
| 7,767,659 | B2 | 8/2010 | Barrasa et al. |
| 7,795,260 | B2 | 9/2010 | Barrasa et al. |
| 7,919,493 | B2 | 4/2011 | Flores et al. |
| 2003/0216397 | A1 | 11/2003 | Flores et al. |
| 2004/0002602 | A1 | 1/2004 | Francesch et al. |
| 2004/0019056 | A1 | 1/2004 | Manzanares et al. |
| 2004/0059112 | A1 | 3/2004 | Rinehart et al. |
| 2004/0108086 | A1 | 6/2004 | Takahashi et al. |
| 2005/0004018 | A1 | 1/2005 | Jimeno et al. |
| 2006/0030571 | A1 | 2/2006 | Rinehart et al. |
| 2006/0094687 | A1 | 5/2006 | Beijnen et al. |
| 2007/0004691 | A1 | 1/2007 | Donald et al. |
| 2007/0082856 | A1 | 4/2007 | Gianni et al. |
| 2007/0128201 | A1 | 6/2007 | D'Incalci et al. |

(Continued)

FOREIGN PATENT DOCUMENTS

EP 0 309 477 B1 11/1991

(Continued)

OTHER PUBLICATIONS http://www.sigmaaldrich.com/chemistry/chemistry-products.html?TablePage=16274965; last accessed Dec. 20, 2010.*

(Continued)

*Primary Examiner* — Jeffrey Murray

(74) *Attorney, Agent, or Firm* — Kenneth H. Sonnenfeld; King & Spalding LLP

(57) ABSTRACT

Derivatives of Et-743 or Et-770 or Et-729 are provided. The derivatives are of the general formula Ia.:

Ia

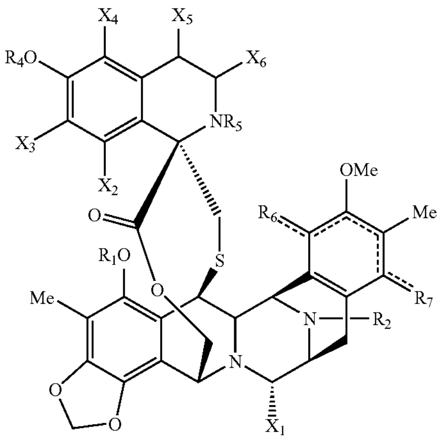

wherein the substituent groups take various permitted meanings.

18 Claims, No Drawings

U.S. PATENT DOCUMENTS

| | | | |
|---|---|---|---|
| 2007/0275942 | A1 | 11/2007 | Cvitkovich et al. |
| 2008/0051407 | A1 | 2/2008 | Manzanares et al. |
| 2008/0076772 | A1 | 3/2008 | Allavena et al. |
| 2008/0234279 | A1 | 9/2008 | Rinehart et al. |
| 2008/0255132 | A1 | 10/2008 | Rowinsky et al. |
| 2008/0293725 | A1 | 11/2008 | Rosell Costa et al. |
| 2009/0076016 | A1 | 3/2009 | Calvo Salve et al. |
| 2009/0117176 | A1 | 5/2009 | Gilles et al. |
| 2009/0170860 | A1 | 7/2009 | Scotto et al. |
| 2009/0247533 | A1 | 10/2009 | Rinehart et al. |
| 2009/0324744 | A1 | 12/2009 | Takahashi et al. |
| 2010/0009906 | A1 | 1/2010 | Ali Elsayed |

FOREIGN PATENT DOCUMENTS

| | | |
|---|---|---|
| JP | 59-225189 | 12/1984 |
| JP | 60-084288 | 5/1985 |
| WO | WO 87/07610 | 12/1987 |
| WO | WO 92/09607 | 6/1992 |
| WO | WO 98/12198 | 3/1998 |
| WO | WO 98/46080 | 10/1998 |
| WO | WO 99/51238 | 10/1999 |
| WO | WO 99/58125 | 11/1999 |
| WO | WO 00/18233 | 4/2000 |
| WO | WO 00/69862 | 11/2000 |
| WO | WO 01/77115 | 10/2001 |
| WO | WO 01/87894 | 11/2001 |
| WO | WO 2009/050303 | 4/2009 |
| WO | WO 2009/138509 | 11/2009 |
| WO | WO 2009/140675 | 11/2009 |

OTHER PUBLICATIONS

U.S. Appl. No. 06/872,189, filed Jun. 9, 1986, Kenneth L. Rinehart.
U.S. Appl. No. 06/898,906, filed Aug. 21, 1986, Kenneth L. Rinehart.
U.S. Appl. No. 07/006,395, filed Jan. 23, 1987, Kenneth L. Rinehart.
U.S. Appl. No. 07/278,629, filed Dec. 1, 1988, Kenneth L. Rinehart.
U.S. Appl. No. 07/548,060, filed Jul. 5, 1990, Kenneth L. Rinehart.
U.S. Appl. No. 07/620,427, filed Nov. 30, 1990, Kenneth L. Rinehart.
U.S. Appl. No. 07/838,149, filed Feb. 18, 1992, Kenneth L. Rinehart.
U.S. Appl. No. 08/161,340, filed Dec. 2, 1993, Kenneth L. Rinehart.
U.S. Appl. No. 08/198,449, filed Feb. 18, 1994, Kenneth L. Rinehart.
U.S. Appl. No. 08/483,182, filed Jun. 7, 1995, Kenneth L. Rinehart.
U.S. Appl. No. 08/715,541, filed Sep. 18, 1996, Elias J. Corey.
U.S. Appl. No. 09/058,499, filed Apr. 10, 1998, Kenneth L. Rinehart.
U.S. Appl. No. 09/165,892, filed Sep. 30, 1998, Elias J. Corey.
U.S. Appl. No. 09/286,242, filed Apr. 5, 1999, Kenneth L. Rinehart.
U.S. Appl. No. 09/309,947, filed May 11, 1999, Kenneth L. Rinehart.
U.S. Appl. No. 09/510,315, filed Feb. 22, 2000, Elias J. Corey.
U.S. Appl. No. 09/546,877, filed Apr. 10, 2000, Kenneth L. Rinehart.
U.S. Appl. No. 09/674,796, filed Dec. 18, 2008, Bullent Kukurtcu Targotay.
U.S. Appl. No. 09/787,461, filed Mar. 2, 2001, Estaban Cvitkovich.
U.S. Appl. No. 09/949,051, filed Sep. 7, 2001, Kenneth L. Rinehart.
U.S. Appl. No. 09/971,852, filed Oct. 3, 2001, Kenneth L. Rinehart.
U.S. Appl. No. 09/979,404, filed Mar. 6, 2002, Carmen Cuevas.
U.S. Appl. No. 10/077,700, filed Feb. 14, 2002, Elias J. Corey.
U.S. Appl. No. 10/213,711, filed Aug. 7, 2002, Elias J. Corey.
U.S. Appl. No. 10/240,963, filed Mar. 19, 2003, Maria Flores.
U.S. Appl. No. 10/257,856, filed Mar. 31, 2003, Andrés Francesch.
U.S. Appl. No. 10/257,857, filed Mar. 31, 2003, Ignacio Manzanares.
U.S. Appl. No. 10/355,500, filed Jan. 31, 2003, Bullent Kukurtcu Targotay.
U.S. Appl. No. 10/406,997, filed Apr. 2, 2003, Kenneth L. Rinehart.
U.S. Appl. No. 10/416,086, filed Sep. 17, 2003, Naoto Takahashi.
U.S. Appl. No. 10/492,320, filed Aug. 18, 2004, José Jimeno.
U.S. Appl. No. 10/503,106, filed Jun. 8, 2005, Valentin Martinez Barrasa.
U.S. Appl. No. 10/524,152, filed Aug. 24, 2005, Beatriz Perez Esteban.
U.S. Appl. No. 10/540,092, filed Sep. 22, 2005, Ana Velasco Iglesias.
U.S. Appl. No. 10/558,133, filed Nov. 15, 2006, Maurizio D'Incalci.
U.S. Appl. No. 10/575,132, filed Jul. 7, 2006, Sarah Donald.
U.S. Appl. No. 10/579,130, filed Aug. 13, 2007, Eric Rowinsky.
U.S. Appl. No. 10/579,160, filed Mar. 1, 2007, Mary Ellen Rybak.
U.S. Appl. No. 10/579,251, filed Oct. 20, 2006, Luca Gianni.
U.S. Appl. No. 10/738,973, filed Dec. 17, 2003, Elias J. Corey.
U.S. Appl. No. 11/009,237, filed Dec. 10, 2004, Kenneth L. Rinehart.
U.S. Appl. No. 11/045,595, filed Jan. 26, 2005, Ignacio Manzanares.
U.S. Appl. No. 11/132,466, filed May 18, 2005, Kenneth L. Rinehart.
U.S. Appl. No. 11/249,172, filed Oct. 11, 2005, Andrés Francesch.
U.S. Appl. No. 11/261,876, filed Oct. 28, 2005, Jacob Hendrik Beijnen.
U.S. Appl. No. 11/571,589, filed Feb. 5, 2007, Rafael Rosell Costa.
U.S. Appl. No. 11/576,115, filed May 14, 2007, Paola Allavena.
U.S. Appl. No. 11/577,790, filed Sep. 24, 2007, Erard Gilles.
U.S. Appl. No. 11/645,356, filed Dec. 22, 2006, Ignacio Manzanares.
U.S. Appl. No. 11/733,606, filed Apr. 10, 2007, Maria Flores.
U.S. Appl. No. 11/769,873, filed Jun. 28, 2007, Esteban Cvitkovich.
U.S. Appl. No. 11/774,890, filed Jul. 9, 2007, Carmen Cuevas.
U.S. Appl. No. 11/929,787, filed Oct. 30, 2007, Kenneth L. Rinehart.
U.S. Appl. No. 12/091,540, filed Jun. 4, 2008, Pilar Calvo Salve.
U.S. Appl. No. 12/094,744, filed Nov. 17, 2008, Kathleen Scotto.
U.S. Appl. No. 12/273,919, filed Nov. 19, 2008, Valentin Martinez Barrasa.
U.S. Appl. No. 12/299,960, filed Mar. 23, 2009, Yusri Ali Elsayed.
U.S. Appl. No. 12/337,756, filed Dec. 18, 2008, Elias J. Corey.
U.S. Appl. No. 12/482,753, filed Jun. 11, 2009, Kenneth L. Rinehart.
U.S. Appl. No. 12/552,347, filed Sep. 2, 2009, Naoto Takahashi.
Suggitt et al., "50 Years of Preclinical Anticancer Drug Screening: Empirical to Target-Driven Approaches," Feb. 1, 2005, pp. 971-981, vol. 11, Clinical Cancer Research.
Cecil Textbook of Medicine, 2000, 21$^{st}$ Edition, pp. 1060-1074, Chapter 198, W.B. Saunders Company.
Arai, T. et al., "The Structure of a Novel Antitumor Antibiotic, Saframycin A", Experientia, vol. 36, pp. 1025-1027 (1980).
Arai, Tadashi et al., "Increased Production of Saframycin A and Isolation of Saframycin S", The Journal of Antibiotics, vol. XXXIII, No. 9, pp. 951-960 (1980).
Arai, Tadashi et al., "Isoquinolineinones from Actinomycetes and Sponges", The Alkaloids Chemistry and Pharmacology, vol. XXI, pp. 56-100 (1983).
Arai, Tadashi et al., "New Antibiotics, Safraycins A, B, C, D and E", The Journal of Antibiotics, vol. XXX, No. 11, pp. 1015-1018 (1977).
Asaoka, Takemitsu et al., "A New Saframycin, Saframycin R", The Journal of Antibiotics, vol. XXXV, No. 12, pp. 1708-1710 (1982).
Barton, Derek H.R. et al, "Synthesis and Properties of a Series of Sterically Hindered Guanidine Bases", Journal of the Chemical Society Perkin Transactions I, No. 9, pp. 2085-2090 (1982).
Brown, J.M., "NCI's Anticancer Drug Screening Program May Not Be Selecting for Clinically Active Compounds," Oncol. Res. 9(5):213-215 (1997).
Cable, Karl M. et al., "The Biosynthesis of Tuberin from Tyrosine and Glycine; Observations on the Stereochemistry Associated with the Conversion of Glycine through Methylenetetrahydrofolate into Methenyltetrahydrofolate", Journal of the Chemical Society Perkins Transactions I, No. 7, pp. 1593-1598 (1987).
Cooper, Raymond et al., "Structure of the Quinone Antibiotic EM5519 and the Behavior of Quinones in Fast Atom Bombardment Mass Spectrometry", The Journal of Antibiotics, vol. XXXVIII, No. 1, pp. 24-30 (1985).
Corey, E.J. et al., "Enantioselective Total Synthesis of Ecteinascidin 743", Journal of the American Chemical Society, vol. 118, No. 38, pp. 9202-9203 (1996).
Cuevas, Carmen et al., "Synthesis of Ecteinascidin ET-743 and Phthalascidin Pt-650 from Cyanosafracin B", Organic Letters, vol. 2, No. 16, pp. 2545-2548 (2000).
Draetta, G. et al., "Annual Reports in Medicinal Chemistry, vol. 31," Academic Press, San Diego, pp. 241-246 (1996).
Eckhardt, S.G. et al., "Activity of ecteinascidin, a novel marine cytotoxic, against primary human tumor colony-forming units", Proceedings of the American Association for Cancer Research, vol. 37, #2791, pp. 409 (1996).
Faircloth, G. et al., "Ecteinascidin-743 (ET743): in vitro (IVT) and in vivo (INV) Results in Tumor Models", The European Journal of Cancer, vol. 32A, Supp. 1, #24 0, pp. S5 (1996).
Flam, Faye, "Chemical Prospectors Scour the Seas for Promising Drugs", Science, vol. 266, pp. 1324-1325 (1994).

Frincke, James M. et al., "Antimicrobial Metabolites of the *Sponge reniera* sp.", Journal of the American Chemical Society, vol. 104, pp. 265-269 (1982).
Fukuyama, Tohru et al., "Stereocontrolled Total Synthesis of (±)-Saframycin B", Journal of American Chemical Society, vol. 104, pp. 4957-4958 (1982).
Fukuyama, Tohru et al., "Total Synthesis of (±)-Saframycin A", Journal of American Chemical Society, vol. 112, pp. 3712-3713 (1990).
Garcia-Rocha, M. et al., "Characterisation of antimitotic products from marine organisms that disorganize the microtubule network: ecteinascidin 743, isohomohalichondrin-B and LL-15", British Journal of Cancer, vol. 73, pp. 875-883 (1996).
Goldwasser, F, et al. "Characterization of ecteinascidin 743-induced DNA damages in cells", Proceedings of the American Association for Cancer Research, vol. 39, #4066, pp. 598, (1998).
Guan, Yue et al., "Molecular and Crystal Structures of Ecteinascidins: Potent Antitumor Compounds from the Caribbean Tunicate *Ecteinascidia turbinata*", Journal of Biomolecular Structure & Dynamics, vol. 10, No. 5, pp. 793-818 (1993).
Gulavita, Nanda K., et al., "Antimicrobial Constituents of a Sponge-Nudibranch Pair from Sri Lanka", Bioactive Compounds from Marine Organisms, Oxford & IBH Publishing Co. Pvt. Ltd., pp. 229-233 (1991).
He, Hai-Yin et al., "Renieramycins E and F from the *Sponge reniera* sp.: Reassignment of the Stereochemistry of the Renieramycins", The Journal of Organic Chemistry, vol. 54, No. 24, pp. 5822-5824 (1989).
Hendriks, H.R. et al., "High antitumor activity of ET743 in human tumor xenograft models", Proceedings of the American Association for Cancer Research, vol. 37, #2653, pp. 389 (1996).
Ikeda, Yoshifumi et al., "Safracins, New Antitumor Antibiotics I. Producing Organism, Fermentation and Isolation", The Journal of Antibiotics, vol. XXXVI, No. 10, pp. 1279-1283 (1983).
Ikeda, Yoshifumi et al., "Safracins, New Antitumor Antibiotics I. Producing Organism, Fermentation and Isolation", The Journal of Antibiotics, vol. XXXVI, No. 10, pp. 1284-1289 (1983).
Ito, Yoichiro, "High-Speed Countercurrent Chromatography", Critical Reviews in Analytical Chemistry, vol. 17, No. 1, pp. 65-143 (1986).
Koenig, Karl E., "The Applicability of Asymmetric Homogeneous Catalytic Hodrogenation", Asymmetric Synthesis, Ed. Morrison, Academic Press, Inc., Orlando, FL, vol. 5, pp. 71(1985).
Kofron, William G. et al., "A Convenient Method for Estimation of Alkyllithium Concentrations", The Journal of Organic Chemistry, vol. 41, No. 10, pp. 1879-1880 (1976).
Kubo, Alcinori et al., "Structure of Saframycin D, A New Dimeric Isoquinolinequinone Antibiotic", Chem. Pharm. Bull., vol. 35, No. 1, pp. 440-442 (1987).
Kuffel, M.J. et al., "Cytochrome P450 catalyzed metabolism of Ecteinascidin 743 by rat and human liver microsomes", Proceedings of the American Association for Cancer Research, vol. 38, #4003, pp. 596 (1997).
Lichter, W. et al., "Biological Activities Exerted by Extracts of *Ecteinascidia turbinata*", Food and Drugs from the Sea Proceedings, pp. 117-127 (1972).
Lown, J. William et al., "Molecular Mechanisms of Binding and Single-Strand Scission of Deoxyribonucleic Acid by the Antitumor Antibiotics Saframycins A and C", Biochemistry, vol. 21, No. 3, pp. 419-428 (1982).
Lown, J. William et al., "Structure and Confirmation of Saframycin R Determined by High Field $^{1}$1-1 and $^{13}$C NMR and its Interactions with DNA in Soloution", The Journal of Antibiotics, vol. XXXVI, No. 9, pp. 1184-1194 (1983).
Martinez et al., "A New, More Efficient, and Effective Process for the Synthesis of a Key Pentacyclic Intermediate for Production of Ecteinascidin and Phthalascidin Antitumor Agents", Organic Letters, 2(7):993-996 (2000).
Martinez et al., "Enantioselective Synthesis of Saframycin A and Evaluation of Antitumor Activity Relative to Ecteinascidin/Saframycin Hybirds", Organic Letters, 1(7):75-77 (1999).
Martinez, Eduardo J. et al., "Phthalascidin, a synthetic antitumor agent with potency and mode of action comparable to ecteinascidin 743", Chemistry, vol. 96, pp. 3496-3501 (1999).
Mikami, Yuzuru et al., "Structural Studies on Minor Components of Saframycin Group Antibiotics Saframycins F, G and H", The Journal of Antibiotics, vol. XLI, No. 6, pp. 734-740 (1988).
Mirsalis, J.C. et al., "Toxicity of Ecteinascidin 743 in female Fischer-344 rats administered i.v. in a multiple-dose regimen", Proceedings of the American Association for Cancer Research, vol. 38, #2073, pp. 309 (1997).
Moore, B.M. et al., "The NMR model of an ecteinascidin 743-DNA adduct", Proceedings of the American Association for Cancer Research, vol. 38, #2105, pp. 314 (1997).
Myers et al., "A Concise, Stereocontrolled Syntheis of (-)-Saframycin A by the Directed Condensation of a-Amino Aldehyde Precursors", J. Am. Chem. Soc., 121:10828-10829 (1999).
Nakagawa, Masako et al., "Total Synthesis of (-)-Eudistomin L and (-)-Debromoeudistomin L", Journal of the American Chemical Society, vol. 111, No. 7, pp. 2721-2722 (1989).
Pommier, Yves et al., "DNA Sequence- and Structure-Selective Allcylation of Guanine N2 in the DNA Minor Groove by Ecteinascidin 743, a Potent Antitumor Compound from the Caribbean Tunicate *Ecteinascidia turbinata*", Biochemistry, vol. 35, pp. 13303-13309 (1996).
Pretsch et al., Tables of Spectral Data for Structure Determination of Organic Compounds, pp. H125 (1983).
Reid, Joel M. et al, "Preclinical pharmacology of ecteinascidin 729, a marine natural product with potent antitumor activity", Cancer Chemotherapy and Pharmacology, vol. 38, No. 4, pp. 329-334 (1996).
Remers, William A., "Saframycins, Renieramycins, and Safracins", The Chemistry of Antitumor Antibiotics, vol. 2, pp. 93-119 (1988).
Rinehart et al., "Novel Bioactive Natural Products from Marine Organisms", Topics in Pharmaceutical Sciences 1989, pp. 613-626, D.D. Breimer, D.J.A. Cromwelin, K.K. Midha, Eds., Amsterdam Medical Press B.V. Noordwijk, The Netherlands (1989).
Rinehart, Kenneth L. et al., "Applications of High-Resolution Tandem FAB Mass Spectrometry", Biological Mass Spectrometry, eds. Burlingame et al., Elsevier Amsterdam, pp. 233-258 (1990).
Rinehart, Kenneth L. et al., "Bioactive Compounds from Aquatic and Terrestrial Sources", Journal of Natural Products, vol. 53, No. 4, pp. 771-792 (1990).
Rinehart, Kenneth L. et al., "Biologically active natural products", Pure and Applied Chemistry, vol. 62, No. 7, pp. 1277-1280 (1990).
Rinehart, Kenneth L. et al., "Ecteinascidins 729, 743, 759A, 759B, and 770: Potent Antitumor Agents from the Caribbean Tunic ate *Exteinascidia turbinata*", The Journal of Organic Chemistry vol. 55, No. 15, pp. 4512-4515 (1990).
Rinehart, Kenneth L., "Antitumor Compounds from Tunicates", Medicinal Research Reviews, vol. 20, No. 1, pp. 1-27 (2000).
Saito, Naoki et al., "Synthesis of Saframycins. 3. Preparation of a Key Tricyclic Lactam Intermediate to Saframycin A", The Journal of Organic Chemistry, vol. 54, No. 22, pp. 5391-5395 (1989).
Sakai, Ryuichi et al., "Additional antitumor ecteinascidins from a Caribbean tunicate: Crystal structures and activities in vivo", Proceedings of the National Academy of Sciences, vol. 89, No. 23, pp. 11456-11460 (1992).
Sakai, Ryuichi et al., "Ecteinascidins: Putative Biosynthetic Precursors and Absolute Stereochemistry", Journal of the American Chemical Society, vol. 118, No. 38, pp. 9017-9023 (1996).
Shamma, Maurice et al., Carbon-13 NMR Shift Assignments of Amines and Alkaloids, pp. 206 (1979).
Still, W. Clark et al., "Rapid Chromatographic Technique for Preparative Separations with Moderate Resolution", Journal of Organic Chemistry, vol. 43, No. 14, pp. 2923-2925 (1978).
Takahaski, Katsuhiro et al., "Microbial Conversion of Saframycin A to 25-Dihydrosaframycin A and 21-Decyano-25-Dihydrosaframycin A (25-Dihydrosaframycin B) and Their Biological Activities", The Journal of Antibiotics, vol. XXXV, No. 2, pp. 196-202 (1982).
Takahaski, Katsuhiro, "New Antibiotics, Saframycins A, B, C, D and E", The Journal of Antibiotics, vol. XXX, No. 11, pp. 1015-1018 (1977).

Trowitzsch-Kienast, Wolfram et al., "Isolierung und Strukturaufklarung der Saframycine Mx 1 und Mx 2, neue antitumoraktive Antibiotika aus *Myxococcus xanthus*", Liebigs Ann. Chem., vol. XXXV, pp. 475-481 (1988).
Witten, Jane L. et al., "Structures of Two Cockroach Neuropeptides Assigned by Fast Atom bombardment Mass Spectrometry", Biochemical and Biophysical Research Communications, vol. 124, No. 2, pp. 350-358 (1984).
Calabresi et al., "Chemotherapy of Neoplastic Diseases", Goodman & Gilman's The Pharmacological Basis of Therapeutics, 9th ed. New York: McGraw-Hill, 1996, pp. 1225-1229.
"Cancer" definition, http://www.medterms.com/script/main/artasp?articlekey+2580, accessed Nov. 27, 2007.
Cecil Textbook of Medicine (Bennet, J.C. and Plum, F., eds.) 20th Edition, vol. 1, pp. 1004-1010 (1996).
Fregeau, Nancy Louise, "Biologically Active Compounds froma Clam and a Tunicate", Thesis, University of Illinois art Urbana-Champaign, 1992.
Greene et al., Protective Groups in Organic Systems, 1999, Table of Contents for Chapters 2 and 7.
Holt, Tom Grady, "The Isolation and Structural Characterization of the Ecteinascidins", Thesis, University of Illinois art Urbana-Champaign, 1986.
"IUPAC Gold Book", http://goldbook.iupac.org/A00123.html, accessed Dec. 26, 2007.
Kania, "The first Enantioselective Total Synthesis of Dolabellatrienone and Ecteinascidin 743", Harvard University, Sep. 1997, pp. 1-225.
Morales, Jose Javier, "Marine Natural Products Chemistry of a Caribbean Tunicate and a Palau Sponge", University of Illinois art Urbana-Champaign, 1999.
Sakai, Ryuichi, "Biologically Active Compounds from Tunicates and a Sponge", Thesis, University of Illinois art Urbana-Champaign, 1991.
Sparidans, Rolf W. et al., "Search for metabolites of ecteinascidin 743, a novel, marine-derived, anti-cancer agent, in man." *Anti-Cancer Drugs*, vol. 12, pp. 653-666.
Valoti et al. Clin. Cancer Res. 4(8): 1977-83 (1998).
Wright, Amy E. et al., "Antitumor Tetrahydroisoquinoline Alkaloids from the Colonial Ascidian *Ecteinascidia turbinata*", The Journal of Organic Chemistry, vol. 55, No. 15, pp. 4508-4512 (1990).
Yazawa, Katsukiyo et al., "Bioconversions of Saframycin A Specific to some Genera of Actinomycetes", The Journal of Antibiotics, vol. XXXV, No. 7, pp. 915-917 (1982).
Yazawa, Katsulciyo etal., "Isolation and Structural Elucidation of New Saframycins Y3, Yd-1, Yd-2, Ad-1, Y2b and Y2b-d", The Journal of Antibiotics, vol. XXXIX, No. 12, pp. 1639-1650 (1986).
Zmijewski, Milton J., Jr. et al., "The in vitro Interaction of Naphthyridinomycin with Deoxyribonucleic Acids", Chernico-Biological Interactions, vol. 52, No. 3, pp. 361-375 (1985).
Vollhardt et al., "Synthesis of Polypeptides: A Challenge in the Application of Protecting Groups," Organic Chemistry, Structure and Function, $5^{th}$ ed., Chapter 26, pp. 1216-1219, 2007.
Internal Medicine, pp. 699-715, Chapters 71-72, $4^{th}$ Edition, Editor-in-Chief Jay Stein, 1994.
Arai, Tadashi et al., "Directed Biosynthesis of New Saframycin Derivatives with Resting Cells of *Streptomyces lavendulae*", Antimicrobial Agents and Chemotherapy, vol. 28, No. 1, pp. 5-11, 1985.
Parulekar, A.H. et al., "Bioactivity and Chemical Ecology of Some Interdial Animals", Bioactivity and Chemical Ecology, pp. 29-35, 1991.

* cited by examiner

ANTITUMORAL DERIVATIVES OF ET-743

This application claims priority under 35 U.S.C. §120 as a continuation from application Ser. No. 10/484,060 filed Mar. 2, 2005 now U.S. Pat. No. 7,759,345, which is a 35 U.S.C. §371 National Phase filing of PCT Application No. PCT/GB02/03288 filed Jul. 17, 2002, which claims priority to United Kingdom Patent Application No. 0117402.8, filed Jul. 17, 2001, the contents of each of which are hereby incorporated by reference.

The present invention relates to derivatives of the ecteinascidins, particularly ecteinascidin743, ET-743.

BACKGROUND OF THE INVENTION

The ecteinascidins such as Et-743 are exceedingly potent antitumor agents isolated from the marine tunicate *Ecteinascidia turbinata*. Several ecteinascidins have been reported previously in the patent and scientific literature. See, for example:

U.S. Pat. No. 5,256,663, which describes pharmaceutical compositions comprising matter extracted from the tropical marine invertebrate, *Ecteinascidia turbinata*, and designated therein as ecteinascidins, and the use of such compositions as antibacterial, anti-viral, and/or antitumor agents in mammals.

U.S. Pat. No. 5,089,273, which describes novel compositions of matter extracted from the tropical marine invertebrate, *Ecteinascidia turbinata*, and designated therein as ecteinascidins 729, 743, 745, 759A, 759B and 770. These compounds are useful as antibacterial and/or antitumor agents in mammals.

U.S. Pat. No. 5,478,932, which describes ecteinascidins isolated from the Caribbean tunicate *Ecteinascidia turbinata*, which provide in vivo protection against P388 lymphoma, B16 melanoma, M5076 ovarian sarcoma, Lewis lung carcinoma, and the LX-1 human lung and MX-1 human mammary carcinoma xenografts.

U.S. Pat. No. 5,654,426, which describes several ecteinascidins isolated from the Caribbean tunicate *Ecteinascidia turbinata*, which provide in vivo protection against P388 lymphoma, B16 melanoma, M5076 ovarian sarcoma, Lewis lung carcinoma, and the LX-1 human lung and MX-1 human mammary carcinoma xenografts.

U.S. Pat. No. 5,721,362, which describes a synthetic process for the formation of ecteinascidin compounds and related structures.

U.S. Pat. No. 6,124,293, which relates to semisynthetic ecteinascidins.

WO 9846080, which provides nucleophile substituted and N-oxide ecteinascidins.

WO 9958125, relating to an ecteinascidin metabolite. WO 0069862, which describes the synthesis of ecteinascidin compounds from cyanosafracin B.

WO 0177115, WO 0187894 and WO 0187895, which describe new synthetic compounds of the ecteinascidin series, their synthesis and biological properties.

See also: Corey, E. J., *J. Am. Chem. Soc.* 1996, 118, 9202-9203; Rinehart, et al., *Journal of National Products* 1990, "Bioactive Compounds from Aquatic and Terrestrial Sources", 53, 771-792; Rinehart et al., *Pure and Appl. Chem.* 1990, "Biologically active natural products", 62, 1277-1280; Rinehart, et al., *J. Org. Chem.* 1990, "Ecteinascidins 729, 743, 745, 759A, 759B, and 770: Potent Antitumor Agents from the Caribbean Tunicate *Ecteinascidia turbinatd",* 55, 4512-4515; Wright et al., *J. Org. Chem.* 1990, "Antitumor Tetrahydroisoquinoline Alkaloids from the Colonial Ascidian *Ecteinascidia turbinata",* 55, 4508-4512; Sakai et al., *Proc. Natl. Acad. Sci. USA* 1992, "Additional antitumor ecteinascidins from a Caribbean tunicate: Crystal structures and activities in vivo", 89, 11456-11460; *Science* 1994, "Chemical Prospectors Scour the Seas for Promising Drugs", 266, 1324; Koenig, K. E., "Asymmetric Synthesis", ed. Morrison, Academic Press, Inc., Orlando, Fla., vol. 5, 1985, pp. 71; Barton, et al., *J. Chem Soc. Perkin Trans.* I 1982, "Synthesis and Properties of a Series of Sterically Hindered Guandidine Bases", 2085; Fukuyama et al., *J. Am Chem. Soc.* 1982, "Stereocontrolled Total Synthesis of (+)—Saframycin B", 104, 4957; Fukuyama et al., *J. Am Chem Soc.* 1990, "Total Synthesis of (+)—Saframycin A", 112, 3712; Saito, et al., *J. Org. Chem.* 1989, "Synthesis of Saframycins. Preparation of a Key Tricyclic Lactam Intermediate to Saframycin A", 54, 5391; Still, et al., *J. Org. Chem.* 1978, "Rapid Chromatographic Technique for Preparative Separations with Moderate Resolution", 43, 2923; Kofron, W. G.; Baclawski, L. M., *J. Org. Chem.* 1976, 41, 1879; Guan et al., *J. Biomolec. Struc. & Dynam.* 1993, 10, 793-817; Shamma et al., "Carbon-13 NMR Shift Assignments of Amines and Alkaloids", p. 206, 1979; Lown et al., Biochemistry 1982, 21, 419-428 ; Zmijewski et al., *Chem. Biol. Interactions* 1985, 52, 361-375; Ito, CRC CRIT. *Rev. Anal. Chem.* 1986, 17, 65-143; Rinehart et al., "Topics in Pharmaceutical Sciences 1989" pp. 613-626, D. D. Breimer, D. J. A. Cromwelin, K. K. Midha, Eds., Amsterdam Medical Press B. V., Noordwijk, The Netherlands (1989); Rinehart et al., "Biological Mass Spectrometry," 233-258 eds. Burlingame et al., Elsevier Amsterdam (1990); Guan et al., *Jour. Biomolec. Struct. & Dynam.* 1993, 10, 793-817; Nakagawa et al., *J. Amer. Chem. Soc.* 1989, 111: 2721-2722; Lichter et al., "Food and Drugs from the Sea Proceedings" (1972), Marine Technology Society, Washington, D.C. 1973, 117-127; Sakai et al., *J. Amer. Chem. Soc.* 1996, 118, 9017; Garcia-Rocha et al., *Brit. J. Cancer* 1996, 73: 875-883; Pommier et al., *Biochemistry* 1996, 35: 13303-13309; Rinehart, K. L. *Med. Res. Rev.* 2000, 20, 1-27 and Manzanares I. et al. *Org. Left.* 2000, 2 (16), 2545-2548; Corey et al., *Proc. Natl. Acad. Sci. USA* 1999, 96, 3496-3501.

SUMMARY OF THE INVENTION

The present invention is directed to compounds of the general formula Ia.:

Ia

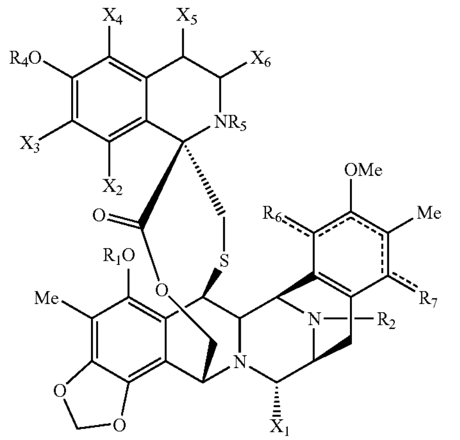

wherein the substituent groups defined by $R_1$, $R_2$, $R_4$, $R_5$ are each independently selected of H, C(═O)R', C(═O)OR' substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl;

wherein $R_6$ and $R_7$ are both =O and the dotted lines indicate a quinone ring, or $R_6$ is —$OR_3$, where $R_3$ is H, C(=O)R', C(=O)OR' substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, $R_7$ is H, and the dotted lines indicate a phenyl ring;

wherein each of the R" groups is independently selected from the group consisting of H, OH, $NO_2$, $NH_2$, SH, CN, halogen, =O, C(=O)H, C(=O)$CH_3$, $CO_2H$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl;

wherein the substituent groups for $X_2$, $X_3$, $X_4$, $X_5$, $X_6$ are independently selected of H, OH, OR', SH, SR', SOR', $SO_2R'$, C(=O)R', C(=O)OR', $NO_2$, $NH_2$, NHR', $N(R')_2$, NHC(O)R', CN, halogen, =O, ', substituted or unsubstituted $C_1$-$C_{24}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted heteroaromatic;

wherein $X_1$ is independently selected of $OR_1$, CN, (=O), or H;

wherein substituent groups for $R_1$, $R_2$, $R_3$, $R_4$, and $R_5$ are each independently selected from the group consisting of H, OH, OR', SH, SR', SOR', $SO_2R'$, C(=O)R', C(=O)OR', $NO_2$, $NH_2$, NHR', $N(R')_2$, NHC(O)R', CN, halogen, =O, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted heterocyclic.

More particularly, the invention provides compounds of formula (I):

I

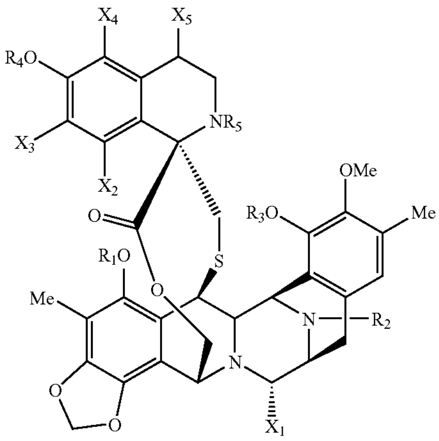

wherein the substituent groups defined by $R_1$, $R_2$, $R_4$, $R_5$ are each independently selected of H, C(=O)R', C(=O)OR' substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, or P=O $(OR')_2$;

where $R_3$ is H, C(=O)R', C(=O)OR' substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, $R_7$ is H, and the dotted lines indicate a phenyl ring;

wherein each of the R' groups is independently selected from the group consisting of H, OH, $NO_2$, $NH_2$, SH, CN, halogen, =O, C(=O)H, C(=O)$CH_3$, alkyloxycarbonyl, $CO_2H$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl;

wherein the substituent groups for $X_2$, $X_3$, $X_4$, $X_5$ are independently selected of H, OH, OR', SH, SR', SOR', $SO_2R'$, C(=O)R', C(=O)OR', $NO_2$, $NH_2$, NHR', $N(R')_2$, NHC(O)R', CN, halogen, =O, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted heteroaromatic;

wherein $X_1$ is independently selected of $OR_1$, CN, (=O), or H;

wherein substituent groups for $R_1$, $R_2$, $R_3$, $R_4$, and $R_5$ are each independently selected from the group consisting of H, OH, OR', SH, SR', SOR', $SO_2R'$, C(=O)R', C(=O)OR', $NO_2$, $NH_2$, NHR', $N(R')_2$, NHC(O)R', CN, halogen, =O, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, substituted or unsubstituted heteroaromatic.

In one aspect, the invention provides compounds of formula (I), wherein:

$R_1$, $R_3$ and $R_4$ are independently selected from hydrogen, R', C=OR', or COOR', where R' is optionally substituted alkyl or alkenyl, the optional substituents being chosen from halo, amino including amino derived from amino acid, aryl or heterocyclic;

$R_2$ is hydrogen, alkyl or C(=O)OR', where R' is alkyl;

$R_5$ is hydrogen, alkyl or C(=O)OR', where R' is alkylene.

$X_1$ is hydrogen, hydroxy, or cyano;

$X_2$, $X_4$ and $X_5$ are hydrogen;

$X_3$ is OR', where R' is alkyl; and $X_6$ is hydrogen or alkyl.

Suitable halogen substituents in the compounds of the present invention include F, Cl, Br and I.

Alkyl groups preferably have from 1 to 24 carbon atoms. One more preferred class of alkyl groups has 1 to about 12 carbon atoms, yet more preferably 1 to about 8 carbon atoms, still more preferably 1 to about 6 carbon atoms, and most preferably 1, 2, 3 or 4 carbon atoms. Another more preferred class of alkyl groups has 12 to about 24 carbon atoms, yet more preferably 12 to about 18 carbon atoms, and most preferably 13, 15 or 17 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred.

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulfinyl groups in the compounds of the present invention include those groups having one or more sulfoxide (SO) groups and from 1 to about 12 carbon atoms, more preferably from 1 to about 8 carbon atoms, and still more preferebly 1 to about 6 carbon atoms. Alkylsulfinyl groups having 1, 2, 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable heterocyclic groups include heteroaromatic and heteroalicyclic groups. Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl such as 2-substituted phenyl, 3-substituted phenyl, 2.3-substituted phenyl, 2.5-substituted phenyl, 2.3.5-substituted and 2.4.5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

References herein to substituted R' groups in the compounds of the present invention refer to the specified moiety, typically alkyl or alkenyl, that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl (e.g., R being a substituted or unsubstituted biphenyl moiety); and aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteratoms or with 10 ring atoms and 1 to 3 heteroatoms.

Preferred R' groups are present in groups of formula R', COR' or OCOR' and include alkyl or alkenyl, that may be substituted at one or more available positions by one or more suitable groups, e.g., halogen such as fluoro, chloro, bromo and iodo, especially co-chloro or perfluoro; aminoalkyl groups such as groups having one or more N atoms and from 1 to about 12 carbon atoms or from 1 to about 6 carbon atoms, and especially including amino acid, notably glycine, alanine, arginine, asparagine, asparaginic acid, cystein, glutamine, glutamic acid, histidine, isoleucine, leucine, lysine, methionine, phenylalanine, proline, serine, threonine, tryptophan, tyrosine or valine, especially protected forms of such amino acids; carbocylic aryl having 6 or more carbons, particularly phenyl; and aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteratoms or with 10 ring atoms and 1 to 3 heteroatoms, the heterocyclic groups optionally being substituted with one or more of the subsitituents permitted for R' and especially amino such as dimethylamino or with keto.

DESCRIPTION OF PREFERRED EMBODIMENTS

One class of preferred compounds of this invention includes compounds of this invention which have one or more of the following substituents:

$R_1$ is hydrogen;

alkyl, more preferably alkyl of 1 to 6 carbon atoms;

C(═O)R', where R' is alkyl, more preferably alkyl of 1 to 24 carbon atoms, especially 1 to 8 or 12 to 18 carbon atoms; haloalkyl, more preferably ω-chloro- or perfluoro- alkyl of 1 to 4 carbon atoms, especially ω-chloroethyl or perfluoromethyl, ethyl or propyl; heterocylicalkyl, more preferably an aylkyl of 1 to 6 carbon atoms with an ω-heterocyclic substituent suitably having 5 to 10 ring atoms and 1 to 4 heteroatoms, including fused heteroalicyclic with 3 hetero atoms, such as biotin; aminoalkyl, more preferably alkyl of 1 to 6 carbon atoms, especially 2 carbon atoms, with an ω-amino group optionally protected for example with alkoxycarbonyl such as $(CH_3)_3C—O—C═O—$ or other protecting group;

arylalkylene, especially cinnamoyl; alkylene, especially vinyl or allyl; aralkyl, such as benzyl; or C(═O)OR', where R' is alkyl, more preferably alkyl of 1 to 6 carbon atoms, especially branched alkyl; alkenyl, more preferably allyl;

$R_2$ is hydrogen, methyl, or a protecting group including alkoxycarbonyl such as $(CH_3)_3C—O—C{=}O—$.

$R_3$ is hydrogen;

alkyl, more preferably alkyl of 1 to 6 carbon atoms;

(C═O)R', where R' is alkoxy, especially with an alkyl group of 1 to 6 carbon atoms; alkyl, more preferably alkyl of 1 to 24 carbon atoms, preferably 1 to 8 or 12 to 18 carbon atoms; haloalkyl, more preferably perfluoroalkyl of 1 to 4 carbon atoms, especially perfluoromethyl, ethyl or propyl; arylalkylene, especially cinnamoyl; heterocylicalkyl, more preferably an alkyl of 1 to 6 carbon atoms with an co heterocyclic substituent suitably having 5 to 12 ring atoms and 1 to 4 heteroatoms, including fused heterocyclic with 3 ring atoms, such as biotin; heterocyclicalkyl, with preferably 1 carbon atom in the alkyl group, and more preferably heteroalicylicmethyl with 5 to 10 ring atoms and 1 to 4 ring atoms, especially fused heterocylic with 1 to 4 heteroatoms, such as dimethylaminocoumarin or coumarin; alkylene, especially allyl; aralkyl, such as benzyl;

(C═O)OR', where R' is alkyl, more preferably alkyl of 1 to 6 carbon atoms; alkylene, especially vinyl or allyl; aralkyl, such as benzyl.

$R_4$ is C(═O)R', where R' is alkyl, more preferably alkyl of 1 to 24 carbon atoms, preferably 1 to 8 or 12 to 18 carbon atoms; haloalkyl, more preferably ω-chloro- or perfluoroalkyl of 1 to 4 carbon atoms, especially ω-chloroethyl or perfluoromethyl, ethyl or propyl; aralkyl, such as benzyl or phenethyl; arylalkylene, especially cinnamoyl; aminoalkyl, especially amino acid, more especially protected amino acid, including protected cysteinine, notably Fm-S $CH_2CH$(NHAlloc)-cys or protected alanine, notably $(CH_3)_3C—O—C{=}O$-ala; heterocyclicalkyl, more preferably an alkyl of 1 to 6 carbon atoms with an ω-heterocyclic substituent suitably having 5 to 12 ring atoms and 1 to 4 heteroatoms, including fused heterocyclic with 3 ring atoms, such as biotin; heterocyclicalkyl, with preferably 1 carbon atom in the alkyl group, and more preferably heteroalicyclicmethyl with 5 to 10 ring atoms and 1 to 4 ring atoms, especially fused heterocylic with 1 to 4 heteroatoms, such as coumarin or dimethylaminocoumarin;

(C═O)OR', where R' is alkyl, more preferably alkyl of 1 to 6 carbon atoms; alkylene, especially vinyl or allyl; aralkyl, such as benzyl;

P═O$(OR')_2$, where R' is benzyl.

$R_5$ is hydrogen;

alkyl, more preferably alkyl of 1 to 6 carbon atoms;

(C═O)OR', where R' is alkylene, especially vinyl.

$X_1$ is hydrogen, hydroxy, or cyano.

$X_2$ is hydrogen.

$X_3$ is OR', where R' is alkyl having 1 to 6 carbon atoms, especially methyl.

$X_4$ is hydrogen.

$X_5$ is hydrogen.

$X_6$ is hydrogen or alkyl, especially hydrogen or alkyl of 1 to 6 carbon atoms, more especially hydrogen.

Compounds where $R_3$ is not hydrogen are one class of preferred compounds. In the article by Corey et al., Proc. Natl. Acad. Sci. USA 1999, 96, 3496-3501, a structure-activity relationship is shown for ecteinascidin-type compounds, indicating that a hydrogen is essential. It is stated on page 3498 that "the protection of the other phenolic hydroxyl group on the E subunit resulted in diminished activity". We find the hydrogen is not essential, see compounds 96, 97 and 98, among many others.

Compounds wherein $R_4$ is an ester or an ether are among the preferred compounds, for example compounds 57, 60, 61, 63, 65, 68 and 76. In general they have improved toxicology properties and thus give a wider therapeutic window.

In particular, compounds wherein both $R_3$ and $R_4$ are not hydrogen are preferred. Of those, compounds with an ester or ether at these positions are most preferred, and in particular esters and carbonates. See compounds 78, 82, 83, 84, 86, 88, 92. Esters with bulky groups (long aliphatic or aromatic residues) give better results. Examples of particularly preferred substituents include octanoic, palmitic, cinnamoyl, hydrocinnamoyl. See compounds 86, 92. Among the carbonates, ter-Butyloxycarbonyl (tBOC) and vinyloxycarbonyl (VOC) are the most preferred substituents for these positions. See compounds 86 and 92, which are among the best in activity and toxicology. For the ether substituents at these positions, ethyl or a bulky group is preferred.

Compounds with ethyl at $R_5$, N 2' are preferred, since there is activity at lower concentrations than those at which the compound begins to be toxic.

Compounds with changes at $R_1$ are part of this invention, especially ester groups, $R_1$═R'CO—, with R' a long aliphatic or aromatic group. See compounds 161, 162, 164, 165, 168, 169, 170, 171, 172, 174, 175. Some of these compounds have substituents at both $R_1$ and $R_3$. They have good activity/toxicity properties. For example 170 is active and in heart and myelo non toxic. Compound 174 is very active (E-10) and toxic at higher concentrations (E-8).

There are compounds that have good ADME properties (absorption-distribution-metabolism-excretion) which are good indicative of pharmacokinetics.

As mentioned above, compounds of the present invention, preferably those with bulky substituted groups, have a good therapeutic window and the estherification of the phenols with different acids and carbonates, results in a general enhancement of the pharmaceutical properties: there is a significant decrease in hepatocyte toxicity, and also a good profile on drug-drug interactions since these derivatives do not show cytochrome inhibition having moreover higher metabolic stability.

In a related aspect of this invention, the compounds have one or more of the following features:

$R_1$ is not acetyl. Preferably it has at least 4, 5 or 6 carbon atoms, for example up to 18 or 24 carbon atoms. Suitable substituents include esters COR', where R' is alkyl, alkenyl, often with one or more substituents. Alkyl, substituted alkyl, alkenyl and arylalkenyl are preferred, with suitable substituents including aryl, heterocyclic. Other defintions for $R_1$ include esters of formula COR' derived from an amino acid, optionally a protected amino acid.

$R_3$ is not hydrogen. Preferably it is R', COR' or COOR' where R' is a substituent with some bulk. Such bulky substituents include those with branched chain groups, unsaturated groups or cyclic groups including aromatic groups. Thus, branched alkyl, cycloalkyl, branched alkenyl, aryl, heteroaromatic and related groups are preferred for inclusion within the structure of the substituent $R_3$. Preferably the total number of carbon atoms in $R_3$ is 2 to 24, more preferably 6 to 18 carbon atoms. Typically $R_3$ is an ester, ether or carbonate, being of formula COR', R' or COOR'.

$R_4$ is not hydrogen. Preferably it is R', COR' or COOR' where R' is a substituent with some bulk. Such bulky substituents include those with branched chain groups, unsaturated groups or cyclic groups including aromatic groups. Thus, branched alkyl, cycloalkyl, branched alkenyl, aryl, heteroaromatic and related groups are preferred for inclusion within the structure of the substituent $R_4$. Preferably the total number of carbon atoms in $R_4$ is 2 to 24, more preferably 6 to 18 carbon atoms. Typically $R_4$ is an ester, ether or carbonate, being of formula COR', R' or COOR'.

Examples of protecting groups for amino and other substituents are given in WO 0069862, and we expressly incorporate that disclosure.

Without being exhaustive, another class of preferred compounds of this invention have one or more of the following definitions:

$X_1$ is H, —CN or —OH, most especially —OH or —CN.

$X_2$ is hydrogen.

$X_3$ is methoxy.

$X_4$ and $X_5$ are hydrogen.

$R_1$ is preferably H or acetyl; arylalkyl, especially benzyl; alkyl-CO— (alkyl being up to 25 carbon atoms, such as up to 17, 19 or 21 carbon atoms and preferably an odd number of carbon atoms corresponding to a fatty acid carboxylic acid of even number of carbon atoms or else a low number of carbon atoms such as 1 to 6) especially $CH_3$—$(CH_2)_n$—CO— where n is for example 1.2.4.6.12.14 or 16; haloalkyl-CO—, especially trifluoromethylcarbonyl; arylalkyl-CO—, especially benzyl-CO—; arylalkenyl-CO—, especially cinnamoyl-CO—; most especially $R_1$ is H, acetyl or cinnamoyl.

$R_2$ is H; alkyl, especially methyl; alkyl-O—CO—, especially t-butyl-O—CO— or alkenyl-O—CO—, especially allyl-O—CO—.

$R_3$ is preferably H or acetyl; alkyl (alkyl being 1 to 6 carbon atoms), especially $C_1$ to $C_3$ alkyl; alkenyl, especially allyl; arylalkyl, especially benzyl; alkyl-CO— (alkyl being up to 25 carbon atoms, such as up to 17, 19 or 21 carbon atoms and preferably an odd number of carbon atoms corresponding to a fatty acid carboxylic acid of even number of carbon atoms or else a low number of carbon atoms such as 1 to 6) especially $CH_3$—$(CH_2)_n$—CO— where n is for example 1.2.4.6.12.14 or 16 and derivatives thereof, as in Biotin-$(CH_2)_4$—CO—; arylalkenyl-CO—, especially cinnamoyl-CO—; alkyl-O—CO—, especially t-butyl-O—CO—; arylalkyl-O—CO—, especially benzyl-O—CO—; alkenyl-O—CO, especially allyl-O—CO—.

$R_4$ is preferably H, acetyl, alkyl (alkyl being 1 to 6 carbon atoms) especially $C_1$ to $C_3$ alkyl; alkenyl, especially allyl; arylalkyl, especialy benzyl; alkyl-CO— (alkyl being up to 25 carbon atoms, such as up to 17, 19 or 21 carbon atoms and preferably an odd number of carbon atoms corresponding to a fatty acid carboxylic acid of even number of carbon atoms or else a low number of carbon atoms such as 1 to 6) especially $CH_3$—$(CH_2)_n$—CO— where n is for example 1.2.4.6.12.14 or 16 and derivatives thereof, as in Biotin-$(CH_2)_4$—CO—; haloalkyl-CO—, especially trifluoromethylcarbonyl; amino acid acyl or a derivative thereof, as in $FmSCH_2CH(NHAlloc)CO$—; arylalkenyl-CO—, especially cinnamoyl-CO—; alkyl-O—CO—, especially tert-butyl-O—CO—; alkenyl-O—CO—, especially allyl-O—CO; arylalkyl-O—CO—, especially benzyl-O—CO—; protecting group as in $PO(OBn)_2$; most especially $R_4$ is H, acyl y cinnamoyl.

$R_5$ is H or alkyl (alkyl being 1 to 6 carbon atoms) and $R_5$ is most especially H or $C_1$ to $C_3$ alkyl.

This application claims priority of a British patent application. We expressly incorporate by reference any disclosure which is in the specification of that British priority application and which is not in the present application.

Furthermore, we expressly incorporate by reference each of WO 0069862, WO 0177115, WO 0187894 and WO 0187895 for their discussion of substituents which correspond to the substituents of the present invention. Any definitions given in any of these earlier applications for a particular substituent can be adopted for a substituent of a compound of this invention.

Furthermore, we do not claim any of the compounds disclosed in the earlier applications, and we expressly disclaim any such compounds. We expressly incorporate by reference each of the earlier applications for the wording of any disclaimer which might be necessary.

In one aspect, this invention is concerend with a derivative of Et-743 or Et-770 or Et-729 which differs in one or more of the following aspects:

$R_1$ is not acetyl, and in particular is a group which is not COR' where R' is hydrogen, methyl or ethyl, or which is not COR' where R' is hydrogen, methyl, ethyl or propyl.

$R_1$ is not R' where R' is methyl or ethyl, or where R' is methyl, ethyl or propyl or where R' is methyl, ethyl, propyl or butyl.

$R_2$ is not methyl.

$R_6$ is $R_3$ and is not hydrogen.

$R_4$ is not hydrogen.

$R_5$ is not hydrogen.

$R_6$ and $R_7$ are =O.

$X_1$ is not hydroxy or cyano.

In one aspect, this invention provides a derivative wherein:

$R_1$ is not acetyl, and in particular is a group which is not COR' where R' is hydrogen, methyl or ethyl, or which is not COR' where R' is hydrogen, methyl, ethyl or propyl; $R_1$ is not R' where R' is methyl or ethyl, or where R' is methyl, ethyl or propyl or where R' is methyl, ethyl, propyl or butyl; and $R_6$ is $R_3$ and is not hydrogen.

In a further aspect, this invention provides a derivative wherein:

$R_1$ is not acetyl, and in particular is a group which is not COR' where R' is hydrogen, methyl or ethyl, or which is not COR' where R' is hydrogen, methyl, ethyl or propyl; $R_1$ is not R' where R' is methyl or ethyl, or where R' is methyl, ethyl or propyl or where R' is methyl, ethyl, propyl or butyl; and $R_4$ is not hydrogen.

In a related aspect, this invention provides a derivative wherein:

$R_6$ is $R_3$ and is not hydrogen; and $R_4$ is not hydrogen.

In yet another aspect, this invention provides a derivative wherein:

$R_1$ is not acetyl, and in particular is a group which is not COR' where R' is hydrogen, methyl or ethyl, or which is not COR' where R' is hydrogen, methyl, ethyl or propyl; $R_1$ is not R' where R' is methyl or ethyl, or where R' is methyl, ethyl or propyl or where R' is methyl, ethyl, propyl or butyl; $R_6$ is $R_3$ and is not hydrogen; $R_4$ is not hydrogen.

The compounds of the present invention can be prepared synthetically from the intermediate compound 15 described in the U.S. Pat. No. 5,721,362, ET-770 and ET-729. Numerous active antitumoral compounds have been prepared from this compound and it is believed that many more compounds can be formed in accordance with the teachings of the present disclosure.

ET-770 (1)

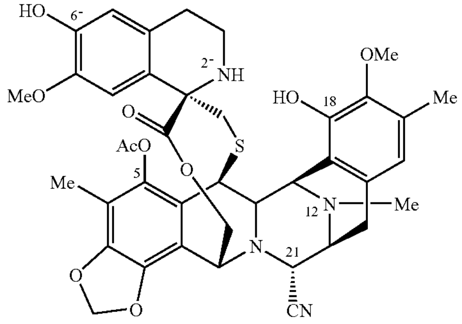

ET-729 (19)

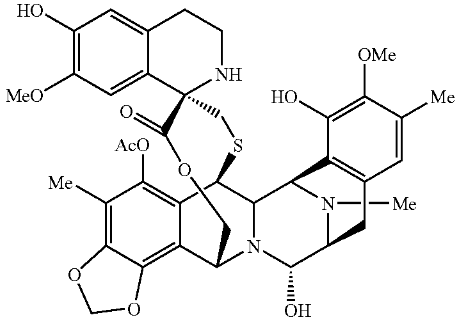

15 (34)

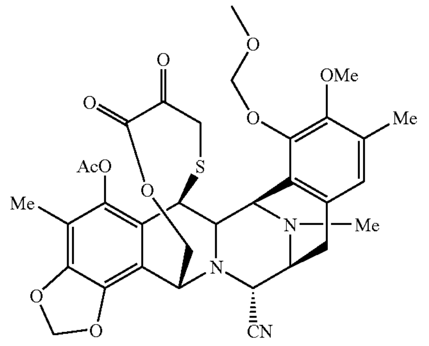

15 (34)

Antitumoral activities of these compounds include leukaemias, lung cancer, colon cancer, kidney cancer, prostate cancer, ovarian cancer, breast cancer, sarcomas and melanomas.

Another especially preferred embodiment of the present invention is pharmaceutical compositions useful as antitumor agents which contain as active ingredient a compound or compounds of the invention, as well as the processes for their preparation.

Examples of pharmaceutical compositions include any solid (tablets, pills, capsules, granules etc.) or liquid (solutions, suspensions or emulsions) with suitable composition or oral, topical or parenteral administration.

Administration of the compounds or compositions of the present invention may be any suitable method, such as intravenous infusion, oral preparation, intraperitoneal and intravenous preparation.

Administration of the compounds or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);

d) drugs which target DNA such as the antracycline drugs adriamycin, doxorubicin, pharmorubicin or epirubicin;

e) drugs which target topoisomerases such as etoposide;

f) hormones and hormone agonists or antagonists such as estrogens, antiestrogens (tamoxifen and related compounds) and androgens, flutamide, leuprorelin, goserelin, cyprotrone or octreotide;

g) drugs which target signal transduction in tumour cells including antibody derivatives such as herceptin;

h) alkylating drugs such as platinum drugs (cis-platin, carbonplatin, oxaliplatin, paraplatin) or nitrosoureas;

i) drugs potentially affecting metastasis of tumours such as matrix metalloproteinase inhibitors;

j) gene therapy and antisense agents;

k) antibody therapeutics;

l) other bioactive compounds of marine origin, notably the didemnins such as aplidine;

m) steroid analogues, in particular dexamethasone;

n) anti-inflammatory drugs, in particular dexamethasone; and o) anti-emetic drugs, in particular dexamethasone.

Examples of biological activities of the compounds of the present invention are included in tables I, II and III at the end of the document.

DETAILED DESCRIPTION OF THE PREFERRED EMBODIMENTS
The preferred methods of producing the compounds are described below in schemes I-VI.
SCHEME I
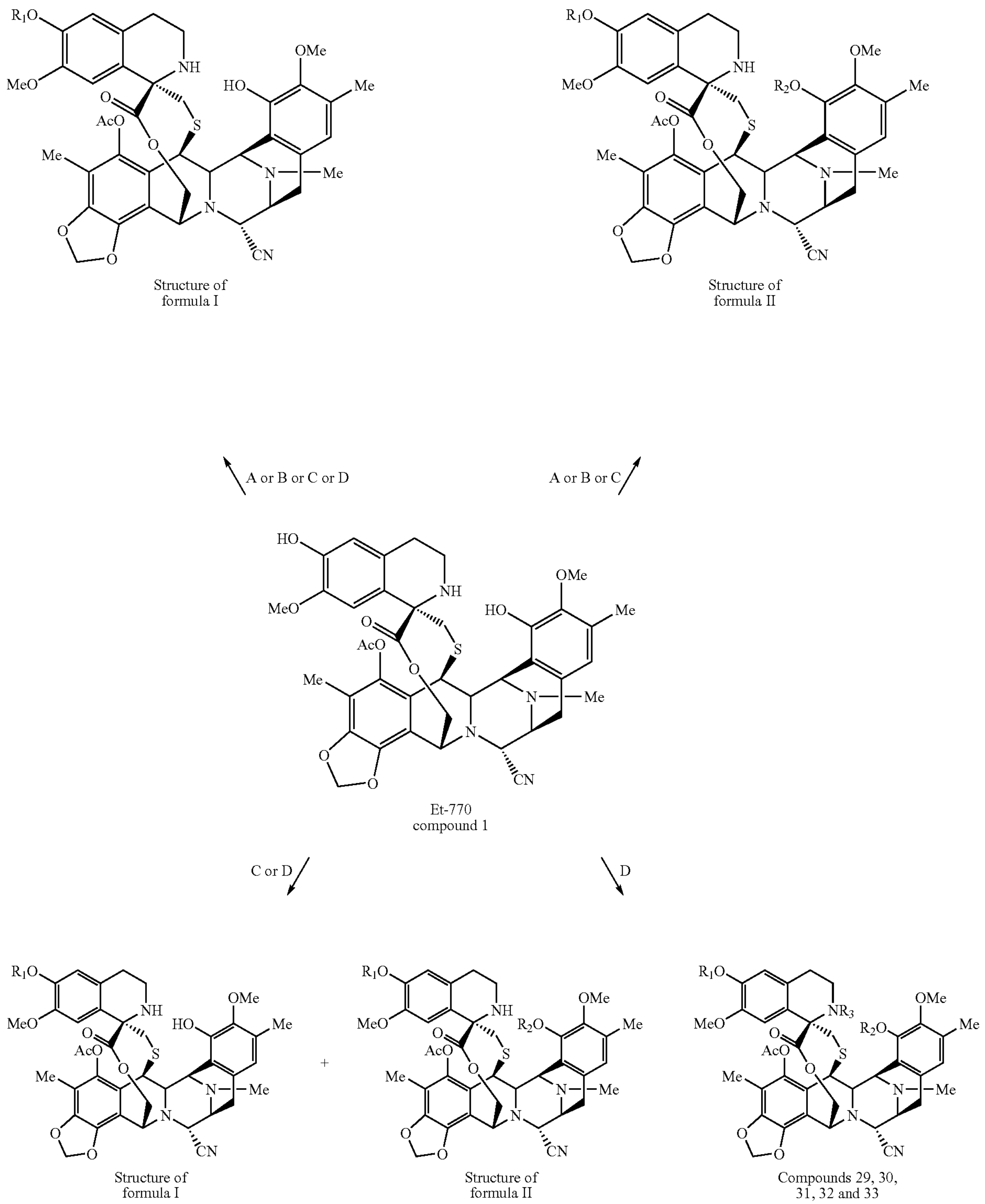
Structure of formula I
Structure of formula II
Et-770 compound 1
Structure of formula I
Structure of formula II
Compounds 29, 30, 31, 32 and 33

-continued

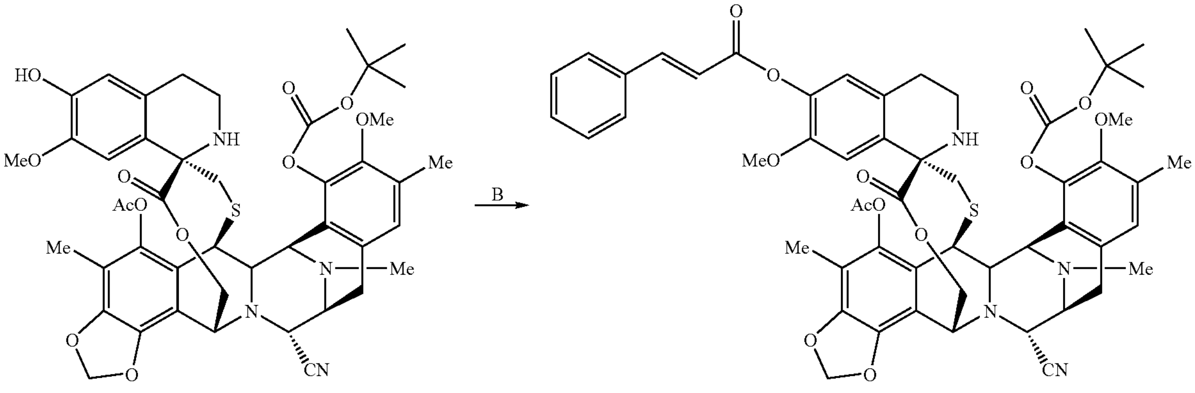

47 49

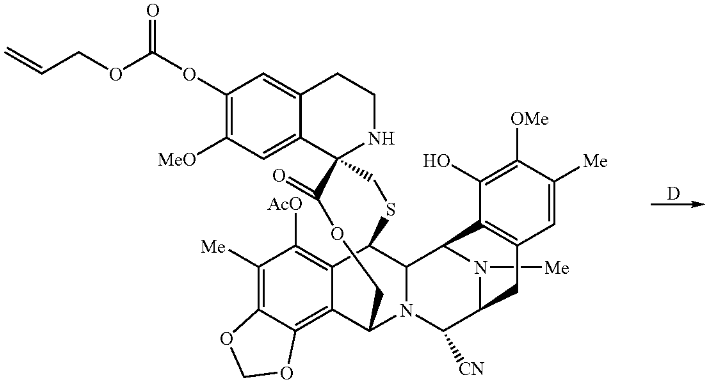

25

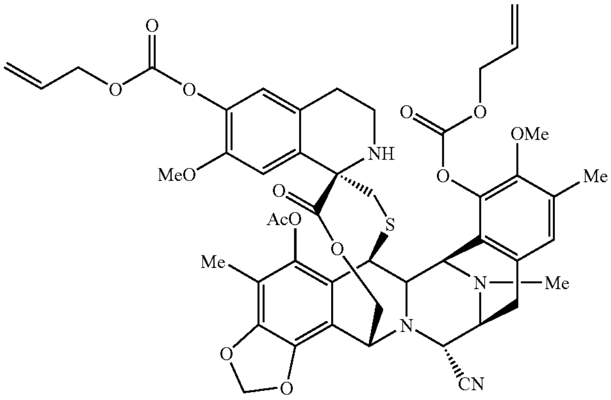

26

Scheme I includes acylation reactions through the different procedures described in the experimental part. Compound 1 corresponds to Et-770. Starting from this compound it is possible to obtain target compounds following acylation methods: A ($(RCO)_2O$/base), B (RCOCl/base), C (RCOOH/DMAP/EDC.HCl) and D (ROCOCl/base). Other acylation reactions have been performed from compound 25 which belongs to the family of the structures of formula I and compound 47 whose structure is described further.

Compounds 29, 30, 31, 32 and 33 are compounds wherein $R_1$, $R_2$ and $R_3$ is a vinyl radical or an hydrogen atom.

SCHEME II

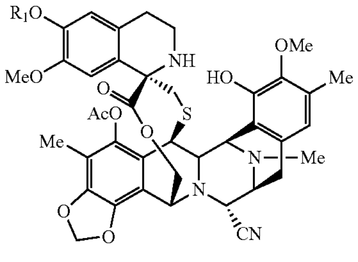

Structure of formula I

+

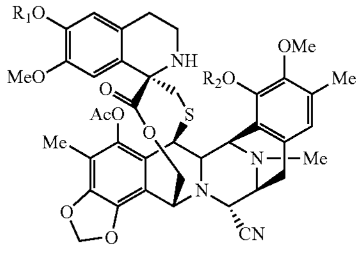

Structure of formula II

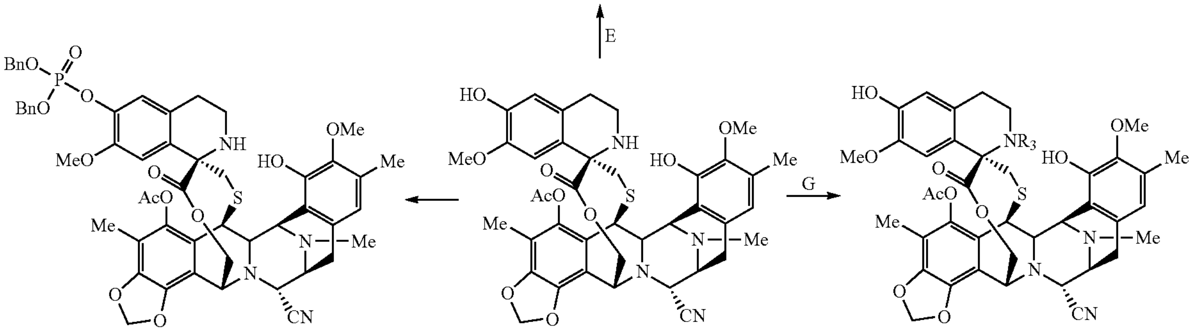

53

Et-770 compound 1

Structure of formula III

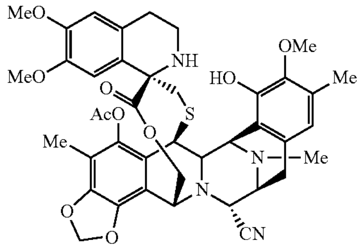

34

+

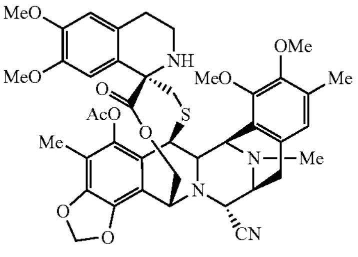

35

+

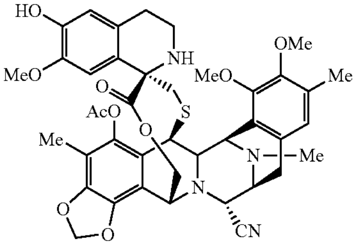

36

In Scheme II method E involves reactions of alkylation ($RBr/Cs_2CO_3$) and method G ($RCHO/NaBCNBH_3/AcOH$) is the reductive alkylation at N-2'. Compounds 34, 35 and 36 are obtained when the alkylation reaction is performed with MeI. With these methodologies we generate N and O-alkyl derivatives starting from compound 1. In compound 53 a phosphate group is introduced at position C-6' using dibenzyl phosphite.

SCHEME III
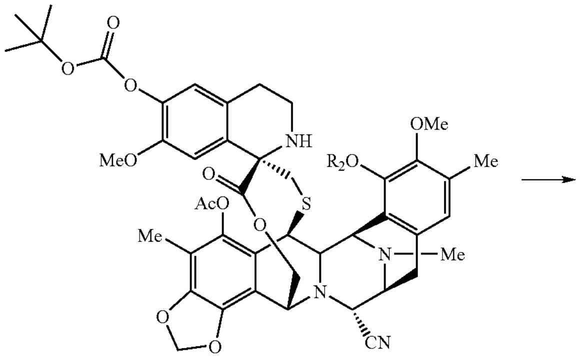
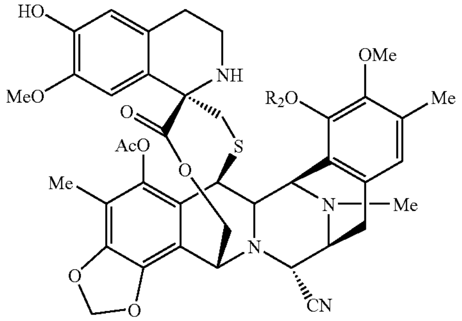
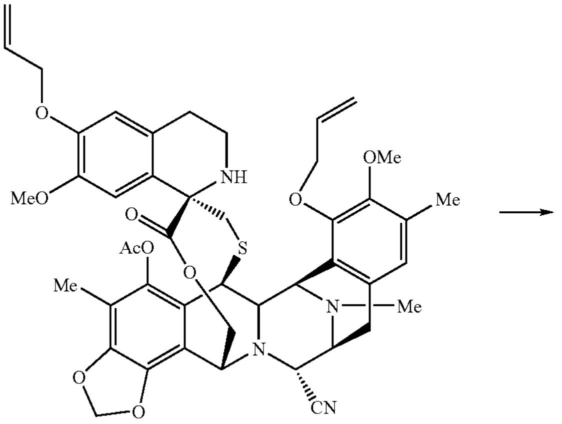
42
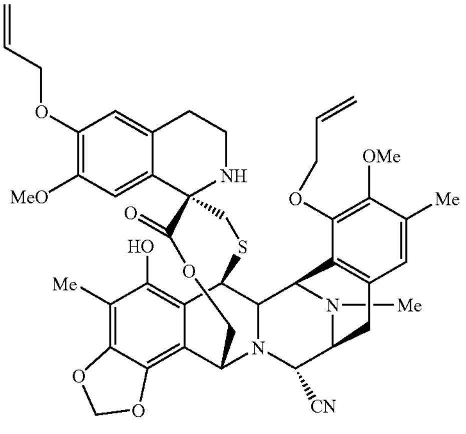
50
-continued
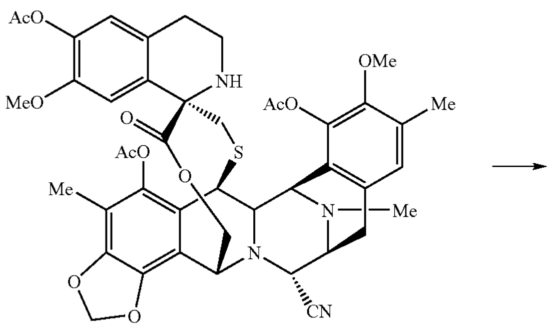
6
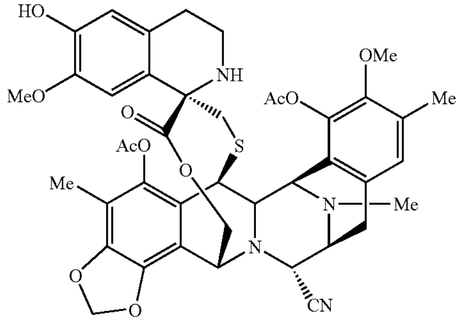
51
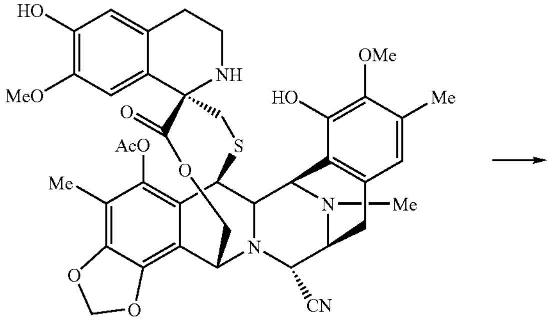
Et-770
compound 1
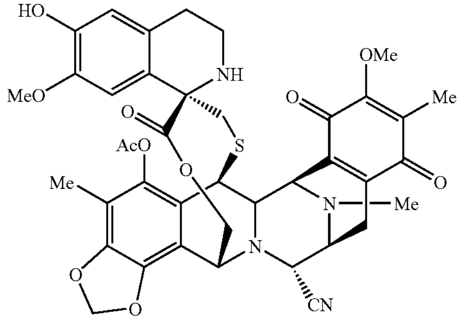
52

Scheme III includes hydrolysis of tert-butylcarbonate in C-6' through method F ($TFA/H_2O/CH_2Cl_2$) and hydrolysis of acetyl groups in C-5 from compound 42 with $KOH/H_2$)/THF and in C-6' from compound 6 with TEA/MeOH/THF. Also is described the formation of compound 52 starting from compound 1 through an oxidation reaction of the right aromatic ring.

SCHEME IV

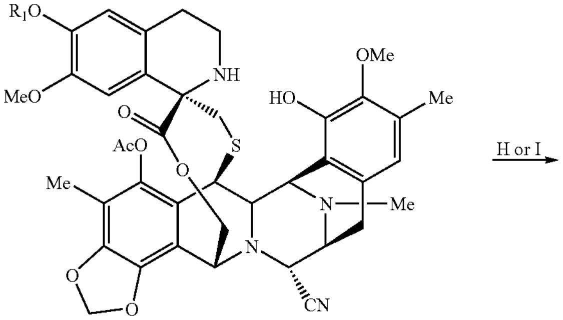

Structure of formula I

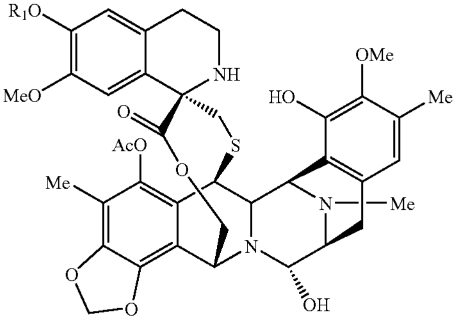

Final compound of the structure of formula I

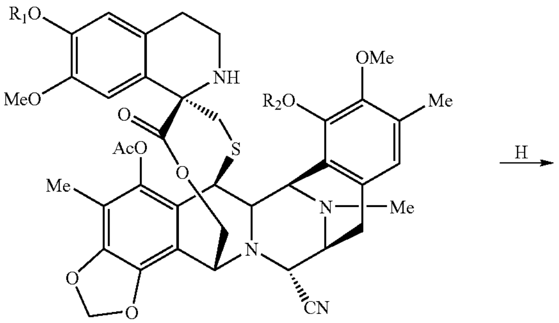

Structure of formula II

-continued

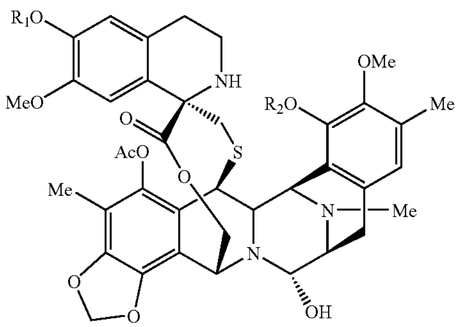

Final compound of the structure of formula II

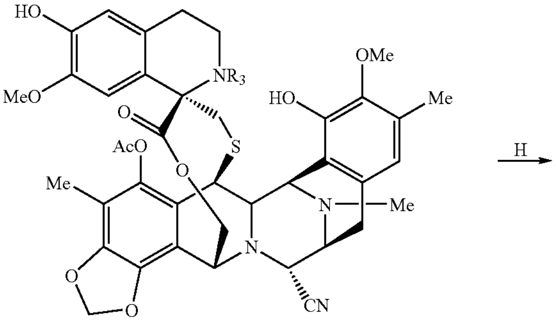

Structure of formula III

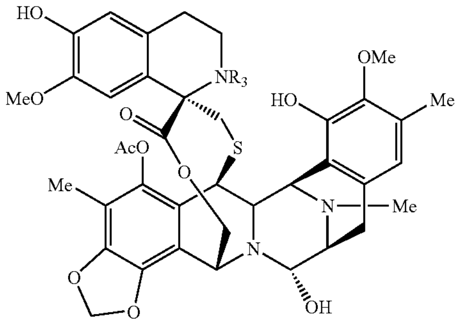

Final compound of the structure of formula III

The different analogs of Et-743 wherein $R_1$, $R_2$ and $R_3$ are acyl, carbonate, carbamate or alkyl groups are prepared following method H ($AgNO_3/CH_3CN/H_2O$) or I (CuBr/THF/$H_2O$) from the derivatives of Et-770 (Scheme IV). In both cases the reaction involves the transformation of the nitrile group in C-21 into the hydroxyl group. Other specific derivatives as compounds 96, 97, 98, 99, 100, 101 and 102 are synthetised from their corresponding analogs of Et-770, compounds 51, 47, 36, 31, 32, 52 and 48 following the same methodology.

SCHEME V
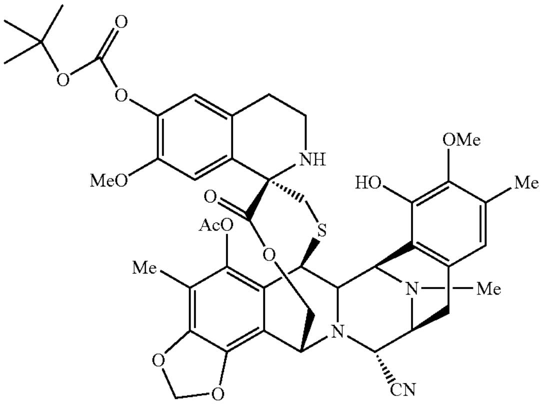
4
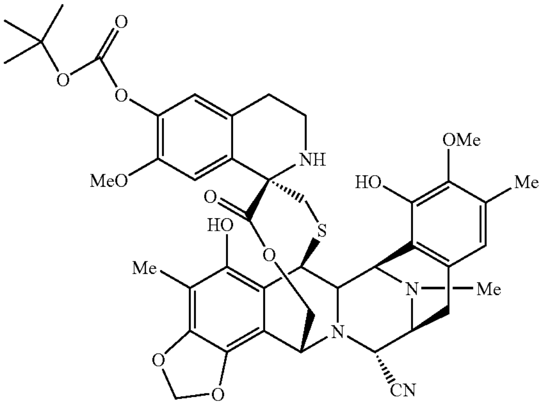
106
A, B, C, or E
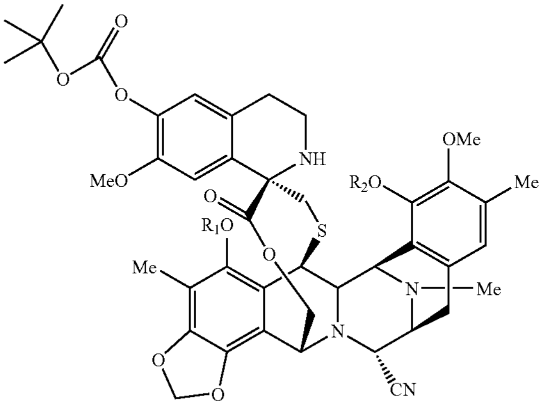
Structure of formula IV
F or J
H -continued

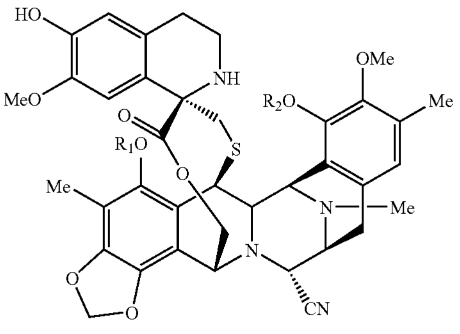

Structure of formula V

H, I or K

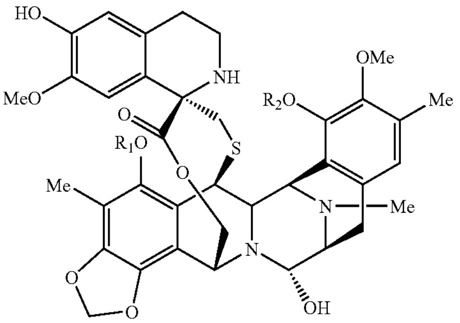

Structure of formula VI

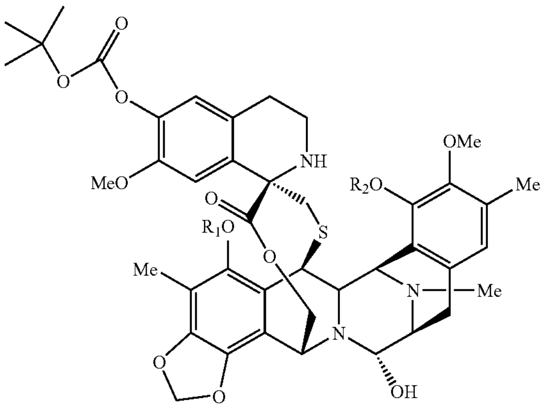

Structure of formula VII

In Scheme V the starting material is compound 106 obtained from compound 4 by hydrolysis of the acetyl group in C-5 with KOH/THF/$H_2O$. From compound 106 and by esterification and alkylation reactions can be prepared derivatives with structures of formula I. The next step includes the hydrolysis of the tert-butylcarbonate group (method F: TFA/$H_2O$/$CH_2Cl_2$ or method J: TMSCl, NaI; $CH_3CN$/$H_2O$) to afford derivatives of structures of formula III which are transformed into the final compounds (structure of formula IV) by conversion of the nitrile group in C-21 into the hydroxyl group. This last step is achieved following method H ($AgNO_3$/$CH_3CN$/$H_2O$), method I (CuBr/THF/$H_2O$) or method K (CuCl/THF/$H_2O$). In the case of derivatives of structure of formula I wherein $R_1$ and $R_2$ are Boc, $R_1$ are Boc, AlaBoc and Voc radicals the hydrolysis of the tert-butylcarbonyl involves also the hydrolysis of these ester functionalities. These compounds are transformed into the final analogs through method H.

SCHEME VI

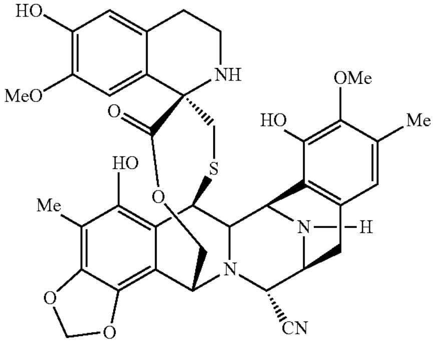

184

-continued
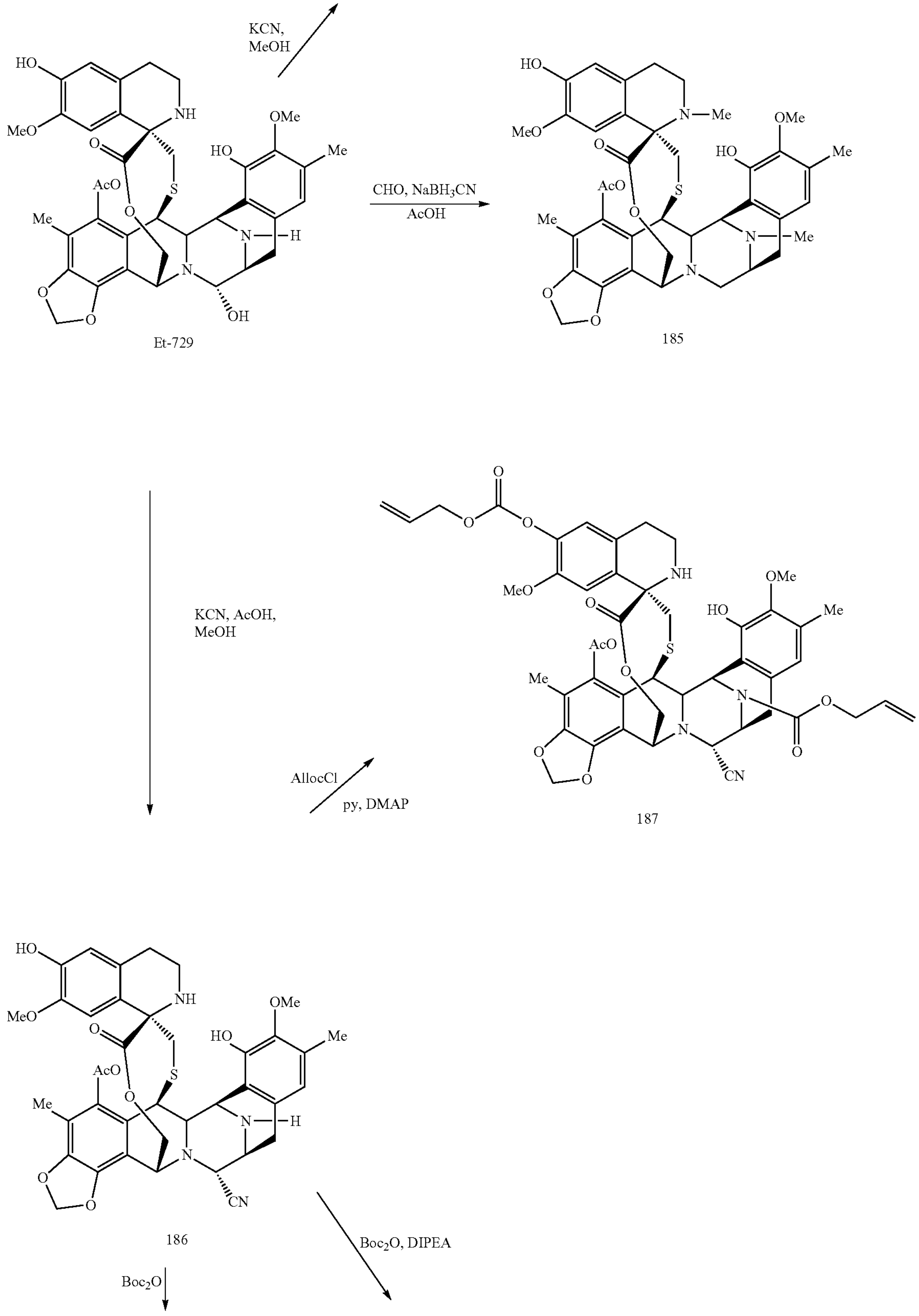
Et-729
185
187
186

-continued
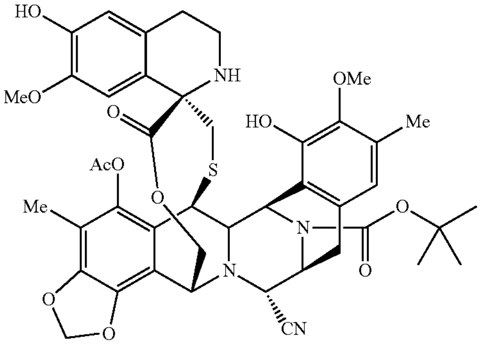
188
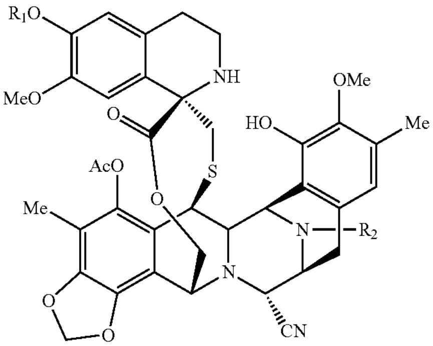
| Compound | $R_1$ | $R_2$ |
| --- | --- | --- |
| 188 | H | Boc |
| 189 | Boc | H |
| 190 | Boc | Boc |
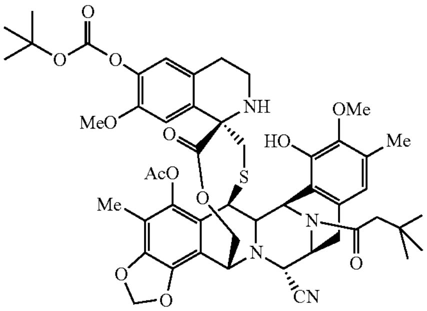
190
$Cs_2CO_3$
AllylBr
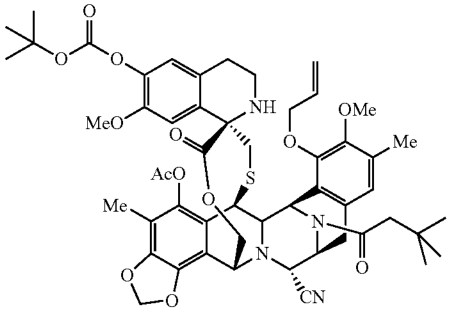
F
199
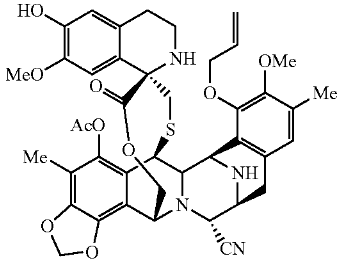
201
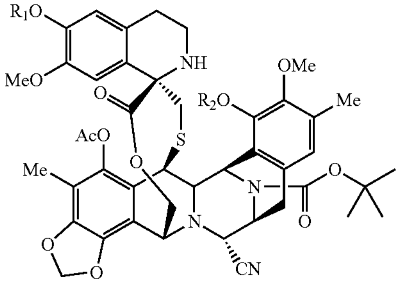
Structure of formula VIII
F
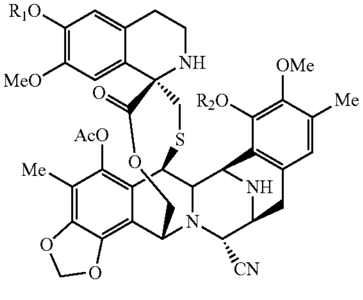
Structure of formula IX
H -continued

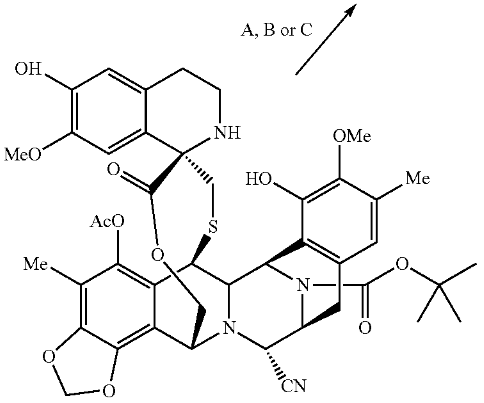

188

A, B or C

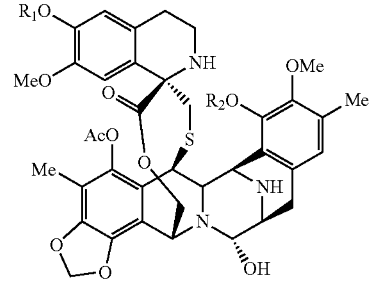

Structure of formula X

NaBH3CN, AcOH

CH3CN, CHO

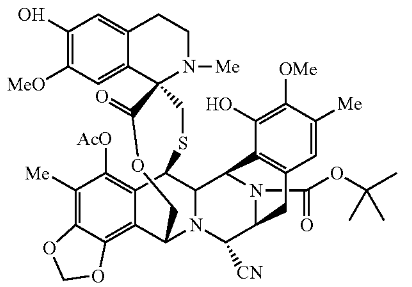

200

F

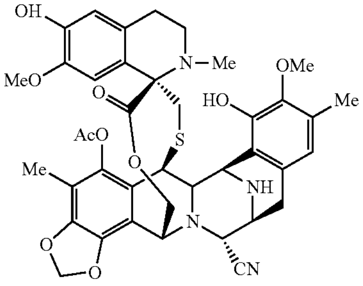

209

H

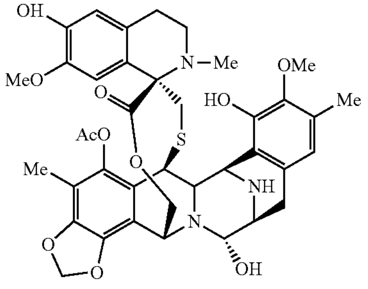

217

From Et-729 it is possible to obtain target compounds through different experimental conditions. In the attempts to prepare compound 186, other two compounds (184 and 185) were isolated as it is described in the scheme VI. Treatment of compound 186 with Alloc chloroformiate, pyridine and DMAP affords compound 187. With Boc anhydride with o without DIPEA we are able to obtain Boc derivatives (compounds 188, 189 and 190). From compound 190 through an alkylation reaction ($Cs_2CO_3$, allyl bromide) is prepared compound 199 which is transformed into compound 201 by hydrolysis of tert-butyl carbonate groups following method F.

From the key compound 188 through esterification reactions it is possible to generate compounds of structure of formula I mono or di substituted. Hydrolysis of tert-butyl carbonate group (method F) and transformation of the nitrile group in C-21 into the hydroxyl group (method H) lead to the compounds of structure of formula III. Also from compound 188 by a reductive methylation it is obtained compound 200 with a methyl group in position N-2'. Hydrolysis of the amide bond (method F) and conversion of the nitrile group into the hydroxyl group (method H) affords compound 217.

SCHEME VII

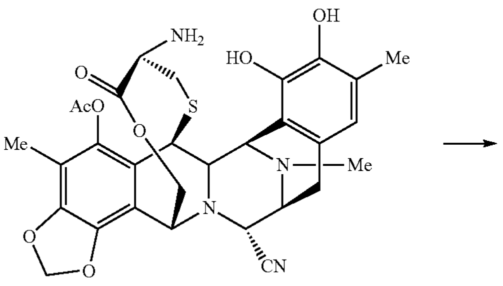

218

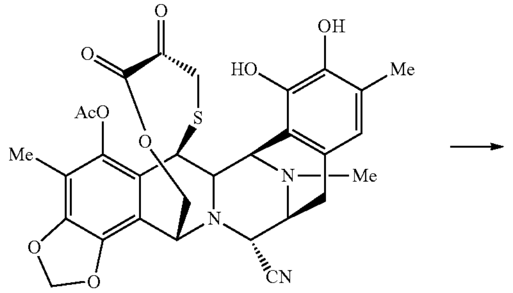

219

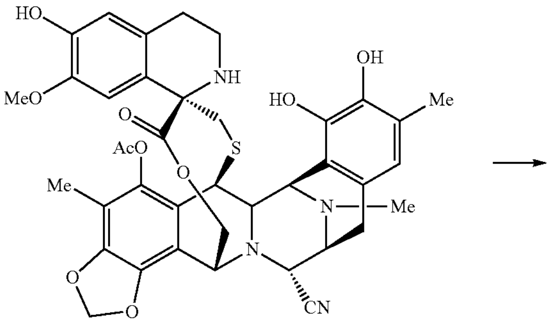

220

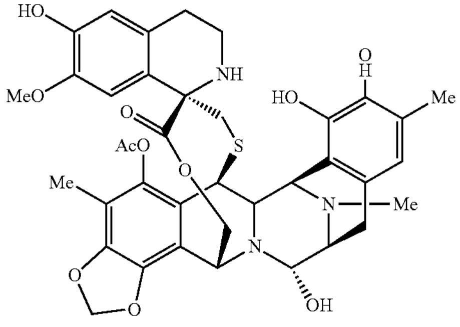

221

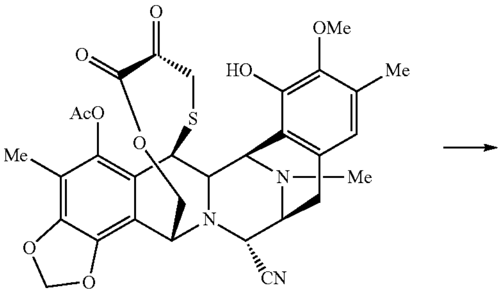

222

-continued

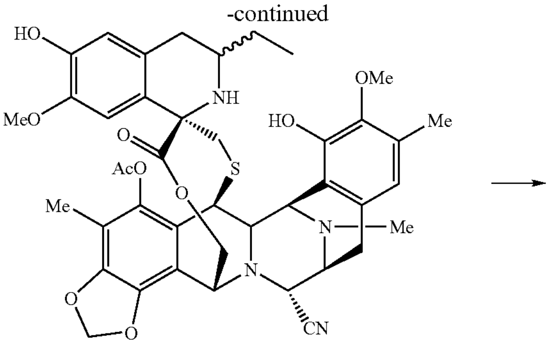

223

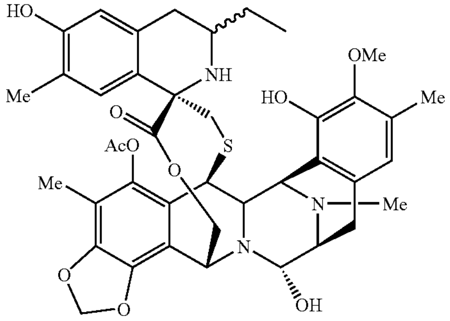

224

In this scheme compound 221 can be obtained from compound 218, described in the Patent WO 01/77115 A1 as compound 24, following a transamination reaction to afford 219 and a Pictect-Spengler cyclization to give compound 220. Final step is the conversion of nitrile group into OH in C-21 with the usual methodology (method K) using $AgNO_3$. Also compound 224 can be obtained from compound 222, described in the WO 00/69862 as compound 36, following a Pictect-Splenger cyclization to give compound 223. Final step is the conversion of nitrile group into OH in C-21 with the usual methodology (method K)

EXPERIMENTAL PART

Method A: To a solution of 1 equiv. of ET-770 (1) in $CH_2Cl_2$ (0.032M) under Argon were added 2 equiv. of the anhydride and 2 equiv. of pyridine. The reaction was followed by TLC and quenched with $NaHCO_3$, extracted with $CH_2Cl_2$ and the organic layers dried over $Na_2SO_4$. Flash chromatography gives pure compounds.

Example 1

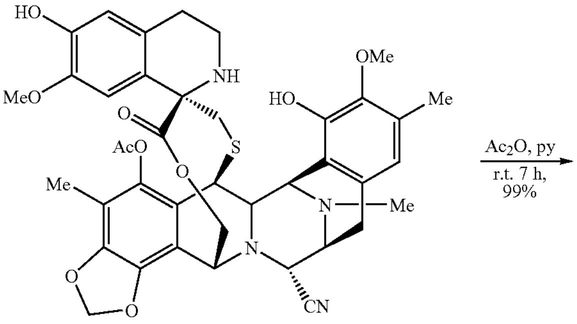

1

-continued
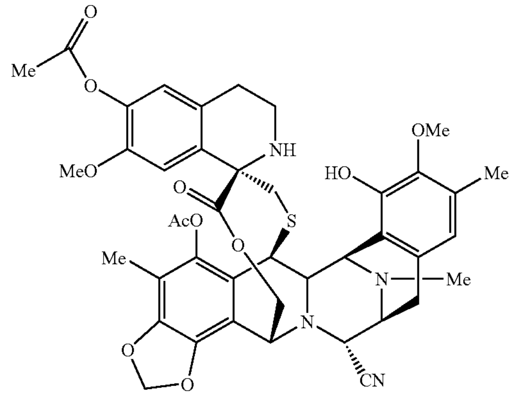
2
2. $^{1}$H-RMN (300 MHz, $CDCl_3$): δ 6.60 (s, 1H); 6.59 (s, 1H); 6.56 (s, 1H); 6.00 (dd, 2H); 5.73 (s, 1H); 5.01 (d, 1H); 4.55 (s, 1H); 4.32 (s, 1H); 4.27 (d, 1H); 4.17 (d, 1H); 4.11 (dd, 1H); 3.78 (s, 3H); 3.55 (s, 3H); 3.51 (d, 1H); 3.42 (s, 1H); 3.16-3.06 (m, 1H); 2.94-2.92 (m, 2H); 2.81-2.75 (m, 1H); 2.64-2.58 (m, 1H); 2.51-2.44 (m, 1H); 2.35-2.12 (m, 2H); 2.31 (s, 3H); 2.26 (s, 3H); 2.23 (s, 3H); 2.19 (s, 3H); 2.03 (s, 3H).
$^{13}$C-RMN (75 MHz, $CDCl_3$): δ 172.1, 168.9, 168.1, 148.4, 147.8, 145.3, 143.0, 141.3, 140.1, 138.5, 132.5, 130.8, 129.3, 128.7, 122.4, 121.0, 120.7, 118.1, 118.0, 114.0, 111.8, 102.0, 101.8, 64.8, 61.1, 60.3, 60.1, 59.5, 55.1, 54.7, 53.3, 42.3, 41.9, 41.6, 39.5, 29.6, 28.6, 24.1, 20.5, 20.3, 15.7, 9.6.
ESI-MS m/z: Calcd for $C_{42}H_{44}N_4O_{10}S$: 812.3 Found ($M+H^+$): 813.3
Example 2
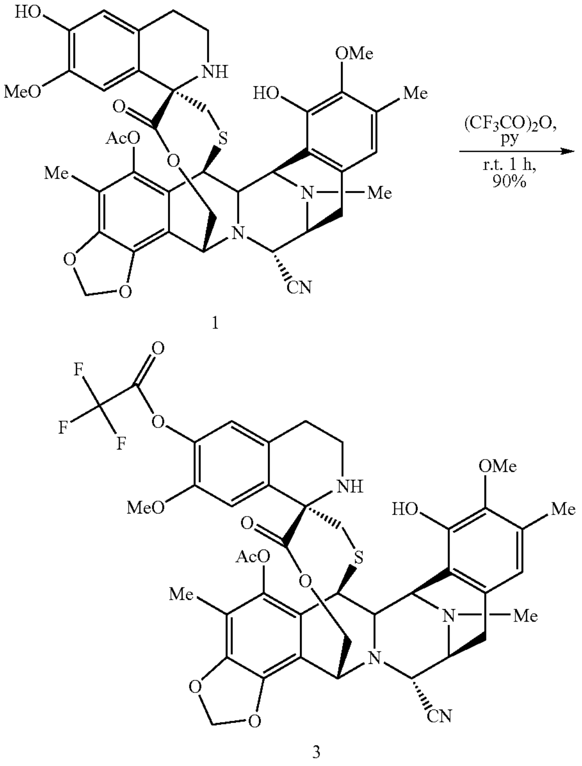
3. $^{1}$H-RMN (300 MHz, $CDCl_3$): δ 6.48 (s, 1H); 6.47 (s, 1H); 6.44 (s, 1H); 6.01 (dd, 2H); 5.70 (s, 1H); 5.50 (s, 1H); 4.70-4.78 (m, 2H); 4.39 (s, 1H); 4.24 (dd, 1H); 4.12-4.08 (m, 2H); 3.80 (s, 3H); 3.59 (s, 3H); 3.55 (d, 1H); 3.42-3.39 (m, 1H); 3.22 (d, 1H); 2.90 (d, 2H); 2.65 (t, 2H); 2.51 (d, 1H); 2.32 (s, 3H); 2.27-2.03 (m, 2H); 2.40 (s, 3H); 2.12 (s, 3H); 2.03 (s, 3H).
$^{13}$C-RMN (75 MHz, $CDCl_3$): δ 168.5, 167.6, 147.3, 145.4, 145.2, 143.1, 141.8, 140.7, 130.8, 129.7, 127.0, 126.3, 125.3, 122.5, 121.4, 118.5, 117.8, 114.3, 114.0, 113.8, 109.5, 102.1, 71.4, 62.2, 61.0, 60.3, 60.2, 60.1, 55.3, 55.1, 54.9, 42.6, 41.9, 39.0, 31.7, 29.3, 24.8, 22.8, 20.5, 15.7, 14.2, 9.9.
ESI-MS m/z: Calcd for $C_{42}H_{41}F_3N_4O_{11}S$: 867.2 Found ($M+H^+$): 866.2
Example 3
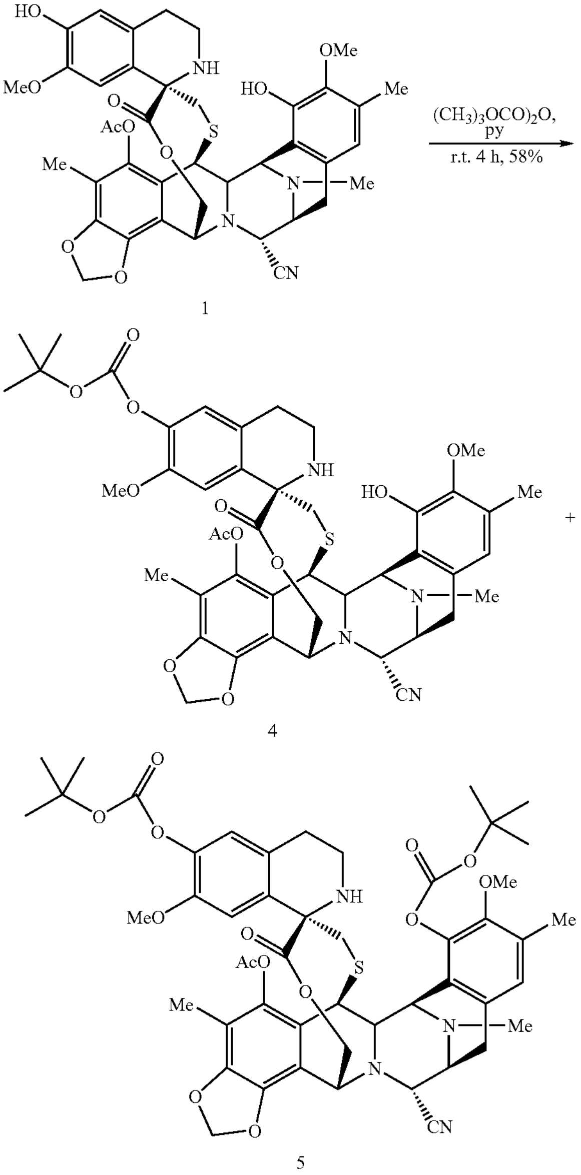

4. $^1$H-RMN (300 MHz, $CDCl_3$): δ 6.68 (s.1H); 6.58 (s, 1H); 6.57 (s, 1H); 6.00 (dd, 2H); 5.74 (s, 1H); 5.00 (d, 1H); 4.54 (s, 1H); 4.31 (s, 1H); 4.26 (dd, 1H); 4.17 (d 1H); 4.11 (dd, 1H); 3.78 (s, 3H); 3.58 (s, 3H); 3.51 (d, 1H); 3.42-3.40 (m, 1H); 3.14-3.06 (m, 1H); 2.94-2.92 (m, 2H); 2.81-2.75 (m, 1H); 2.64-2.58 (m, 1H); 2.51-2.44 (m, 1H); 2.35-2.21 (m, 2H); 2.31 (s, 3H); 2.26 (s, 3H); 2.19 (s, 3H); 2.03 (s, 3H); 1.50 (s, 9H).

$^{13}$C-RMN (75 MHz, $CDCl_3$): δ 172.0, 168.0, 151.5, 148.5, 147.8, 145.3, 143.0, 141.2, 140.0, 138.8, 132.4, 130.7, 129.2, 128.6, 122.1, 122.0, 120.6, 118.1, 118.0, 113.9, 111.9, 101.8, 83.3, 64.7, 61.0, 60.2, 60.0, 59.6, 59.5, 55.2, 54.6, 54.5, 42.2, 41.8, 41.5, 39.5, 28.6, 27.5, 24.1, 20.3, 15.7, 9.6.

ESI-MS m/z: Calcd for $C_{45}H_{50}N_4O_{12}S$: 870.3 Found ($M+H^+$): 871.3

5: $^1$H-RMN (300 MHz, $CDCl_3$): δ 6.92 (s, 1H); 6.69 (s, 1H); 6.55 (s, 1H); 6.00 (dd, 2H); 5.73 (s, 1H); 5.00 (d, 1H); 4.44 (s, 1H); 4.32 (s, 1H); 4.18 (d, 1H); 4.09 (dd, 1H); 3.93 (d, 1H); 3.79 (s, 3H); 3.58 (s, 3H); 3.53 (d, 1H); 3.46-3.44 (m, 1H); 3.12-3.04 (m, 1H); 2.97 (d, 2H); 2.83-2.77 (m, 1H); 2.65-2.58 (m, 1H); 2.51-2.46 (m, 1H); 2.32-2.03 (m, 2H); 2.32 (s, 3H); 2.31 (s, 3H); 2.17 (s, 3H); 2.04 (s, 3H); 1.53 (s, 9H); 1.50 (s, 9H).

$^{13}$C-RMN (75 MHz, $CDCl_3$): δ 172.0, 168.4, 151.5, 151.2, 148.5, 148.1, 145.6, 144.0, 141.3, 140.1, 138.9, 132.3, 131.3, 130.3, 128.7, 126.9, 124.3, 122.2, 121.0, 117.8, 113.8, 111.8, 101.9, 83.4, 83.2, 64.9, 61.1, 60.0, 59.9, 59.6, 59.1, 55.6, 55.2, 54.4, 42.2, 41.9, 41.5, 39.5, 28.6, 27.6, 27.5, 23.9, 20.1, 15.7, 9.6.

ESI-MS m/z: Calcd for $C_{50}H_{58}N_4O_{14}S$: 970.1 Found ($M+H^+$): 971.3

Example 4

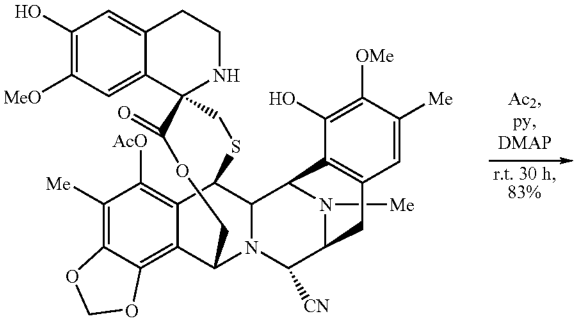

1

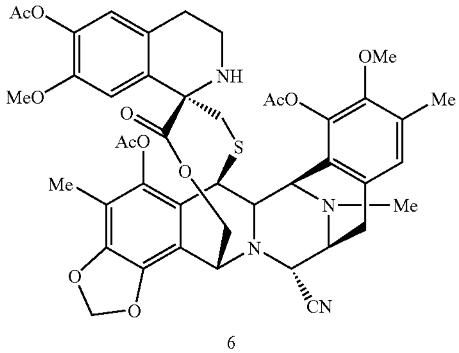

6

Compound 6 is obtained with 45 equiv of $Ac_2O$ and 113 equiv. of pyridine and catalytic amount of DMAP.

6. $^1$H-NMR (300 MHz, $CDCl_3$): δ 6.95 (s, 1H), 6.62 (s, 1H), 6.54 (s, 1H), 6.02 (dd, 2H), 5.01 (d, 1H), 4.44 (bs, 1H), 4.32 (s, 1H), 4.19 (d, 1H), 4.12 (dd, 1H), 3.82 (d, 1H), 3.77 (s, 3H), 3.65 (s, 3H), 3.53 (bd, 1H), 3.47-3.43 (m, 1H), 3.14-3.05 (m, 1H), 3.00-2.97 (m, 2H), 2.86-2.78 (m, 1H), 2.69-2.58 (m, 1H), 2.52-2.44 (m, 1H), 2.38-2.15 (m, 2H), 2.38 (s, 3H), 2.32 (s, 3H), 2.30 (s, 3H), 2.24 (s, 3H), 2.15 (s, 3H), 2.04 (s, 3H).

ESI-MS m/z: Calcd for $C_{44}H_{46}N_4O_{12}S$: 854.3 Found ($M+H^+$): 855.3

Example 5

Method B: To a solution of 1 equiv. of Et-770 (1) in $CH_2Cl_2$ (0.032M) under Argon at room temperature were added 2 equiv. of base and 2 equiv. of the acid chloride. The reaction was followed by TLC and quenched with $NaHCO_3$, extracted with $CH_2Cl_2$ and the organic layers dried with $Na_2SO_4$. Flash chromatography gives pure compounds.

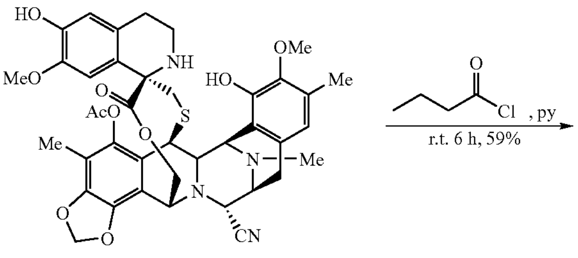

1

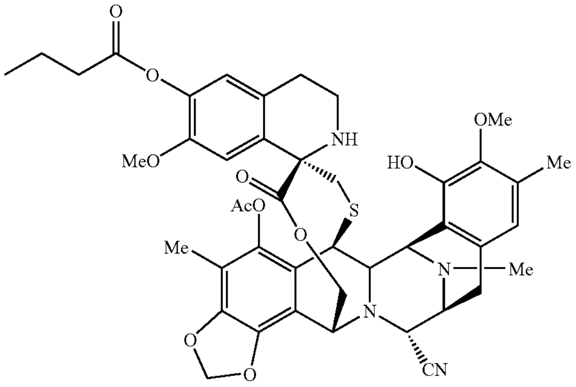

7

After chromatographic purification 25% of starting material was recuperated.

7. $^1$H-NMR (300 MHz, $CDCl_3$): δ 6.59 (s, 2H); 6.56 (s, 1H); 6.00 (dd, 2H); 5.74 (s, 1H); 5.01 (d, 1H); 4.55 (s, 1H); 4.32 (s, 1H); 4.27 (dd, 1H); 4.17 (d, 1H); 4.11 (dd, 1H); 3.78 (s, 3H); 3.54 (s, 3H); 3.51 (d, 1H); 3.42 (s, 1H); 3.16-3.05 (m, 1H); 2.94-2.93 (m, 2H); 2.81-2.75 (m, 1H); 2.64-2.58 (m, 1H); 2.51-2.44 (m, 1H); 2.48 (t, 2H); 2.35-2.11 (m, 2H); 2.31 (s, 3H); 2.26 (s, 3H); 2.19 (s, 3H); 2.03 (s, 3H); 1.73 (m, 2H); 1.00 (t, 3H).

$^{13}$C-NMR (75 MHz, $CDCl_3$): δ 172.1, 168.9, 168.1, 148.4, 147.8, 145.3, 143.0, 141.3, 140.1, 132.4, 130.8, 129.3, 128.6, 122.4, 121.0, 120.7, 118.1, 114.0, 111.7, 107.2, 101.8, 64.8, 61.0, 60.3, 60.0, 59.6, 59.5, 55.1, 54.7, 54.6, 42.3, 41.9, 41.6, 39.5, 35.8, 33.7, 29.6, 28.6, 24.1, 20.3, 18.5, 15.7, 14.0, 9.6.

ESI-MS m/z: Calcd. for $C_{44}H_{48}N_4O_{11}S$: 840.3 Found ($M+H^+$): 841.3.

Example 6

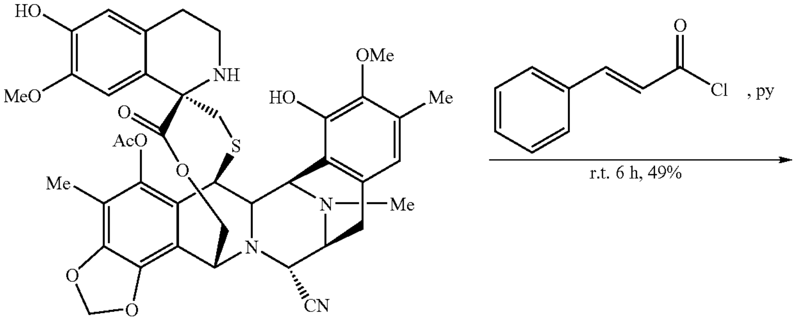

1

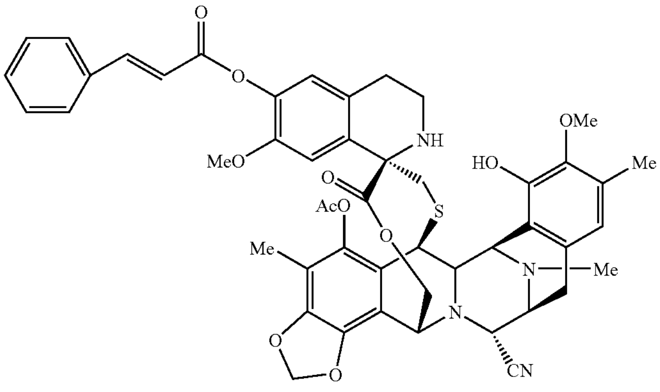

8

After chromatographic purification 28% of starting material was recuperated.

8. $^{1}$H-NMR (300 MHz, $CDCl_3$): δ 7.80 (d, 1H); 7.56-7.54 (m, 2H); 7.41-7.39 (m, 3H); 6.69 (s, 1H); 6.60 (s, 2H); 6.59 (d, 1H); 6.00 (dd, 2H); 5.74 (s, 1H); 5.03 (d, 1H); 4.56 (s, 1H); 4.33 (s, 1H); 4.28 (dd, 1H); 4.17 (d, 1H); 4.11 (dd, 1H); 3.79 (s, 3H); 3.58 (s, 3H); 3.52 (d, 1H); 3.42-3.40 (m, 1H); 3.16-3.06 (m, 1H); 2.96-2.93 (m, 2H); 2.82-2.75 (m, 1H); 2.64-2.59 (m, 1H); 2.54-2.46 (m, 1H); 2.38-2.12 (m, 2H); 2.32 (s, 3H); 2.28 (s, 3H); 2.20 (s, 3H); 2.04 (s, 3H).

$^{13}$C-NMR (75 MHz, $CDCl_3$): δ 172.1, 169.0, 148.4, 147.8, 145.3, 143.0, 141.3, 140.1, 138.5, 132.5, 130.8, 129.3, 128.9, 128.6, 127.4, 127.3, 122.4, 121.0, 120.7, 118.1, 114.0, 111.7, 101.8, 64.8, 61.1, 60.3, 60.1, 59.6, 59.5, 55.1 54.7, 54.6, 42.3, 41.9, 41.6, 39.5, 29.7, 28.6, 24.1, 20.6, 20.4, 15.8, 9.7.

ESI-MS m/z: Calcd. for $C_{49}H_{48}N_4O_{11}S$: 900.3 Found ($M+H^+$): 901.3

Example 7

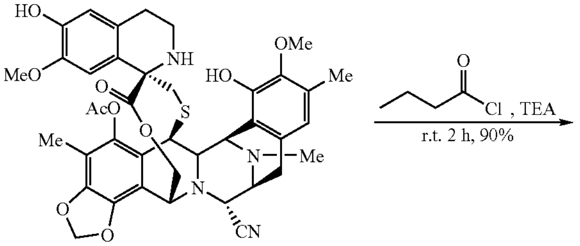

1

-continued

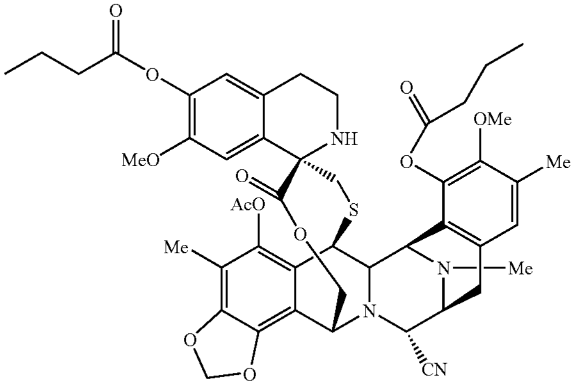

9

9 was obtained using 10 equiv. of butyryl chloride and 10 equiv. of TEA.

$^{1}$H-NMR (300 MHz, $CDCl_3$): δ 6.95 (s, 1H); 6.60 (s, 1H); 6.54 (s, 1H); 6.01 (dd, 2H); 5.01 (d, 1H); 4.45 (s, 1H); 4.32 (s, 1H); 4.17 (d, 1H); 4.09 (dd, 1H); 3.80 (d, 1H); 3.75 (s, 3H); 3.54 (s, 3H); 3.51 (d, 1H); 3.44 (s, 1H); 3.16-3.05 (m, 1H); 2.99-2.97 (m, 2H); 2.85-2.79 (m, 1H); 2.64-2.58 (m, 1H); 2.61 (t, 2H); 2.51-2.44 (m, 1H); 2.48 (t, 2H); 2.33-2.02 (m, 2H); 2.32 (s, 3H); 2.29 (s, 3H); 2.15 (s, 3H); 2.04 (s, 3H); 1.86 (m, 2H); 1.73 (m, 2H); 1.09 (t, 3H); 1.00 (t, 3H).

ESI-MS m/z: Calcd. for $C_{48}F_{54}N_4O_{12}S$: 910.3 Found ($M+H^+$): 911.3.

Example 8
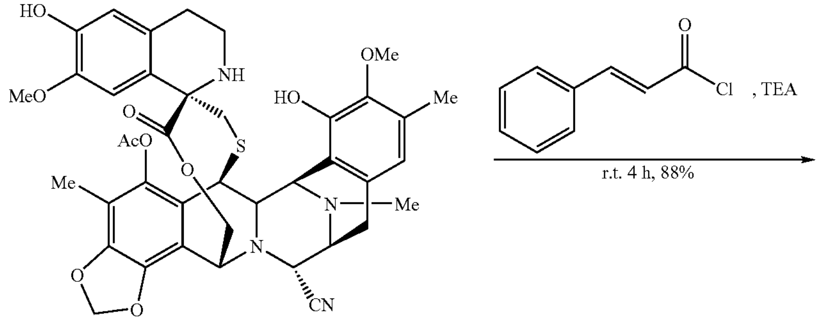
1
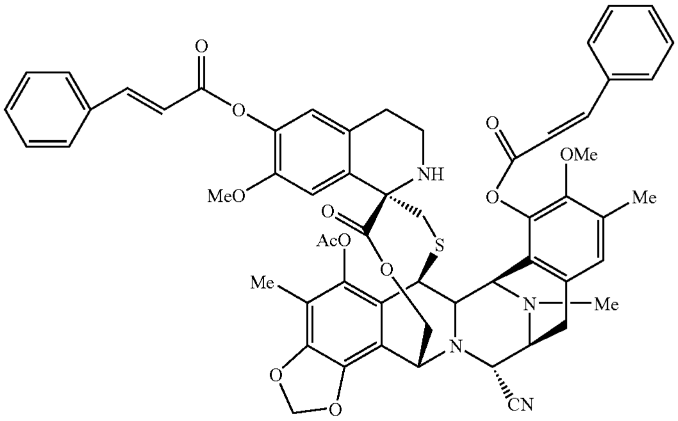
10
10. $^{1}$H-NMR (300 MHz, $CDCl_3$): δ 7.94 (d, 1H); 7.81 (d, 1H); 7.63-7.54 (m, 4H); 7.46-7.39 (m, 6H); 6.99 (s, 1H); 6.70 (s, 1H); 6.66 (d, 1H); 6.60 (d, 1H); 6.59 (s, 1H); 6.02 (dd, 2H); 5.04 (d, 1H); 4.55 (s, 1H); 4.35 (s, 1H); 4.21 (d, 1H); 4.13 (dd, 1H); 3.92 (d, 1H); 3.79 (s, 3H); 3.57 (s, 3H); 3.54 (d, 1H); 3.48-3.45 (m, 1H); 3.20-3.10 (m, 1H); 3.01-2.99 (m, 2H); 2.88-2.80 (m, 1H); 2.74.2.62 (m, 1H); 2.56-2.50 (m, 1H); 2.41-2.15 (m, 2H); 2.35 (s, 3H); 2.34 (s, 3H); 2.19 (s, 3H); 2.06 (s, 3H).
ESI-MS m/z: Calcd. for $C_{58}H_{54}N_4O_{12}S$: 1030.3 Found $(M+H^+)$:1031.3.
Example 9
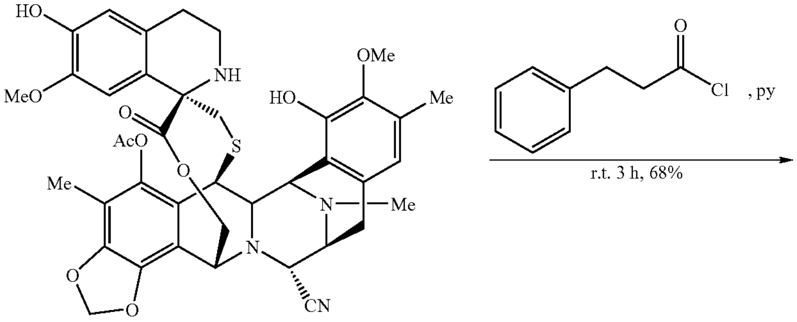
1

-continued

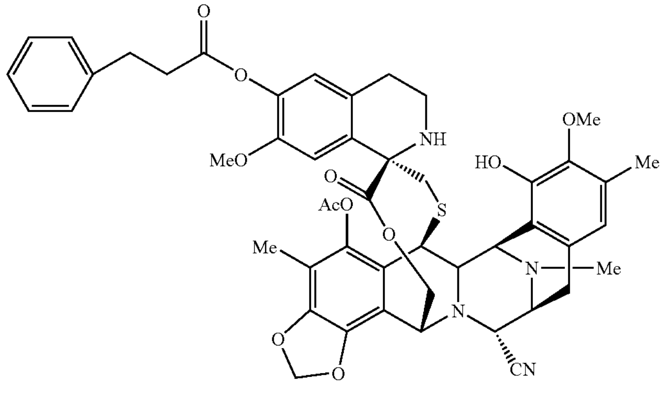

11

The reaction was performed using 4 equiv. of hydrocynamoyl chloride and 2 equiv. of pyridine. After chromatographic purification 25% of starting material was recuperated.

11. $^1$H-NMR (300 MHz, $CDCl_3$): δ 7.31-7.20 (m, 5H); 6.59 (s, 1H); 6.55 (s, 1H); 6.53 (s, 1H); 6.03 (s, 1H); 5.97 (s, 1H); 5.76 (s, 1H); 5.01 (d, 1H); 4.56 (s, 1H); 4.32 (s, 1H); 4.28 (d, 1H); 4.17 (d, 1H); 4.11 (dd, 1H); 3.78 (s, 3H); 3.56-3.50 (m, 1H); 3.51 (s, 3H); 3.42 (s, 1H); 3.14-2.92 (m, 3H); 3.02 (t, 2H); 2.87-2.78 (m, 1H); 2.83 (t, 2H); 2.67-2.43 (m, 4H); 2.3.2.25 (m, 1H); 2.31 (s, 3H); 2.27 (s, 3H); 2.19 (s, 3H); 2.03 (s, 3H).

$^{13}$C-RMN (75 MHz, $CDCl_3$): δ 172.2, 171.2, 148.6, 148.0, 145.5, 143.2, 141.5, 140.4, 140.3, 138.7, 132.6, 131.0, 129.6, 128.8, 128.7, 128.6, 128.5, 126.5, 122.6, 121.2, 120.9, 118.3, 118.2, 114.2, 111.9, 102.1, 65.0, 61.3, 60.5, 60.3, 59.8, 59.7, 55.3, 54.8, 54.7, 42.3, 42.1, 41.8, 39.6, 35.6, 35.5, 31.4, 30.9, 29.9, 28.6, 24.3, 20.6, 16.0, 9.9.

ESI-MS m/z: Calcd. for $C_{49}H_{50}N_4O_{11}S$: 902.3 Found ($M+H^+$): 903.2.

Example 10

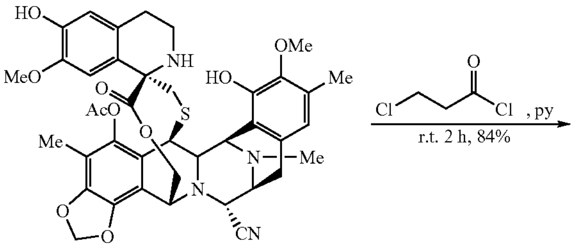

1

-continued

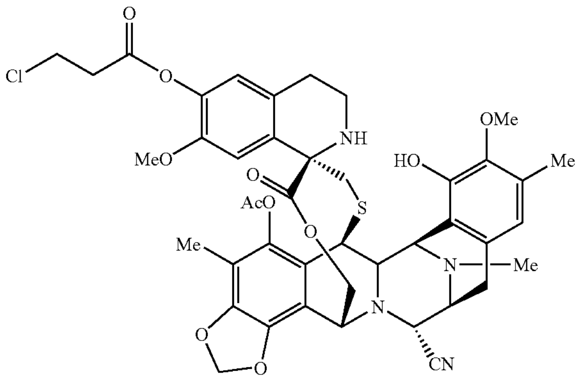

12

12. $^1$H-NMR (300 MHz, $CDCl_3$): δ 6.68 (s, 1H); 6.58 (s, 1H); 6.47 (s, 1H); 6.06 (d, 1H); 5.97 (d, 1H); 5.02 (d, 1H); 4.59 (s, 1H); 4.37 (s, 1H); 4.29 (d, 1H); 4.19-4.16 (m, 2H); 3.85 (s, 2H); 3.75 (s, 3H); 3.55 (s, 3H); 3.53 (s, 1H); 3.43 (d, 1H); 3.07-2.80 (m, 5H); 3.00 (t, 2H); 2.83 (t, 2H); 2.61-2.57 (m, 1H); 2.44-2.33 (m, 1H); 2.37 (m, 3H); 2.29 (s, 3H); 2.21 (s, 3H); 2.03 (s; 3H). ESI-MS m/z: Calcd. for $C_{43}H_{45}ClN_4O_{11}S$: 860.2 Found ($M+H^+$): 861.3.

Example 11

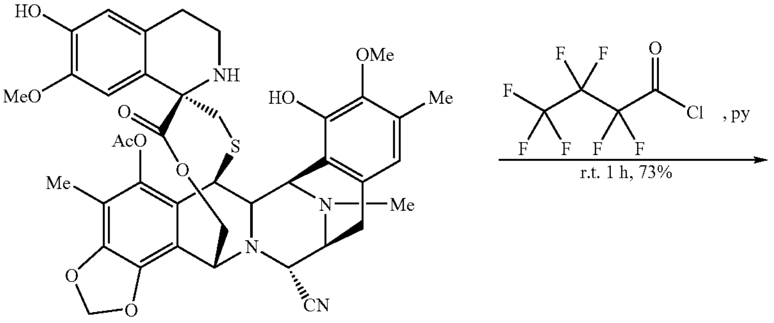

1

-continued

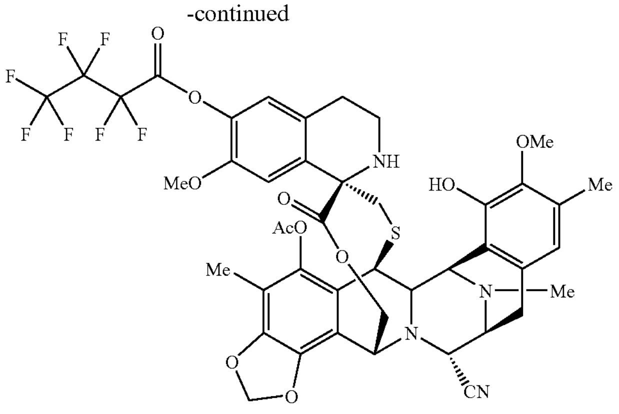

13

13. $^{1}$H-NMR (300 MHz, $CDCl_3$): δ 6.69 (s, 1H); 6.63 (s, 1H); 6.59 (s, 1H); 6.04 (s, 1H); 5.96 (s, 1H); 5.74 (s, 1H);5.02 (d, 1H); 4.58 (s, 1H); 4.33 (s, 1H); 4.28 (d, 1H); 4.18 (d, 1H); 4.13 (dd, 1H); 3.78 (s, 3H); 3.57 (s, 3H); 3.51 (d, 1H); 3.42 (s, 1H); 3.14-3.06 (m, 1H); 2.94 (d, 2H); 2.82-2.76 (m, 1H); 2.69-2.59 (m, 1H); 2.54-2.48 (m, 1H); 2.36-2.14 (m, 1H); 2.32 (s, 3H); 2.26 (s, 3H); 2.19 (s, 3H); 2.03 (s, 3H).

ESI-MS m/z: Calcd. for $C_{44}H_{41}F_7N_4O_{11}S$: 966.2 Found ($M+H^+$): 967.3.

Example 12

Method C: To a solution of 1 equiv. of ET-770 (1) in $CH_2Cl_2$ (0.032M) under Argon were added 2 equiv. of acid, 2 equiv. of DMAP and 2 equiv. of EDC.HCl. The reaction was stirred at room temperature for 2 h. After this time was diluted with $CH_2Cl_2$, washed with brine and the organic layer dried with $Na_2SO_4$. Flash chromatography gives pure compounds.

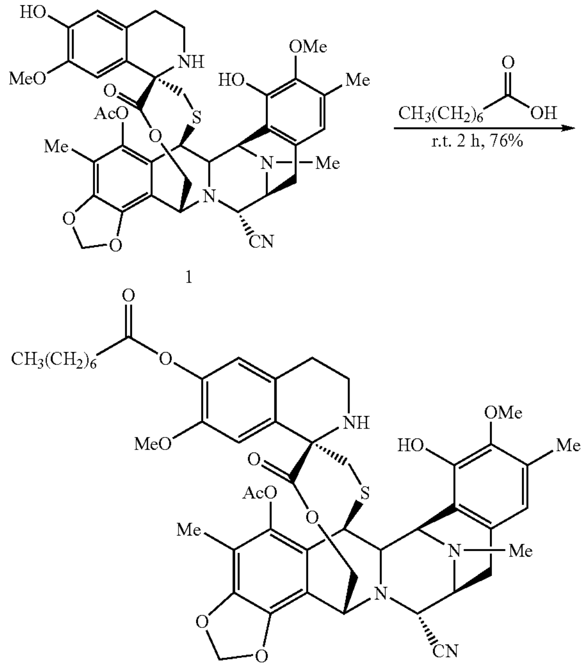

1

14

14. $^{1}$H-NMR (300 MHz, $CDCl_3$): δ 6.59 (s, 2H); 6.56 (s, 1H); 6.00 (dd, 2H); 5.72 (s, 1H); 5.01 (d, 1H); 4.55 (s, 1H); 4.32 (s, 1H); 4.27 (dd, 1H); 4.17 (d 1H); 4.10 (dd, 1H); 3.79 (s, 3H); 3.54 (s, 3H); 3.51 (d, 1H); 3.42 (s, 1H); 3.16-3.05 (m, 1H); 2.94-2.93 (m, 2H); 2.81-2.75 (m, 1H); 2.64-2.58 (m, 1H); 2.51-2.44 (m, 1H); 2.49 (t, 2H); 2.35-2.11 (m, 2H); 2.32 (s, 3H); 2.27 (s, 3H); 2.19 (s, 3H); 2.03 (s, 3H); 1.73-1.68 (m, 2H); 1.25-1.15 (m, 8H); 1.02 (t, 3H).

$^{13}$C-NMR (75 MHz, $CDCl_3$): δ 172.1, 171.8, 148.4, 147.8, 145.3, 143.0, 141.3, 140.1, 138.6, 132.4, 130.8, 129.3, 128.6, 122.9, 122.4, 121.0, 120.7, 120.6, 118.1, 114.0, 111.7, 101.8, 64.8, 61.0, 60.3, 60.0, 59.6, 59.5, 55.1, 54.7, 54.6, 42.3, 41.8, 41.5, 39.5, 33.9, 33.7, 31.9, 31.6, 30.1, 29.3, 28.9, 28.8, 28.6, 26.9, 24.9, 24.1, 22.6, 22.5, 20.3, 15.7, 14.0, 9.6.

ESI-MS m/z: Calcd. for $C_{48}F_{56}N_4O_{11}S$: 896.3 Found ($M+H^+$):897.3.

Example 13

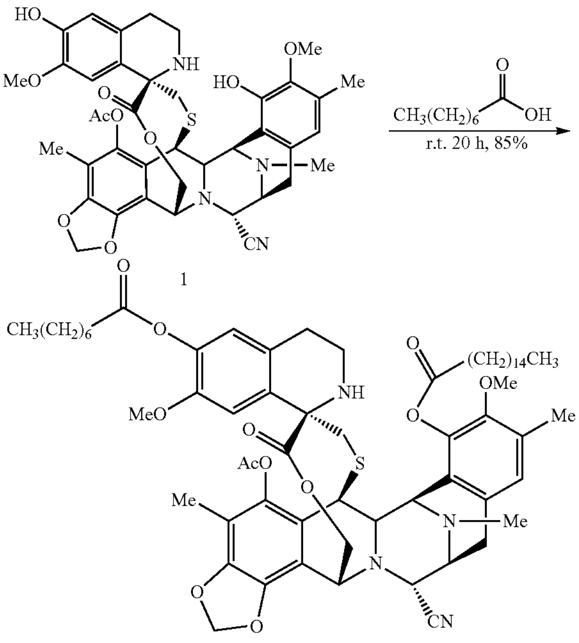

1

15

Compound 15 is obtained following method C, using 10 equiv. of octanoic acid and 10 equiv. of EDC.HCl and 10 equiv. of DMAP):

15. $^1$H-NMR (300 MHz, $CDCl_3$): δ 6.94 (s, 1H); 6.59 (s, 1H); 6.53 (s, 1H); 6.01 (dd, 2H); 5.01 (d, 1H); 4.45 (s, 1H); 4.32 (s, 1H); 4.18 (d, 1H); 4.10 (dd, 1H); 3.80 (d, 1H); 3.74 (s, 3H); 3.54 (s, 3H); 3.51 (d, 1H); 3.44 (s, 1H); 3.16-3.05 (m, 1H); 2.99-2.97 (m, 2H); 2.88-2.79 (m, 1H); 2.64-2.58 (m, 1H); 2.61 (t, 2H); 2.51-2.44 (m, 1H); 2.49 (t, 2H); 2.35-2.15 (m, 2H); 2.32 (s, 3H); 2.29 (s, 3H); 2.15 (s, 3H); 2.03 (s, 3H); 1.88-1.78 (m, 2H); 1.74-1.56 (m, 4H); 1.39-1.24 (m, 20H).

$^{13}$C-NMR (75 MHz, $CDCl_3$): δ 182.1, 172.2, 172.0 171.4, 148.7, 148.2, 145.7, 143.9, 141.5, 140.4, 138.9, 132.3, 131.7, 130.8, 128.8, 127.4, 124.6, 122.8, 121.0, 118.0, 114.1, 111.9, 102.2, 65.1, 61.3, 60.3, 60.2, 59.8, 59.4, 56.1, 55.3, 54.6, 42.6, 42.3, 41.8, 39.7, 34.4, 34.1, 33.8, 31.8, 29.9, 29.4, 29.2, 29.1, 29.0, 28.7, 25.4, 25.2, 24.9, 24.2, 22.7, 20.5, 16.0, 14.2, 9.8.

ESI-MS m/z: Calcd. for $C_{56}H_{70}N_4O_{12}S$: 1022.4 Found (M+H$^+$): 1023.5.

Example 14

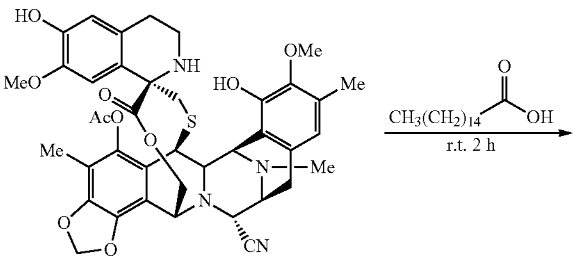

1

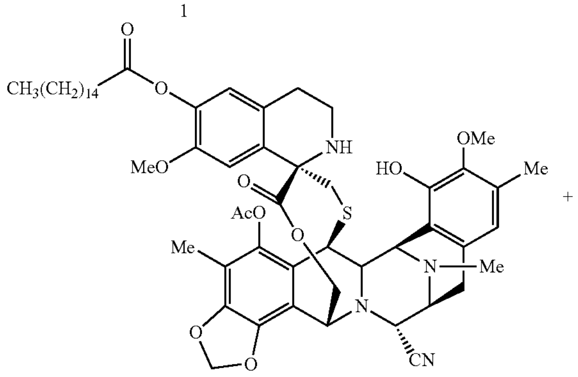

16

15%

-continued

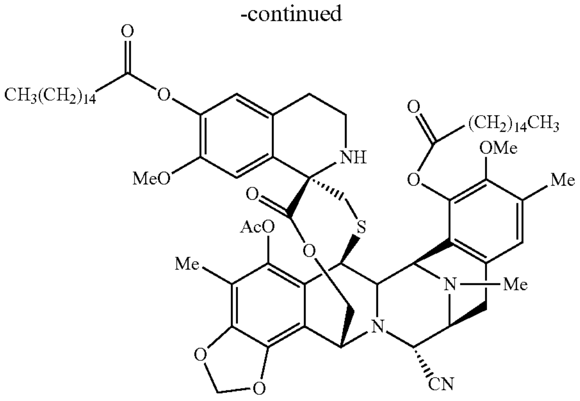

17

81%

Compounds 16 and 17 were obtained using Method C.

16: $^1$H-NMR (300 MHz, $CDCl_3$): δ 6.61 (s, 2H); 6.56 (s, 1H); 6.00 (dd, 2H); 5.75 (s, 1H); 5.01 (d, 1H); 4.56 (s, 1H); 4.32 (s, 1H); 4.27 (dd, 1H); 4.17 (d, 1H); 4.09 (dd, 1H); 3.79 (s, 3H); 3.53 (s, 3H); 3.50 (d, 1H); 3.41 (s, 1H); 3.16-3.05 (m, 1H); 2.95-2.93 (m, 2H); 2.81-2.75 (m, 1H); 2.68-2.55 (m, 1H); 2.51-2.44 (m, 1H); 2.49 (t, 2H); 2.39-2.11 (m, 2H); 2.32 (s, 3H); 2.28 (s, 3H); 2.19 (s, 3H); 2.03 (s, 3H); 1.73-1.64 (m, 2H); 1.40-1.17 (m, 27H).

$^{13}$C-NMR (75 MHz, $CDCl_3$): δ 172.0, 171.8, 168.0, 148.4, 147.8, 145.3, 143.0, 141.3, 140.1, 138.6, 132.3, 130.8, 129.8, 129.3, 128.6, 122.4, 121.0, 120.7, 118.0, 114.0, 111.7, 101.8, 64.8, 61.0, 60.2, 60.0, 59.6, 59.5, 55.1, 54.6, 54.6, 42.2, 41.8, 41.5, 39.5, 33.9, 31.8, 29.7, 29.63, 29.60, 29.44, 29.30, 29.21, 29.07, 28.9, 28.5, 24.9, 24.1, 22.6, 20.3, 15.7, 14.0, 9.6.

ESI-MS m/z: Calcd. for $C_{56}H_{72}N_4O_{11}S$: 1008.4 Found (M+H$^+$): 1009.5.

17: $^1$H-NMR (300 MHz, $CDCl_3$): δ 6.94 (s, 1H); 6.59 (s, 1H); 6.54 (s, 1H); 6.02 (dd, 2H); 5.01 (d, 1H); 4.45 (s, 1H); 4.33 (s, 1H); 4.18 (d 1H); 4.10 (dd, 1H); 3.79 (d, 1H); 3.75 (s, 3H); 3.54 (s, 3H); 3.52 (d, 1H); 3.49 (s, 1H); 3.15-3.05 (m, 1H); 2.99-2.97 (m, 2H); 2.83-2.75 (m, 1H); 2.68-2.55 (m, 1H); 2.62 (t, 2H); 2.51-2.44 (m, 1H); 2.49 (t, 2H); 2.36-2.11 (m, 2H); 2.32 (s, 3H); 2.29 (s, 3H); 2.16 (s, 3H); 2.04 (s, 3H); 1.86-1.78 (m, 2H); 1.72-1.75 (m, 2H); 1.40-1.10 (m, 54H).

ESI-MS m/z: Calcd. for $C_{72}H_{102}N_4O_{12}S$: 1246.7 Found (M+H$^+$): 1247.6.

Example 15

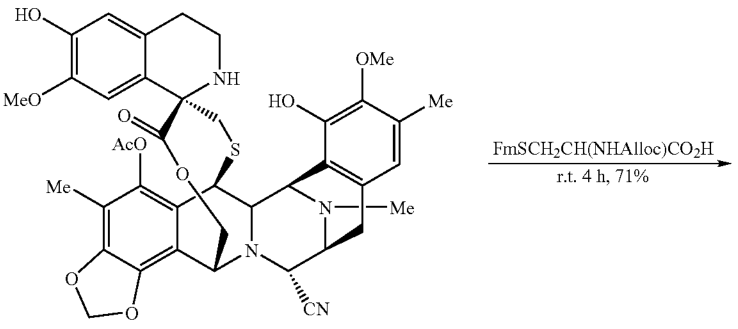

1

-continued
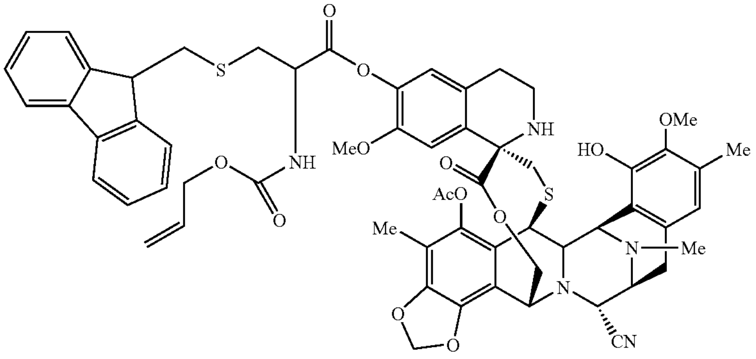
18
Compound 18 is obtained with 1.5 equiv. of acid, 2.5 equiv. of DMAP and 2.5 equiv. of EDC.HCl (Method C)
18 $^1$H-NMR (300 MHz, $CDCl_3$): δ 7.74 (d, 2H), 7.64 (t, 2H), 7.38 (t, 2H), 7.31-7.27 (m, 2H), 6.60 (s, 1H), 6.57 (s, 1H), 6.55 (s, 1H), 5.98 (d, 2H), 5.96-5.83 (m, 1H), 5.72 (s, 1H), 5.58 (d, 1H), 5.37-5.18 (m, 2H), 5.04 (d, 1H), 4.88-4.79 (m, 1H), 4.58 (bd, 3H), 4.32 (s, 1H), 4.25 (d, 1H), 4.18 (d, 1H), 4.12-4.08 (m, 2H), 3.79 (s, 3H), 3.51 (d, 1H), 3.45 (s, 3H), 3.45-3.42 (m, 1H), 3.16-3.11 (m, 5H), 2.95-2.93 (m, 2H), 2.82-2.75 (m, 1H), 2.63-2.50 (m, 1H), 2.46-2.41 (m, 1H), 2.32-2.13 (m, 2H), 2.32 (s, 3H), 2.27 (s, 3H), 2.20 (s, 3H), 2.03 (s, 3H).
ESI-MS m/z: Calcd. for $C_{61}H_{61}N_5O_{13}S_2$: 1135.4 Found ($M+H^+$): 1136.3.
Example 16
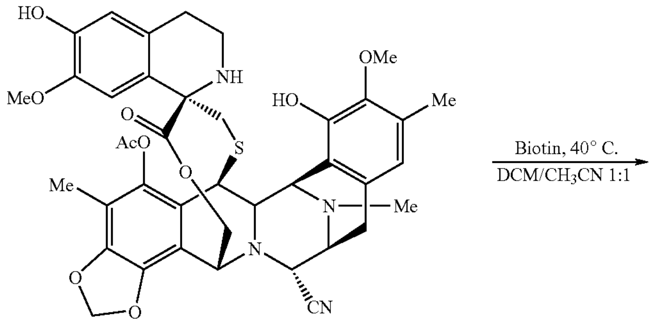
1
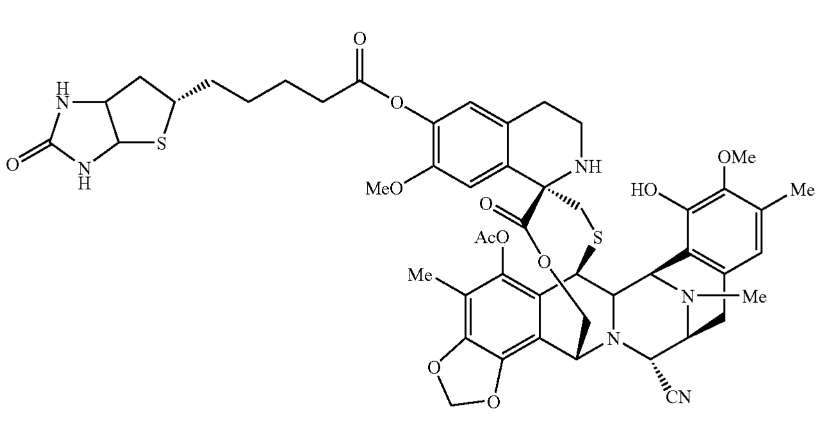
19
46%
+

-continued

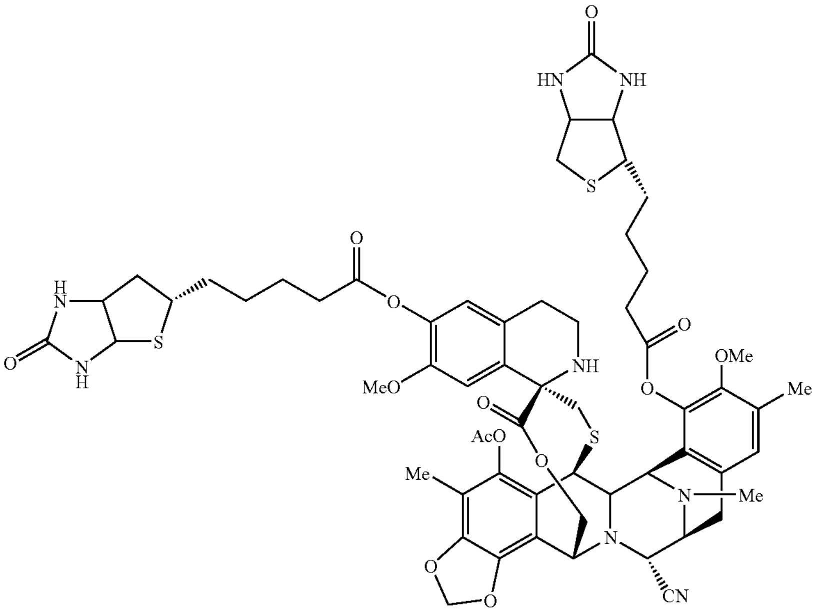

20

31%

A mixture of compounds 19 and 20 were obtained with 1.5 equiv. of biotin, 2.5 equiv. of DMAP and 2.5 equiv. of EDC.HCl. (Method C)

19: $^1$H-NMR (300 MHz, $CDCl_3$): δ 6.59 (s, 2H), 6.56 (s, 1H), 6.00 (d, 2H), 5.81 (bs, 1H), 5.26 (bs, 1H), 5.02 (d, 1H), 4.83 (bs, 1H), 4.57 (bs, 3H), 4.51-4.47 (m, 1H), 4.33-4.29 (m, 3H), 4.18 (d, 1H), 4.14-4.11 (m, 1H), 3.79 (s, 3H), 3.55 (s, 3H), 3.52-3.50 (m, 1H), 3.49-3.42 (m, 1H), 3.19-3.13 (m, 2H), 2.94-2.87 (m, 3H), 2.78-2.70 (m, 2H), 2.62-2.48 (m, 4H), 2.38-2.16 (m, 2H), 2.32 (s, 3H), 2.27 (s, 3H), 2.20 (s, 3H), 2.03 (s, 3H), 1.79-1.50 (m, 6H).

ESI-MS m/z: Calcd. for $C_{50}H_{56}N_6O_{12}S_2$: 996.3 Found (M+H$^+$): 997.3.

20: $^1$H-NMR (300 MHz, $CDCl_3$): δ 6.95 (s, 1H), 6.62 (s, 1H), 6.52 (bs, 1H), 6.01 (d, 2H), 5.57 (bs, 1H), 5.40 (bs, 1H), 5.01 (d, 1H), 4.99 (bs, 1H), 4.92 (bs, 1H), 4.51-4.28 (m, 6H), 4.18 (d, 1H), 4.13-4.09 (m, 1H), 3.80-3.77 (m, 4H), 3.55 (s, 3H), 3.55-3.52 (m, 1H), 3.46-3.42 (m, 1H), 3.24-3.12 (m, 3H), 3.02-2.52 (m, 13H), 2.33-2.15 (m, 2H), 2.33 (s, 6H), 2.15 (s, 3H), 2.05 (s, 3H), 1.87-1.47 (m, 12H).

ESI-MS m/z: Calcd. for $C_{60}H_{70}N_8O_{14}S_3$: 1222.4 Found (M+H$^+$): 1223.3.

Example 17

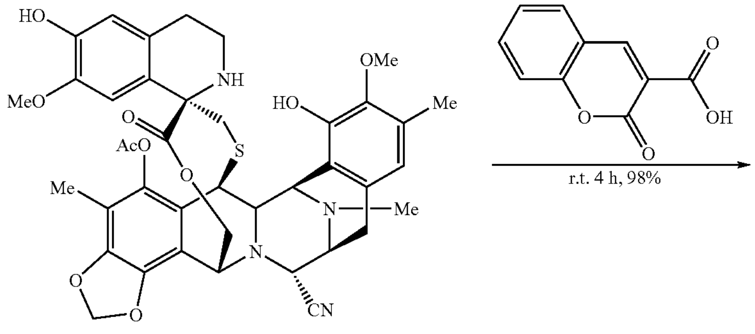

1

-continued
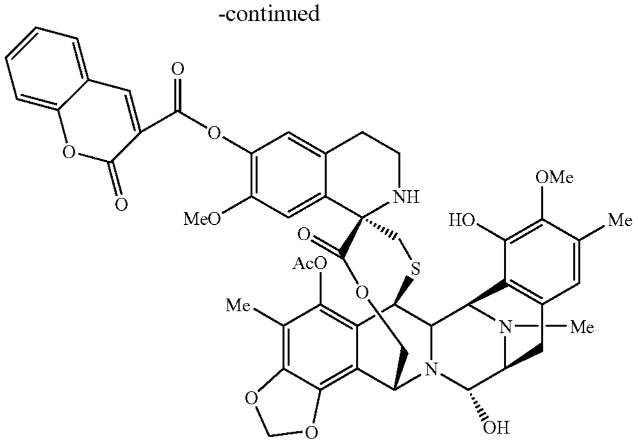
21
21. Was obtained using Method C
$^1$H-NMR (300 MHz, $CDCl_3$): δ 8.66 (s, 1H); 7.66-7.59 (m, 2H); 7.35-7.29 (m, 2H); 6.74 (s, 1H); 6.60 (s, 1H); 6.59 (s, 1H); 6.01 (d, 1H); 5.94 (d, 1H); 5.81 (s, 1H); 5.02 (d, 1H); 4.55 (s, 1H); 4.31 (s, 1H); 4.26 (d, 1H); 4.18 (d, 1H); 4.13-4.06 (m, 2H); 3.77 (s, 3H); 3.55 (s, 3H); 3.50 (d, 1H); 3.41 (s, 1H); 3.15-3.06 (m, 1H); 2.94 (d, 2H); 2.80-2.75 (m, 1H); 2.68-2.58 (m, 1H); 2.52-2.47 (m, 1H); 2.37-2.11 (m, 1H); 2.31 (s, 3H); 2.26 (s, 3H); 2.18 (s, 3H); 2.02 (s, 3H).
ESI-MS m/z: Calcd. for $C_{50}H_{46}N_4O_{13}S$: 942.8 Found (M+Na+): 965.1.
Example 18
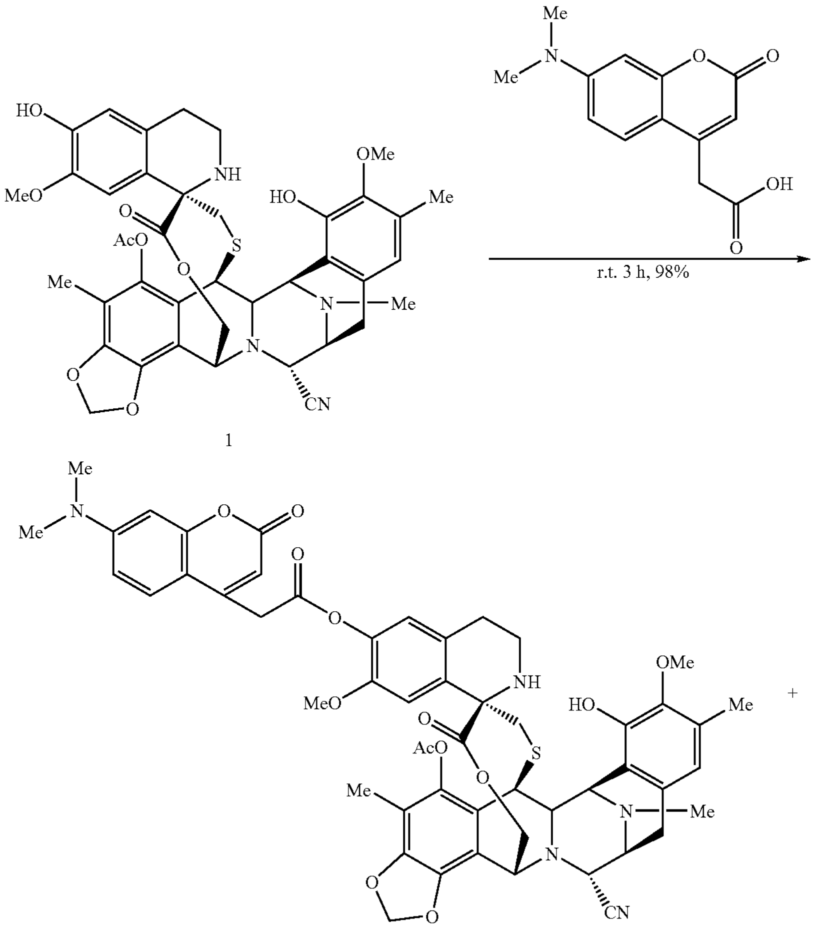
1
22

-continued
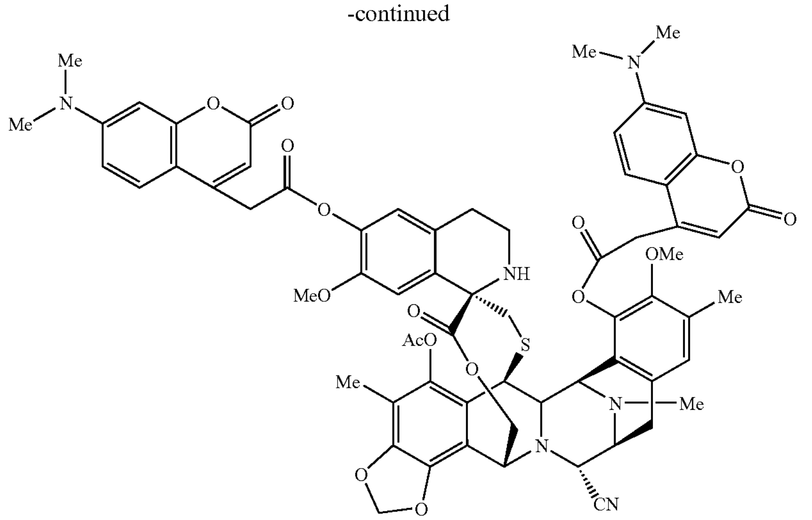
23
Compounds 22 and 23 are obtained using Method C as a mixture 3:1 and described together in $^1$H-RMN.
22, 23. $^1$H-NMR (300 MHz, $CDCl_3$): δ 7.46 (d, 1H); 7. 43 (d, 1H); 6.89 (s, 1H); 6.64-6.34 (m, 9H); 6.19 (s, 1H); 6.18 (s, 1H); 6.03 (s, 1H); 6.02 (d, 1H); 5.97 (d, 1H); 5.95 (d, 1H); 5.80 (s, 1H); 5.01 (d, 1H); 4.99 (d, 1H); 4.55 (s, 2H); 4.30 (s, 2H); 4.27-4.23 (m 2H); 4.19-4.15 (m, 2H); 4.10 (dd, 1H); 4.09 (dd, 1H); 4.01-3.90 (m, 2H); 3.85 (s, 4H); 3.77 (s, 6H); 3.68 (s, 2H); 3.59 (s, 1H); 3.56-3.46 (m, 2H); 3.49 (s, 6H); 3.40 (s, 2H); 3.13-3.06 (m, 2H); 3.04 (s, 12H); 2.96 (s, 6H); 2.92 (d, 4H); 2.81-2.73 (m, 2H); 2.63-2.56 (m, 2H); 2.49-2.41 (m, 2H); 2.30 (s, 3H); 2.28 (s, 3H); 2.25 (s, 3H); 2.18 (s, 3H); 2.10 (s, 3H); 2.09 (s, 3H); 2.02 (s, 3H); 2.01 (s, 3H).
ESI-MS m/z: Calcd. for $C_{53}H_{33}N_5O_{13}S$ (22) 1000.08 and Calcd. for $C_{66}H_{64}N_6O_{16}S$ (23) 1229.3. Found (M±): 1000.2 (22) and 1229.2 (23).
Example 19
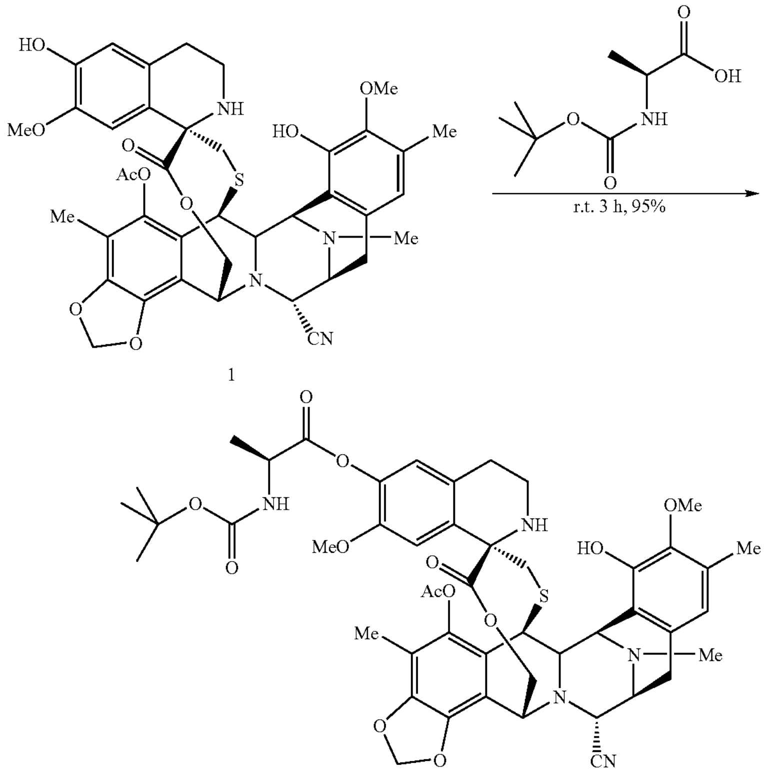
1
24

24 was obtained using Method C.

$^1$H-NMR (300 MHz, $CDCl_3$): δ 6.61 (s, 1H), 6.58 (s, 1H), 6.56 (s, 1H), 5.98 (d, 2H), 5.84 (s, 1H), 5.09 (bd, 1H), 5.00 (d, 1H), 4.54-4.51 (m, 2H), 4.31 (s, 1H), 4.27 (d, 1H), 4.17 (d, 1H), 4.12-4.07 (m, 1H), 3.77 (s, 3H), 3.53 (s, 3H), 3.50 (d, 1H), 3.42-3.39 (m, 1H), 3.13-3.04 (m, 1H), 2.94-2.92 (m, 2H), 2.79-2.75 (m, 1H), 2.66-2.56 (m, 1H), 2.50-2.45 (m, 1H), 2.35-2.02 (m, 2H), 2.31 (s, 3H), 2.26 (s, 3H), 2.18 (s, 3H), 2.02 (s, 3H), 1.48 (d, 3H), 1.43 (s, 9H).

$^{13}$C-NMR (75 MHz, $CDCl_3$): δ 172.0, 171.5, 168.1, 154.9, 148.1, 147.8, 145.3, 142.9, 141.2, 140.0, 138.2, 132.7, 130.7, 129.3, 128.6, 122.2, 120.9, 120.6, 118.0, 113.9, 113.3, 111.7, 101.8, 79.8, 64.8, 61.0, 60.2, 60.1, 59.5, 59.5, 55.1, 54.6, 54.5, 42.1, 41.8, 41.5, 39.4, 28.5, 28.2, 24.1, 20.4, 18.7, 15.7, 9.6.

ESI-MS m/z: Calcd. for $C_{48}H_{55}N_5O_{13}S$: 941.3 Found ($M+H^+$): 942.3.

Example 20

Method D: To a solution of 1 equiv. of starting material in $CH_2Cl_2$ (0.032M) under Argon were added 2 equiv. of chloroformiate and 2 equiv. of base and the mixture was stirred at room temperature. The reaction was followed by TLC and quenched with $NaHCO_3$, extracted with $CH_2Cl_2$ and the organic layers dried with $Na_2SO_4$. Flash chromatography gives pure compounds.

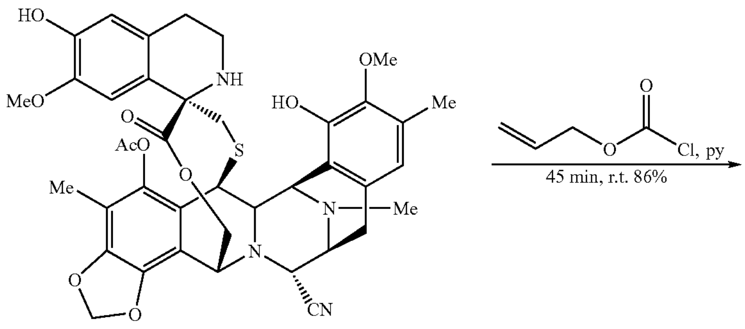

1

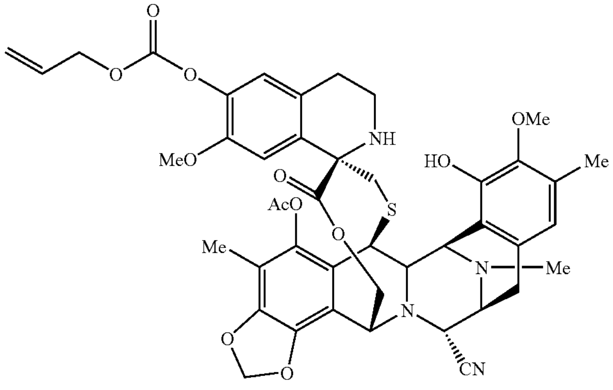

25

The reaction is performed with 3.3 equiv. of Alloc chloride and 3.3 equiv. of pyridine.

25. $^1$H-NMR (300 MHz, $CDCl_3$): δ 6.70 (s, 1H), 6.59 (s, 1H), 6.57 (s, 1H), 6.07-5.89 (m, 1H), 6.00 (d, 2H), 5.76 (s, 1H), 5.42-5.27 (m, 2H), 5.01 (d, 1H), 4.69-4.66 (m, 2H), 4.56 (bs, 1H), 4.33 (s, 1H), 4.27 (d, 1H), 4.17 (d, 1H), 4.01 (dd, 1H), 3.79 (s, 3H), 3.58 (s, 3H), 3.51 (bd, 1H), 3.45-3.40 (m, 1H), 3.16-3.06 (m, 1H), 2.97-2.91 (m, 2H), 2.85-2.75 (m, 1H), 2.70-2.57 (m, 1H), 2.53-2.45 (m, 1H), 2.37-2.12 (m, 2H), 2.32 (s, 3H), 2.27 (s, 3H), 2.20 (s, 3H), 2.04 (s, 3H).

ESI-MS m/z: Calcd. for $C_{44}H_{46}N_4O_{12}S$: 854.3 Found ($M+H^+$): 855.0.

Example 21

The reaction was performed with excess of Alloc Chloride and pyridine and catalytic DMAP (method D). Some starting material was recovered after chromatographic purification.

26. $^1$H-NMR (300 MHz, $CDCl_3$): δ 6.96 (s, 1H), 6.70 (s, 1H), 6.56 (s, 1H), 6.06-5.89 (m, 2H), 6.01 (d, 2H), 5.44-5.27 (m, 4H), 5.00 (d, 1H), 4.82-4.67 (m, 4H), 4.47 (bs, 1H), 4.34 (s, 1H), 4.19-4.09 (m, 2H), 3.94 (d, 1H), 3.79 (s, 3H), 3.57 (s, 3H), 3.54-3.45 (m, 2H), 3.15-3.03 (m, 1H), 2.99-2.97 (m, 2H), 2.84-2.77 (m, 1H), 2.70-2.59 (m, 1H), 2.53-2.44 (m, 1H), 2.32-2.17 (m, 8H), 2.17 (s, 3H), 2.05 (s, 3H).

ESI-MS m/z: Calcd. for $C_{48}H_{50}N_4O_{14}S$: 938.3 Found ($M+H^+$): 939.3.

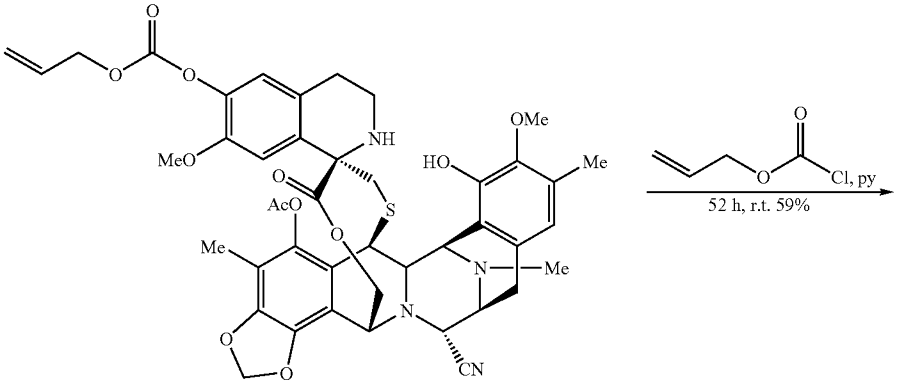

25

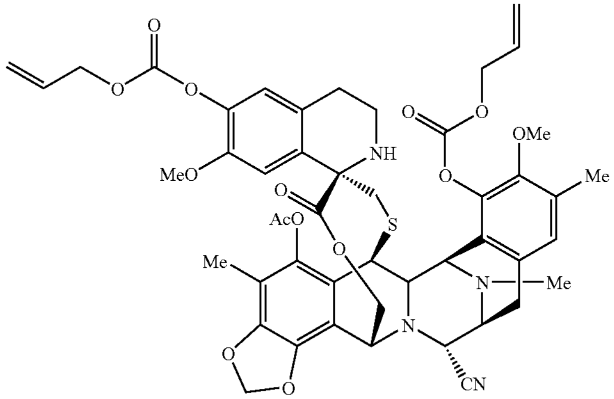

26

Example 22
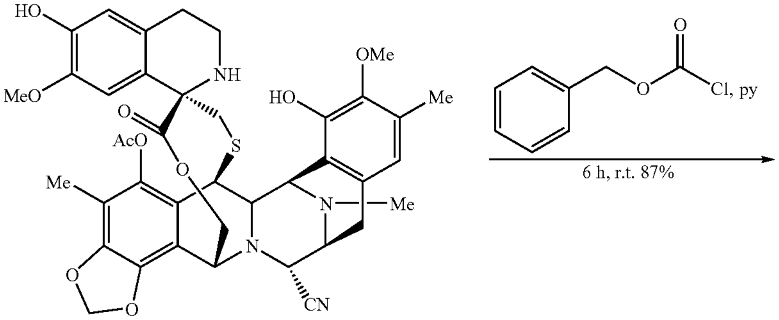
1
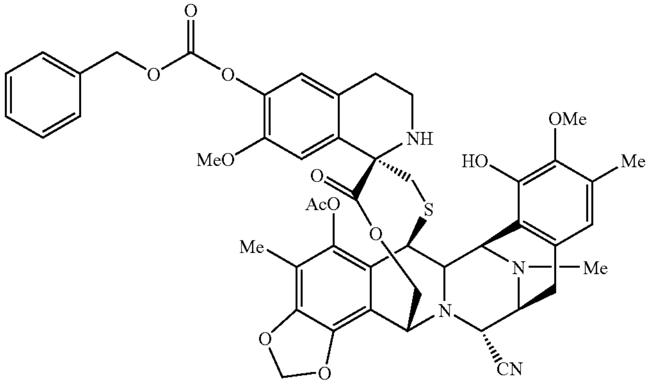
27
The reaction was performed with 3.0 equiv. of pyridine (Method D).
27. $^1$H-NMR (300 MHz, $CDCl_3$): δ 7.38-7.33 (m, 5H); 6.69 (s, 1H); 6.59 (s, 1H); 6.57 (s, 1H); 5.99 (dd, 2H); 5.75 (s, 1H); 5.21 (s, 2H); 5.00 (d, 1H); 4.56 (s, 1H); 4.32 (s, 1H); 4.27 (dd, 1H); 4.17 (d, 1H); 4.10 (dd, 1H); 3.78 (s, 3H); 3.54 (s, 3H); 3.51 (d, 1H); 3.41 (s, 1H); 3.16-3.06 (m, 1H); 2.94-2.93 (m, 2H); 2.81-2.75 (m, 1H); 2.68-2.58 (m, 1H); 2.49-2.44 (m, 1H); 2.35-2.13 (m, 2H); 2.31 (s, 3H); 2.26 (s, 3H); 2.19 (s, 3H); 2.03 (s, 3H).
$^{13}$C-NMR (75 MHz, $CDCl_3$): δ 172.0, 168.1, 148.4, 147.8, 145.3, 143.0, 141.3, 140.1, 138.9, 134.9, 132.8, 130.7, 129.3, 128.7, 128.5, 128.3, 121.9, 121.0, 120.7, 118.0, 114.0, 111.9, 101.8, 70.2, 64.8, 61.0, 60.3, 60.1, 59.6, 59.5, 55.1, 54.7, 54.6, 42.2, 41.8, 41.5, 39.5, 29.6, 28.6, 24.1, 20.3, 15.7, 9.6.
ESI-MS m/z: Calcd. for $C_{48}F_{48}N_4O_{12}S$: 904.3 Found ($M+H^+$): 905.3.
Example 23
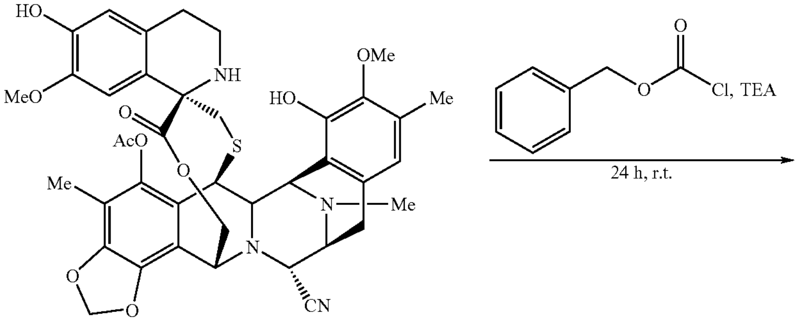
1

-continued
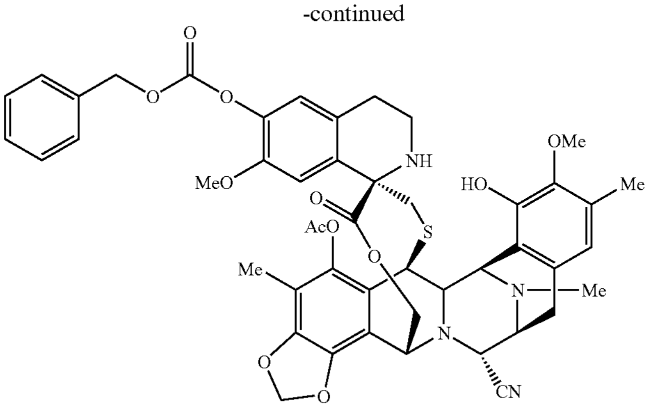
+
27
32%
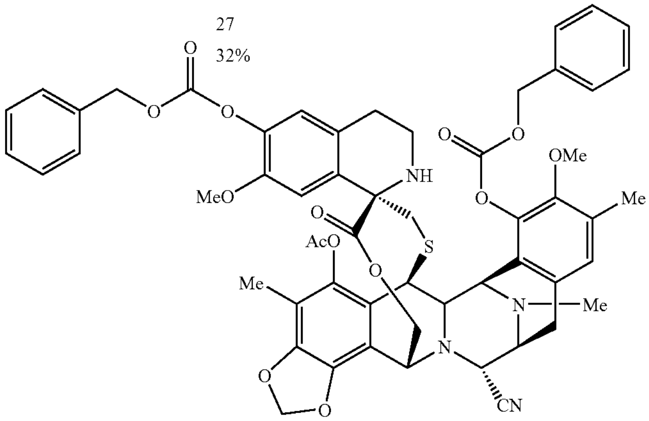
28
66%
28: Was obtained following Method C using TEA as base.
$^1$H-NMR (300 MHz, $CDCl_3$): δ 7.40-7.34 (m, 10H); 6.95 (s, 1H); 6.69 (s, 1H); 6.54 (s, 1H); 5.99 (dd, 2H); 5.33 (d, 1H); 5.23 (s, 1H); 5.21 (s, 2H); 5.00 (d, 1H); 4.43 (s, 1H); 4.32 (s, 1H); 4.17 (d, 1H); 4.10 (dd, 1H); 3.90 (d, 1H); 3.75 (s, 3H); 3.53 (s, 3H); 3.50 (d, 1H); 3.44 (s, 1H); 3.20-3.01 (m, 1H); 2.97-2.96 (m, 2H); 2.82-2.75 (m, 1H); 2.68-2.56 (m, 1H); 2.51-2.42 (m, 1H); 2.28-2.00 (m, 2H); 2.31 (s, 3H); 2.19 (s, 3H); 2.12 (s.3H); 2.03 (s, 3H).
$^{13}$C-NMR (75 MHz, $CDCl_3$): δ 172.2, 168.7, 153.4, 153.1, 148.6, 148.2, 145.7, 144.3, 141.5, 140.4, 139.1, 135.1, 132.8, 131.7, 130.8, 129.0, 128.9, 128.8, 128.7, 128.5, 128.4, 127.5, 124.5, 122.4, 122.2, 121.1, 117.9, 114.0, 113.6, 112.1, 102.1, 70.7, 70.5, 65.2, 61.3, 60.4, 60.2, 59.8, 59.4, 55.7, 55.3, 54.6, 42.4, 42.1, 41.7, 39.7, 28.8, 24.1, 20.2, 15.9, 9.8.
ESI-MS m/z: Calcd. for $C_{56}H_{54}N_4O_{14}S$: 1038.3 Found $(M+H^+)$: 1039.8.
Example 24
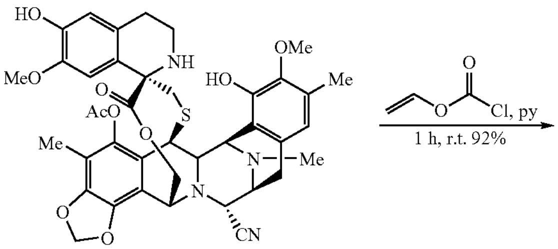
1
-continued
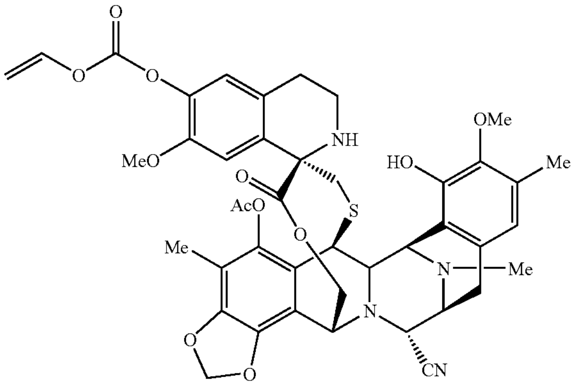
29
29. was obtained using Method D.
$^1$H-NMR (300 MHz, $CDCl_3$): δ 7.08 (dd, 1H); 6.72 (s, 1H); 6.60 (s, 1H); 6.59 (s, 1H); 6.03 (s, 1H); 5.96 (s, 1H); 5.77 (s, 1H); 5.01 (d, 1H); 4.99 (dd, 1H); 4.63 (dd, 1H); 4.56 (s, 1H); 4.32 (s, 1H); 4.27 (d, 1H); 4.17 (d, 1H); 4.11 (dd, 1H); 3.78 (s, 3H); 3.58 (s, 3H); 3.51 (d, 1H); 3.42 (s, 1H); 3.15-3.06 (m, 1H); 2.93 (d, 2H); 2.82-2.75 (m, 1H); 2.68-2.57 (m, 1H); 2.52-2.46 (m, 1H); 2.36-2.14 (m, 1H); 2.31 (s, 3H); 2.26 (s, 3H); 2.19 (s, 3H); 2.02 (s, 3H).

ESI-MS m/z: Calcd. for $C_{43}H_{44}N_4O_{12}S$: 840.2 Found ($M+H^+$): 841.3.

Example 25

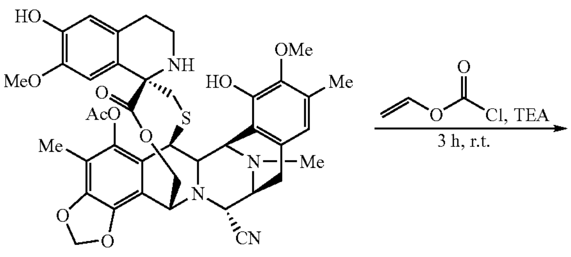

1

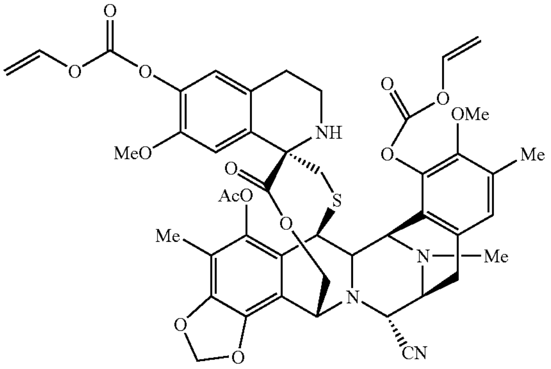

+

30
34%

-continued

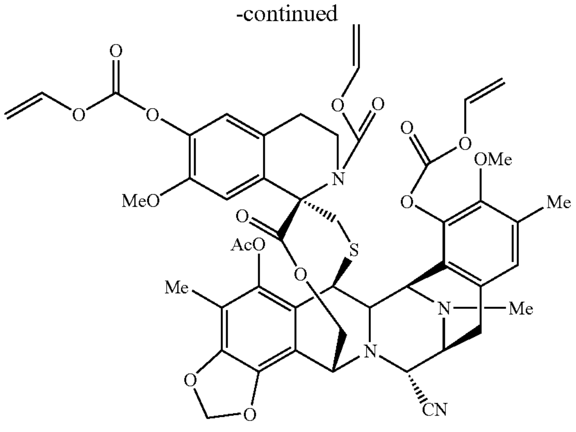

31
16%

The reaction was performed with 5.0 equiv. of TEA and 10 equiv. of vinylchloroformiate (method D).

30: $^1$H-NMR (300 MHz, $CDCl_3$): δ 7.14 (dd, 1H); 7.08 (dd, 1H); 6.99 (s, 1H); 6.73 (s, 1H); 6.58 (s, 1H); 6.04 (d, 1H); 5.97 (d, 1H); 5.03-4.97 (m, 2H); 4.70 (dd, 1H); 4.63 (dd, 1H); 4.48 (s, 1H); 4.33 (s, 1H); 4.17 (d, 1H); 4.13 (dd, 1H); 3.95 (d, 1H); 3.80 (s, 3H); 3.59 (s, 3H); 3.54 (d, 1H); 3.46 (s, 1H); 3.13-3.05 (m, 1H); 2.99 (d, 2H); 2.88-2.77 (m, 1H); 2.70-2.59 (m, 1H); 2.52-2.46 (m, 1H); 2.27-2.12 (m, 2H); 2.35 (s, 3H); 2.33 (s, 3H); 2.17 (s, 3H); 2.05 (s, 3H).

ESI-MS m/z: Calcd. for $C_{46}H_{46}N_4O_{14}S$: 910.2 Found ($M+H^+$): 911.2.

31: $^1$H-NMR (300 MHz, $CDCl_3$): δ 7.17 (dd, 1H); 7.07 (dd, 1H); 7.02 (dd, 1H); 6.86 (s, 1H); 6.74 (s, 1H); 6.33 (s, 1H); 6.07 (d, 1H); 5.95 (d, 1H); 5.01 (dd, 1H); 4.99 (dd, 1H); 4.83 (d, 1H); 4.75 (dd, 1H); 4.68 (dd, 1H); 4.65 (dd, 1H); 4.51 (s, 1H); 4.43 (dd, 1H); 4.35 (s, 1H); 4.12 (d, 1H); 4.05 (dd, 1H); 3.92 (d, 1H); 3.83 (s, 3H); 3.56 (s, 3H); 3.52 (d, 1H); 3.46-3.44 (m, 1H); 3.34 (d, 1H); 3.02-2.88 (m, 2H); 2.77-2.66 (m, 1H); 2.52-2.27 (m, 3H); 2.41 (s, 3H); 2.23 (s, 3H); 2.14 (s, 3H); 2.04 (s, 3H).

ESI-MS m/z: Calcd. for $C_{49}H_{48}N_4O_{16}S$: 980.2 Found ($M+Na^+$): 1003.2.

Example 26

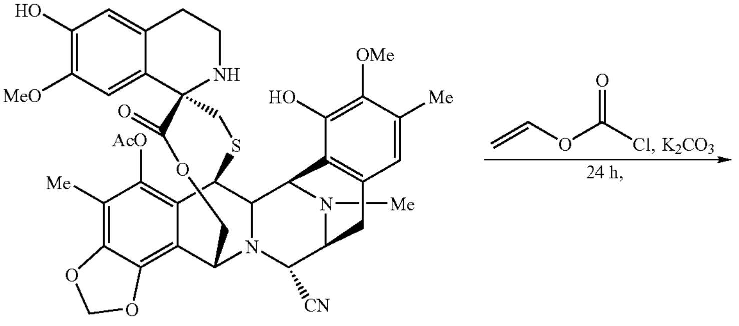

1

-continued
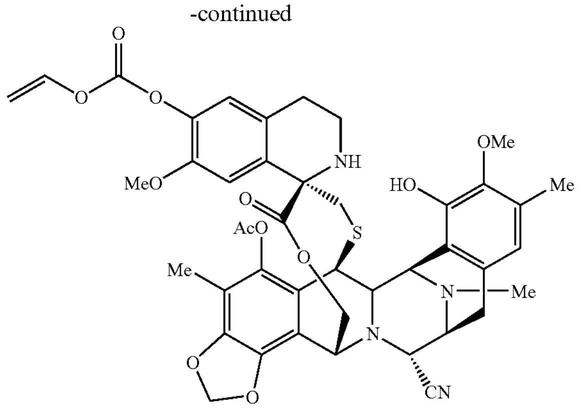
+
29
9%
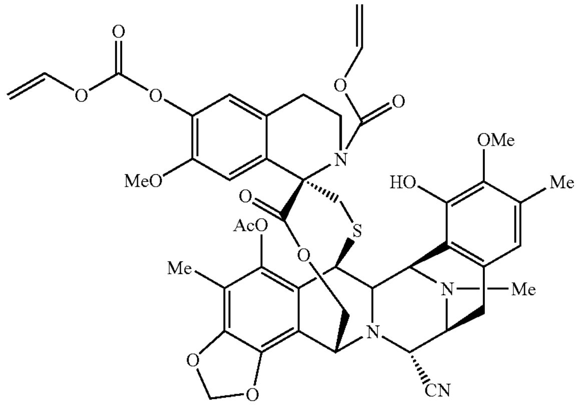
+
32
47%
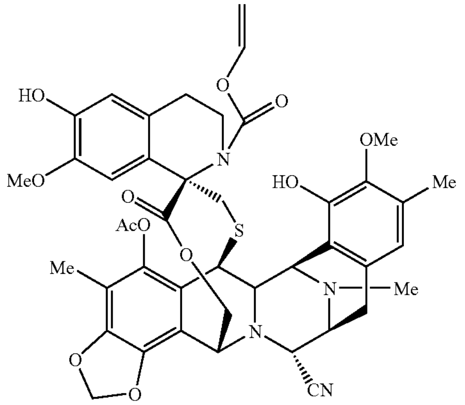
33
40%
32: $^1$H-NMR (300 MHz, $CDCl_3$): δ 7.07 (dd, 1H); 7.01 (dd, 1H); 6.72 (s, 1H); 6.47 (s, 1H); 6.35 (s, 1H); 6.06 (s, 1H); 5.94 (s, 1H); 5.74 (s, 1H); 5.00 (dd, 1H); 4.84 (d, 1H); 4.72 (d, 1H); 4.65 (dd, 1H); 4.62 (s, 1H); 4.41 (dd, 1H); 4.34 (s, 1H); 4.25 (d, 1H); 4.15-3.99 (m, 3H); 3.80 (s, 3H); 3.55 (s, 3H); 3.51-3.27 (m, 3H); 2.96-2.82 (m, 2H); 2.77-2.66 (m, 1H); 2.54-2.44 (m, 3H); 2.33 (s, 3H); 2.21 (s, 3H); 2.16 (s, 3H); 2.01 (s, 3H).
ESI-MS m/z: Calcd. for $C_{46}H_{46}N_4O_{14}S$: 910.2 Found $(M+H^+)$: 911.2.
33: $^1$H-NMR (300 MHz, $CDCl_3$): δ 7.02 (dd, 1H); 6.46 (s, 1H); 6.46 (s, 1H); 6.17 (s, 1H); 6.06 (d, 1H); 5.95 (d, 1H); 5.75 (s, 1H); 5.47 (s, 1H); 4.82 (d, 1H); 4.72 (d, 1H); 4.62 (s, 1H); 4.40 (dd, 1H); 4.33 (s, 1H); 4.25 (d, 1H); 4.11 (d, 1H); 4.01 (dd, 1H); 4.03-3.96 (m, 1H); 3.80 (s, 3H); 3.59 (s, 3H); 3.51-3.38 (m, 3H); 3.22 (d, 1H); 2.96-2.82 (m, 2H); 2.72-2.62 (m, 1H); 2.52-2.40 (m, 2H); 2.33 (s, 3H); 2.28-2.18 (m, 1H); 2.22 (s, 3H); 2.16 (s, 3H); 2.03 (s, 3H).
ESI-MS m/z: Calcd. for $C_{43}H_{44}N_4O_{12}S$: 840.2 Found (M+Na'): 863.2.

Example 27

Method E: To a solution of 1 equiv. of Et-770 (1), or compound 4 in DMF (0.032M) under Argon at room temperature were added 2 equiv. of $Cs_2CO_3$ and 2 equiv. of the alkyl halide. The reaction was followed by TLC and quenched with $NaHCO_3$, extracted with $CH_2Cl_2$ and the organic layers dried with $Na_2SO_4$. Flash chromatography gives pure compounds.

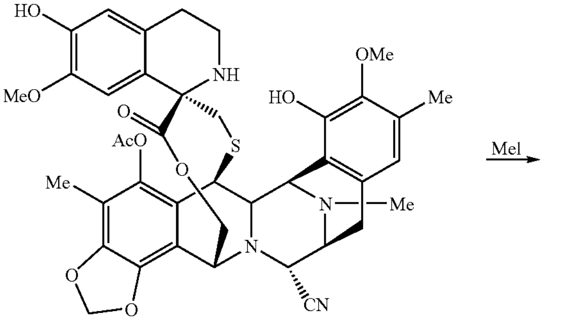

1

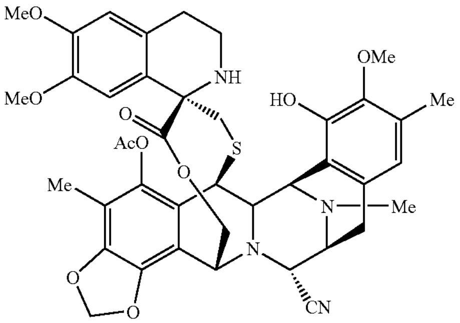

34

25%

+

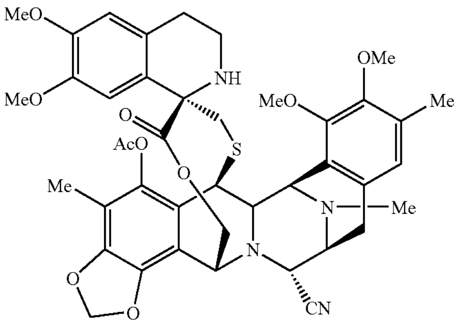

35

15%

+

-continued

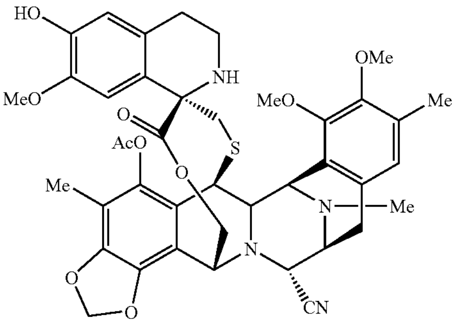

36

11%

This mixture of compounds is obtained with 1.5 equiv. of MeI and 1.0 equiv. of $Cs_2CO_3$. After chromatographic purification is recovered 21% of starting material and a fraction of the mixture of the three compounds.

34: $^1$H-NMR (300 MHz, $CDCl_3$): δ d 6.60 (s, 1H), 6.48 (s, 1H), 6.40 (s, 1H), 6.01 (d, 2H), 5.72 (s, 1H), 5.02 (d, 1H), 4.57 (bp, 1H), 4.34 (s, 1H), 4.28 (d, 1H), 4.18 (d, 1H), 4.13-4.11 (m, 1H), 3.80 (s, 3H), 3.76 (s, 3H), 3.61 (s, 3H), 3.51 (d, 1H), 3.44-3.41 (m, 1H), 3.17-3.10 (m, 1H), 2.95-2.94 (m, 2H), 2.82-2.78 (m, 1H), 2.70-2.62 (m, 1H), 2.52-2.47 (m, 1H), 2.38-2.04 (m, 2H), 2.33 (s, 3H), 2.26 (s, 3H), 2.20 (s, 3H), 2.04 (s, 3H).

ESI-MS m/z: Calcd. for $C_{41}H_{44}N_4O_{10}S$: 784.8 Found $(M+H^+)$: 785.3.

35: $^1$H-NMR (300 MHz, $CDCl_3$): δ d 6.78 (s, 1H), 6.46 (s, 1H), 6.40 (s, 1H), 6.02 (d, 2H), 5.02 (d, 1H), 4.47 (bp, 1H), 4.34 (s, 1H), 4.23 (d, 1H), 4.20 (d, 1H), 4.13-4.11 (m, 1H), 3.91 (s, 3H), 3.82 (s, 3H), 3.76 (s, 3H), 3.60 (s, 3H), 3.51 (d, 1H), 3.45-3.42 (m, 1H), 3.17-3.09 (m, 1H), 2.96-2.93 (m, 2H), 2.85-2.81 (m, 1H), 2.71-2.61 (m, 1H), 2.53-2.48 (m, 1H), 2.34-2.01 (m, 2H), 2.28 (s, 3H), 2.24 (s, 3H), 2.20 (s, 3H), 2.04 (s, 3H).

ESI-MS m/z: Calcd. for $C_{42}H_{46}N_4O_{10}S$: 798.3 Found $(M+H^+)$: 799.2

36: $^1$H-NMR (300 MHz, $CDCl_3$): δ 6.76 (s, 1H), 6.47(s, 1H), 6.42 (s, 1H), 6.01 (d, 2H), 5.41 (bs, 1H), 5.01 (d, 1H), 4.47 (bp, 1H), 4.33 (s, 1H), 4.22 (d, 1H), 4.20 (d, 1H), 4.12 (dd, 1H), 3.90 (s, 3H), 3.82 (s, 3H), 3.61 (s, 3H), 3.50 (d, 1H), 3.44-3.42 (m, 1H), 3.14-3.06 (m, 1H), 3.00-2.87 (m, 2H), 2.82-2.78 (m, 1H), 2.67-2.56 (m, 1H), 2.50-2.44 (m, 1H), 2.32-2.11 (m, 2H), 2.28 (s, 3H), 2.23 (s, 3H), 2.20 (s, 3H), 2.04 (s, 3H).

$^{13}$C-NMR (75 MHz, $CDCl_3$): δ 172.6, 168.1, 164.3, 151.7, 148.6, 145.3, 144.5, 144.2, 141.2, 140.1, 131.4, 130.2, 129.0, 127.6, 125.6, 124.3, 121.3, 118.1, 114.1, 109.7, 101.8, 64.7, 61.2, 60.0, 59.7, 59.4, 59.1, 55.1, 54.9, 54.5, 42.2, 41.9, 41.7, 39.5, 28.7, 24.1, 20.2, 15.8, 9.7.

ESI-MS m/z: Calcd. for $C_{41}H_{44}N_4O_{10}S$: 784.8 Found $(M+H^+)$: 785.3.

Example 28

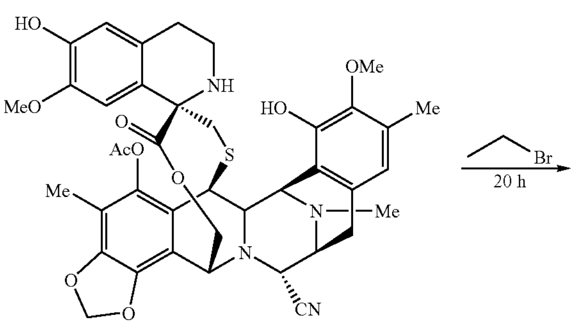

1

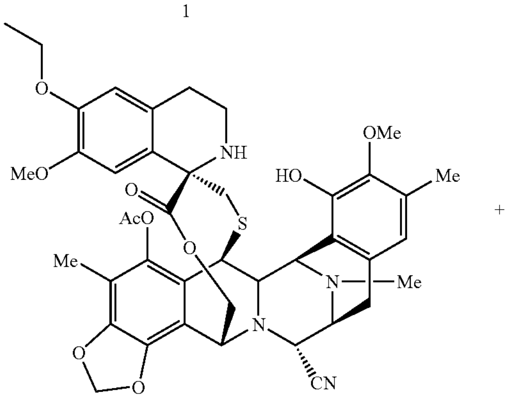

37

56%

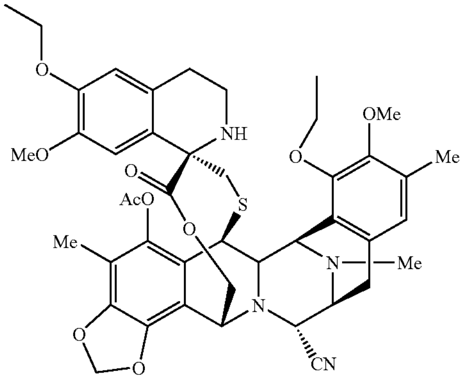

38

45%

37. (Method E) $^1$H-NMR (300 MHz, $CDCl_3$): δ 6.59 (s, 1H); 6.47 (s, 1H); 6.40 (s, 1H); 6.01 (dd, 2H); 5.76 (s, 1H); 5.02 (d, 1H); 4.55 (s, 1H); 4.32 (s, 1H); 4.27 (d, 1H); 4.19 (d, 1H); 4.12 (dd, 1H); 3.98 (q, 2H); 3.78 (s, 3H); 3.59 (s, 3H); 3.51 (d, 1H); 3.42 (s, 1H); 3.15-3.06 (m, 1H); 2.94-2.92 (m, 2H); 2.81-2.75 (m, 1H); 2.68-2.58 (m, 1H); 2.56-2.42 (m, 1H); 2.39-2.10 (m, 2H); 2.32 (s, 3H); 2.26 (s, 3H); 2.19 (s, 3H); 2.03 (s, 3H); 1.37 (t, 3H).

$^{13}$C-NMR (75 MHz, $CDCl_3$): δ 172.8, 167.9, 148.0, 147.5, 146.3, 143.2, 141.7, 141.6, 141.5, 132.7, 131.0, 130.1, 129.5, 129.0, 128.6, 121.3, 120.9, 118.3, 114.2, 112.8, 111.3, 102.1, 68.3, 64.3, 61.3, 60.5, 60.2, 59.8, 55.4, 54.9, 54.8, 39.9, 29.6, 29.1, 24.4, 22.8, 20.6, 16.0, 14.3, 9.6.

ESI-MS m/z: Calcd. for $C_{42}H_{46}N_4O_{10}S$: 798.2 Found $(M+H^+)$: 799.3.

38. (Method E): $^1$H-NMR (300 MHz, $CDCl_3$): δ 6.72 (s, 1H); 6.47 (s, 1H); 6.40 (s, 1H); 6.02 (dd, 2H); 5.02 (d, 1H); 4.50 (s, 1H); 4.32 (s, 1H); 4.24 (d, 1H); 4.20 (d, 1H); 4.13 (dd, 1H); 3.99 (q, 2H); 3.96 (q, 2H); 3.83 (s, 3H); 3.60 (s, 3H); 3.51 (d, 1H); 3.42 (s, 1H); 3.15-3.06 (m, 1H); 2.96-2.93 (m, 2H); 2.84-2.78 (m, 1H); 2.70-2.58 (m, 1H); 2.53-2.42 (m, 1H); 2.33-2.11 (m, 2H); 2.28 (s, 3H); 2.25 (s, 3H); 2.20 (s, 3H); 2.04 (s, 3H); 1.40 (t, 3H); 1.37 (s, 3H).

$^{13}$C-NMR (75 MHz, $CDCl_3$): δ 172.8, 168.2, 151.0, 147.5, 147.0, 145.5, 141.4, 140.4, 131.4, 130.4, 129.0, 128.5, 128.4, 124.4, 121.5, 118.3, 114.2, 112.8, 111.0, 102.0, 68.3, 64.3, 61.5, 60.0, 59.4, 55.4, 55.3, 54.9, 54.5, 42.2, 42.1, 41.9, 39.8, 29.5, 29.2, 24.4, 22.8, 20.4, 16.4, 16.0, 14.3, 9.8.

ESI-MS m/z: Calcd. for $C_{44}H_{50}N_4O_{10}S$: 826.3 Found $(M+H^+)$: 827.3.

Example 29

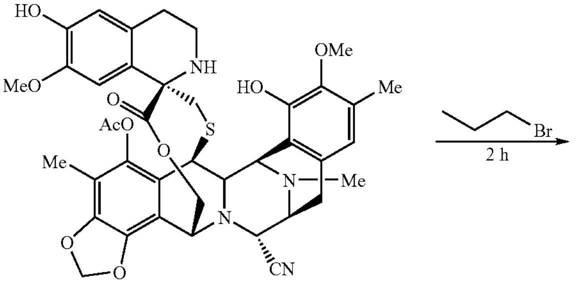

1

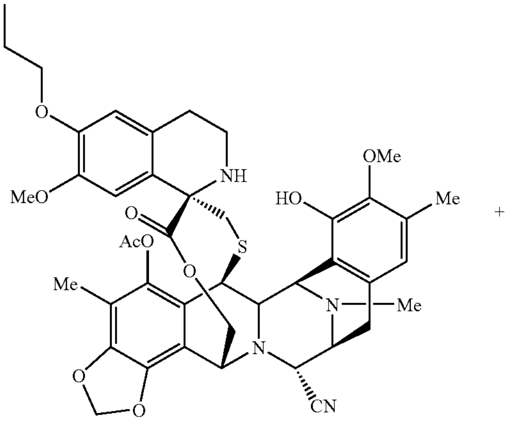

39

53%

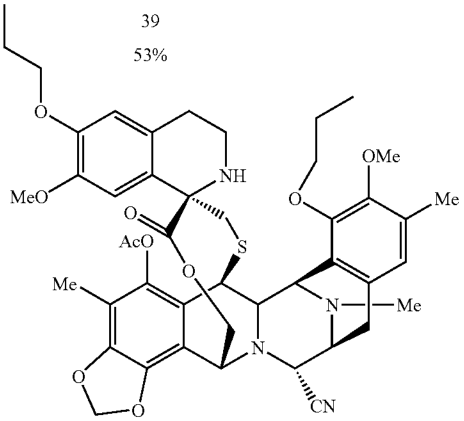

40

49%

39. (Method E) $^1$H-NMR (300 MHz, $CDCl_3$): δ 6.59 (s, 1H); 6.48 (s, 1H); 6.40 (s, 1H); 6.01 (dd, 2H); 5.74 (s, 1H); 5.02 (d, 1H); 4.55 (s, 1H); 4.31 (s, 1H); 4.27 (d, 1H); 4.18 (d, 1H); 4.11 (dd, 1H); 3.84 (q, 2H); 3.78 (s, 3H); 3.59 (s, 3H); 3.51 (d, 1H); 3.41 (s, 1H); 3.16-3.06 (m, 1H); 2.96-2.92 (m, 2H); 2.81-2.73 (m, 1H); 2.68-2.58 (m, 1H); 2.54-2.42 (m, 1H); 2.39-2.10 (m, 2H); 2.31 (s, 3H); 2.25 (s, 3H); 2.19 (s, 3H); 2.03 (s, 3H); 1.80-1-71 (m, 2H); 0.96 (s, 3H).

$^{13}$C-NMR (75 MHz, $CDCl_3$): δ 172.8, 167.9, 148.0, 147.5, 146.3, 143.2, 141.7, 141.6, 141.5, 131.0, 130.1, 129.5, 129.0, 128.6, 121.3, 120.9, 118.3, 114.2, 112.8, 111.3, 102.1, 70.5, 61.3, 60.5, 60.2, 60.0, 59.8, 59.7, 55.5, 54.9, 54.8, 42.3, 42.1, 41.8, 39.9, 29.9, 24.4, 22.5, 20.6, 16.0, 10.5, 9.9.

ESI-MS m/z: Calcd. for $C_{43}H_{48}N_4O_{10}S$: 812.3 Found (M+H$^+$): 813.3.

40. (Method E). $^1$H-NMR (300 MHz, $CDCl_3$): δ 6.77 (s, 1H); 6.47 (s, 1H); 6.40 (s, 1H); 6.03 (dd, 2H); 5.02 (d, 1H); 4.52 (s, 1H); 4.32 (s, 1H); 4.22 (d, 1H); 4.19 (d, 1H); 4.12 (dd, 1H); 3.87-3.80 (m, 4H); 3.82 (s, 3H); 3.59 (s, 3H); 3.51 (d, 1H); 3.43 (s, 1H); 3.15-3.06 (m, 1H); 2.96-2.93 (m, 2H); 2.84-2.74 (m, 1H); 2.68-2.58 (m, 1H); 2.53-2.42 (m, 1H); 2.38-2.07 (m, 2H); 2.28 (s, 3H); 2.24 (s, 3H); 2.20 (s, 3H); 2.04 (s, 3H); 1.83-1.72 (m, 4H); 1.10 (t, 3H); 0.96 (s, 3H).

$^{13}$C-NMR (75 MHz, $CDCl_3$): δ 172.8, 168.2, 151.2, 147.8, 147.1, 145.5, 141.7, 141.4, 131.4, 130.4, 128.6, 127.8, 125.4, 124.4, 121.5, 118.3, 114.2, 113.0, 111.3, 102.0, 74.3, 70.5, 61.4, 60.0, 59.6, 59.5, 55.5, 55.4, 54.9, 42.2, 42.1, 41.9, 39.8, 31.7, 29.9, 24.4, 24.2, 22.8, 22.5, 20.4, 16.0, 14.3, 11.1, 10.5, 9.8.

ESI-MS m/z: Calcd. for $C_{46}H_{54}N_4O_{10}S$: 854.3 Found (M+H$^+$): 855.3.

Example 30

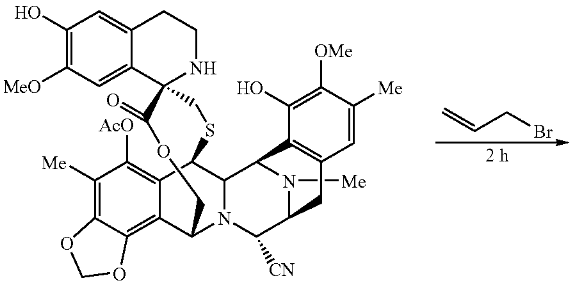

1

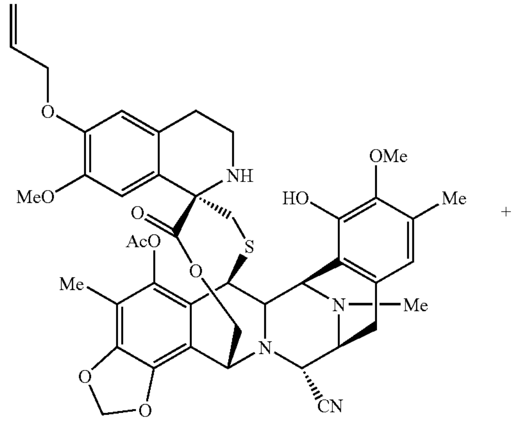

41

35%

-continued

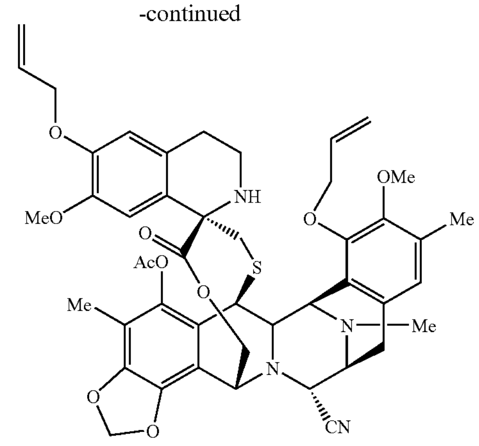

42

32%

Compounds 41 and 42 were obtained using Method E.

41: $^1$H-NMR (300 MHz, $CDCl_3$): δ 6.59 (s, 1H); 6.48 (s, 1H); 6.40 (s, 1H); 6.04-5.92 (m, 1H); 6.01 (dd, 2H); 5.72 (s, 1H); 5.31 (dd, 1H); 5.22 (dd, 1H); 5.02 (d, 1H); 4.55 (s, 1H); 4.49 (d, 2H); 4.32 (s, 1H); 4.27 (d, 1H); 4.18 (d, 1H); 4.12 (dd, 1H); 3.78 (s, 3H); 3.60 (s, 3H); 3.51 (d, 1H); 3.41 (s, 1H); 3.16-3.06 (m, 1H); 2.95-2.92 (m, 2H); 2.82-2.74 (m, 1H); 2.67-2.58 (m, 1H); 2.52-2.42 (m, 1H); 2.37-2.10 (m, 2H); 2.32 (s, 3H); 2.26 (s, 3H); 2.19 (s, 3H); 2.03 (s, 3H).

$^{13}$C-NMR (75 MHz, $CDCl_3$): δ 172.8, 167.9, 148.0, 147.2, 143.2, 141.5, 140.3, 133.4, 131.0, 129.5, 128.6, 126.8, 121.3, 120.9, 118.4, 118.3, 117.9, 114.2, 113.4, 111.2, 102.1, 69.9, 64.7, 61.3, 60.5, 60.2, 59.8, 59.7, 55.5, 54.9, 54.8, 42.4, 42.0, 41.9, 41.8, 39.9, 29.9, 29.2. 24.4, 20.6, 16.0, 9.9.

ESI-MS m/z: Calcd. for $C_{43}H_{46}N_4O_{10}S$: 810.2 Found (M+H$^+$): 811.2.

42: $^1$H-NMR (300 MHz, $CDCl_3$): δ 6.79 (s, 1H); 6.48 (s, 1H); 6.40 (s, 1H); 6.16-5.92 (m, 2H); 6.03 (dd, 2H); 5.45 (dd, 1H); 5.31 (dd, 1H); 5.24 (dd, 1H); 5.21 (dd, 1H); 5.02 (d, 1H); 4.82-4.77 (m, 1H); 4.53 (s, 1H); 4.49 (d, 2H); 4.37-4.31 (m, 1H); 4.32 (s, 1H); 4.24 (d, 1H); 4.17 (d, 1H); 4.12 (dd, 1H); 3.82 (s, 3H); 3.60 (s, 3H); 3.51 (d, 1H); 3.42 (s, 1H); 3.15-3.06 (m, 1H); 2.96-2.93 (m, 2H); 2.84-2.74 (m, 1H); 2.68-2.58 (m, 1H); 2.53-2.42 (m, 1H); 2.34-2.11 (m, 2H); 2.28 (s, 3H); 2.23 (s, 3H); 2.19 (s, 3H); 2.03 (s, 3H).

$^{13}$C-NMR (75 MHz, $CDCl_3$): δ 172.8, 169.5, 150.7, 149.0, 147.2, 146.3, 141.5, 140.3, 134.8, 133.4, 131.4, 130.5, 128.5, 124.9, 124.7, 121.4, 118.2, 118.0, 116.9, 114.2, 113.4, 111.2, 102.1, 73.1, 69.8, 61.4, 60.0, 59.6, 59.5, 55.4, 55.3, 54.8, 42.3, 42.1, 41.9, 39.8, 29.9, 29.1, 24.4, 20.5, 16.0, 9.8.

ESI-MS m/z: Calcd. for $C_{46}H_{50}N_4O_{10}S$: 850.3 Found (M+H$^+$): 851.3.

Example 31

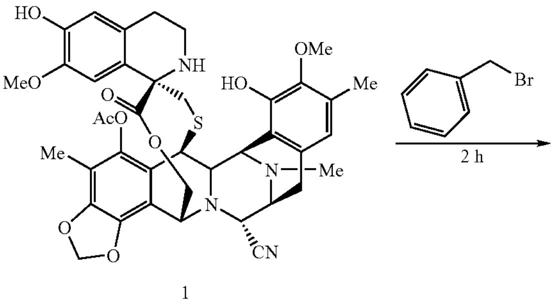

1

-continued

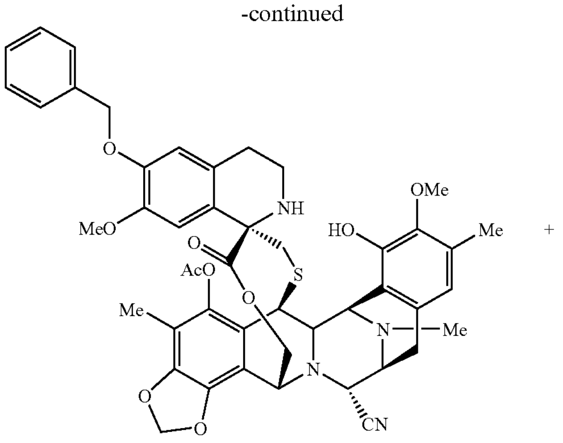

43

33%

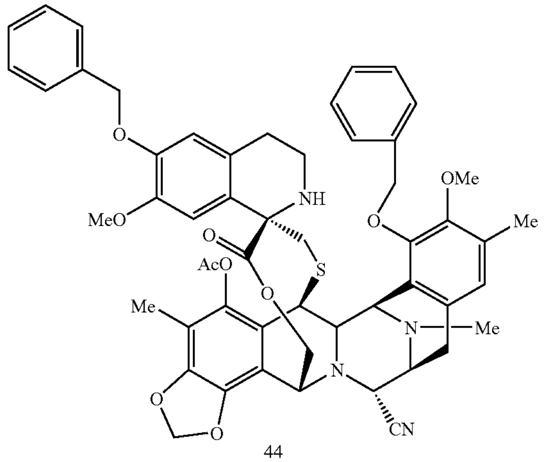

44

62%

Compounds 43 and 44 were obtained using Method E 64

43: $^1$H-NMR (300 MHz, $CDCl_3$): δ 7.38-7.26 (m, 5H); 6.59 (s, 1H); 6.51 (s, 1H); 6.41 (s, 1H); 6.02 (dd, 2H); 5.73 (s, 1H); 5.03 (s, 2H); 5.01 (d, 1H); 4.56 (s, 1H); 4.32 (s, 1H); 4.27 (d, 1H); 4.18 (d, 1H); 4.12 (dd, 1H); 3.78 (s, 3H); 3.61 (s, 3H); 3.51 (d, 1H); 3.42 (s, 1H); 3.13-3.06 (m, 1H); 2.94-2.92 (m, 2H); 2.80-2.72 (m, 1H); 2.62-2.53 (m, 1H); 2.47-2.37 (m, 1H); 2.34-2.10 (m, 2H); 2.32 (s, 3H); 2.26 (s, 3H); 2.19 (s, 3H); 2.03 (s, 3H).

$^{13}$C-NMR (75 MHz, $CDCl_3$): δ 172.8, 169.5, 168.3, 148.0, 147.3, 145.5, 143.2, 141.5, 140.3, 137.3, 132.4, 131.0, 128.6, 127.9, 127.3, 127.0, 121.3, 120.9, 118.3, 114.2, 113.9, 111.4, 102.1, 70.9, 64.7, 61.3, 60.5, 60.2, 59.8, 59.7, 55.5, 54.9, 54.8, 42.3, 42.0, 41.8, 39.9, 29.9, 29.1, 24.4, 20.6, 16.0, 9.9.

ESI-MS m/z: Calcd. for $C_{47}H_{48}N_4O_{10}S$: 860.3 Found ($M+H^+$): 861.3.

44: $^1$H-NMR (300 MHz, $CDCl_3$): δ 7.47-7.25 (m, 10H); 6.81 (s, 1H); 6.48 (s, 1H); 6.41 (s, 1H); 6.01 (dd, 2H); 5.32 (d, 1H); 5.03 (s, 2H); 5.01 (d, 1H); 4.84 (d, 1H); 4.50 (s, 1H); 4.32 (s, 1H); 4.21 (d, 1H); 4.19 (d, 1H); 4.13 (dd, 1H); 3.86 (s, 3H); 3.60 (s, 3H); 3.49 (d, 1H); 3.40 (s, 1H); 3.15-3.06 (m, 1H); 2.96-2.93 (m, 2H); 2.81-2.71 (m, 1H); 2.64-2.51 (m, 1H); 2.50-2.40 (m, 1H); 2.33-2.11 (m, 2H); 2.32 (s, 3H); 2.04 (s, 3H); 2.02 (s, 3H); 2.00 (s, 3H).

$^{13}$C-NMR (75 MHz, $CDCl_3$): δ 172.7, 168.3, 149.2, 147.4, 147.3, 145.5, 141.4, 140.3, 138.1, 137.2, 131.5, 130.3, 128.8, 128.7, 128.6, 128.2, 128.1, 127.9, 127.3, 127.0, 125.0, 124.9, 121.4, 118.2, 114.2, 114.0, 111.3, 102.0, 74.3, 70.9, 64.9, 61.4, 60.1, 60.0, 59.7, 59.5, 55.5, 55.4, 54.8, 42.2, 42.1, 41.7, 39.7, 31.7, 29.9, 24.4, 22.8, 20.1, 16.0, 14.3, 9.8.

ESI-MS m/z: Calcd. for $C_{54}H_{54}N_4O_{10}S$: 950.3 Found ($M+H^+$): 951.3.

Example 32

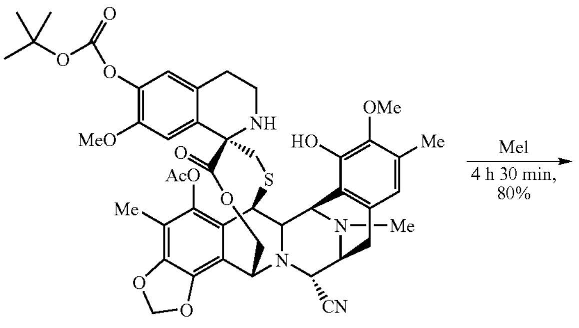

4

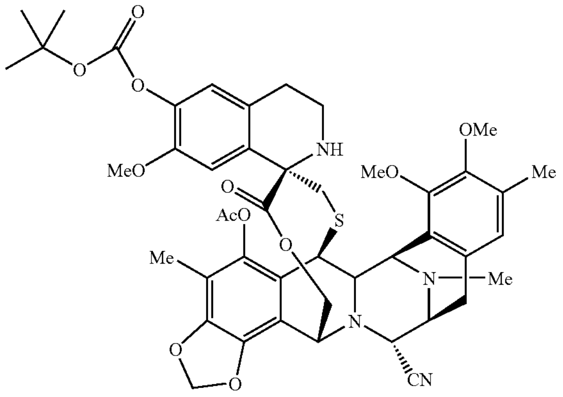

45

The reaction was performed with 1.0 equiv. of MeI and 1.0 equiv. of $Cs_2CO_3$ (Method E). After chromatographic purification starting material (16%) was recuperated.

45. $^1$H-NMR (300 MHz, $CDCl_3$): d 6.76 (s, 1H), 6.47(s, 1H), 6.42 (s, 1H), 6.01 (d, 2H), 5.41 (bs, 1H), 5.01 (d, 1H), 4.47 (bp, 1H), 4.33 (s, 1H), 4.22 (d, 1H), 4.20 (d, 1H), 4.12 (dd, 1H), 3.90 (s, 3H), 3.82 (s, 3H), 3.61 (s, 3H), 3.50 (d, 1H), 3.44-3.42 (m, 1H), 3.14-3.06 (m, 1H), 3.00-2.87 (m, 2H), 2.82-2.78 (m, 1H), 2.67-2.56 (m, 1H), 2.50-2.44 (m, 1H), 2.32-2.11 (m, 2H), 2.28 (s, 3H), 2.23 (s, 3H), 2.20 (s, 3H), 2.04 (s, 3H).

$^{13}$C-NMR (75 MHz, $CDCl_3$): 172.6, 168.1, 164.3, 151.7, 148.6, 145.3, 144.5, 144.2, 141.2, 140.1, 131.4, 130.2, 129.0, 127.6, 125.6, 124.3, 121.3, 118.1, 114.1, 109.7, 101.8, 64.7, 61.2, 60.0, 59.7, 59.4, 59.1, 55.1, 54.9, 54.5, 42.2, 41.9, 41.7, 39.5, 28.7, 24.1, 20.2, 15.8, 9.7.

ESI-MS m/z: Calcd. for $C_{46}H_{52}N_4O_{12}S$: 884.3 Found $(M+H^+)$: 985.3.

Example 33

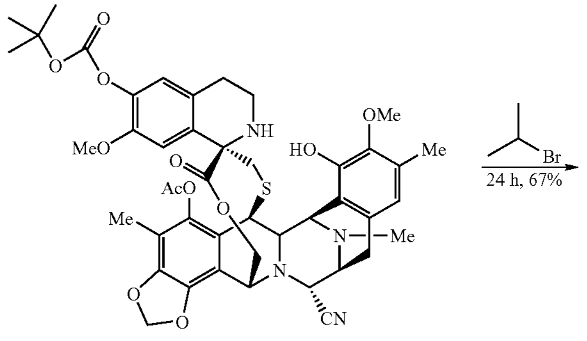

4

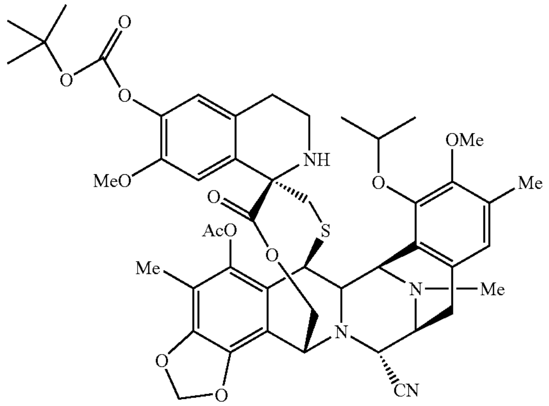

46

Compound 46 was obtained with 15 equiv. of isopropyl bromide and 15 equiv, of $Cs_2CO_3$ (Method E)

46. $^1$-H-NMR (300 MHz, $CDCl_3$): d 6.75 (s, 1H), 6.68 (s, 1H), 6.57 (s, 1H), 6.03 (d, 1H), 5.96(d, 1H); 4.99 (d, 1H), 4.86-4.80 (m, 1H); 4.51 (s, 1H), 4.35-4.31 (m, 2H), 4.18 (s, 1H), 4.11 (d, 1H), 3.80 (s, 3H), 3.58 (s, 3H), 3.48 (d, 1H), 3.41 (s, 1H), 3.15-3.08 (m, 1H), 2.95-2.93 (m, 2H), 2.82-2.74 (m, 1H), 2.68-2.48 (m, 2H); 2.27 (s, 3H), 2.26 (s, 3H), 2.23 (s, 3H), 2.17-2.12 (m, 1H); 2.04 (s, 3H); 1.50 (s, 9H); 1.45 (d, 3H); 1.14 (d, 3H).

ESI-MS m/z: Calcd. for $C_{48}H_{56}N_4O_{12}S$: 912.3 Found $(M+H^+)$: 913.3.

Example 34

Method F: To a solution of 1 equiv. of starting material in $CH_2Cl_2/H_2O/TFA$ 2:1:3.3 (0.013M) was stirred at room temperature for 15 min. The reaction was followed by TLC and neutralised with $NaHCO_3$, extracted with $CH_2Cl_2$ and the organic layers dried with $Na_2SO_4$. Flash chromatography gives pure compounds.

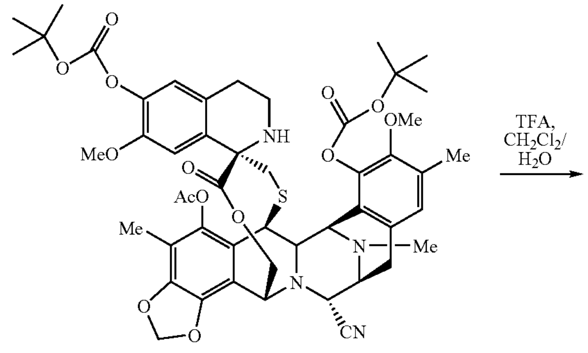

5

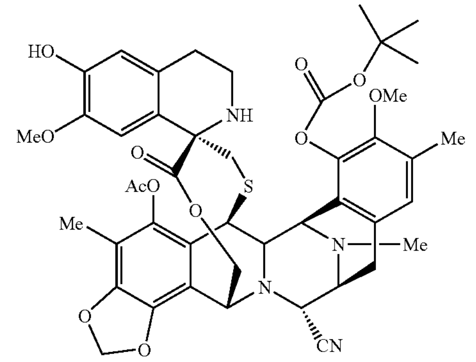

47
32%

+

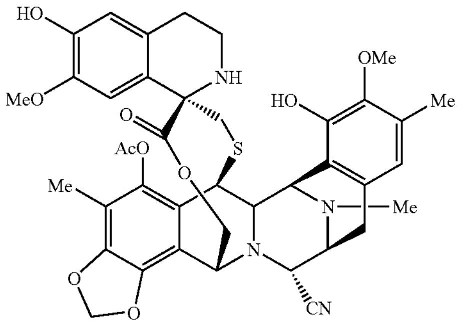

1
56%

47. was obtained using Method F $^1$H-NMR (300 MHz, $CDCl_3$): δ 6.93 (s, 1H); 6.48 (s, 1H); 6.42 (s, 1H); 6.02 (dd, 2H); 5.39 (s, 1H); 5.02 (d, 1H); 4.47 (s, 1H); 4.33 (s, 1H); 4.18 (d, 1H); 4.13 (dd, 1H); 3.93 (d, 1H); 3.79 (s, 3H); 3.62 (s, 3H); 3.52 (d, 1H); 3.46-3.44 (m, 1H); 3.12-3.04 (m, 1H); 2.98 (d, 2H); 2.83-2.76 (m, 1H); 2.64-2.57 (m, 1H); 2.51-2.46 (m, 1H); 2.24-2.03 (m, 2H); 2.32 (s, 3H); 2.31 (s, 3H); 2.17 (s, 3H); 2.06 (s, 3H); 1.56 (s, 9H).

$^{13}$C-NMR (75 MHz, $CDCl_3$): δ 172.0, 168.4, 151.3, 148.3, 145.6, 144.8, 144.5, 141.5, 140.4, 131.6, 130.5, 129.4, 127.1, 125.7, 124.5, 121.4, 118.1, 114.3, 114.2, 113.6, 109.9, 102.0, 83.4, 67.4, 61.4, 60.2, 60.0, 59.8, 59.3, 55.9, 55.8, 54.7, 42.4, 42.1, 41.8, 39.8, 29.9, 29.0, 27.8, 24.2, 20.3, 16.0, 9.8.

ESI-MS m/z: Calcd. for $C_{45}H_{50}N_4O_{12}S$: 870.3 Found ($M+H^+$): 871.3.

Example 35

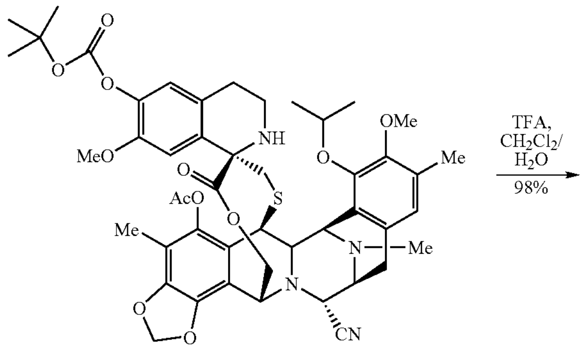

46

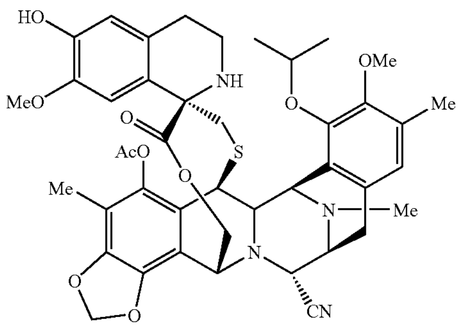

48

48 was obtained using Method F. $^1$-NMR (300 MHz, $CDCl_3$): d 6.76 (s, 1H), 6.46 (s, 1H), 6.44 (s, 1H), 6.04 (d, 1H), 5.97 (d, 1H); 5.42 (s, 1H); 5.01 (d, 1H), 4.89-4.80 (m, 1H); 4.53 (s, 1H), 4.34 (dd, 1H); 4.31 (s, 1H), 4.19 (d, 1H), 4.12 (dd, 1H), 3.80 (s, 3H), 3.61 (s, 3H), 3.49 (d, 1H), 3.42 (s, 1H), 3.12-3.04 (m, 1H), 2.95 (d, 2H), 2.78-2.73 (m, 1H), 2.64-2.47 (m, 2H); 2.30-2.10 (m, 2H); 2.28 (s, 3H), 2.25 (s, 3H), 2.23 (s, 3H), 2.04 (s, 3H); 1.45 (d, 3H); 1.14 (d, 3H).

ESI-MS m/z: Calcd. for $C_{43}H_{48}N_4O_{10}S$: 812.3 Found ($M+H^+$): 813.3.

Example 36

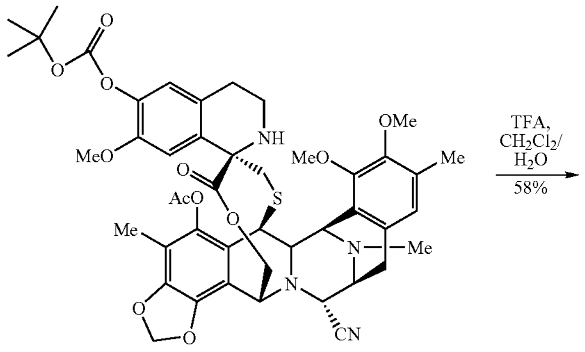

45

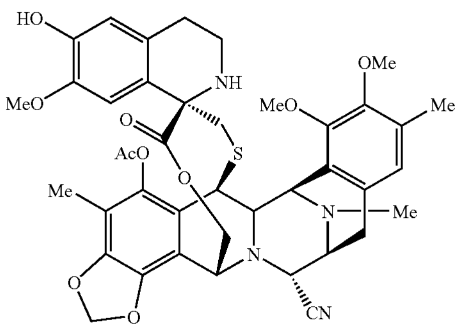

36

After chromatographic purification, starting material (33%) was recuperated. Compound 36 has been previously described.

Other chemical transformations:

Example 37

Compound 47 was acylated following method B.

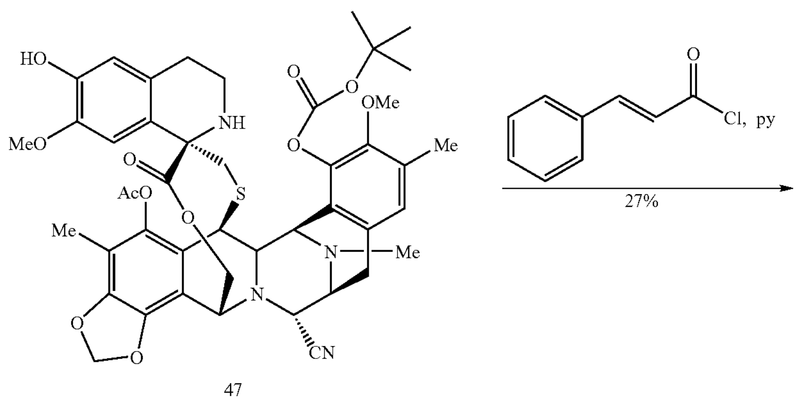

47

-continued

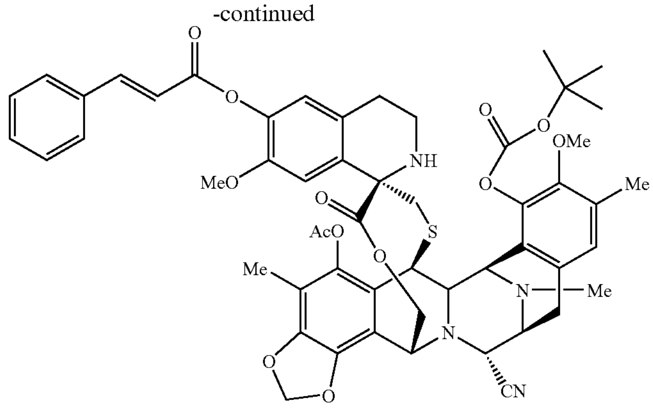

49

49. $^1$H-NMR (300 MHz, $CDCl_3$): δ 7.80 (d, 1H); 7.56-7.54 (m, 2H); 7.41-7.39 (m, 3H); 6.93 (s, 1H); 6.69 (s, 1H); 6.60 (d, 1H); 6.57 (s, 1H); 6.00 (dd, 2H); 5.02 (d, 1H); 4.45 (s, 1H); 4.34 (s, 1H); 4.18 (d, 1H); 4.13 (dd, 1H); 3.93 (d, 1H); 3.80 (s, 3H); 3.56 (s, 3H); 3.52 (d, 1H); 3.46-3.43 (m, 1H); 3.15-3.06 (m, 1H); 2.98-2.96 (m, 2H); 2.86-2.80 (m, 1H); 2.64-2.59 (m, 1H); 2.54-2.46 (m, 1H); 2.35-2.05 (m, 2H); 2.33 (s, 3H); 2.31 (s, 3H); 2.18 (s, 3H); 2.05 (s, 3H); 1.53 (s, 9H).

ESI-MS m/z: Calcd. for $C_{54}H_{56}N_4O_{13}S$: 1000.3 Found $(M+H^+)$: 1001.3.

Example 38

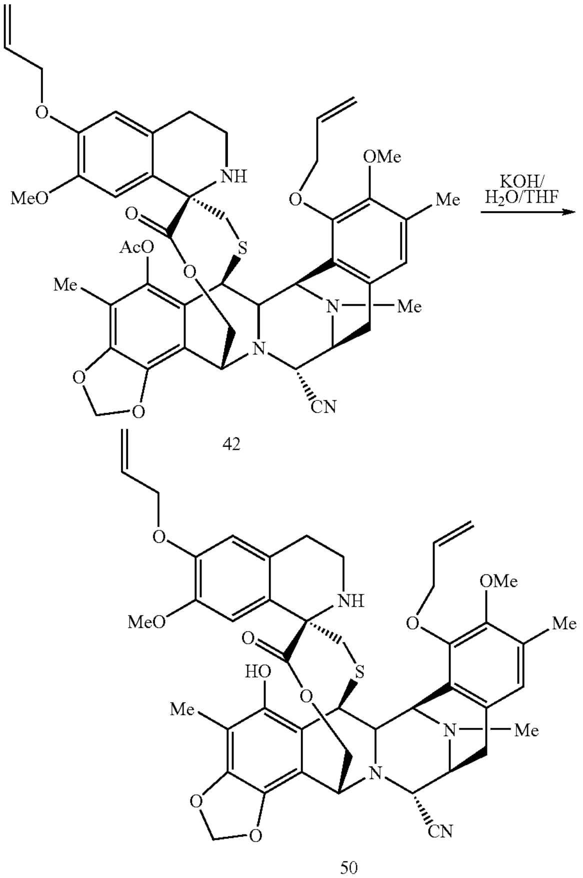

42

50

To a solution of compound 42 in THF/MeOH 1:1 were added 2 equiv of KOH. The reaction mixture was stirred at room temperature for 5 h. After this time the reaction was quenched with NaCl or diluted aqueous solution of HCl, extracted with $CH_2Cl_2$. The organic layer was dried with $Na_2SO_4$. Chromatography gives pure compound 50 (79%).

50. $^1$H-NMR (300 MHz, $CDCl_3$): δ 6.81 (s, 1H), 6.47 (s, 1H), 6.43 (s, 1H), 6.17-5.90 (m, 2H), 5.94 (d, 2H), 5.45-5.22 (m, 4H), 4.98 (d, 1H), 4.83-4.77 (m, 1H), 4.56-4.27 (m, 5H), 4.16-4.02 (m, 3H), 3.84 (s, 3H), 3.58 (bs, 4H), 3.44-3.40 (m, 1H), 3.20-2.16 (m, 8H), 2.31 (s, 3H), 2.25 (s, 3H), 2.19 (s, 3H).

ESI-MS m/z: Calcd. for $C_{44}H_{48}N_4O_9S$: 808.3 Found $(M+H^+)$: 809.2.

Example 39

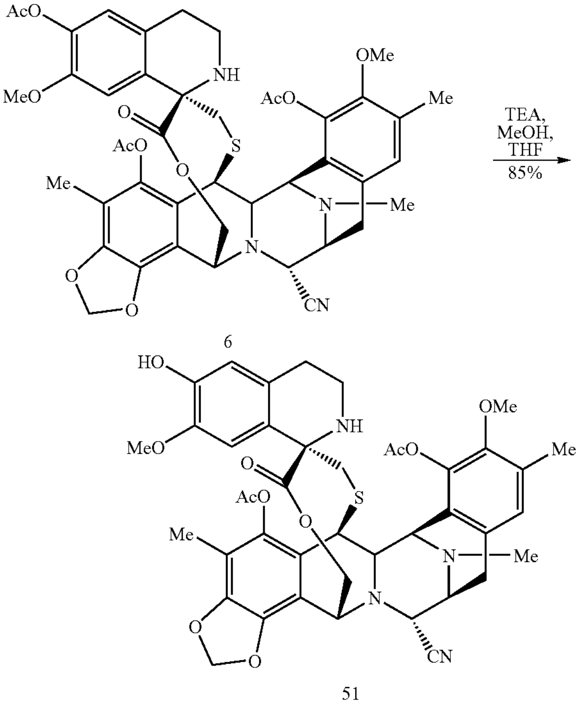

6

51

To a solution of compound 6 in MeOH/THF 3:4 (0.011M) at room temperature were added 150 equiv. of $Et_3N$. After 7 days the solvent was evaporated. Flash chromatography gives pure compound 51.

51. $^1$H-NMR (300 MHz, $CDCl_3$): δ 6.95 (s, 1H), 6.49 (s, 1H), 6.40 (bs, 1H), 6.02 (dd, 2H), 5.42 (bs, 1H), 5.02 (d, 1H), 4.45 (bs, 1H), 4.35 (s, 1H), 4.21-4.10 (m, 2H), 3.84-3.68 (m, 4H), 3.62 (s, 3H), 3.53 (bd, 1H), 3.48-3.44 (m, 1H), 3.16-2.75 (m, 4H), 2.67-2.14 (m, 4H), 2.38 (s, 3H), 2.35 (s, 3H), 2.31 (s, 3H), 2.16 (s, 3H), 2.01 (s, 3H).

ESI-MS m/z: Calcd. for $C_{42}H_{44}N_4O_{11}S$: 812.3 Found ($M+H^+$): 813.3.

Example 40

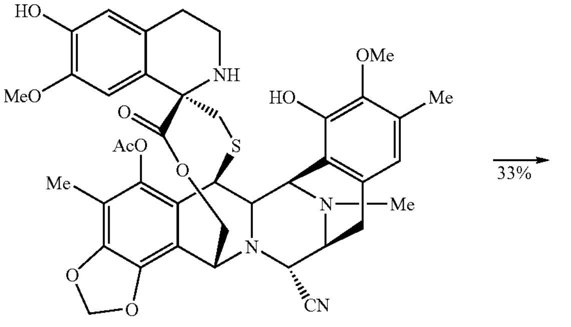

1

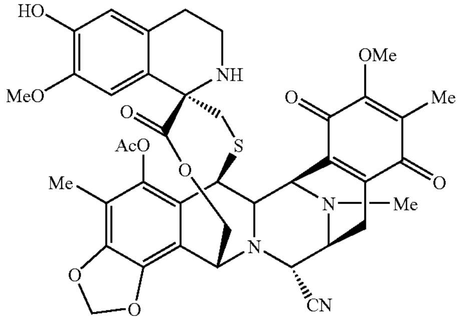

52

To a solution of Et-770 (1) (1.0 equiv.) in MeOH (0.032M) at room temperature under Argon, were added $RuCl_2(PPh_3)_3$ (0.1 equiv.) and $H_2O_2$ (8 equiv.). The reaction mixture was stirred at room temperature for 4 h. After this time, it was diluted with $CH_2Cl_2$, washed with brine and the organic layer was dried over $Na_2SO_4$. Flash chromatography gives compound 52.

52. $^1$H-NMR (300 MHz, $CDCl_3$): δ 6.48(s, 1H); 6.43(s, 1H); 6.05(s, 1H); 5.99(s, 1H); 5.42(s, 1H); 4.92(d, 1H); 4.50 (s, 1H); 4.22(s, 1H); 4.18-4.15(m, 1H); 4.12-3.98(m, 2H); 4.10(s, 3H); 3.61(s, 3H); 3.58-3.55(m, 1H); 3.42-3.37(m, 2H); 3.12-3.03(m, 1H); 2.90-2.59(m, 3H); 2.55-2.27(m, 4H); 2.24(s, 3H); 2.21(s, 3H); 2.04(s, 3H); 2.02(s, 3H).

ESI-MS m/z: Calcd. for $C_{40}H_{40}N_4O_{11}S$: 784.2. Found ($M+Na^+$): 807.2.

Example 41

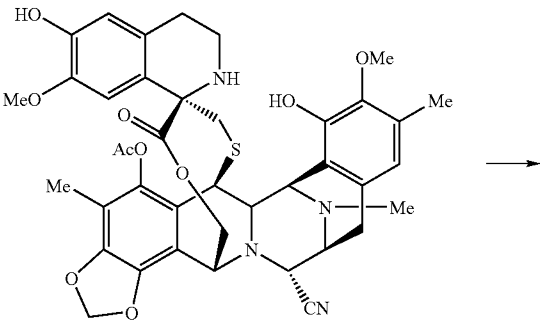

1

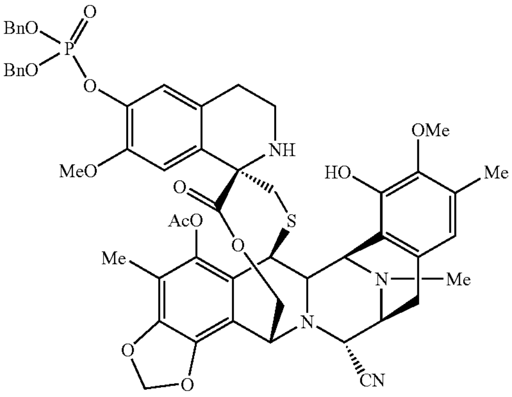

53

A suspension of 1, coevaporated twice with anhydrous toluene, in $CH_3CN$ (0.03M) under Argon was cooled at −10° C. At this temperature were added 5 equiv. of $CCl_4$, 2.1 equiv. of $^iPr_2NEt$, 0.1 equiv. of DMAP and 1.45 equiv of dibenzyl phosphite. After 1 h the reaction was quenched with 1.2 equiv. of $KH_2PO_4$ (0.5M). The reaction mixture was warmed up to room temperature, stirred for 5 min, diluted with EtOAc and washed with water. The organic layers were dried with $Na_2SO_4$. Flash chromatography gives pure compound 53 (75%).

53. $^1$H-NMR (300 MHz, $CDCl_3$): δ 7.29 (s, 10H), 6.71 (s, 1H), 6.59 (s, 1H), 6.52 (s, 1H), 6.00 (d, 2H), 5.76 (s, 1H), 5.12-5.07 (m, 2H), 5.02 (d, 1H), 4.57 (bs, 1H), 4.32 (s, 1H), 4.27 (d, 1H), 4.18 (d, 1H), 4.11 (bd, 1H), 3.78 (s, 3H), 3.50 (bs, 4H), 3.44-3.39 (m, 1H), 3.12-3.03 (m, 1H), 2.95-2.92 (m, 2H), 2.81-2.72 (m, 1H), 2.60-2.04 (m, 4H), 2.32 (s, 3H), 2.27 (s, 3H), 2.20 (s, 3H), 2.04 (s, 3H).

ESI-MS m/z: Calcd. for $C_{54}H_{55}N_4O_{13}PS$: 1030.3 Found ($M+H^+$): 1031.3.

Example 42

Method G: To a solution of Et-770 (1) in $CH_3CN$ (0.016M) at room temperature under Argon, were added 200 equiv. of the aldehyde (37 wt. % in water) and 10 equiv. of $NaCNBH_3$. After 1 h 10 min 40 equiv. of acetic acid were added. The reaction mixture was stirred for 2 h more. After this time, it was diluted with $CH_2Cl_2$, neutralised with $NaHCO_3$ and extracted with $CH_2Cl_2$. The organic layers were dried over $Na_2SO_4$. Flash chromatography gives pure compounds.

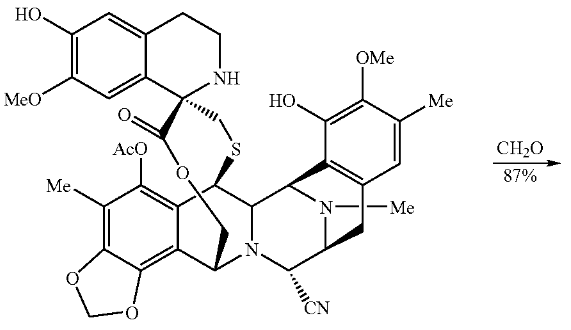

1

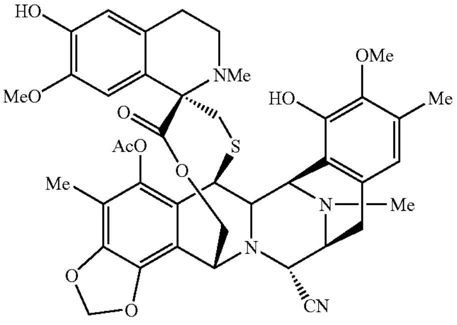

54

54 was obtained following method G. $^1$H-NMR (300 MHz, $CDCl_3$): δ 6.47 (s, 1H), 6.45 (s, 1H), 6.17 (s, 1H), 6.02 (dd, 2H), 5.73 (bs, 1H), 5.44 (bs, 1H), 4.94 (d, 1H), 4.60 (bs, 1H), 4.35 (d, 1H), 4.26 (d, 1H), 4.07 (d 1H), 3.88-3.82 (m, 1H), 3.79 (s, 3H), 3.56 (s, 3H), 3.52 (bd, 1H), 3.42-3.39 (m, 1H), 3.20 (bp, 1H), 3.00-2.44 (m, 5H), 2.35-2.16 (m, 2H), 2.31 (s, 3H), 2.24 (s, 3H), 2.21 (bs, 3H), 2.16 (s, 3H), 2.02 (s, 3H).

ESI-MS m/z: Calcd. for $C_{41}H_{44}N_4O_{10}S$: 784.3. Found (M+H$^+$): 785.2.

Example 43

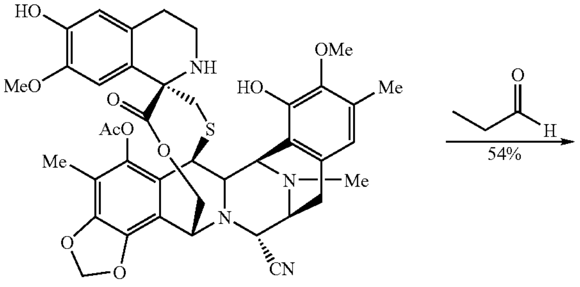

1

-continued

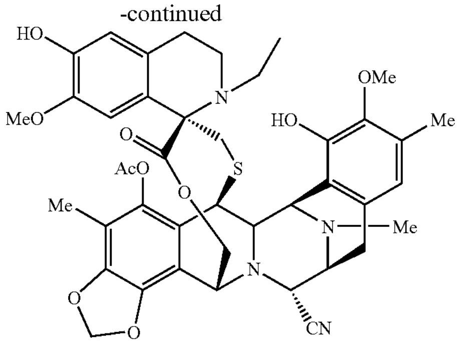

55

55 was obtained following method G $^1$H-NMR (300 MHz, $CD_3OD$): δ 6.41 (s, 1H), 6.35 (s, 1H), 6.21 (s, 1H), 6.09 (d, 2H), 4.97 (d, 1H), 4.67 (bs, 1H), 4.36 (bs, 2H), 4.27 (d, 1H), 3.95 (dd 1H), 3.73 (s, 3H), 3.53 (s, 3H), 3.45-3.41 (m, 2H), 2.98-2.47 (m, 6H), 2.37-2.03 (m, 4H), 2.33 (s, 3H), 2.25 (s, 3H), 2.07 (s, 3H), 2.03 (s, 3H), 0.88 (t, 3H).

ESI-MS m/z: Calcd. for $C_{42}H_{46}N_4O_{10}S$: 798.3. Found (M+H$^+$): 799.2.

Example 44

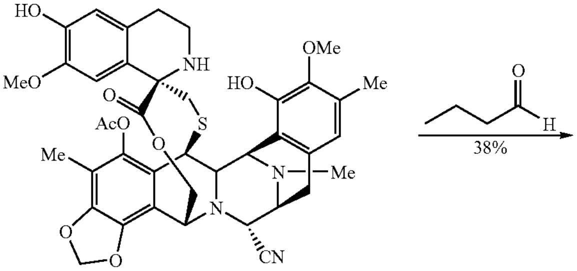

1

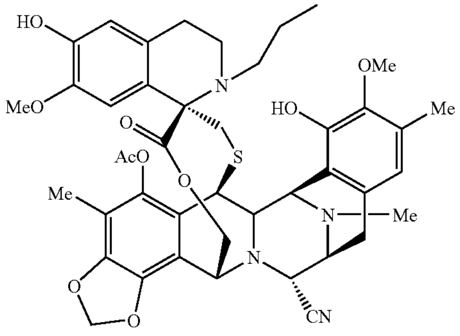

56

56 was obtained following method G. $^1$H-NMR (300 MHz, $CDCl_3$): δ 6.46 (s, 1H), 6.43 (s, 1H), 6.23 (s, 1H), 6.03 (d, 2H), 5.86 (s, 1H), 5.43 (s, 1H), 4.96 (d, 1H), 4.63 (bs, 1H), 4.46 (d, 1H), 4.27 (d, 1H), 4.08 (d 1H), 3.95-3.85 (m, 1H), 3.84 (s, 3H), 3.56 (d, 1H), 3.52 (s, 3H), 3.46-3.41 (m, 1H), 3.00-2.85 (m, 3H), 2.72-2.64 (m, 2H), 2.50-2.42 (m, 1H), 2.36-2.03 (m, 4H), 2.33 (s, 6H), 2.07 (s, 3H), 2.03 (s, 3H), 1.35-1.24 (m, 2H), 0.87 (t, 3H).

ESI-MS m/z: Calcd. for $C_{43}H_{48}N_4O_{10}S$: 812.3. Found (M+H$^+$): 813.3.

Example 45

Method H: To a solution of 1 equiv. of starting material in $CH_3CN/H_2O$ 3:2 (0.009M) were added 30 equiv. of $AgNO_3$. After 24 h the reaction was quenched with a mixture 1:1 of saturated solutions of brine and $NaHCO_3$, stirred for 10 min and diluted and extracted with $CH_2Cl_2$. The organic layer was dried over $Na_2SO_4$. Chromatography gives pure compounds.

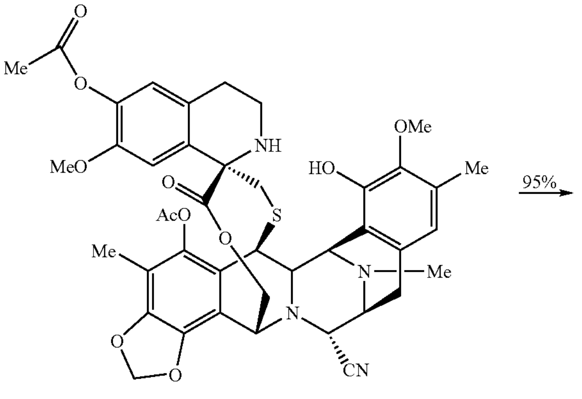

2

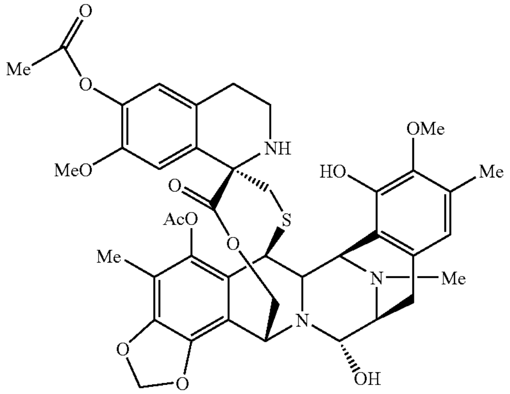

57

57 was obtained using Method H. $^1$H-NMR (300 MHz, $CDCl_3$): δ 6.60 (s, 2H); 6.57 (s, 1H); 5.97 (dd, 2H); 5.70 (s, 1H); 5.12 (d, 1H); 4.82 (s, 1H); 4.48 (d, 1H); 4.47 (s, 1H); 4.16 (d, 1H); 4.04 (dd, 1H); 3.79 (s, 3H); 3.58 (d, 1H); 3.54 (s, 3H); 3.23-3.20 (m, 1H); 3.18-3.09 (m, 1H); 2.88-2.86 (m, 2H); 2.86-2.78 (m, 1H); 2.66-2.58 (m, 1H); 2.52-2.44 (m, 1H); 2.35-2.12 (m, 2H); 2.32 (s, 3H); 2.27 (s, 3H); 2.23 (s, 3H); 2.17 (s, 3H); 2.01 (s, 3H).

$^{13}$C-NMR (75 MHz, $CDCl_3$): δ 172.0, 168.9, 148.3, 147.6, 145.1, 141.2, 140.4, 139.1, 138.4, 131.4, 130.8, 128.7, 128.6, 122.9, 122.3, 121.6, 120.9, 120.6, 115.8, 111.7, 101.6, 82.0, 64.9, 61.4, 60.3, 57.8, 57.6, 55.9, 55.0, 54.9, 42.1, 41.3, 39.5, 29.6, 24.0, 20.5, 15.7, 9.6.

ESI-MS m/z: Calcd. for $C_{41}H_{43}N_3O_{12}S$: 803.2 Found ($M-H_2O+H^+$): 786.2.

Example 46

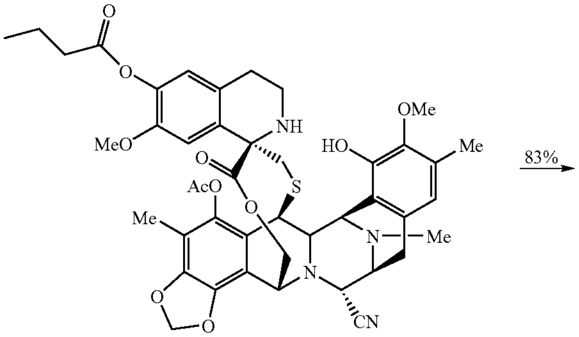

7

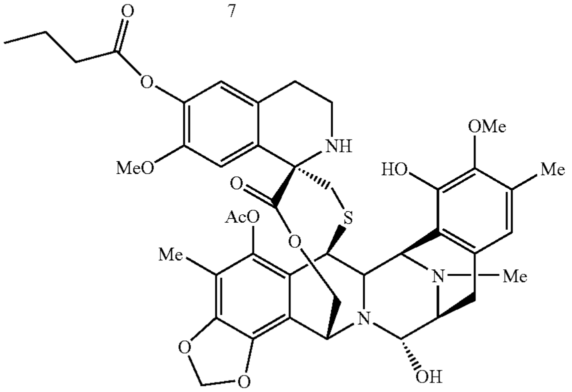

58

58 was obtained using Method H$^1$H-NMR (300 MHz, $CDCl_3$): δ 6.60 (s, 1H); 6.59 (s, 1H); 6.57 (s, 1H); 5.97 (dd, 2H); 5.72 (s, 1H); 5.12 (d, 1H); 4.81 (s, 1H); 4.47 (d, 1H); 4.47-4.45 (m, 1H); 4.16 (d, 1H); 4.03 (dd, 1H); 3.79 (s, 3H); 3.58 (d, 1H); 3.53 (s, 3H); 3.26-3.20 (m, 1H); 3.18-3.09 (m, 1H); 2.88-2.86 (m, 2H); 2.86-2.78 (m, 1H); 2.69-2.58 (m, 1H); 2.52-2.44 (m, 1H); 2.48 (t, 2H); 2.35-2.12 (m, 2H); 2.32 (s, 3H); 2.27 (s, 3H); 2.17 (s, 3H); 2.01 (s, 3H); 1.78-1.67 (m, 2H); 1.00 (t, 3H).

$^{13}$C-NMR (75 MHz, $CDCl_3$): δ 171.8, 167.2, 148.6, 147.9, 145.4, 141.5, 141.5, 140.7, 138.7, 132.9, 132.4, 131.7, 131.0, 130.5, 128.8, 127.8, 122.6, 121.1, 120.8, 116.2, 112.0, 101.9, 82.3, 65.1, 61.6, 60.5, 58.0, 56.1, 55.3, 55.1, 42.5, 41.6, 39.8, 29.9, 28.9, 24.3, 22.8, 20.6, 18.7, 16.0, 14.3, 13.7, 9.8.

ESI-MS m/z: Calcd. for $C_{43}H_{49}N_3O_{12}S$: 814.3 Found ($M+-H_2O$): 796.3.

Example 47

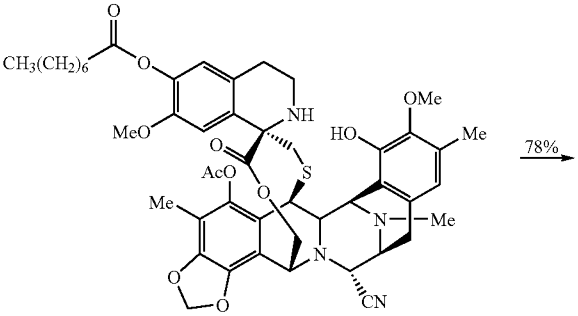

14

-continued

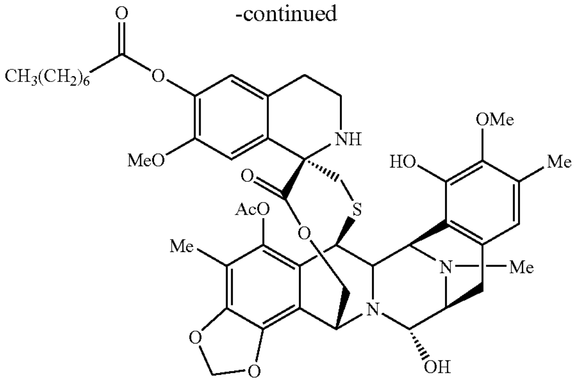

59

59 was obtained using Method H$^1$H-NMR (300 MHz, $CDCl_3$): δ 6.59 (s, 1H); 6.58 (s, 1H); 6.55 (s, 1H); 5.96 (dd, 2H); 5.69 (s, 1H); 5.11 (d, 1H); 4.80 (s, 1H); 4.47-4.45 (m, 2H); 4.14 (d, 1H); 4.02 (dd, 1H); 3.78 (s, 3H); 3.56 (d, 1H); 3.53 (s, 3H); 3.24-3.18 (m, 1H); 3.14-3.04 (m, 1H); 2.86-2.84 (m, 2H); 2.86-2.78 (m, 1H); 2.69-2.58 (m, 1H); 2.52-2.44 (m, 1H); 2.48 (t, 2H); 2.35-2.12 (m, 2H); 2.31 (s, 3H); 2.26 (s, 3H); 2.16 (s, 3H); 2.01 (s, 3H); 1.73-1.61 (m, 2H); 1.40-1.14 (m, 11H).

$^{13}$C-NMR (75 MHz, $CDCl_3$): δ 172.0, 171.8, 148.4, 147.7, 145.1, 142.9, 141.3, 140.5, 138.5, 132.7, 131.5, 129.9, 128.6, 122.4, 121.7, 120.9, 115.8, 111.7, 101.6, 82.1, 64.9, 61.4, 60.3, 57.8, 57.7, 55.9, 55.1, 54.9, 42.2, 41.4, 39.6, 33.9, 31.6, 29.6, 28.9, 28.6, 21.0, 24.0, 22.5, 20.4, 15.7, 14.0, 9.6.

ESI-MS m/z: Calcd. for $C_{47}H_{57}N_3O_{12}S$: 888.0 Found ($M^+-H_2O$): 870.3.

Example 48

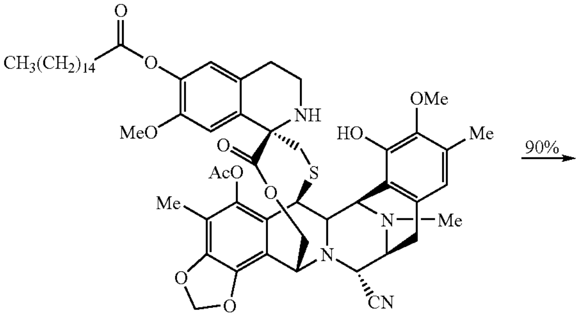

16

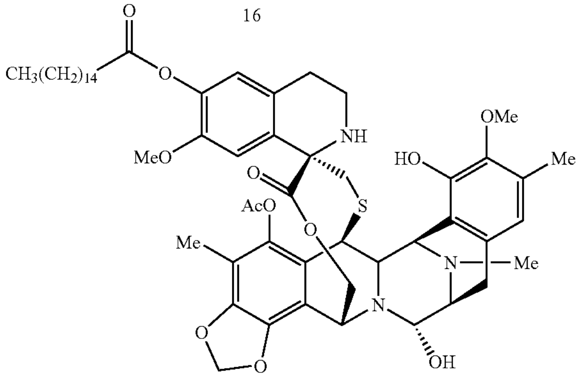

60

60 was obtained using Method H$^1$H-NMR (300 MHz, $CDCl_3$): δ 6.60 (s, 1H); 6.58 (s, 1H); 6.56 (s, 1H); 5.96 (dd, 2H); 5.72 (s, 1H); 5.12 (d, 1H); 4.81 (s, 1H); 4.48 (d, 1H); 4.47-4.45 (m, 1H); 4.16 (d, 1H); 4.03 (dd, 1H); 3.79 (s, 3H); 3.58 (d, 1H); 3.53 (s, 3H); 3.24-3.19 (m, 1H); 3.14-3.09 (m, 1H); 2.87-2.84 (m, 2H); 2.86-2.78 (m, 1H); 2.69-2.58 (m, 1H); 2.52-2.44 (m, 1H); 2.49 (t, 2H); 2.37-2.12 (m, 2H); 2.31 (s, 3H); 2.27 (s, 3H); 2.17 (s, 3H); 2.01 (s, 3H); 1.73-1.62 (m, 2H); 1.40-1.20 (m, 27H).

$^{13}$C-NMR (75 MHz, $CDCl_3$): δ 172.2, 172.0, 168.5, 148.6, 147.9, 145.4, 143.2, 141.5, 140.7, 138.8, 132.8, 131.7, 129.4, 128.8, 125.3, 122.6, 121.9, 121.1, 116.0, 111.9, 101.9, 82.3, 65.1, 61.6, 60.5, 58.0, 57.8, 56.1, 55.3, 55.1, 53.6, 42.4, 41.5, 39.8, 34.2, 32.1, 31.7, 29.89, 29.85, 29.82, 29.7, 29.5, 29.4, 29.3, 29.2, 28.8, 25.3, 22.9, 22.8, 20.6, 16.0, 14.3, 9.8.

ESI-MS m/z: Calcd. for $C_{55}H_{73}N_3O_{12}S$: 1000.2 Found ($M^+-H_2O$): 982.4.

Example 49

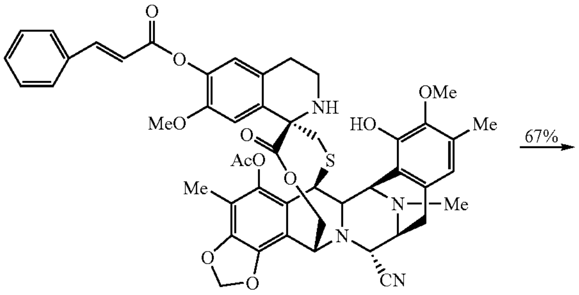

8

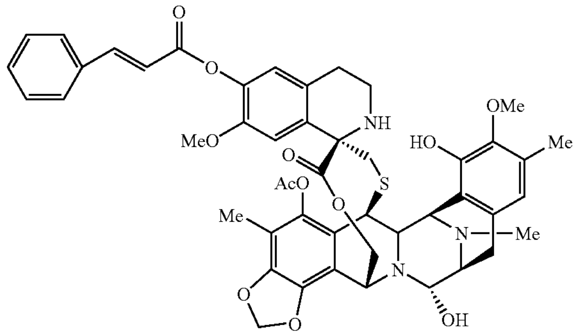

61

61 was obtained using Method H. $^1$H-NMR (300 MHz, $CDCl_3$): δ 7.80 (d, 1H); 7.57-7.54 (m, 2H); 7.40-7.38 (m, 3H); 6.68 (s, 1H); 6.60 (s, 2H); 6.59 (d, 1H); 5.96 (dd, 2H); 5.70 (s, 1H); 5.13 (d, 1H); 4.82 (s, 1H); 4.48 (d, 1H); 4.48-4.46 (m, 1H); 4.16 (d, 1H); 4.05 (dd, 1H); 3.79 (s, 3H); 3.59 (d, 1H); 3.55 (s, 3H); 3.25-3.20 (m, 1H); 3.18-3.09 (m, 1H); 2.88-2.85 (m, 2H); 2.86-2.78 (m, 1H); 2.70-2.60 (m, 1H); 2.56-2.44 (m, 1H); 2.35-2.08 (m, 2H); 2.32 (s, 3H); 2.28 (s, 3H); 2.17 (s, 3H); 2.01 (s, 3H).

ESI-MS m/z: Calcd. for $C_{48}H_{49}N_3O_{12}S$: 892.3 Found ($M^+-H_2O$): 874.3.

Example 50
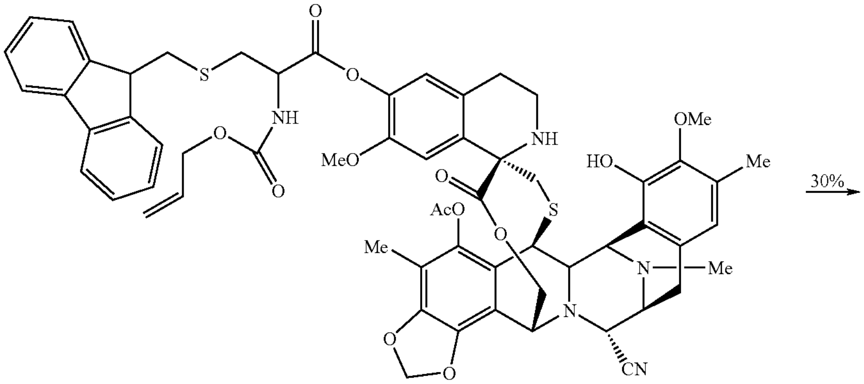
18
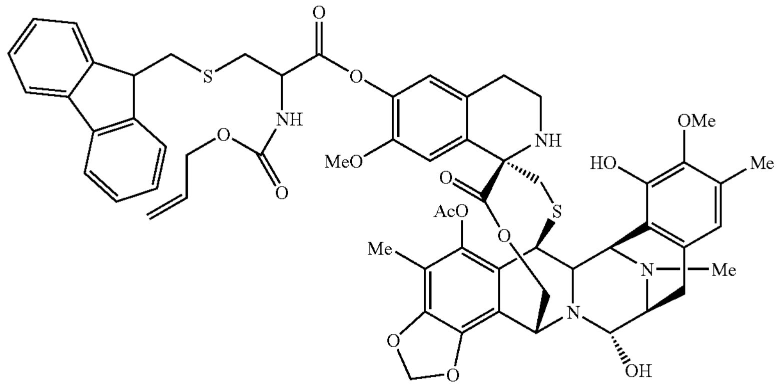
62
62 was obtained using Method H $^1$H-NMR (300 MHz, $CDCl_3$): δ 7.75-7.73 (d, 2H), 7.66-7.61 (m, 2H), 7.40-7.33 (t, 2H), 7.30-7.27 (m, 2H), 6.63 (s, 1H), 6.57 (s, 1H), 6.54 (s, 1H), 5.96 (d, 2H), 5.98-5.85 (m, 1H), 5.58 (d, 1H), 5.30-5.18 (m, 2H), 5.10 (d, 1H), 4.87-4.02 (m, 9H), 3.80 (s, 3H), 3.64-3.57 (m, 1H), 3.44 (s, 3H), 3.16-2.42 (m, 11H), 2.34-2.17 (m, 2H), 2.34 (s, 3H), 2.27 (s, 3H), 2.17 (s, 3H), 2.04 (s, 3H).
ESI-MS m/z: Calcd. for $C_{60}H_{62}N_4O_{14}S_2$: 1126.4 Found ($M-H_2O+H^+$): 1109.3.
Example 51
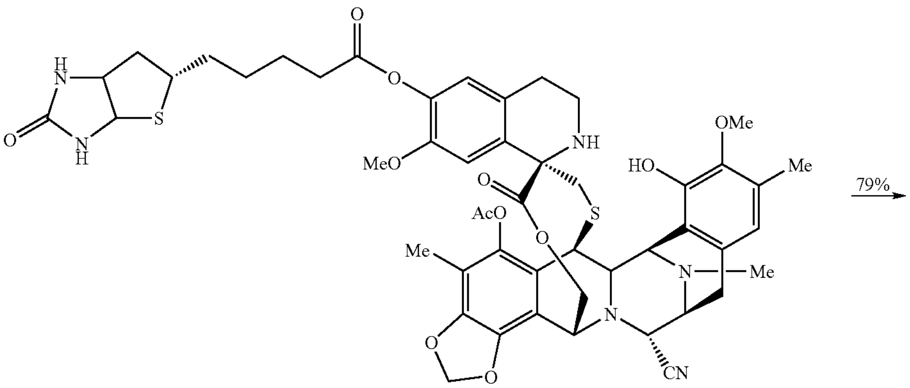
19

-continued

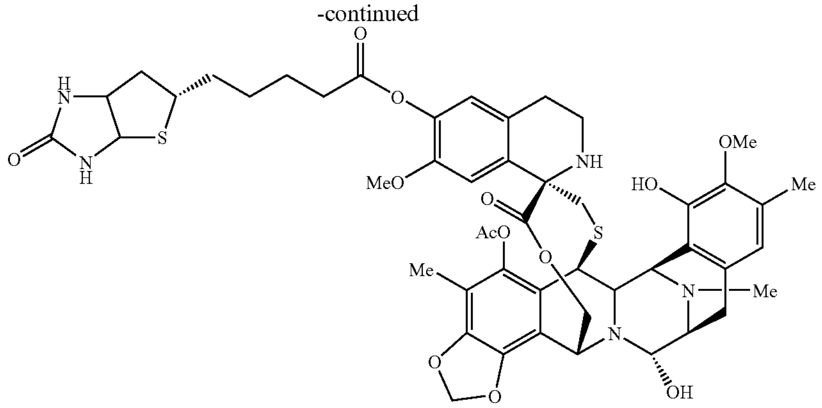

63

63 was obtained using Method H$^1$H-NMR (300 MHz, $CDCl_3$): δ 6.59 (s, 2H), 6.56 (s, 1H), 5.96 (d, 2H), 5.96 (bs, 1H), 5.77 (s, 1H), 5.13 (s, 1H), 5.11 (d, 1H), 4.80 (bs, 1H), 4.47-4.43 (m, 3H), 4.28 (dd, 1H), 4.16 (d, 1H), 4.03 (dd, 1H), 3.78 (s, 3H), 3.57 (d, 1H), 3.53 (s, 3H), 3.22-3.10 (m, 3H), 2.92-2.46 (m, 9H), 2.36-2.17 (m, 2H), 2.31 (s, 3H), 2.26 (s, 3H), 2.17 (s, 3H), 2.01 (s, 3H), 1.76-1.65 (m, 3H), 1.50-148 (m, 3H).

$^{13}$C-NMR (75 MHz, $CDCl_3$): δ 172.0, 171.7, 168.5, 163.3, 148.2, 147.7, 145.1, 142.9, 141.2, 140.4, 138.3, 132.8, 131.5, 129.2, 128.6, 122.4, 121.6, 120.8, 118.0, 115.8, 111.6, 101.7, 82.0, 64.9, 61.9, 61.4, 60.3, 60.0, 57.7, 57.6, 55.9, 55.4, 55.1, 54.8, 42.2, 41.4, 40.5, 39.5, 33.5, 28.6, 28.1, 24.7, 24.0, 20.4, 15.8, 9.6.

ESI-MS m/z: Calcd. for $C_{49}H_{57}O_{13}S_2$: 987.3 Found ($M-H_2O+H^+$): 970.2.

64 was obtained using Method H $^1$H-NMR (300 MHz, $CDCl_3$): δ 6.70 (s, 1H), 6.60 (s, 1H), 6.59 (s, 1H), 6.04-5.89 (m, 1H), 5.97 (dd, 2H), 5.69 (s, 1H), 5.42-5.27 (m, 2H), 5.12 (d, 1H), 4.81 (s, 1H), 4.68 (d, 2H), 4.48-4.45 (m, 2H), 4.16 (d, 1H), 4.03 (dd, 1H), 3.79 (s, 3H), 3.57 (s, 3H), 3.59-3.57 (m, 1H), 3.21-3.10 (m, 2H), 2.93-2.79 (m, 3H), 2.68-2.60 (m, 1H), 2.52-2.47 (m, 1H), 2.32 (s, 3H), 2.38-2.17 (m, 2H), 2.27 (s, 3H), 2.17 (s, 3H), 2.02 (s, 3H).

$^{13}$C-NMR (75 MHz, $CDCl_3$): δ 172.0, 168.4, 153.1, 148.3, 147.7, 145.1, 142.9, 141.3, 140.5, 138.7, 133.2, 131.5, 131.2, 129.1, 128.6, 122.0, 121.7, 120.9, 119.1, 117.9, 115.8, 111.9, 101.7, 82.1, 69.1, 64.9, 61.5, 60.3, 57.7, 57.7, 55.9, 55.2, 54.9, 42.2, 41.4, 39.5, 28.7, 24.0, 20.4, 15.8, 9.6.

ESI-MS m/z: Calcd. for $C_{43}H_{47}N_3O_{13}S$: 845.3 Found ($M-H_2O+H^+$): 828.3.

Example 52

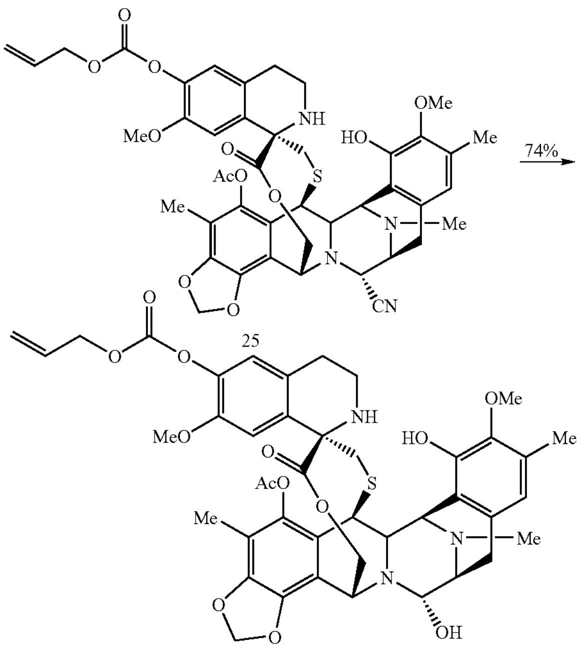

25

64

Example 53

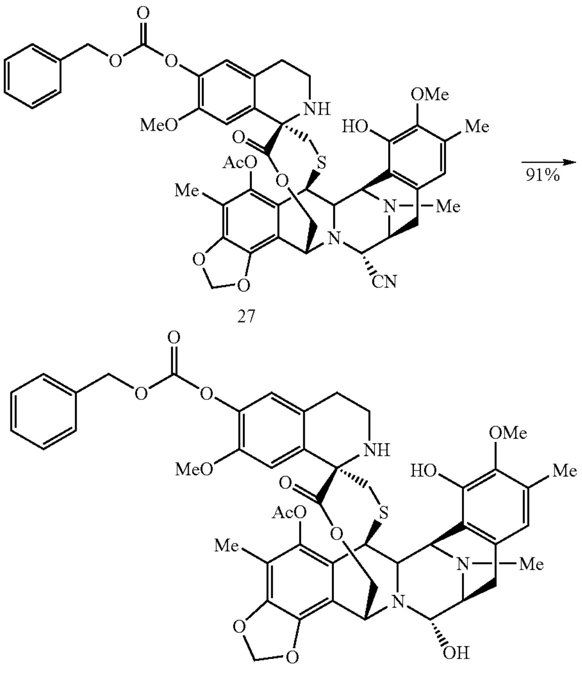

27

65

65 was obtained using Method H $^1$H-NMR (300 MHz, $CDCl_3$): δ 7.40-7.33 (m, 5H); 6.69 (s, 1H); 6.60 (s, 1H); 6.57 (s, 1H); 5.96 (dd, 2H); 5.70 (s, 1H); 5.21 (s, 2H); 5.11 (d, 1H); 4.81 (s, 1H); 4.47 (d, 1H); 4.47-4.45 (m, 1H); 4.15 (d, 1H); 4.03 (dd, 1H); 3.79 (s, 3H); 3.58 (d, 1H); 3.54 (s, 3H); 3.23-3.20 (m, 1H); 3.18-3.09 (m, 1H); 2.87-2.85 (m, 2H); 2.86-2.78 (m, 1H); 2.69.2.58 (m, 1H); 2.52-2.44 (m, 1H); 2.36-2.12 (m, 2H); 2.31 (s, 3H); 2.27 (s, 3H); 2.17 (s, 3H); 2.01 (s, 3H).

$^{13}$C-NMR (75 MHz, $CDCl_3$): δ 172.0, 168.9, 148.3, 147.6, 145.1, 141.2, 140.4, 139.1, 138.7, 131.4, 130.8, 128.7, 128.5, 122.1, 121.9, 121.1, 120.9, 120.6, 116.0, 112.1, 101.9, 82.3, 70.5, 65.1, 61.7, 60.5, 58.0, 57.9, 56.1, 55.3, 55.1, 42.4, 41.6, 39.7, 29.9, 29.5, 24.2, 22.9, 20.6, 16.0, 9.8.

ESI-MS m/z: Calcd. for $C_{47}H_{49}N_3O_{13}S$: 895.9 Found ($M-H_2O+H^+$): 878.6.

Example 54

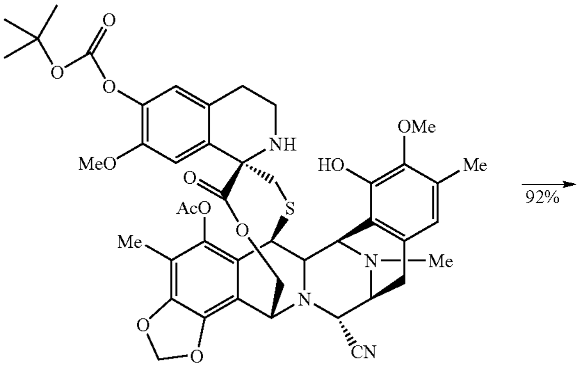

4

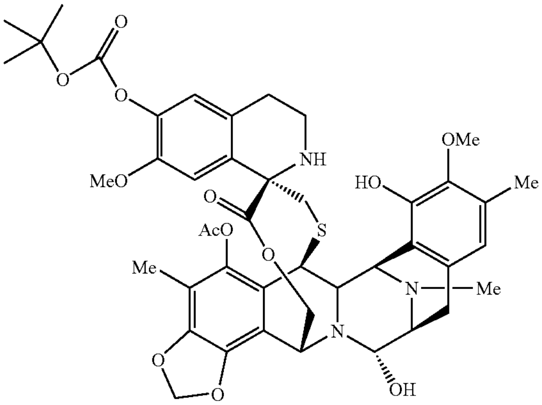

66

66 was obtained using Method H $^1$H-NMR (300 MHz, $CDCl_3$): δ 6.68 (s, 1H); 6.60 (s, 1H); 6.57 (s, 1H); 5.97 (dd, 2H); 5.70 (s, 1H); 5.11 (d, 1H); 4.81 (s, 1H); 4.47 (d, 1H); 4.46 (s, 1H); 4.16 (d, 1H); 4.02 (dd, 1H); 3.79 (s, 3H); 3.58-3.56 (m, 1H); 3.57 (s, 3H); 3.23-3.20 (m, 1H); 3.18-3.09 (m, 1H); 2.87-2.84 (m, 2H); 2.86-2.78 (m, 1H); 2.66-2.58 (m, 1H); 2.52-2.44 (m, 1H); 2.36-2.12 (m, 2H); 2.32 (s, 3H); 2.27 (s, 3H); 2.17 (s, 3H); 2.02 (s, 3H); 1.50 (s, 9H).

$^{13}$C-NMR (75 MHz, $CDCl_3$): δ 172.2, 168.6, 151.8, 148.7, 147.9, 145.4, 143.1, 141.5, 140.7, 139.0, 133.0, 131.7, 129.4, 128.8, 122.3, 121.8, 121.1, 116.0, 112.1, 101.9, 83.6, 82.3, 65.1, 61.6, 60.5, 58.0, 57.8, 56.1, 55.4, 55.1, 42.4, 41.2, 39.8, 29.9, 28.9, 27.8, 24.2, 20.6, 16.0, 9.8.

ESI-MS m/z: Calcd. for $C_{44}H_{51}N_3O_{13}S$: 861.9 Found ($M-H_2O+H^+$): 844.2.

Example 55

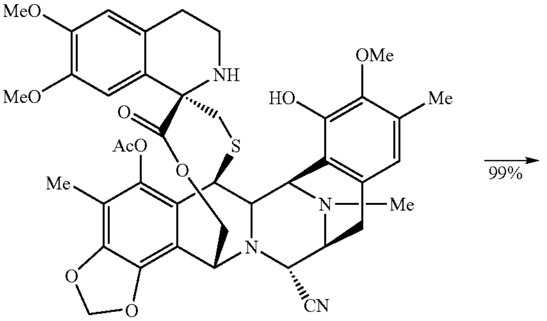

34

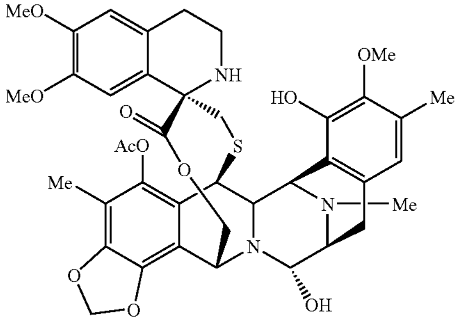

67

67 was obtained using Method H$^1$H-NMR (300 MHz, $CDCl_3$): δ 6.61 (s, 1H), 6.47 (s, 1H), 6.40 (s, 1H), 5.98 (dd, 2H), 5.70 (s, 1H), 5.13 (d, 1H), 4.82 (s, 1H), 4.49-4.46 (m, 2H), 4.17 (bd, 1H), 4.05 (dd, 1H), 3.80 (s, 3H), 3.76 (s, 3H), 3.60 (s, 3H), 3.60-3.51 (m, 1H), 3.22-3.13 (m, 2H), 2.94-2.82 (m, 3H), 2.70-2.62 (m, 1H), 2.53-2.47 (m, 1H), 2.39-2.07 (m, 2H), 2.32 (s, 3H), 2.26 (s, 3H), 2.18 (s, 3H), 2.02 (s, 3H).

$^{13}$C-NMR (75 MHz, $CDCl_3$): δ 172.7, 148.0, 147.9, 146.7, 145.3, 143.1, 141.4, 140.7, 131.7, 129.3, 128.5, 126.6, 121.9, 121.1, 118.2, 116.0, 111.2, 110.6, 101.9, 82.3, 64.8, 61.5, 60.5, 58.0, 57.9, 56.1, 55.9, 55.1, 42.3, 41.6, 39.9, 29.2, 24.2, 20.6, 16.0, 9.8.

ESI-MS m/z: Calcd. for $C_{40}H_{45}N_3O_{11}S$: 775.8 Found ($M-H_2O+H^+$): 758.2.

Example 56

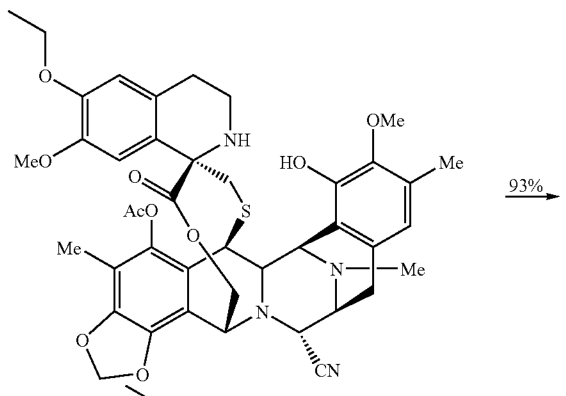

37

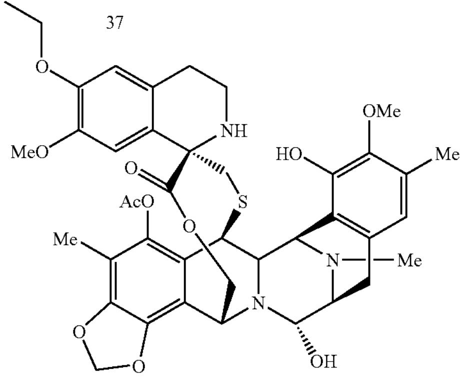

68

68 was obtained using Method H $^1$H-NMR (300 MHz, $CDCl_3$): δ 6.61 (s, 1H); 6.47 (s, 1H); 6.40 (s, 1H); 5.97 (dd, 2H); 5.69 (s, 1H); 5.12 (d, 1H); 4.82 (s, 1H); 4.48 (d, 1H); 4.47 (s, 1H); 4.16 (d, 1H); 4.04 (dd, 1H); 3.97 (q, 2H); 3.79 (s, 3H); 3.65 (d, 1H); 3.58 (s, 3H); 3.23-3.20 (m, 1H); 3.18-3.09 (m, 1H); 2.88-2.86 (m, 2H); 2.86-2.78 (m, 1H); 2.66-2.58 (m, 1H); 2.52-2.44 (m, 1H); 2.35-2.12 (m, 2H); 2.32 (s, 3H); 2.26 (s, 3H); 2.17 (s, 3H); 2.02 (s, 3H); 1.37 (t, 3H).

$^{13}$C-NMR (75 MHz, $CDCl_3$): δ 172.2, 168.8, 165.4, 148.1, 145.8, 143.4, 141.2, 141.0, 135.0, 131.4, 130.1, 129.8, 129.0, 127.9, 121.0, 120.9, 120.7, 118.6, 115.4, 112.9, 102.0, 81.7, 61.9, 60.6, 58.0, 57.9, 57.7, 56.2, 55.2, 52.2, 42.4, 41.5, 32.9, 32.8, 23.8, 20.7, 19.4, 18.2, 16.6, 9.7.

ESI-MS m/z: Calcd. for $C_{41}H_{47}N_3O_{11}S$: 789.8 Found ($M-H_2O+H^+$): 772.2.

Example 57

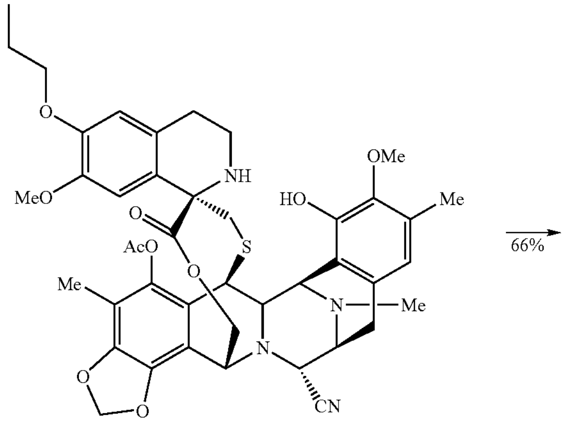

39

-continued

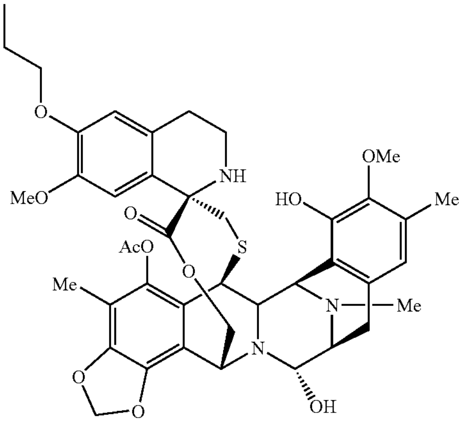

69

69 was obtained using Method H H-NMR (300 MHz, $CDCl_3$): δ 6.60 (s, 1H); 6.48 (s, 1H); 6.40 (s, 1H); 5.97 (dd, 2H); 5.69 (s, 1H); 5.12 (d, 1H); 4.81 (s, 1H); 4.48 (d, 1H); 4.47-4-46 (m, 1H); 4.16 (d, 1H); 4.04 (dd, 1H); 3.84 (q, 2H); 3.79 (s, 3H); 3.61-3.54 (m, 1H); 3.58 (s, 3H); 3.22-3.18 (m, 1H); 3.18-3.09 (m, 1H); 2.88-2.84 (m, 2H); 2.86-2.78 (m, 1H); 2.68-2.58 (m, 1H); 2.52-2.44 (m, 1H); 2.39-2.12 (m, 2H); 2.32 (s, 3H); 2.26 (s, 3H); 2.17 (s, 3H); 2.02 (s, 3H); 1.80-1.73 (m, 2H); 0.96 (t, 3H). $^{13}$C-NMR (75 MHz, $CDCl_3$): δ 172.9, 147.9, 147.6, 147.0, 145.4, 143.1, 141.4, 140.7, 131.7, 128.5, 126.6, 121.9, 121.1, 116.0, 112.7, 111.1, 101.9, 82.3, 70.4, 64.8, 61.5, 60.5, 58.0, 57.8, 56.1, 55.4, 55.1, 42.3, 41.6, 39.9, 32.1, 28.8, 29.2, 24.2, 22.9, 22.5, 20.6, 16.0, 14.3, 10.6, 9.8.

ESI-MS m/z: Calcd. for $C_{42}H_{49}N_3O_{11}S$: 803.9 Found ($M-H_2O+H^+$): 786.2.

Example 58

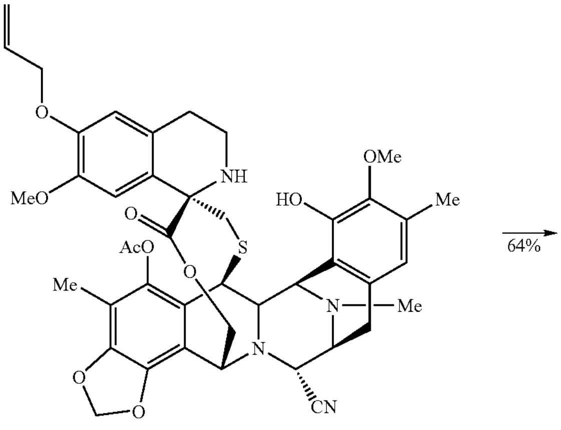

41

-continued

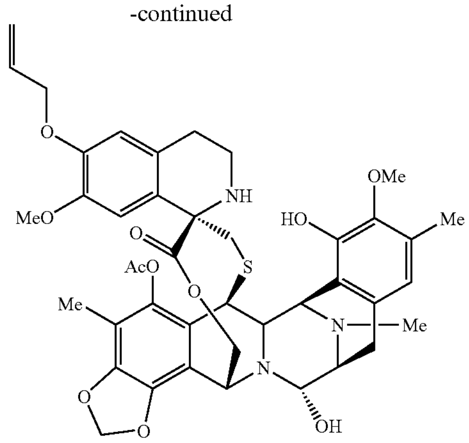

70

70 was obtained using Method H[1]H-NMR (300 MHz, $CDCl_3$): δ 6.60 (s, 1H); 6.48 (s, 1H); 6.40 (s, 1H); 6.03-5.94 (m, 1H); 5.97 (dd, 2H); 5.72 (s, 1H); 5.32 (dd, 1H); 5.21 (dd, 1H); 5.12 (d, 1H); 4.81 (s, 1H); 4.50-4.47 (m, 4H); 4.16 (d 1H); 4.04 (dd, 1H); 3.79 (s, 3H); 3.61 (d, 1H); 3.59 (s, 3H); 3.22-3.18 (m, 1H); 3.18-3.09 (m, 1H); 2.88-2.84 (m, 2H); 2.86-2.78 (m, 1H); 2.68-2.58 (m, 1H); 2.52-2.44 (m, 1H); 2.33-2.12 (m, 2H); 2.32 (s, 3H); 2.26 (s, 3H); 2.17 (s, 3H); 2.02 (s, 3H).

ESI-MS m/z: Calcd. for $C_{42}H_{47}N_3O_{11}S$: 801.2 Found $(M-H_2O+H^+)$: 784.2.

Example 59

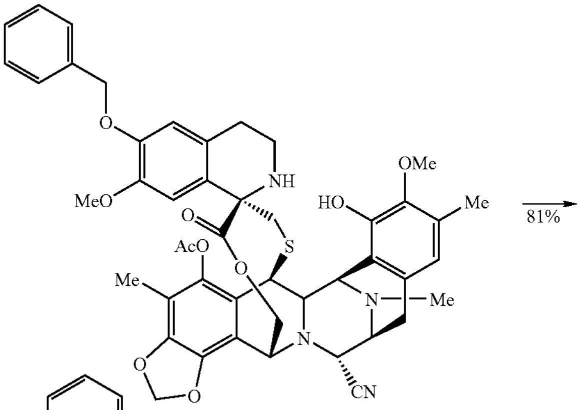

43

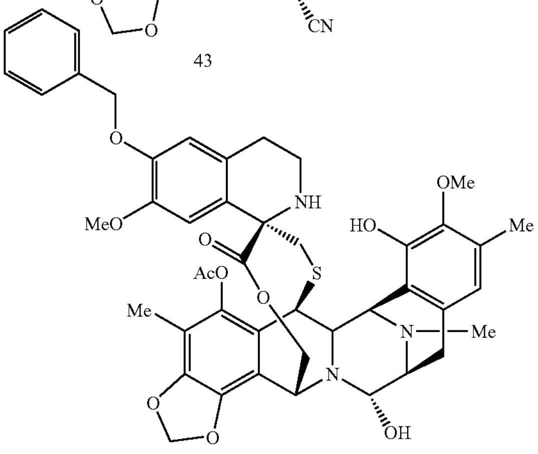

71

71 was obtained using Method H $^1$H-NMR (300 MHz, $CDCl_3$): δ 7.36-7.25 (m, 5H); 6.60 (s, 1H); 6.50 (s, 1H); 6.41 (s, 1H); 5.98 (dd, 2H); 5.69 (s, 1H); 5.12 (d, 1H); 5.02 (s, 2H); 4.81 (s, 1H); 4.48 (d, 1H); 4.48-4.46 (m, 1H); 4.16 (d 1H); 4.04 (dd, 1H); 3.78 (s, 3H); 3.60 (s, 3H); 3.22-3.18 (m, 1H); 3.18-3.09 (m, 1H); 2.88-2.84 (m, 2H); 2.86-2.78 (m, 1H); 2.64-2.58 (m, 1H); 2.46-2.40 (m, 1H); 2.34-2.12 (m, 2H); 2.31 (s, 3H); 2.26 (s, 3H); 2.17 (s, 3H); 2.03 (s, 3H).

ESI-MS m/z: Calcd. for $C_{46}H_{47}N_3O_{11}S$: 851.9 Found $(M-H_2O+H^+)$: 834.3.

Example 60

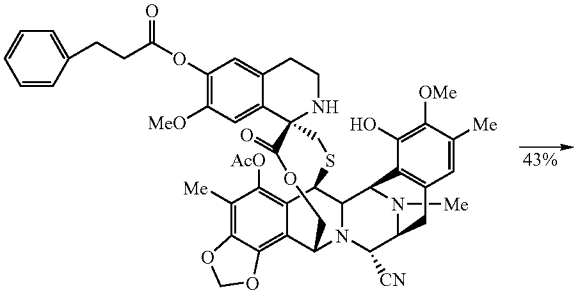

11

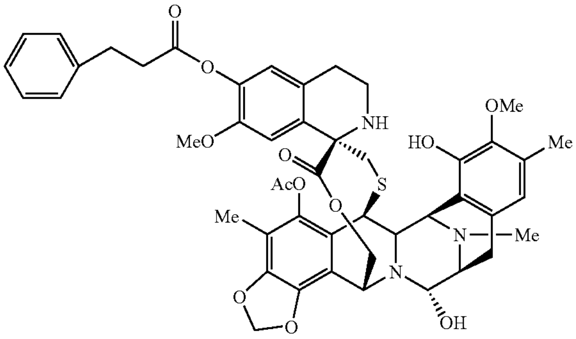

72

Compound 11 (31%) was recovered after chromatographic purification.

72 was obtained using Method H[1]H-NMR (300 MHz, $CDCl_3$): δ 7.31-7.20 (m, 5H); 6.60 (s, 1H); 6.55 (s, 1H); 6.53 (s, 1H); 6.00 (d, 1H); 5.93 (d, 1H); 5.70(s, 1H); 5.11 (d, 1H); 4.81 (s, 1H); 4.47 (d, 1H); 4.16 (d, 1H); 4.02 (dd, 1H); 3.79 (s, 3H); 3.58 (d, 1H); 3.50 (s, 3H); 3.21-3.08 (m, 2H); 3.02 (t, 2H); 2.87-2.80 (m, 5H); 2.66-2.44 (m, 3H); 2.36-2.22 (m, 1H); 2.31 (s, 3H); 2.27 (s, 3H); 2.17 (s, 3H); 2.01 (s, 3H).

ESI-MS m/z: Calcd. for $C_{48}H_{51}N_3O_{12}S$: 893.2 Found $(M-H_2O+H^+)$: 876.5.

Example 61

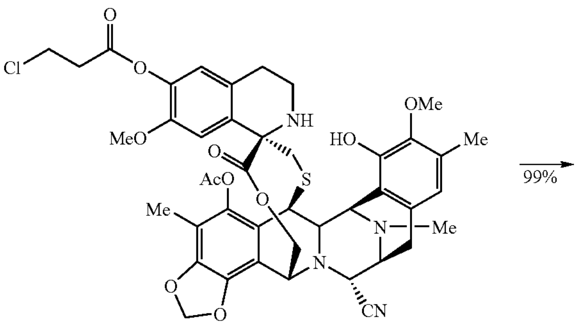

12

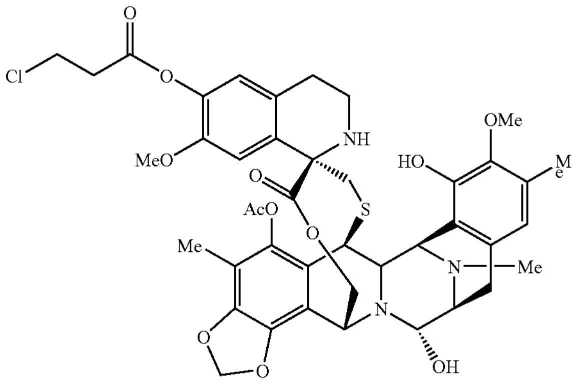
73

73 was obtained using Method H. $^1$H-NMR (300 MHz, $CDCl_3$): δ 6.61 (s, 1H); 6.60 (s, 1H); 6.57 (s, 1H); 6.00 (d, 1H); 5.93 (d, 1H); 5.73 (s, 1H); 5.11 (d, 1H); 4.82 (s, 1H); 4.84 (s, 2H); 4.17-4.15 (m, 1H); 4.03 (dd, 1H); 3.80 (t, 2H); 3.79 (s, 3H); 3.65-3.58 (m, 1H); 3.54 (s, 3H); 3.23-3.10 (m, 2H); 2.99 (t, 2H); 2.88-2.80 (m, 4H); 2.68-2.46 (m, 3H); 2.37-2.17 (m, 1H); 2.31 (s, 3H); 2.26 (s, 3H); 2.18 (s, 3H); 2.01 (s, 3H).

$^{13}$C-NMR (75 MHz, $CDCl_3$): δ 172.2, 168.6, 148.4, 147.9, 145.4, 143.2, 141.5, 140.7, 138.3, 133.3, 131.6, 129.8, 129.7, 129.5, 128.8, 122.5, 121.8, 121.1, 115.9, 112.0, 101.9, 82.3, 65.1, 61.6, 60.5, 58.0, 57.8, 56.1, 55.3, 55.1, 42.4, 41.5, 39.7, 39.0, 37.5, 29.9, 28.8, 27.1, 24.3, 20.6, 16.0, 9.9.

ESI-MS m/z: Calcd. for $C_{42}H_{46}ClN_3O_{12}S$: 851.2 Found $(M-H_2O+H^+)$: 834.2.

Example 62

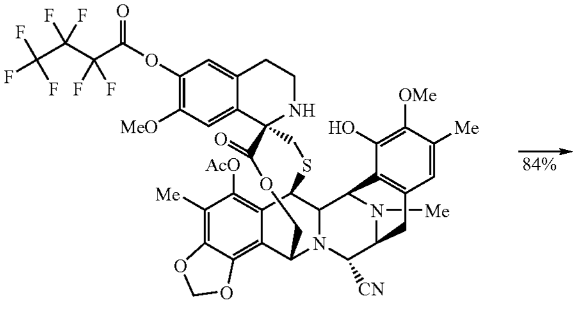

13

-continued

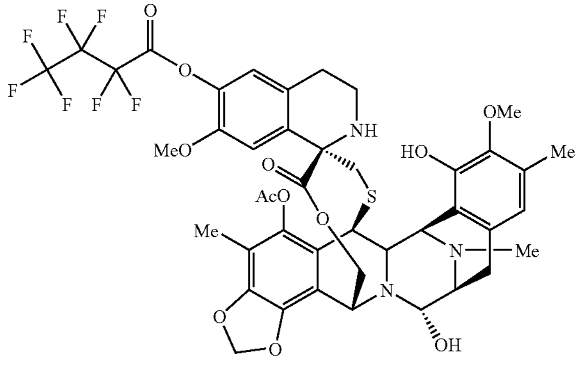
74

74 was obtained using Method H. $^1$H-NMR (300 MHz, $CDCl_3$): δ 6.60 (s, 1H); 6.46 (s, 1H); 6.44 (s, 1H); 6.01 (d, 1H); 5.93 (d, 1H); 5.73 (s, 1H); 5.12 (d, 1H); 4.81 (s, 1H); 4.48 (s, 2H); 4.16 (d, 1H); 4.04 (dd, 1H); 3.78 (s, 3H); 3.60 (s, 3H); 3.58-3.56 (m, 1H); 3.22-3.08 (m, 2H); 2.93-2.75 (m, 3H); 2.65-2.44 (m, 2H); 2.37-2.14 (m, 1H); 2.31 (s, 3H); 2.25 (s, 3H); 2.17 (s, 3H); 2.02 (s, 3H).

$^{13}$C-NMR (75 MHz, $CDCl_3$): δ 172.7, 147.9, 145.3, 144.6, 144.4, 143.1, 141.4, 140.7, 131.7, 131.1, 129.4, 129.2, 129.0, 122.0, 121.1, 116.1, 114.2, 110.0, 101.8, 82.3, 65.7, 64.8, 61.5, 60.5, 58.0, 57.9, 56.1, 55.3, 55.1, 42.3, 41.6, 39.8, 29.9, 29.5, 29.0, 24.2, 22.9, 20.6, 19.4, 16.0, 14.3, 9.8.

ESI-MS m/z: Calcd. for $C_{43}H_{42}F_7N_3O_{12}S$: 957.2 Found $(M-C_4F_7O—H_2O+2H^+)$: 744.2.

Example 63

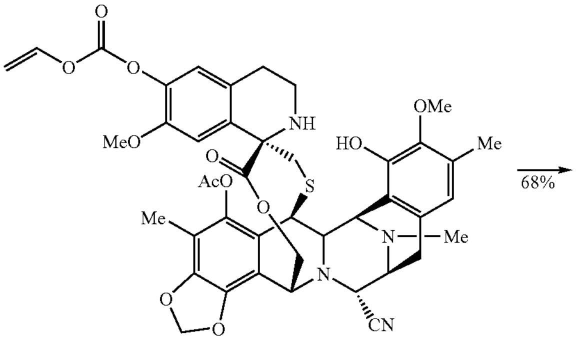

29

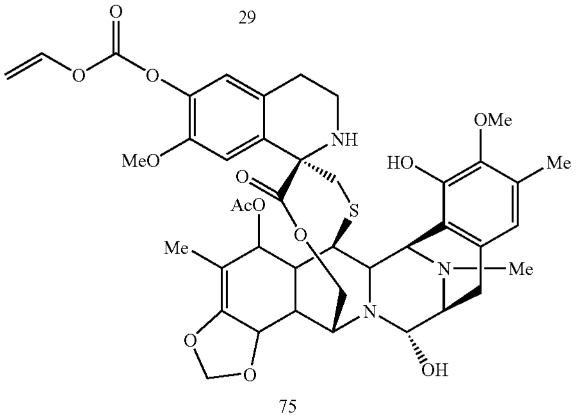
75

75 was obtained using Method H. $^1$H-NMR (300 MHz, $CDCl_3$): δ 7.08 (dd, 1H); 6.71 (s, 1H); 6.60 (s, 2H); 6.00 (d, 1H); 5.92 (d, 1H); 5.74 (s, 1H); 5.12 (d, 1H); 4.99 (dd, 1H); 4.81 (s, 1H); 4.63 (dd, 1H); 4.48 (d, 2H); 4.17 (dd, 1H); 3.79 (s, 3H); 3.60-3.57 (m, 1H); 3.57 (s, 3H); 3.24-3.22 (m, 1H); 3.17-3.09 (m, 1H); 2.93-2.78 (m, 3H); 2.68-2.46 (m, 2H); 3.37-2.22 (m, 1H); 2.31 (s, 3H); 2.26 (s, 3H); 2.17 (s, 3H); 2.01 (s, 3H).

$^{13}$C-NMR (75 MHz, $CDCl_3$): δ 172.1, 151.0, 148.4, 147.9, 145.4, 142.9, 141.5, 140.7, 138.5, 133.7, 131.6, 129.5, 128.9, 122.0, 121.8, 121.1, 118.0, 116.0, 112.2, 101.9, 98.7, 82.3, 65.1, 61.7, 60.5, 58.0, 57.8, 56.1, 55.4, 55.1, 42.2, 41.6, 39.7, 29.9, 28.8, 24.2, 20.6, 16.0, 9.8.

ESI-MS m/z: Calcd. for $C_{42}H_{45}N_3O_{13}S$: 831.2 Found $(M-H_2O+H^+)$: 814.2.

Example 64

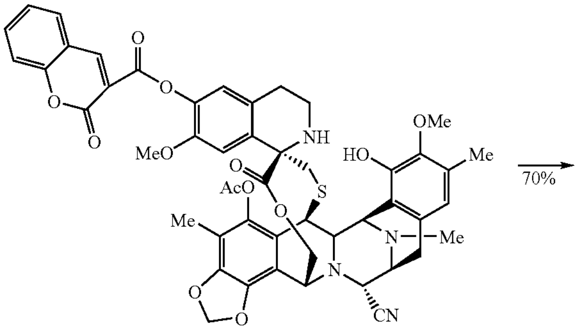

21

-continued

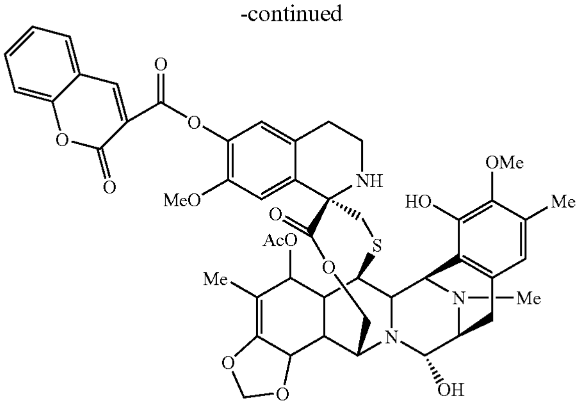

76

Compound 21 (17%) was recovered after chromatographic purification. 76 was obtained using Method H. $^1$H-NMR (300 MHz, $CDCl_3$): δ 8.66 (s, 1H); 7.67-7.70 (m, 2H); 7.36-7.29 (m, 2H); 6.74 (s, 1H); 6.60 (s, 2H); 5.99 (d, 1H); 5.92 (d, 1H); 5.76 (s, 1H); 5.13 (d, 1H); 4.81 (s, 1H); 4.47 (s, 2H); 4.15 (d, 1H); 4.04 (d, 1H); 3.78 (s, 3H); 3.57-3.56 (m, 1H); 3.54 (s, 3H); 3.47-3.44 (m, 1H); 3.21-3.10 (m, 2H); 2.92-2.79 (m, 3H); 2.70-2.48 (m, 2H); 2.38-2.19 (m, 1H); 2.31 (s, 3H); 2.27 (s, 3H); 2.16 (s, 3H); 2.01 (s, 3H).

$^{13}$C-NMR (75 MHz, $CDCl_3$): δ 172.2, 160.9, 156.5, 155.6, 150.0, 148.4, 147.9, 145.3, 143.1, 141.5, 140.7, 138.3, 134.9, 133.5, 131.7, 129.9, 129.4, 128.9, 125.1, 122.6, 121.9, 121.1, 118.2, 118.0, 117.4, 117.0, 116.0, 112.0, 101.9, 82.3, 65.2, 61.7, 60.5, 58.0, 57.9, 56.1, 55.4, 55.1, 42.4, 41.6, 39.7, 29.9, 28.8, 24.2, 20.6, 16.0, 9.8.

ESI-MS m/z: Calcd. for $C_{49}H_{47}N_3O_{14}S$: 933.2 Found $(M-H_2O+H^+)$: 916.3.

Example 65

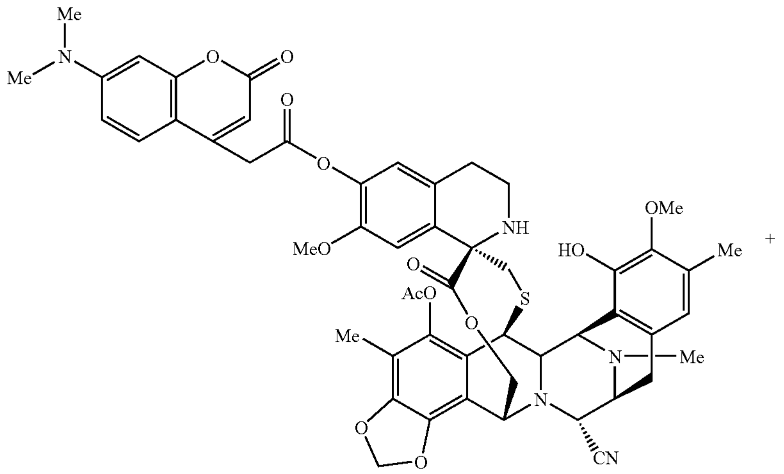

22

-continued
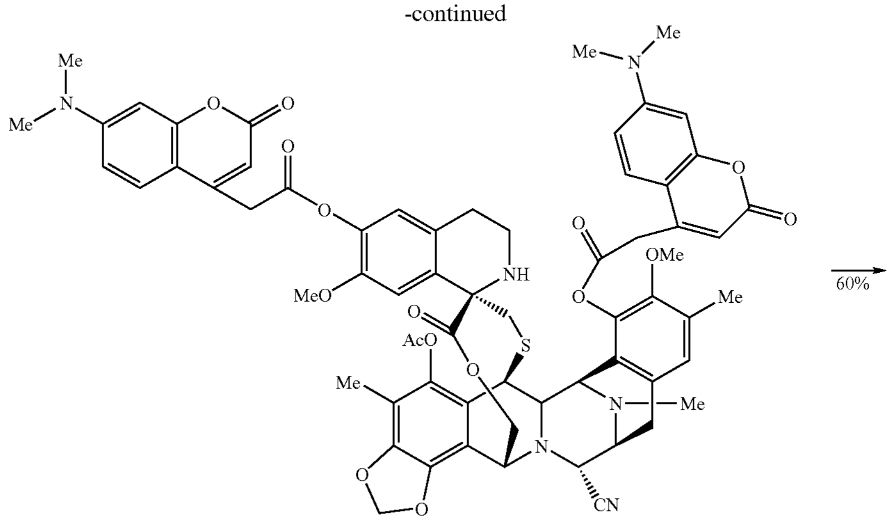
23
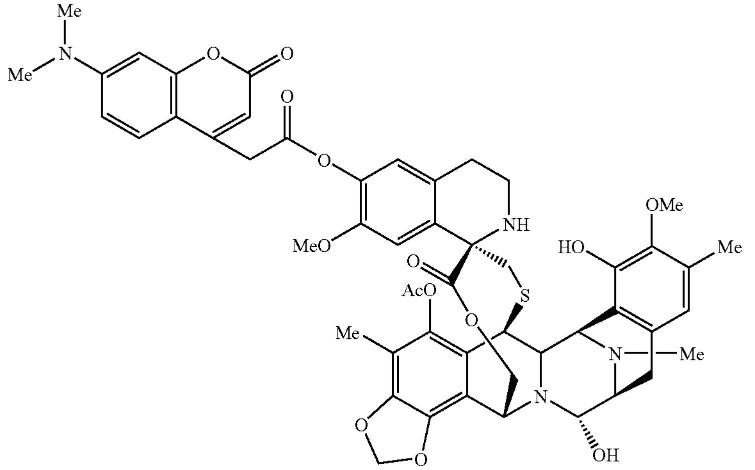
77
+
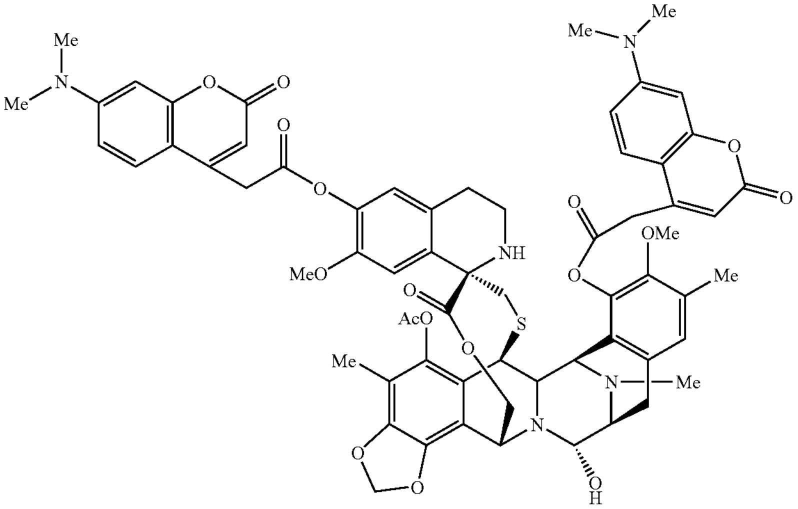
78
The reaction was performed with a mixture of compound 22 and 23 (3:1) using Method H, thus compounds 77 and 78 were isolated after chromatographic as pure compounds.
77: $^{1}$H-NMR (300 MHz, $CDCl_3$): δ 7.44 (d, 1H); 6.61-6.51 (m, 5H); 6.19 (s, 1H); 6.00 (s, 1H); 5.92 (s, 1H); 5.73 (s, 1H); 5.10 (d, 1H); 4.79 (s, 1H); 4.45 (s, 2H); 4.15-4.14 (m, 1H); 4.01 (d, 1H); 3.85 (s, 2H); 3.78 (s, 3H); 3.57-3.56 (m, 1H); 3.49 (s, 3H); 3.21-3.00 (m, 3H); 3.04 (s, 6H); 2.86-2.78 (m, 3H); 2.64-2.43 (m, 2H); 2.30 (s, 3H); 2.25 (s, 3H); 2.16 (s, 3H); 2.00 (s, 3H).

$^{13}C$-NMR (75 MHz, $CDCl_3$): δ 171.9, 167.1, 161.6, 155.8, 152.9, 148.0, 147.9, 147.6, 145.1, 142.9, 141.2, 140.4, 138.1, 133.2, 131.5, 129.1, 128.6, 125.2, 122.0, 121.6, 120.8, 117.8, 115.7, 111.7, 110.7, 108.8, 108.4, 101.6, 98.3, 82.0, 64.9, 61.4, 60.3, 57.7, 55.9, 55.0, 54.8, 42.1, 41.3, 40.1, 39.4, 37.6, 29.6, 28.6, 24.0, 20.4, 15.7, 14.1, 9.6.

ESI-MS m/z: Calcd. for $C_{52}H_{54}N_4O_{14}S$: 990.3 Found ($M-H_2O+H^+$): 973.3.

78: $^1H$-NMR (300 MHz, $CDCl_3$): δ 7.69 (s, 1H); 7.51 (d, 1H); 7.45 (d, 1H); 6.92 (s, 1H); 6.61-6.48 (m, 5H); 6.33 (s, 1H); 6.21 (s, 1H); 6.19 (s, 1H); 6.01 (s, 1H); 5.94 (s, 1H); 5.08 (d, 1H); 4.74 (s, 1H); 4.47 (s, 1H); 4.32-4.28 (m, 2H); 4.04-3.94 (m, 3H); 3.85 (s, 2H); 3.67 (s, 3H); 3.61 (d, 1H); 3.47 (s, 3H); 3.26-2.80 (m, 5H); 3.05 (s, 6H); 2.97 (s, 6H); 2.60-2.42 (m, 2H); 2.29 (s, 6H); 2.19 (s, 3H); 2.06 (s, 3H).

ESI-MS m/z: Calcd. for $C_{65}H_{65}N_3O_{17}S$: 1220.3 Found ($M+H^+$): 1221.3.

Example 66

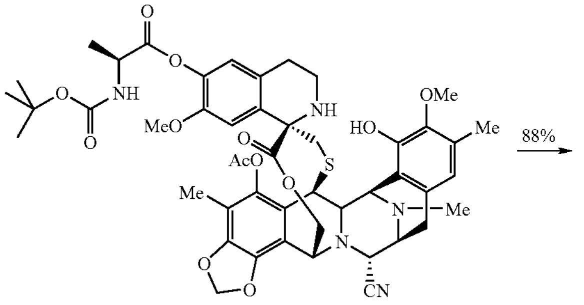

24

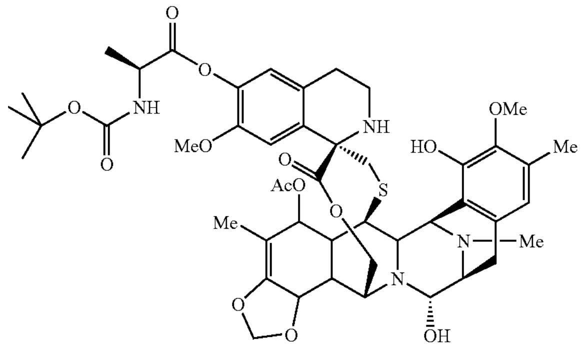

79

79 was obtained using Method H $^1H$-NMR (300 MHz, $CDCl_3$): δ 6.62 (s, 1H), 6.61 (s, 1H), 6.57 (s, 1H), 5.97 (d, 2H), 5.72 (s, 1H), 5.12 (d, 1H), 5.08 (bd, 1H), 4.82 (s, 1H), 4.55-4.44 (m, 3H), 4.17 (d, 1H), 4.03 (dd, 1H), 3.79 (s, 3H), 3.59 (d, 1H), 3.53 (s, 3H), 3.25-3.20 (m, 1H), 3.15-3.09 (m, 1H), 2.92-2.78 (m, 3H), 2.67-2.59 (m, 1H), 2.52-2.47 (m, 1H), 2.37-2.18 (m, 2H), 2.32 (s, 3H), 2.27 (s, 3H), 2.18 (s, 3H), 2.02 (s, 3H), 1.50 (d, 3H), 1.44 (s, 9H).

ESI-MS m/z: Calcd. for $C_{47}H_{56}N_4O_{14}S$: 932.3 Found ($M-H_2O+H^+$): 915.3.

Example 67

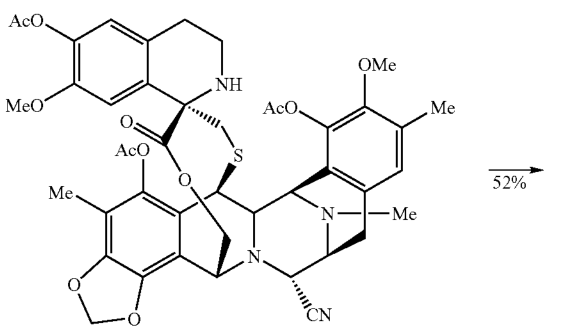

6

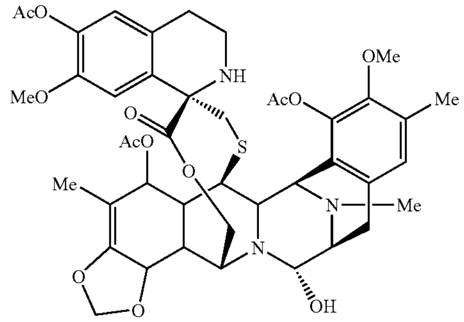

80

Compound 6 (42%) was recuperatd after chromatographic purification.

80 was obtained using Method H $^1H$-NMR (300 MHz, $CDCl_3$): δ 6.96 (s, 1H), 6.61 (s, 1H), 6.54 (s, 1H), 5.98 (dd, 2H), 5.12 (d, 1H), 4.83 (s, 1H), 4.49 (d, 1H), 4.33 (bs, 1H), 4.03 (dd, 1H), 3.78 (s, 3H), 3.70 (d, 1H), 3.60 (d, 1H), 3.55 (s, 3H), 3.29-3.24 (m, 1H), 3.18-3.09 (m, 1H), 3.03-2.80 (m, 3H), 2.69-2.59 (m, 1H), 2.53-2.05 (m, 1H), 2.42-2.13 (m, 2H), 2.37 (s, 3H), 2.33 (s, 3H), 2.31 (s, 3H), 2.24 (s, 3H), 2.13 (s, 3H), 2.03 (s, 3H).

ESI-MS m/z: Calcd. for $C_{43}H_{47}N_3O_{13}S$: 845.3 Found ($M+H^+$): 846.3.

Example 68

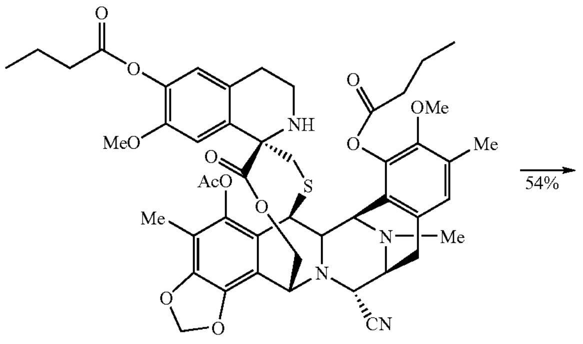

9

-continued

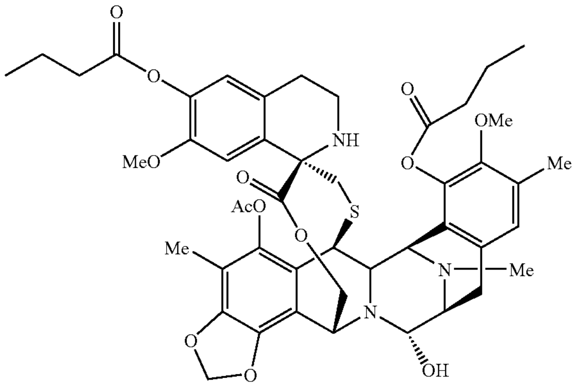

81

Compound 9 was recovered (25%) after chromatographic purification.

81 was obtained using Method H $^{1}$H-NMR (300 MHz, $CDCl_3$): δ 6.95 (s, 1H); 6.59 (s, 2H); 6.54 (d, 1H); 6.01 (dd, 1H); 5.94 (dd, 2H); 5.12 (d, 1H); 4.81 (s, 1H); 4.49 (d, 1H); 4.34 (s, 1H); 4.02 (dd, 1H); 3.75 (s, 3H); 3.67 (d, 1H); 3.58 (d, 1H); 3.53 (s, 3H); 3.25-3.23 (m, 1H); 3.17-3.12 (m, 1H); 2.92-2.80 (m, 3H); 2.69-2.63 (m, 1H); 2.60 (t, 2H); 2.54-2.50 (m, 1H); 2.48 (t, 2H); 2.32 (s, 3H); 2.29 (s, 3H); 2.13 (s, 3H); 2.03 (s, 3H); 1.91-1.80 (m, 2H); 1.79-1.68 (m, 2H); 1.09 (t, 3H); 1.00 (t, 3H).

$^{13}$C-NMR (75 MHz, $CDCl_3$): δ 172.1, 171.9, 171.4, 148.6, 148.0, 145.5, 143.7, 141.4, 140.8, 138.8, 132.7, 131.6, 131.5, 128.8, 127.6, 124.5, 122.6, 121.7, 116.0, 111.9, 102.0, 82.0, 65.2, 61.5, 60.3, 57.9, 57.8, 56.4, 56.2, 55.2, 42.6, 41.6, 39.8, 36.3, 36.0, 29.9, 29.5, 28.8, 24.2, 20.5, 18.9, 18.7, 16.0, 14.0, 13.7, 9.8.

ESI-MS m/z: Calcd. for $C_{47}H_{55}N_3O_{13}S$: 901.3 Found ($M-H_2O+H^+$): 884.5.

Example 69

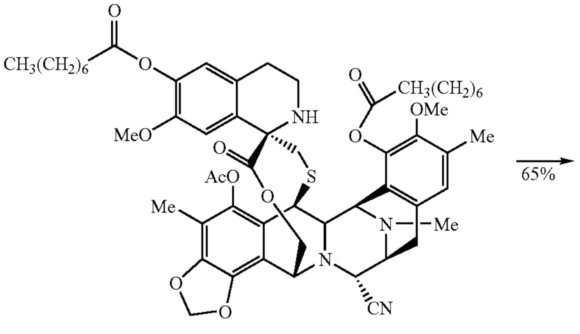

15

-continued

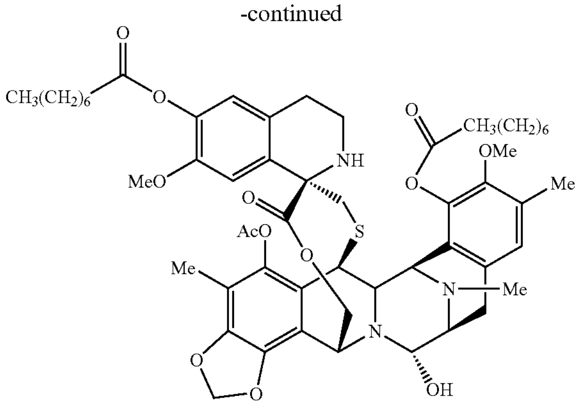

82

82 was obtained using Method H $^{1}$H-NMR (300 MHz, $CDCl_3$): δ 6.95 (s, 1H); 6.59 (s, 1H); 6.54 (s, 1H); 6.02 (d, 1H); 5.94 (s, 1H); 5.12 (d, 1H); 4.81 (s, 1H); 4.49 (s, 1H); 4.35 (s, 1H); 4.02 (d, 1H); 3.75 (s, 3H); 3.68-3.67 (m, 1H); 3.58-3.56(m, 1H); 3.53 (s, 3H); 3.26-3.24 (m, 1H); 3.14-3.08 (m, 1H); 2.92-2.80 (m, 3H); 2.61 (t, 2H); 2.49 (t, 2H); 2.32 (s, 3H); 2.29 (s, 3H); 2.13 (s, 3H); 2.03 (s, 3H); 1.83-1.59 (m, 4H); 1.42-1.14 (m, 20H).

ESI-MS m/z: Calcd. for $C_{55}H_{71}N_3O_{13}S$: 1013.4 Found ($M-H_2O+H^+$): 996.5.

Example 70

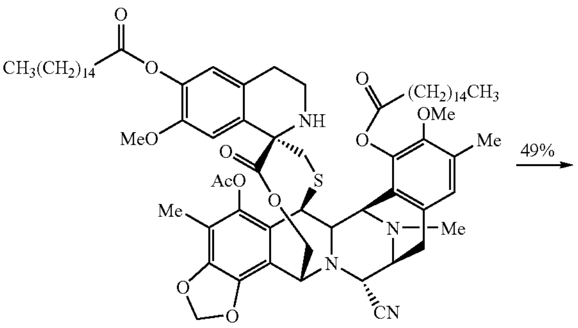

17

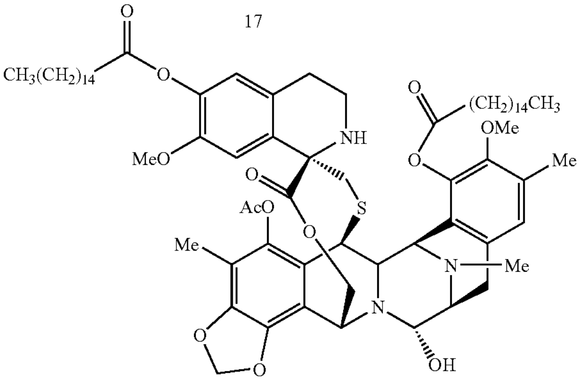

83

83 was obtained using Method H $^{1}$H-NMR (300 MHz, $CDCl_3$): δ 6.95 (s, 1H); 6.59 (s, 1H); 6.54 (s, 1H); 5.98 (dd, 2H); 5.12 (d, 1H); 4.81 (s, 1H); 4.48 (d, 1H); 4.47-4.45 (m, 1H); 4.17 (d, 1H); 4.01 (dd, 1H); 3.75 (s, 3H); 3.66 (d, 1H); 3.59-3.56(m, 1H); 3.53 (s, 3H); 3.26-3.21 (m, 1H); 3.18-3.09 (m, 1H); 2.93-2.90 (m, 2H); 2.86-2.78 (m, 1H); 2.69-2.58 (m, 1H); 2.61(t, 2H); 2.52-2.44 (m, 1H); 2.49 (t, 2H); 2.37-2.12 (m, 2H); 2.31 (s, 3H); 2.29 (s, 3H); 2.12 (s, 3H); 2.03 (s, 3H); 1.84-1.80 (m, 2H); 1.71-1.64(m, 2H); 1.40-1.17 (m, 54H).

Example 71
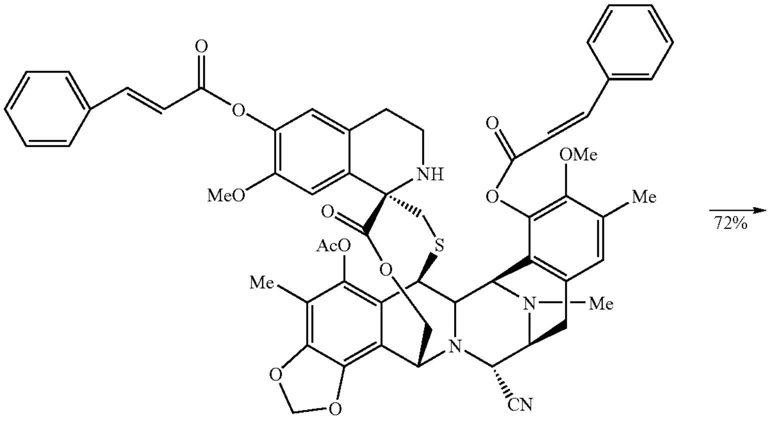
10
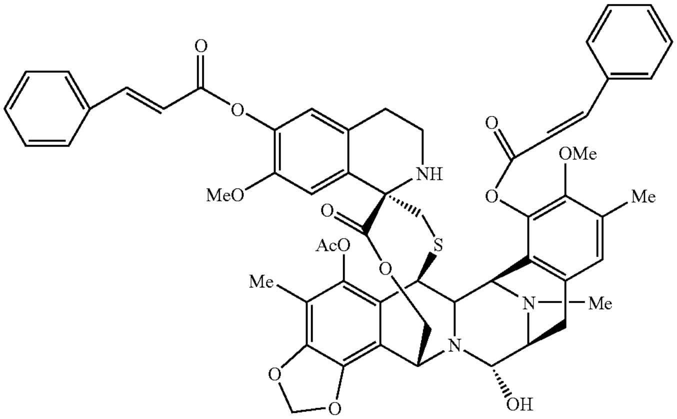
84
84 was obtained using Method H $^{1}$H-NMR (300 MHz, $CDCl_3$): δ 7.94 (d, 1H); 7.81 (d, 1H); 7.61-7.53 (m, 4H); 7.45-7.39 (m, 6H); 6.99 (s, 1H); 6.67 (d, 1H); 6.66 (d, 1H); 6.60 (s, 1H); 6.57 (d, 1H); 6.02 (s, 1H); 5.94 (d, 1H); 5.15 (d, 1H); 4.83 (s, 1H); 4.51 (d, 1H); 4.48-4.46 (m, 1H); 4.05 (dd, 1H); 3.79 (s, 3H); 3.62-3.61 (m, 1H); 3.56 (s, 3H); 3.27-3.16 (m, 1H); 2.96-2.88 (m, 3H); 2.70-2.50 (m, 2H); 2.43-2.39 (m, 2H); 2.35 (s, 3H); 2.234 (s, 3H); 2.17 (s, 3H); 2.05 (s, 3H).
$^{13}$C-NMR (75 MHz, $CDCl_3$): δ 172.0, 164.9, 164.5, 148.5, 148.0, 146.8, 146.5, 145.3, 143.4, 141.2, 140.6, 138.5, 134.2, 134.0, 131.4, 130.8, 130.5, 129.0, 128.9, 128.7, 128.2, 127.5, 125.0, 124.4, 122.5, 116.9, 115.8, 111.7, 101.7, 81.7, 67.6, 65.0, 61.2, 60.2, 57.7, 56.0, 55.1, 42.5, 41.4, 39.6, 32.6, 31.9, 29.6, 26.3, 28.6, 23.9, 22.6, 20.4, 15.8, 14.1, 9.6.
ESI-MS m/z: Calcd. for $C_{55}H_{55}N_3O_{13}S$: 1021.4 Found ($M-H_2O+H^+$): 1004.6.
Example 72
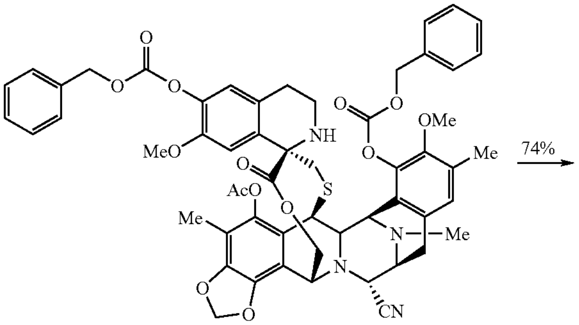
28

-continued

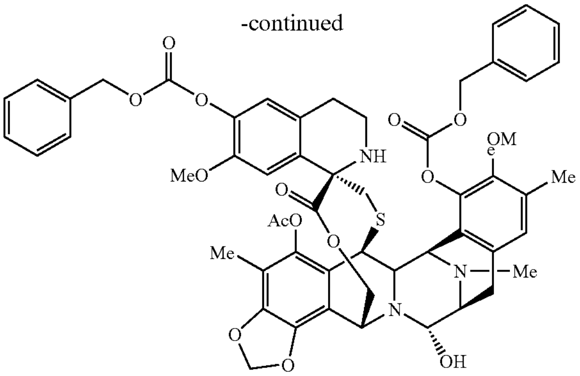

85

85 was obtained using Method H $^1$H-NMR (300 MHz, $CDCl_3$): δ 7.41-7.34 (m, 10H); 6.95 (s, 1H); 6.69 (s, 1H); 6.54 (s, 1H); 6.01 (d, 1H); 5.93 (s, 1H); 5.35-5.25(m, 2H); 5.11 (d, 1H); 4.80 (s, 1H); 4.47 (s, 1H); 4.32 (s, 1H); 4.03 (dd, 1H); 3.75 (s, 3H); 3.52 (s, 3H); 3.24 (s, 1H); 3.14-3.06 (m, 1H); 2.90-2.78 (m, 3H); 2.66-2.45 (m, 2H); 2.31 (s, 3H); 2.26-2.16 (m, 2H); 2.20 (s, 3H); 2.09 (s, 3H); 2.02 (s, 3H).

$^{13}$C-NMR (75 MHz, $CDCl_3$): δ 172.1, 153.5, 153.2, 148.5, 148.0, 145.5, 144.1, 141.5, 140.7, 139.0, 135.2, 135.1, 133.1, 131.6, 128.9, 128.8, 128.8, 128.7, 128.6, 128.4, 127.7, 122.2, 115.8, 112.0, 101.9, 82.0, 70.6, 70.5, 65.3, 61.6, 60.4, 57.8, 56.2, 55.9, 55.3, 42.4, 41.5, 39.7, 31.8, 29.9, 28.8, 24.1, 22.8, 20.3, 15.9, 14.3, 9.8.

ESI-MS m/z: Calcd. for $C_{55}H_{55}N_3O_{15}S$: 1029.3 Found ($M-H_2O+H^+$): 1012.4.

Example 73

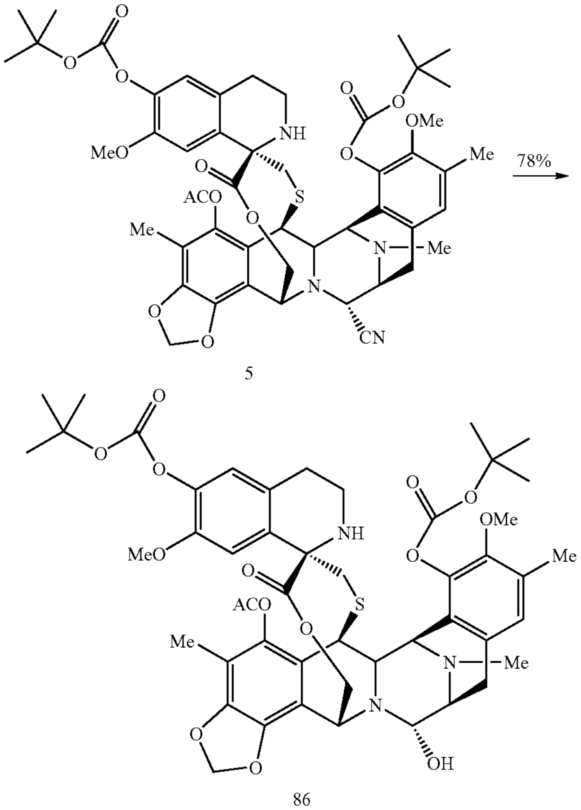

5

86

86 was obtained using Method H $^1$H-NMR (300 MHz, $CDCl_3$): δ 6.92 (s, 1H); 6.69 (s, 1H); 6.55 (s, 1H); 5.97 (dd, 2H); 5.12 (d, 1H); 4.81 (s, 1H); 4.49 (d, 1H); 4.33 (s, 1H); 4.03 (dd, 1H); 3.80 (s, 3H); 3.60-3.56 (m, 1H); 3.57 (s, 3H); 3.26-3.24 (m, 1H); 3.16-3.06 (m, 1H); 2.90-2.89 (m, 2H); 2.88-2.78 (m, 1H); 2.69-2.58 (m, 1H); 2.53-2.44 (m, 1H); 2.34-2.26 (m, 2H); 2.33 (s, 3H); 2.31 (s, 3H); 2.14 (s, 3H); 2.04 (s, 3H); 1.53 (s, 9H); 1.50 (s, 9H).

$^{13}$C-NMR (75 MHz, $CDCl_3$): δ 172.2, 151.8, 151.4, 148.7, 148.1, 145.5, 141.2, 141.5, 140.8, 139.0, 132.8, 131.3, 128.9, 127.3, 124.4, 122.4, 121.9, 116.0, 112.1, 101.9, 83.5, 83.2, 82.0, 65.4, 61.5, 60.2, 57.9, 56.3, 56.0, 55.4, 42.4, 41.6, 39.5, 29.9, 28.9, 27.8, 27.7, 24.1, 20.3, 15.9, 14.3, 9.7.

ESI-MS m/z: Calcd. for $C_{49}H_{59}N_3O_{13}S$: 961.4 Found ($M-H_2O+H^+$) 944.4.

Example 74

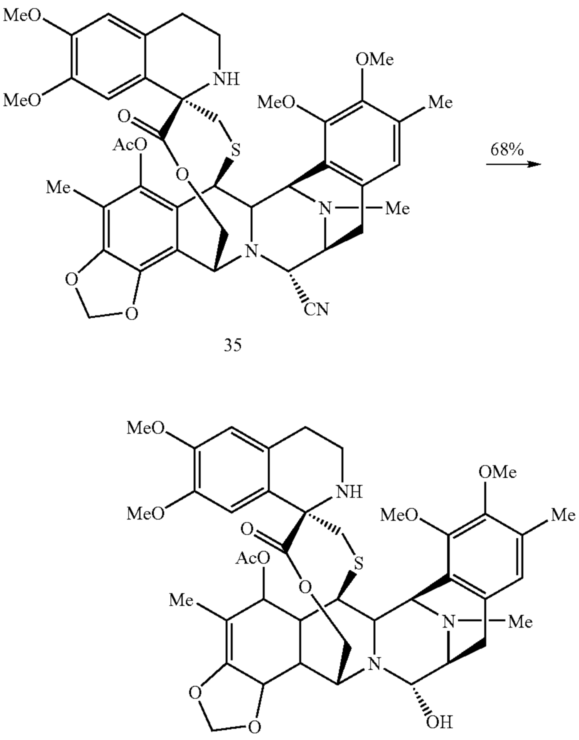

35

87

87 was obtained using Method H $^1$H-NMR (300 MHz, $CDCl_3$): δ 6.76 (s, 1H); 6.45 (s, 1H); 6.39 (s, 1H); 6.02 (d, 1H); 5.93 (d, 1H); 5.13 (d, 1H); 4.81 (s, 1H); 4.49 (d, 1H); 4.36 (s, 1H); 4.18(d, 1H); 4.11(d, 1H); 4.03(d, 1H); 3.90 (s, 3H); 3.81 (s, 3H); 3.75 (s, 3H); 3.58 (s, 3H); 3.58-3.56(m, 1H); 3.23-3.11 (m, 2H); 2.94-2.81 (m, 3H); 2.71-2.61 (m, 1H); 2.53-2.47(m, 1H); 2.35-2.27 (m, 1H); 2.27 (s, 3H); 2.22 (s, 3H); 2.16 (s, 3H); 2.01 (s, 3H).

$^{13}$C-NMR (75 MHz, $CDCl_3$): δ 172.7, 151.8, 148.7, 148.0, 146.6, 145.4, 141.4, 140.7, 131.4, 131.3, 128.5, 126.6, 124.6, 124.4, 122.0, 116.1, 111.2, 110.6, 101.9, 81.7, 64.9, 61.3, 60.2, 59.6, 58.0, 57.9, 56.2, 55.9, 55.3, 55.2, 42.3, 41.7, 39.9, 31.8, 29.9, 29.2, 24.3, 22.8, 20.4, 16.0, 14.3, 9.8.

ESI-MS m/z: Calcd. for $C_{41}H_{47}N_3O_{11}S$: 789.2 Found $(M-H_2O+H^+)$: 772.2.

Example 75

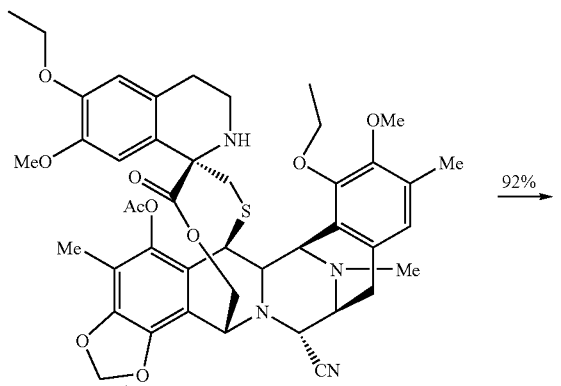

38

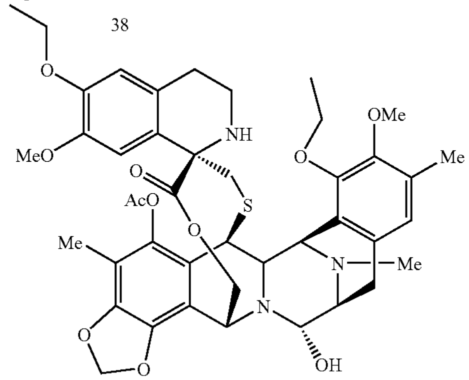

88

88 was obtained using Method H $^1$H-NMR (300 MHz, $CDCl_3$): δ 6.77 (s, 1H); 6.46 (s, 1H); 6.40 (s, 1H); 5.97 (dd, 2H); 5.13 (d, 1H); 4.81 (s, 1H); 4.49 (d, 1H); 4.39 (s, 1H); 4.10 (d 1H); 4.03 (dd, 1H); 3.99 (q, 2H); 3.96 (q, 2H); 3.83 (s, 3H); 3.61-3.54 (m, 1H); 3.58 (s, 3H); 3.24-3.18 (m, 1H); 3.18-3.09 (m, 1H); 2.88-2.85 (m, 2H); 2.86-2.78 (m, 1H); 2.69-2.58 (m, 1H); 2.54-2.44 (m, 1H); 2.35-2.12 (m, 2H); 2.28 (s, 3H); 2.25 (s, 3H); 2.17 (s, 3H); 2.03 (s, 3H); 1.40 (t, 3H); 1.36 (t, 3H).

ESI-MS m/z: Calcd. for $C_{43}H_{51}N_3O_{11}S$: 817.3 Found $(M-H_2O+H^+)$: 800.3.

Example 76

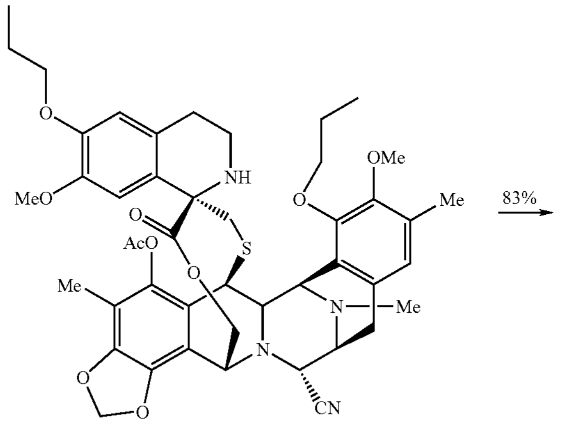

40

-continued

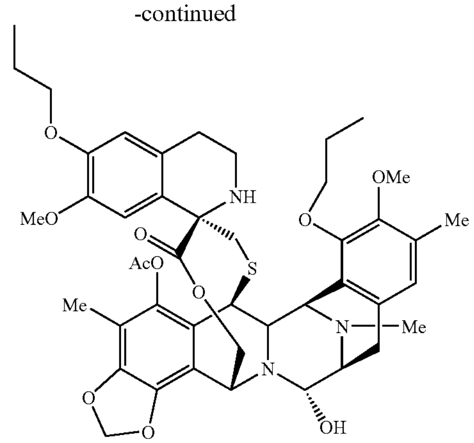

89

89 was obtained using Method H $^1$H-NMR (300 MHz, $CDCl_3$): δ 6.79 (s, 1H); 6.48 (s, 1H); 6.40 (s, 1H); 5.98 (dd, 2H); 5.13 (d, 1H); 4.81 (s, 1H); 4.48 (d, 1H); 4.42 (s, 1H); 4.10 (d, 1H); 4.04 (dd, 1H); 3.86 (q, 2H); 3.84 (q, 2H); 3.79 (s, 3H); 3.60 (s, 3H); 3.60-3.58 (m, 1H); 3.24-3.18 (m, 1H); 3.18-3.09 (m, 1H); 2.88-2.84 (m, 2H); 2.86-2.78 (m, 1H); 2.68-2.58 (m, 1H); 2.52-2.44 (m, 1H); 2.39-2.12 (m, 2H); 2.28 (s, 3H); 2.25 (s, 3H); 2.18 (s, 3H); 2.02 (s, 3H); 1.84-1.74 (m, 4H); 1.10 (t, 3H); 0.96 (t, 3H).

ESI-MS m/z: Calcd. for $C_{45}H_{55}N_3O_{11}S$: 845.3 Found $(M-H_2O+H^+)$: 828.0.

Example 77

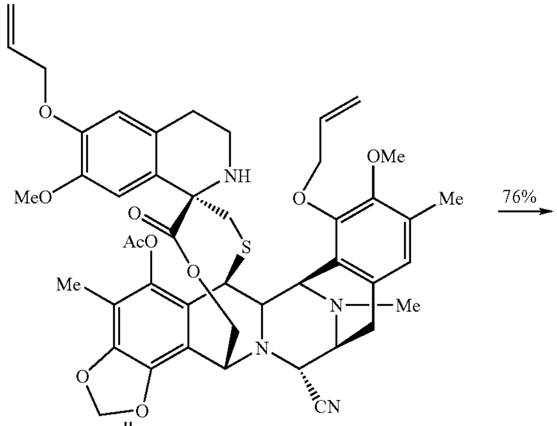

42

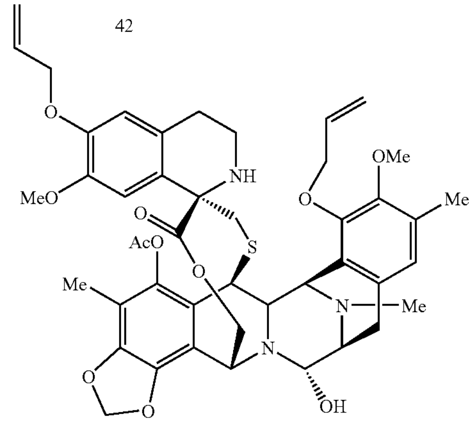

90

90 was obtained using Method H $^1$H-NMR (300 MHz, $CDCl_3$): δ 6.79 (s, 1H); 6.47 (s, 1H); 6.40 (s, 1H); 6.16-5.92 (m, 2H); 5.97 (dd, 2H); 5.45 (dd, 1H); 5.31 (dd, 1H); 5.24 (dd, 1H); 5.50 (dd, 1H); 5.12 (d, 1H); 4.80 (s, 1H); 4.78 (dd, 1H); 4.49 (d, 2H); 4.30 (s, 1H); 4.35 (dd, 1H); 4.11 (d, 1H); 4.04 (dd, 1H); 3.83 (s, 3H); 3.59 (s, 3H); 3.59-3.58 (m, 1H); 3.24-3.18 (m, 1H); 3.18-3.09 (m, 1H); 2.90-2.88 (m, 2H); 2.88-2.78 (m, 1H); 2.68-2.58 (m, 1H); 2.52-2.44 (m, 1H); 2.37-2.12 (m, 2H); 2.28 (s, 3H); 2.23 (s, 3H); 2.16 (s, 3H); 2.02 (s, 3H).

ESI-MS m/z: Calcd. for $C_{45}H_{51}N_3O_{11}S$: 841.3 Found ($M-H_2O+H^+$): 824.3.

Example 78

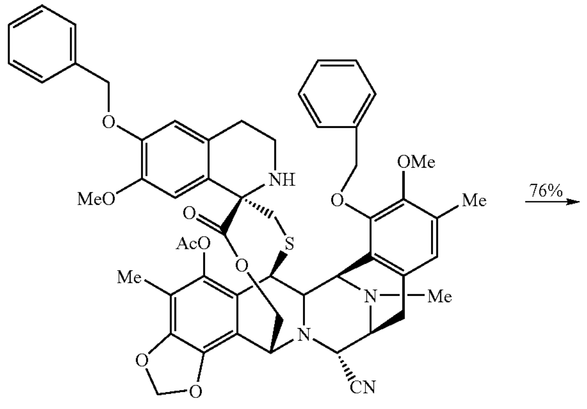

44

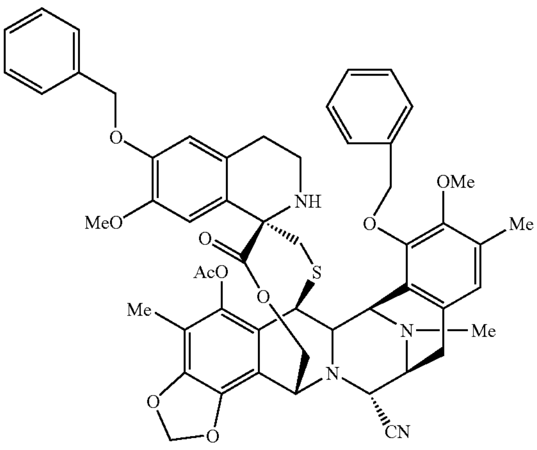

91

91 was obtained using Method H $^1$H-NMR (300 MHz, $CDCl_3$): δ 7.48-7.25 (m, 10H); 6.82 (s, 1H); 6.48 (s, 1H); 6.41 (s, 1H); 5.98 (dd, 2H); 5.32 (d, 1H); 5.12 (d, 1H); 5.02 (s, 2H); 4.84 (d, 1H); 4.80 (s, 1H); 4.48 (d, 1H); 4.45 (s, 1H); 4.50-4.00 (m, 2H); 3.85 (s, 3H); 3.61-3.57 (m, 1H); 3.60 (s, 3H); 3.24-3.18 (m, 1H); 3.18-3.09 (m, 1H); 2.88-2.84 (m, 2H); 2.86-2.78 (m, 1H); 2.64-2.58 (m, 1H); 2.46-2.40 (m, 1H); 2.36-2.12 (m, 2H); 2.30 (s, 3H); 2.03 (s, 9H).

$^{13}$C-NMR (75 MHz, $CDCl_3$): δ 172.6, 150.5, 149.1, 147.3, 145.4, 141.4, 140.7, 138.4, 137.3, 131.4, 131.3, 128.7, 128.6, 128.5, 128.1, 128.0, 127.9, 127.3, 125.1, 124.9, 122.1, 116.2, 116.1, 113.9, 11.3, 101.8, 82.0, 74.2, 71.0, 64.9, 61.4, 59.8, 58.1, 58.0, 56.2, 55.7, 55.4, 42.4, 42.2, 41.5, 39.8, 29.9, 29.1, 24.3, 20.1, 16.0, 9.8.

ESI-MS m/z: Calcd. for $C_{53}H_{55}N_3O_{11}S$: 941.4 Found ($M-H_2O+H^+$): 924.3.

Example 79

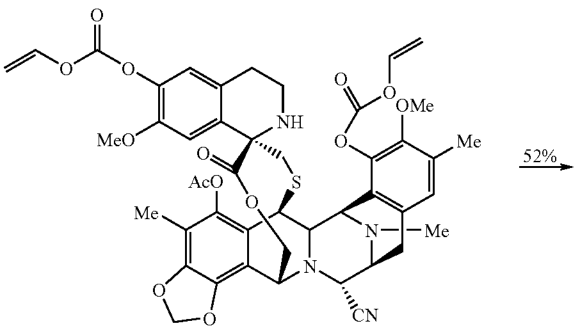

30

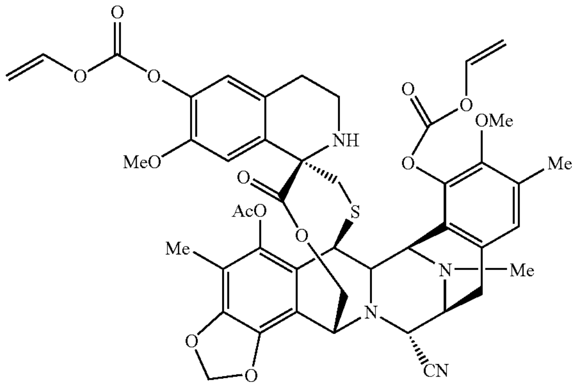

92

Compound 30 (15%) was recovered after chromatographic purification.

92 was obtained using Method H $^1$H-NMR (300 MHz, $CDCl_3$): δ 7.17 (dd, 1H); 7.08 (dd, 1H); 6.96 (s, 1H); 6.72 (s, 1H); 6.58 (s, 1H); 6.02 (d, 1H); 5.94 (d, 1H); 5.12 (d, 1H); 4.99 (dd, 2H); 4.82 (s, 1H); 4.69 (dd, 1H); 4.63 (dd, 1H); 4.50-4.48 (m, 1H); 4.39-4.37 (m, 1H); 4.05 (dd, 1H); 3.84-3.79 (m, 1H); 3.80 (s, 3H); 3.61-3.59 (m, 1H); 3.58 (s, 3H); 3.29-3.26 (m, 1H); 3.18-3.09 (m, 1H); 2.93-2.80 (m, 3H); 2.70-2.47 (m, 2H); 2.53 (s, 3H); 2.33 (s, 3H); 2.30-2.24 (m, 1H); 2.15 (s, 3H); 2.04 (s, 3H).

$^{13}$C-NMR (75 MHz, $CDCl_3$): δ 172.1, 168.8, 151.0, 150.8, 148.4, 147.9, 145.5, 143.8, 143.1, 142.9, 141.5, 140.8, 138.5, 133.5, 131.8, 129.0, 128.1, 124.2, 122.1, 121.6, 115.8, 112.8, 112.2, 102.0, 98.7, 82.0, 65.3, 61.6, 60.6, 57.8, 56.2, 56.0, 55.3, 42.5, 41.5, 39.7, 29.9, 28.9, 24.1, 20.4, 15.9, 9.8.

ESI-MS m/z: Calcd. for $C_{45}H_{47}N_3O_{15}S$: 901.2 Found ($M-H_2O+H^+$): 884.3.

Example 80

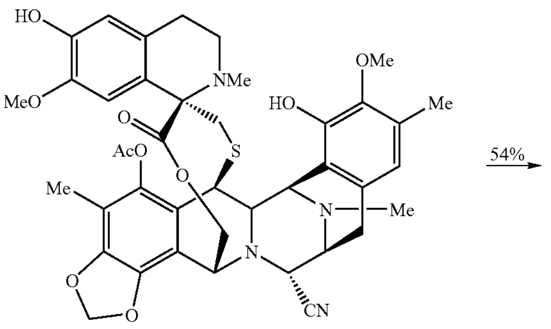

54

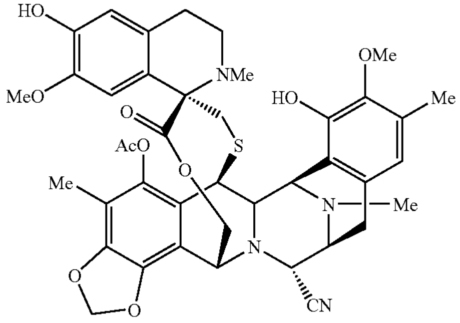

93

93 was obtained using Method H $^1$H-NMR (300 MHz, $CDCl_3$): δ 6.47 (s, 1H), 6.44 (s, 1H), 6.19 (s, 1H), 5.98 (dd, 2H), 5.70 (bp, 1H), 5.01 (d, 1H), 4.83 (d, 1H), 4.48 (bp, 1H), 4.42 (d, 1H), 4.14 (dd, 1H), 3.79 (s, 3H), 3.78 (dd, 1H), 3.58 (d, 1H), 3.53 (s, 3H), 3.23-3.20 (m, 2H), 2.91-2.70 (m, 2H), 2.63-2.47 (m, 5H), 2.30 (s, 3H), 2.23 (s, 6H), 2.15 (s, 3H), 2.01 (s, 3H).

$^{13}$C-NMR (75 MHz, $CDCl_3$): δ 168.7, 147.4, 145.4, 144.4, 144.1, 142.6, 141.7, 140.8, 131.3, 129.6, 129.1, 127.1, 122.1, 121.3, 118.0, 116.1, 113.8, 111.6, 110.5, 101.7, 83.2, 71.2, 62.5, 60.1, 59.2, 57.7, 55.3, 54.9, 49.0, 43.1, 42.1, 41.6, 38.9, 28.5, 24.8, 20.3, 15.6, 9.7.

ESI-MS m/z: Calcd. for $C_{40}H_{45}N_3O_{11}S$: 775.3. Found ($M+H^+$): 776.1.

Example 81

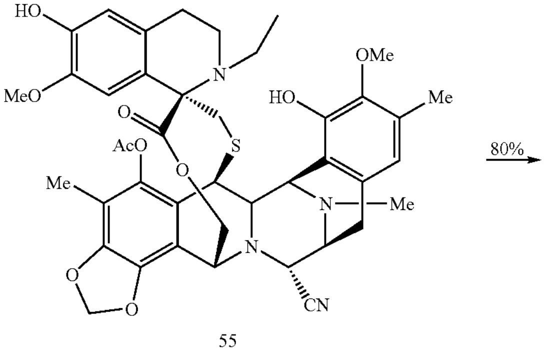

55

-continued

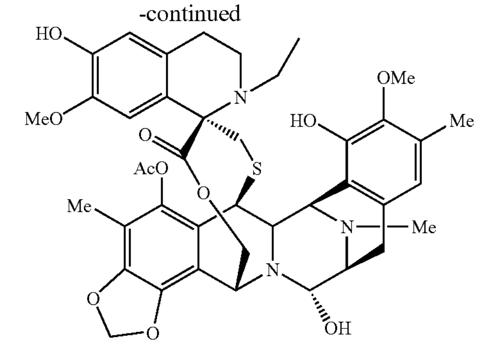

94

94 was obtained using Method H $^1$H-NMR (300 MHz, $CDCl_3$): δ 6.48 (s, 1H), 6.44 (s, 1H), 6.21 (s, 1H), 5.98 (d, 2H), 5.69 (bs, 1H), 4.99 (d, 1H), 4.87 (d, 1H), 4.50-4.44 (m, 2H), 4.17-4.12 (m, 1H), 3.89-3.84 (m 1H), 3.80 (s, 3H), 3.58-3.55 (m, 1H), 3.55 (s, 3H), 3.26-3.22 (m, 1H), 3.02-2.42 (m, 6H), 2.37-2.02 (m, 4H), 2.31 (s, 3H), 2.28 (s, 3H), 2.12 (s, 3H), 2.05 (s, 3H), 0.88 (t, 3H).

ESI-MS m/z: Calcd. for $C_{41}H_{47}N_3O_{11}S$: 789.3. Found ($M-H_2O+H^+$): 772.3.

Example 82

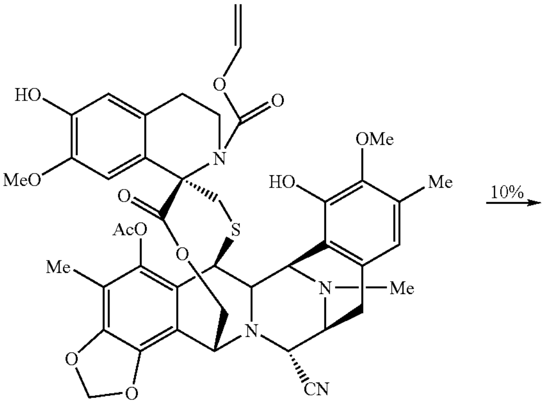

32

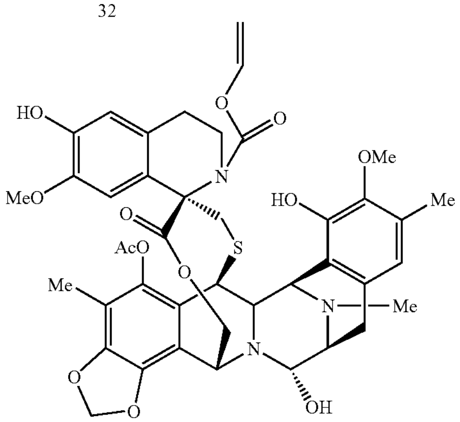

95

Compound 32 was recovered after chromatographic purification (15%).

95 was obtained using Method H $^1$H-NMR (300 MHz, $CDCl_3$): δ 7.05 (dd, 1H); 6.48 (s, 1H); 6.46 (s, 1H); 6.15 (s, 1H); 6.03 (s, 1H); 5.92 (s, 1H); 5.73 (s, 1H); 4.91 (dd, 1H); 4.83 (s, 1H); 4.72 (dd, 1H); 4.45-4.48 (m, 3H); 4.13 (d, 1H); 4.01-3.94 (m, 2H); 3.81 (s, 3H); 3.71-3.66 (m, 2H); 3.59 (s, 3H); 3.23-3.20 (m, 3H); 2.83-2.81 (m, 2H); 2.72-2.62 (m, 1H); 2.54-2.42 (m, 2H); 2.33 (s, 3H); 2.22 (s, 3H); 2.14 (s, 3H); 2.02 (s, 3H).

ESI-MS m/z: Calcd. for $C_{42}H_{45}N_3O_{13}S$: 831.3. Found ($M-H_2O+H^+$): 814.2.

Example 83

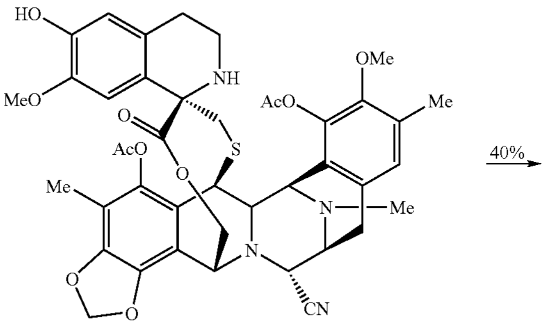

51

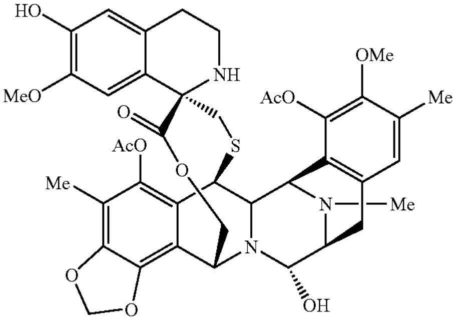

96

96 was obtained using Method H. $^1$H-NMR (300 MHz, $CDCl_3$): δ 7.00 (bs, 1H), 6.49 (s, 1H), 6.42 (bs, 1H), 6.00 (dd, 2H), 5.40 (bs, 1H), 5.12 (d, 1H), 4.84-3.69 (m, 4H), 3.84-3.50 (m, 5H), 3.50 (s, 3H), 3.24-2.57 (m, 7H), 2.42-2.13 (m, 2H), 2.40 (s, 3H), 2.33 (s, 3H), 2.29 (s, 3H), 2.13 (s, 3H), 2.03 (s, 3H).

ESI-MS m/z: Calcd. for $C_{41}H_{45}N_3O_{12}S$: 803.3 Found ($M-H_2O+H^+$): 804.

Example 84

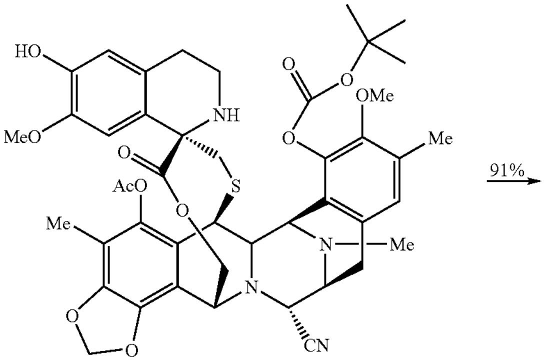

47

-continued

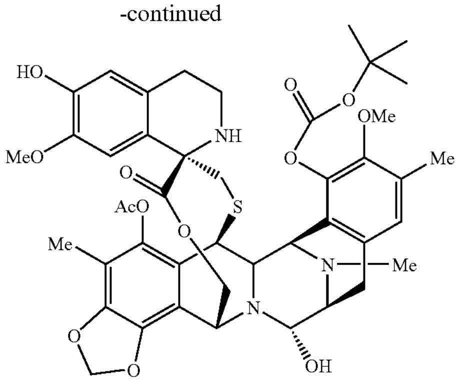

97

97 was obtained using Method H $^1$H-NMR (300 MHz, $CDCl_3$): δ 6.93 (s, 1H); 6.47 (s, 1H); 6.42 (s, 1H); 5.98 (dd, 2H); 5.13 (d, 1H); 4.81 (s, 1H); 4.50 (d, 1H); 4.36 (s, 1H); 4.05 (dd, 1H); 3.79 (s, 3H); 3.62-3.58 (m, 1H); 3.61 (s, 3H); 3.27-3.24 (m, 1H); 3.18-3.06 (m, 1H); 2.91-2.89 (m, 2H); 2.86-2.78 (m, 1H); 2.68-2.56 (m, 1H); 2.52-2.44 (m, 1H); 2.33-2.12 (m, 2H); 2.32 (s, 3H); 2.31 (s, 3H); 2.14 (s, 3H); 2.04 (s, 3H); 1.53 (s, 9H).

$^{13}$C-NMR (75 MHz, $CDCl_3$): δ 172.6, 151.4, 148.1, 145.4, 144.6, 144.4, 144.2, 141.5, 140.0, 131.4, 131.3, 129.4, 127.3, 126.1, 124.4, 122.1, 116.0, 114.2, 110.0, 101.8, 83.2, 82.0, 65.1, 61.4, 60.2, 57.9, 56.3, 56.1, 55.3, 42.4, 41.3, 39.8, 32.1, 30.6, 29.9, 29.5, 29.0, 27.8, 24.1, 22.8, 20.3, 15.5, 14.2, 9.8.

ESI-MS m/z: Calcd. for $C_{44}H_{51}N_3O_{13}S$: 861.2 Found ($M-H_2O+H^+$): 844.2.

Example 85

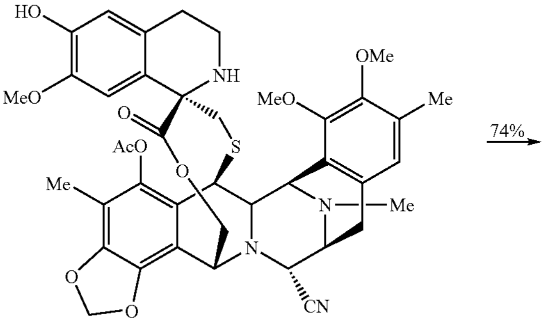

36

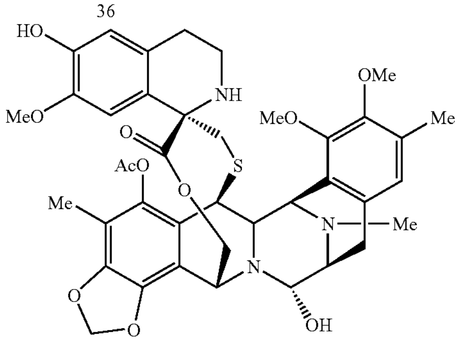

98

Compound 36 (11%) was recovered after chromatographic purification.

98 was obtained using Method H $^1$H-NMR (300 MHz, $CDCl_3$): δ d 6.77 (s, 1H), 6.47 (s, 1H), 6.42 (s, 1H), 5.98 (dd, 2H), 5.40 (bp, 1H), 5.13 (d, 1H), 4.81 (s, 1H), 4.49 (bs, 1H), 4.37 (bp, 1H), 4.11 (d, 1H), 4.03 (dd, 1H), 3.91 (s, 3H), 3.82 (s, 3H), 3.60 (s, 3H), 3.58-3.56 (m, 1H), 3.23-3.21 (m, 1H), 3.16-3.09 (m, 1H), 2.95-2.79 (m, 3H), 2.67-2.57 (m, 1H), 2.50-2.45 (m, 1H), 2.34-2.13 (m, 2H), 2.28 (s, 3H), 2.23 (s, 3H), 2.17 (s, 3H), 2.03 (s, 3H).

$^{13}$C-NMR (75 MHz, $CDCl_3$): δ 172.5, 168.1, 151.6, 148.5, 145.1, 144.4, 144.2, 141.2, 140.5, 131.2, 131.0, 129.1, 126.0, 124.5, 124.2, 122.0, 115.9, 114.0, 109.8, 101.6, 81.7, 64.8, 61.1, 60.0, 59.4, 57.8, 57.7, 56.0, 55.1, 55.1, 42.2, 42.2, 41.5, 39.6, 28.8, 24.1, 20.2, 15.8, 9.6.

ESI-MS m/z: Calcd. for $C_{40}H_{45}N_3O_{11}S$: 775.8 Found $(M-H_2O+H^+)$: 758.7.

Example 86

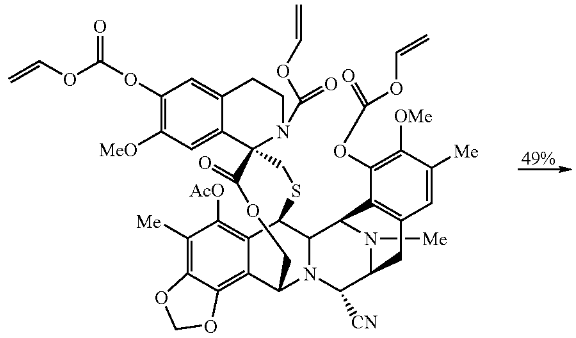

31

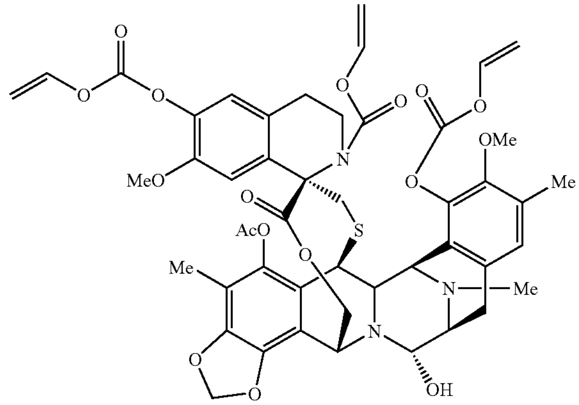

99

99 was obtained using Method H $^1$H-NMR (300 MHz, $CDCl_3$): δ 7.18 (dd, 1H); 7.08 (dd, 1H); 7.04 (dd, 1H); 6.87 (s, 1H); 6.73 (s, 1H); 6.31 (s, 1H); 6.04 (d, 1H); 5.91 (d, 1H); 5.01 (dd, 1H); 4.99 (dd, 1H); 4.92 (d, 1H); 4.83 (s, 1H); 4.75 (d, 1H); 4.69-4.63 (m, 2H); 4.45-4.42 (m, 2H); 4.01-3.96 (m, 2H); 3.84 (s, 3H); 3.81-3.89 (m, 1H); 3.60-3.57 (m, 1H); 3.55 (s, 3H); 3.37-3.25 (m, 2H); 2.90-2.87 (m, 2H); 2.77-2.67 (m, 1H); 2.53-2.28 (m, 3H); 2.41 (s, 3H); 2.23 (s, 3H); 2.12 (s, 3H); 2.03 (s, 3H).

ESI-MS m/z: Calcd. for $C_{48}H_{49}N_3O_{17}S$: 971.2 Found $(M-H_2O+H^+)$: 954.3.

Example 87

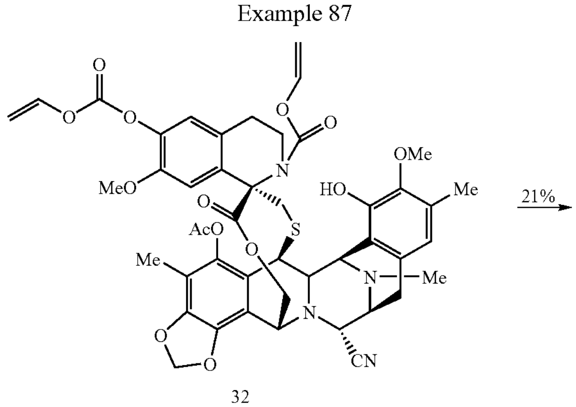

32

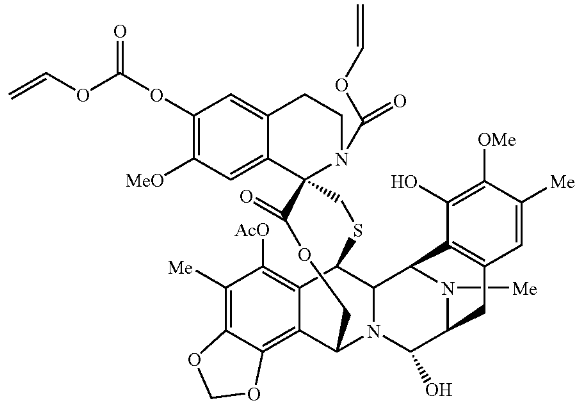

100

100 was obtained using Method H $^1$H-NMR (300 MHz, $CDCl_3$): δ 7.08 (dd, 1H); 7.04 (dd, 1H); 6.72 (s, 1H); 6.49 (s, 1H); 6.34 (s, 1H); 6.04 (s, 1H); 5.91 (s, 1H); 5.73 (s, 1H); 5.00 (dd, 1H); 4.93 (dd, 1H); 4.83 (s, 1H); 4.73 (d, 1H); 4.64 (dd, 1H); 4.51 (s, 1H); 4.44-4.40 (m, 2H); 4.14 (d, 1H); 4.07-4.01 (m, 1H); 3.96 (dd, 1H); 3.81 (s, 3H); 3.58-3.49 (m, 2H); 3.55 (s, 3H); 3.35-3.20 (m, 2H); 2.81 (d, 2H); 2.76-2.66 (m, 1H); 2.56-2.46 (m, 2H); 2.33 (s, 3H); 2.22 (s, 3H); 2.14 (s, 3H); 2.01 (s, 3H).

ESI-MS m/z: Calcd. for $C_{45}H_{47}N_3O_{15}S$: 901.9 Found $(M-H_2O+H^+)$: 884.2.

Example 88

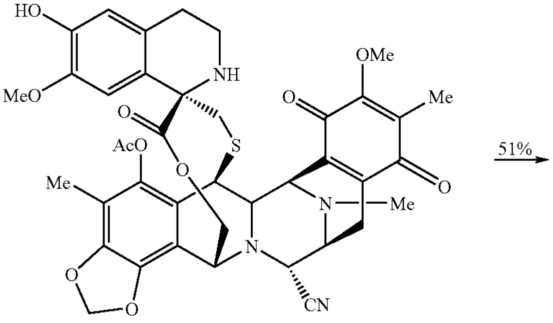

52

-continued

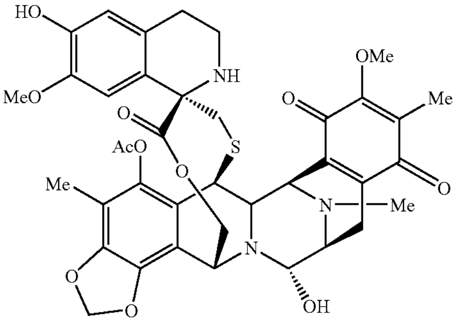

101

Compound 52 (19%) was recovered after chromatographic purification.

101 was obtained using Method H $^1$H-NMR (300 MHz, $CDCl_3$): δ 6.48 (s, 1H); 6.44 (s, 1H); 6.03 (d, 1H); 5.93 (d, 1H); 5.39 (s, 1H); 5.01 (d, 1H); 4.72 (s, 1H); 4.41-4.39 (m, 2H); 4.11-3.99 (m, 3H); 4.10 (s, 3H); 3.64-3.61 (m, 1H); 3.61 (s, 3H); 3.26-3.06 (m, 3H); 2.81-2.29 (m, 8H); 2.23 (s, 3H); 2.18 (s, 3H); 2.05 (s, 3H); 2.03 (s, 3H).

ESI-MS m/z: Calcd. for $C_{39}H_{41}N_3O_{12}S$: 775.2 Found (M+Na$^+$): 798.2.

Example 89

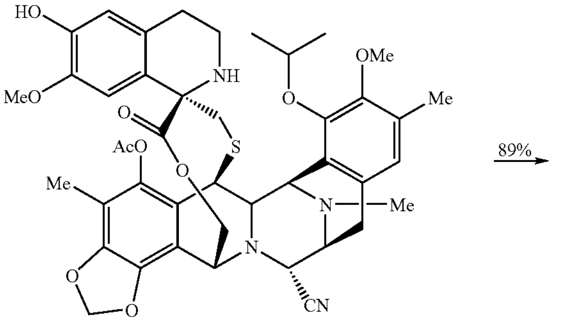

48

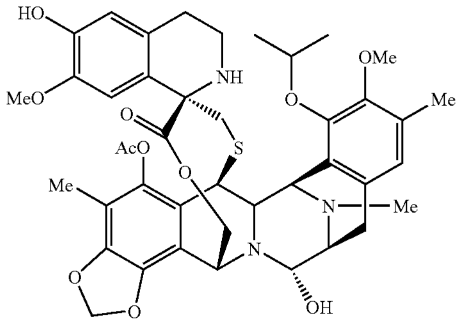

102

102 was obtained using Method H. $^1$H-NMR (300 MHz, $CDCl_3$): δ 6.77 (s, 1H), 6.46 (s, 1H), 6.44 (s, 1H), 6.01 (d, 1H), 5.94 (d, 1H); 5.13 (d, 1H), 4.89-4.80 (m, 1H); 4.80 (s, 1H), 4.48 (d, 1H); 4.42 (s, 1H), 4.21 (d, 1H), 4.05 (dd, 1H), 3.81 (s, 3H), 3.61 (s, 3H), 3.55 (d, 1H), 3.20 (s, 1H), 3.16-3.08 (m, 1H), 2.89-2.86 (m, 2H), 2.80-2.76 (m, 1H), 2.64-2.47 (m, 2H); 2.32-2.12 (m, 2H); 2.28 (s, 3H), 2.25 (s, 3H), 2.20 (s, 3H), 2.03 (s, 3H); 1.45 (d, 3H); 1.14 (d, 3H).

$^{13}$C-NMR (75 MHz, $CDCl_3$): δ 172.7, 168.5, 149.3, 148.8, 145.2, 144.6, 144.4, 141.3, 140.7, 135.8, 131.1, 129.2, 128.6, 126.3, 124.3, 116.1, 114.2, 109.9, 101.8, 81.9, 73.3, 64.9, 61.2, 59.1, 58.2, 58.1, 56.2, 55.3, 42.2, 42.1, 41.7, 39.6, 31.8, 29.9, 29.0, 24.2, 23.8, 22.8, 20.5, 16.0, 14.3, 9.8.

ESI-MS m/z: Calcd. for $C_{42}H_{49}N_3O_{11}S$: 803.4 Found (M+H$^+$): 804.4.

Example 90

Method I: To a solution of 1 equiv. of compound 3 in THF/$H_2O$ 4.5:0.5 (0.0052M) were added 5 equiv. of CuBr. After 24 h the reaction was quenched with $NaHCO_3$, diluted and extracted with $CH_2Cl_2$. The organic layer was dried with $Na_2SO_4$. Chromatography gives pure compound 104 (50%).

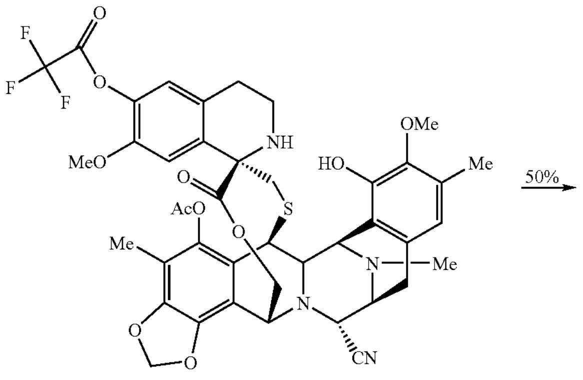

3

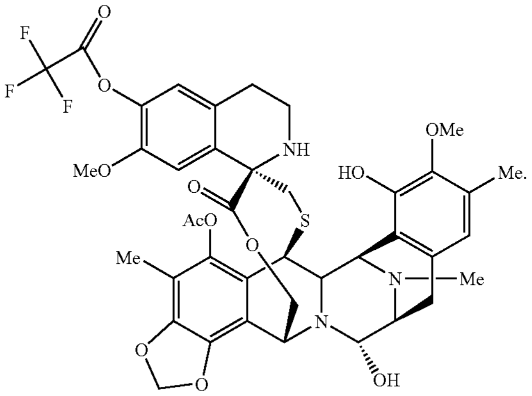

104

104 was obtained using Method I $^1$H-NMR (300 MHz, $CDCl_3$): δ 6.47 (s, 2H); 6.45 (s, 1H); 5.98 (dd, 2H); 5.68 (s, 1H); 4.87 (s, 1H); 4.77 (d, 1H); 4.57 (s, 1H); 4.45 (d, 1H); 4.15 (d, 1H); 4.05 (dd, 1H); 3.79 (s, 3H); 3.64 (d, 1H); 3.58 (s, 3H); 3.25-3.20 (m, 2H); 2.80-2.82 (m, 3H); 2.67-2.63 (m, 2H); 2.52-2.44 (m, 1H); 2.32-2.12 (m, 2H); 2.31 (s, 3H); 2.24 (s, 3H); 2.12 (s, 3H); 2.02 (s, 3H).

$^{13}$C-NMR (75 MHz, $CDCl_3$): δ 172.0, 168.9, 148.3, 147.6, 145.1, 141.2, 140.4, 139.1, 138.4, 131.4, 130.8, 128.7, 128.6, 122.9, 122.3, 121.6, 120.9, 120.6, 115.8, 111.7, 101.6, 82.0, 64.9, 61.4, 60.3, 57.8, 57.6, 55.9, 55.0, 54.9, 42.1, 41.3, 39.5, 29.6, 24.0, 20.5, 15.7, 9.6.

ESI-MS m/z: Calcd. for $C_{41}H_{42}F_3N_3O_{12}S$: 857.8 Found (M-$H_2O$+H$^+$): 840.2.

Example 91

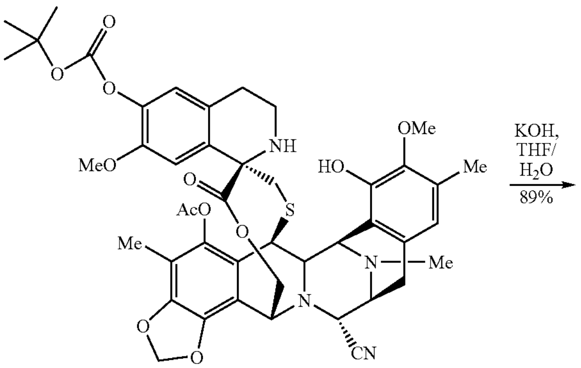

4

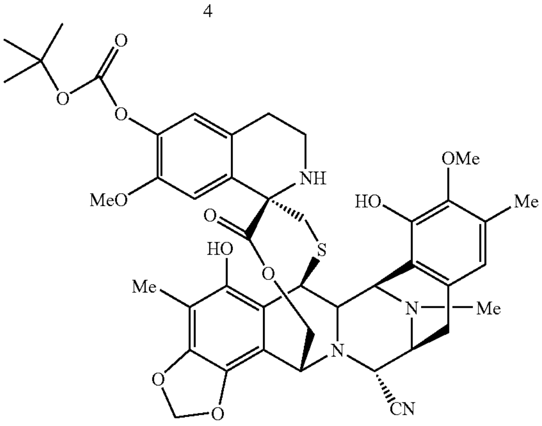

106

To a solution of compound 4 in THF/$H_2O$ 3:1 (0.027M) were added 15 equiv. of KOH. The reaction mixture was stirred at room temperature for 5 h. After this time the reaction was quenched with NaCl or diluted aqueous solution of HCl, extracted with $CH_2Cl_2$. The organic layer was dried with $Na_2SO_4$. Chromatography gives pure compound 106.

106. $^1$H-NMR (300 MHz, $CDCl_3$): δ 6.70 (s, 1H); 6.61 (s, 1H); 6.53 (s, 1H); 5.92 (dd, 2H); 5.84 (s, 1H); 5.41 (s, 1H); 4.97 (d, 1H); 4.48 (d, 1H); 4.34 (s, 1H); 4.31 (dd, 1H); 4.16 (d 1H); 4.03 (dd, 1H); 3.80 (s, 3H); 3.59 (d, 1H); 3.55 (s, 3H); 3.43-3.40 (m, 1H); 3.18-3.08 (m, 1H); 2.95-2.93 (m, 2H); 2.81-2.75 (m, 1H); 2.69-2.58 (m, 1H); 2.45-2.24 (m, 2H); 2.34 (s, 3H); 2.19 (s, 3H); 2.15 (s, 3H); 1.50 (s, 9H).

$^{13}$C-NMR (75 MHz, $CDCl_3$): δ 171.7, 148.6, 148.0, 146.2, 146.0, 143.1, 139.0, 136.1, 132.4, 130.7, 129.4, 128.7, 122.4, 122.7, 118.2, 118.1, 113.1, 111.6, 101.2, 83.5, 64.4, 60.9, 60.7, 60.4, 59.8, 59.3, 55.2, 54.7, 54.6, 51.7, 43.1, 41.5, 39.5, 30.1, 29.8, 29.7, 28.6, 27.6, 25.5, 24.2, 15.9, 8.7.

ESI-MS m/z: Calcd. for $C_{43}H_{48}N_4O_{11}S$: 828.9 Found (M+H$^+$):829.3.

Example 92

Method A: To a solution of 1 equiv. of compound 106 in $CH_2Cl_2$ (0.032M) under Argon were added 2 equiv. of the anhydride and 2 equiv. of pyridine. The reaction was followed by TLC and quenched with $NaHCO_3$, extracted with $CH_2Cl_2$ and the organic layers dried with $Na_2SO_4$. Flash chromatography gives pure compounds.

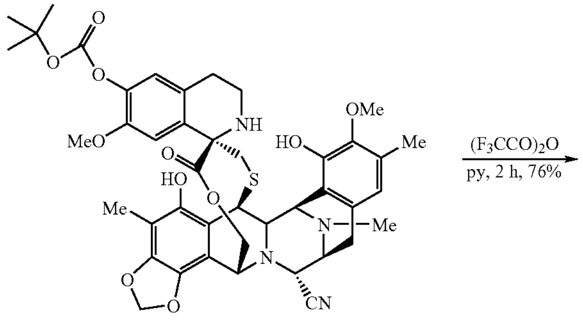

106

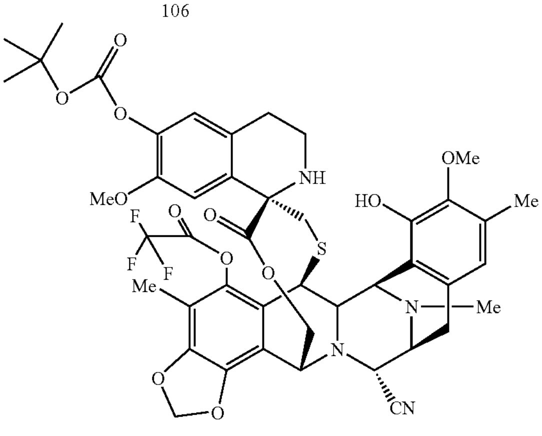

107

107 was obtained using Method A. $^1$H-NMR (300 MHz, $CDCl_3$): δ 6.70 (s, 1H); 6.59 (s, 1H); 6.58 (s, 1H); 6.04 (dd, 2H); 5.69 (s, 1H); 5.02 (d, 1H); 4.58 (s, 1H); 4.34 (s, 1H); 4.29 (dd, 1H); 4.21 (d 1H); 4.13 (dd, 1H); 3.76 (s, 3H); 3.59 (s, 3H); 3.50 (dd, 1H); 3.44-3.41 (m, 1H); 3.19-3.10 (m, 1H); 2.94 (d, 2H); 2.81-2.73 (m, 1H); 2.69-2.58 (m, 1H); 2.54-2.46 (m, 1H); 2.34-2.04 (m, 2H); 2.31 (s, 3H); 2.20 (s, 3H); 2.06 (s, 3H); 1.50 (s, 9H).

$^{13}$C-NMR (75 MHz, $CDCl_3$): δ 172.0, 168.0, 157.9, 151.7, 149.0, 148.2, 145.8, 143.4, 141.4, 139.4, 130.7, 122.7, 120.7, 118.1, 117.8, 114.7, 113.1, 112.0, 102.5, 97.6, 83.7, 64.7, 61.3, 60.4, 60.0, 59.4, 55.7, 54.8, 54.6, 41.8, 41.7, 39.6, 32.1, 29.9, 29.5, 27.8, 24.1, 20.8, 16.0, 14.3, 9.4.

ESI-MS m/z: Calcd. for $C_{45}H_{47}F_3N_4O_{12}S$: 924.3 Found (M+H$^+$): 925.3.

Example 93

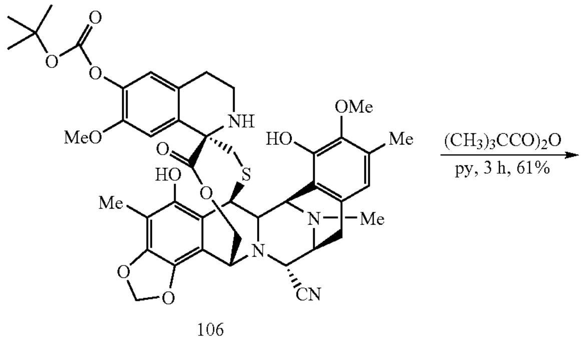

106

-continued

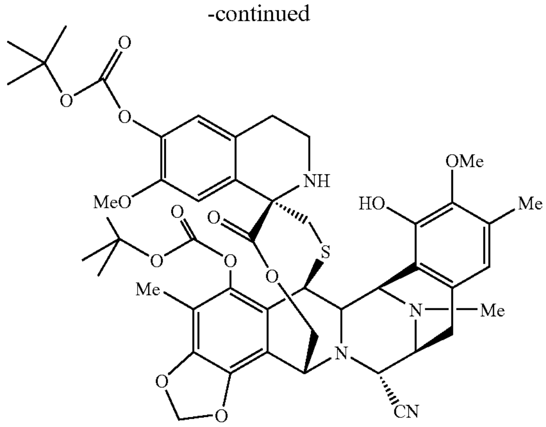

108

108 was obtained using Method A. $^{1}$H-NMR (300 MHz, $CDCl_3$): δ 6.69 (s, 1H); 6.60 (s, 1H); 6.58 (s, 1H); 6.03 (d, 1H); 5.96 (d, 1H); 5.69 (s, 1H); 5.00 (d, 1H); 4.68 (s, 1H); 4.29-4.27 (m, 2H); 4.16-4.09 (m, 2H); 3.78 (s, 3H); 3.59 (s, 3H); 3.50 (d, 1H); 3.41 (s, 1H); 3.15-3.06 (m, 1H); 2.98-2.94 (m, 2H); 2.80-2.74 (m, 1H); 2.69-2.59 (m, 1H); 2.50-2.45 (m, 1H); 2.37-2.21 (m, 2H); 2.31 (s, 3H); 2.18 (s, 3H); 2.08 (s, 3H); 1.51 (s, 9H); 1.47 (s, 9H).

ESI-MS m/z: Calcd. for $C_{48}H_{56}N_4O_{13}S$: 928.4 Found ($M+H^+$): 929.3.

Example 94

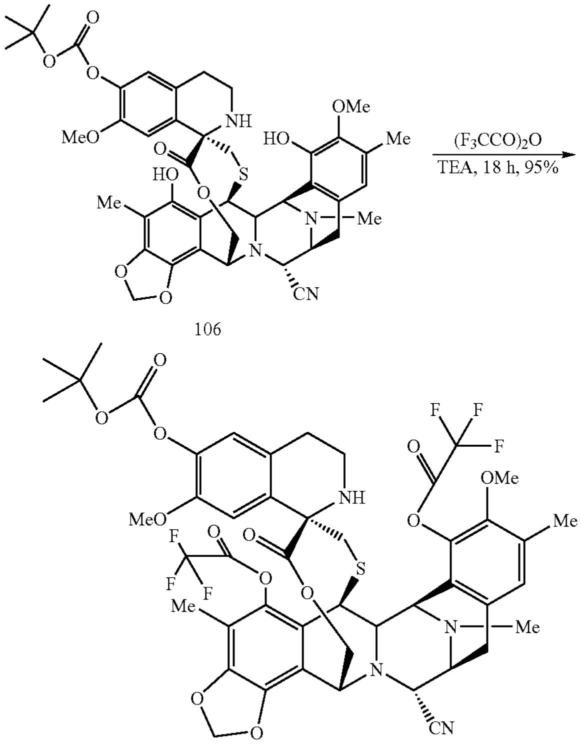

106

109

If the acylation reaction of compound 106 is performed with TEA (10 equiv.) as base instead of pyridine compound 109 is obtained (Method A).

109. $^{1}$H-NMR (300 MHz, $CDCl_3$): δ 6.89 (s, 1H); 6.72 (s, 1H); 6.18 (s, 1H); 6.16 (d, 1H); 6.04 (d, 1H); 4.76 (d, 1H); 4.54 (s, 1H); 4.41 (s, 1H); 4.12 (d, 1H); 4.08 (dd, 1H); 3.79-3.70 (m, 2H); 3.77 (s, 3H); 3.57 (d, 1H); 3.55 (s, 3H); 3.47 (d, 1H); 3.29 (d, 1H); 2.97 (d, 2H); 2.73-2.68 (m, 2H); 2.54 (d, 1H); 2.26 (s, 3H); 2.24-2.12 (m, 1H); 2.08 (s, 3H); 2.05 (s, 3H); 1.51 (s, 9H).

$^{13}$C-NMR (75 MHz, $CDCl_3$): δ 167.0, 151.5, 149.8, 147.4, 146.2, 142.1, 141.9, 139.8, 139.7, 132.8, 132.6, 131.1, 129.2, 126.7, 123.3, 122.7, 121.5, 117.9, 114.4, 112.4, 111.3, 102.8, 84.1, 71.5, 62.0, 60.6, 60.3, 59.6, 55.4, 54.5, 42.7, 42.2, 41.8, 39.0, 29.0, 27.7, 24.4, 15.8, 9.6.

ESI-MS m/z: Calcd. for $C_{47}H_{46}F_6N_4O_{13}S$: 1020.2 Found ($M+H^+$): 1021.3.

Example 95

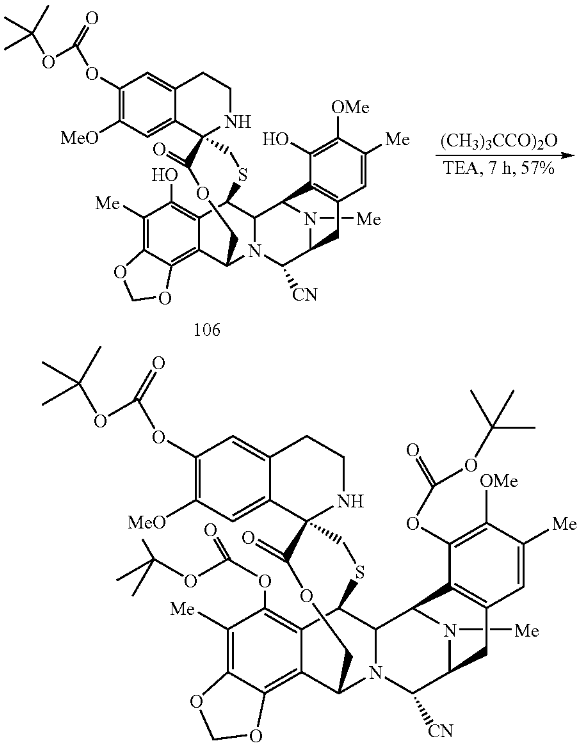

106

110

The reaction is performed with 6 equiv. of anhydride and 9 equiv. of base (Method A). Traces of compound 110 is also obtained when the acylation reaction is performed with pyridine as base and compound 108 is the main product.

110. $^{1}$H-NMR (300 MHz, $CDCl_3$): δ 6.92 (s, 1H); 6.69 (s, 1H); 6.58 (s, 1H); 6.03 (d, 1H); 5.96 (d, 1H); 4.99 (d, 1H); 4.64 (s, 1H); 4.27 (s, 2H); 4.13 (s, 1H); 4.12 (dd, 1H); 3.97 (d, 1H); 3.80 (s, 3H); 3.59 (s, 3H); 3.53 (d, 1H); 3.43-3.41 (m, 1H); 3.15-3.05 (m, 1H); 2.97-2.95 (m, 2H); 2.80-2.74 (m, 1H); 2.70-2.60 (m, 1H); 2.50-2.45 (m, 1H); 2.37-2.18 (m, 1H); 2.31 (s, 3H); 2.17 (s, 3H); 2.09 (s, 3H); 1.53 (s, 9H); 1.51 (s, 9H); 1.48 (s, 9H).

ESI-MS m/z: Calcd. for $C_{53}H_{64}N_4O_{15}S$: 1028.4 Found ($M+H^+$): 1029.3.

Example 96

Method B: To a solution of 1 equiv. of compound 106 in $CH_2Cl_2$ (0.032M) under Argon at room temperature were added 2 equiv. of base and 2 equiv. of the acid chloride. The reaction was followed by TLC and quenched with $NaHCO_3$, extracted with $CH_2Cl_2$ and the organic layers dried with $Na_2SO_4$. Flash chromatography gives pure compounds.

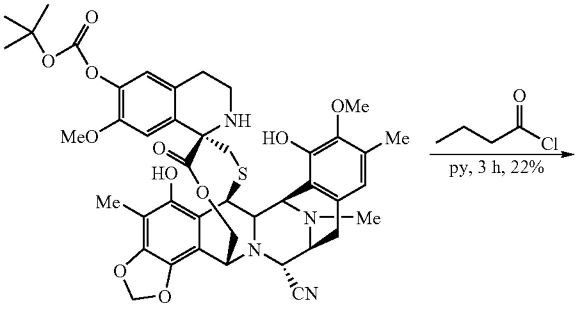

106

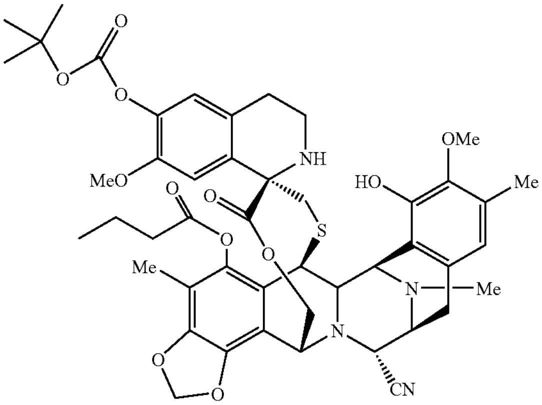

111

111 was obtained using Method B. $^1$H-NMR (300 MHz, $CDCl_3$): δ 6.68 (s, 1H); 6.58 (s, 1H); 6.56 (s, 1H); 6.00 (dd, 2H); 5.67 (s, 1H); 5.00 (d, 1H); 4.58 (s, 1H); 4.36 (s, 1H); 4.27 (dd, 1H); 4.19 (d 1H); 4.12 (dd, 1H); 3.77 (s, 3H); 3.59 (s, 3H); 3.51 (d, 1H); 3.43-3.40 (m, 1H); 3.17-3.08 (m, 1H); 2.92 (d, 2H); 2.86-2.78 (m, 1H); 2.72-2.60 (m, 1H); 2.52-2.44 (m, 1H); 2.50 (t, 2H); 2.34-2.04 (m, 2H); 2.32 (s, 3H); 2.18 (s, 3H); 2.01 (s, 3H); 1.82-1.67 (m, 2H); 1.50 (s, 9H); 1.00 (t, 3H).

ESI-MS m/z: Calcd. for $C_{47}H_{54}N_4O_{12}S$: 898.3 Found $(M+H^+)$: 899.3.

Example 97

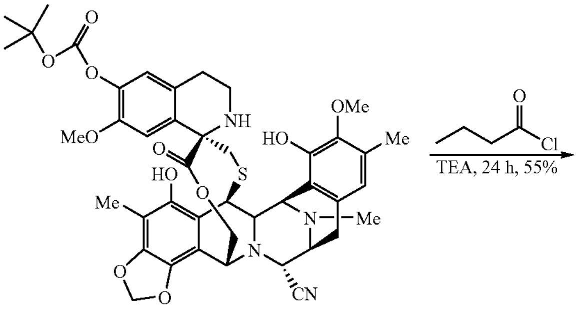

106

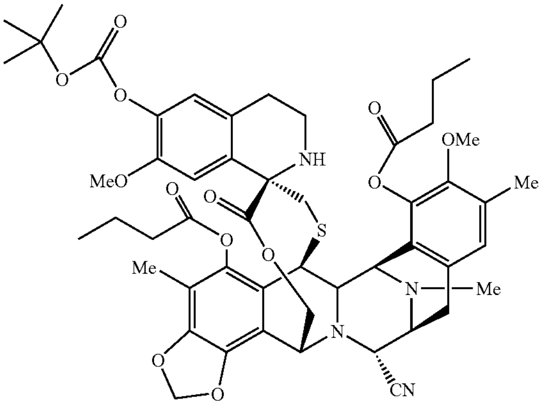

112

Compound 111 is also isolated as minor compound in these reaction conditions (10 equiv. of butyryl chloride and 10 equiv. of TEA).

112 was obtained using Method B. $^1$H-NMR (300 MHz, $CDCl_3$): δ 6.93 (s, 1H); 6.69 (s, 1H); 6.54 (s, 1H); 6.05 (s, 1H); 5.97 (s, 1H); 4.99 (d, 1H); 4.54 (s, 1H); 4.32 (s, 1H); 4.16 (d, 1H); 4.07 (dd, 1H); 3.79 (d, 1H); 3.74 (s, 3H); 3.69-3.31 (m, 1H); 3.58 (s, 3H); 3.52 (d, 1H); 3.43 (s, 1H); 3.18-3.08 (m, 1H); 2.98 (d, 2H); 2.85-2.79 (m, 1H); 2.68-2.44 (m, 2H); 2.60 (t, 2H); 2.55 (t, 2H); 2.31 (s, 3H); 2.14 (s, 3H); 2.02 (s, 3H); 1.89-1.74 (m, 4H); 1.50 (s, 9H); 1.08 (t, 3H); 1.01 (t, 3H).

$^{13}$C-NMR (75 MHz, $CDCl_3$): δ 172.1, 171.3, 151.8, 148.8, 148.2, 145.7, 143.9, 141.5, 140.3, 139.1, 132.4, 131.7, 130.9, 128.8, 127.4, 124.6, 122.4, 120.8, 119.9, 118.1, 114.0, 112.0, 105.0, 102.2, 83.7, 61.2, 60.3, 59.9, 59.6, 56.1, 55.4, 54.5, 42.6, 42.2, 41.8, 39.8, 36.3, 36.0, 29.9, 28.7, 27.8, 24.3, 18.9, 18.5, 16.0, 14.1, 14.0, 10.0.

ESI-MS m/z: Calcd. for $C_{51}H_{60}N_4O_{13}S$: 968.3 Found $(M+H^+)$: 969.3.

Example 98
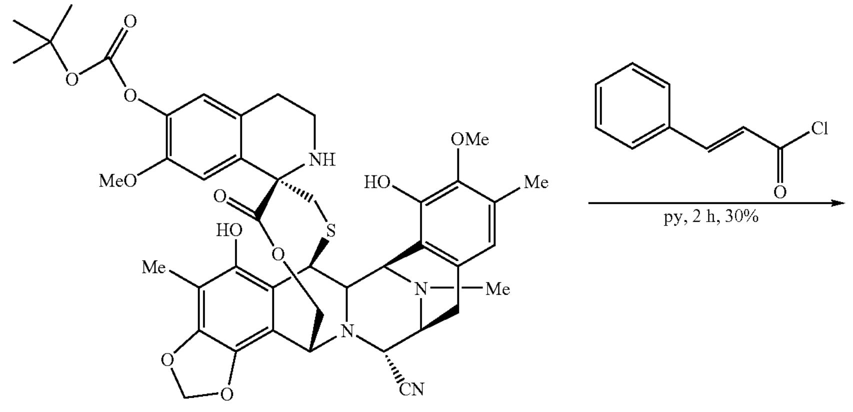
106
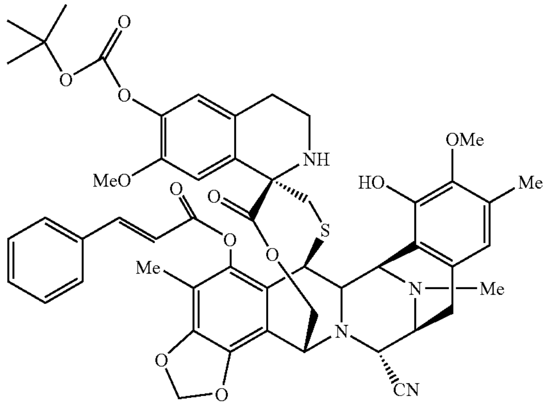
113
113 was obtained using Method B. $^{1}$H-NMR (300 MHz, $CDCl_3$): δ 7.88 (d, 1H); 7.62-7.58 (m, 2H); 7.47-7.44 (m, 3H); 6.70 (s, 1H); 6.59 (d, 1H); 6.58 (s, 1H); 6.54 (s, 1H); 6.03 (dd, 2H); 5.42 (s, 1H); 5.01 (d, 1H); 4.58 (s, 1H); 4.36 (s, 1H); 4.26 (dd, 1H); 4.19 (d 1H); 4.12 (dd, 1H); 3.61 (s, 3H); 3.55 (d, 1H); 3.46 (s, 3H); 3.43-3.40 (m, 1H); 3.16-3.08 (m, 1H); 2.92 (d, 2H); 2.86-2.78 (m, 1H); 2.72-2.60 (m, 1H); 2.52-2.44 (m, 1H); 2.34-2.04 (m, 2H); 2.47 (s, 3H); 2.17 (s, 3H); 2.08 (s, 3H); 1.50 (s, 9H).
$^{13}$C-NMR (75 MHz, $CDCl_3$): δ 172.2, 151.8, 148.8, 147.9, 145.6, 143.2, 141.3, 141.6, 140.4, 139.1, 134.4, 132.6, 131.0, 129.6, 129.3, 129.1, 128.8, 128.4, 122.4, 121.5, 120.7, 118.3, 118.1, 116.8, 114.3, 112.1, 102.1, 83.6, 65.2, 61.4, 60.2, 59.9, 59.5, 55.4, 54.8, 54.7, 42.4, 42.3, 41.8, 39.8, 29.9, 28.7, 27.8, 24.3, 15.9, 10.0.
ESI-MS m/z: Calcd. for $C_{52}H_{54}N_4O_{12}S$: 958.3 Found: $(M+H^+)$: 959.3.
Example 99
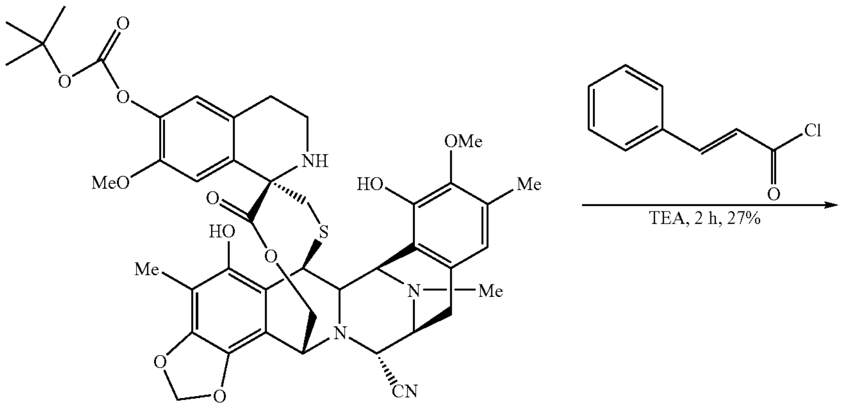
106

-continued
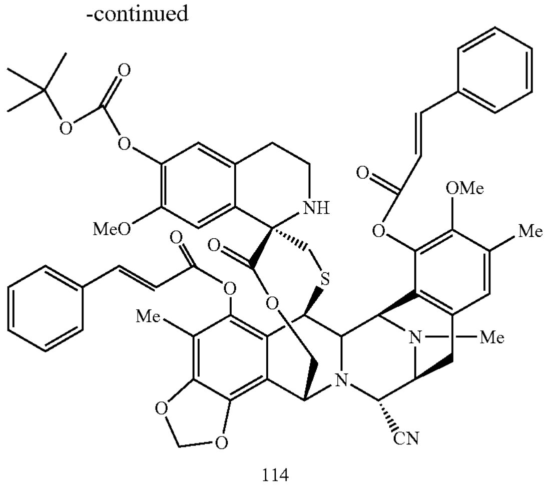
114
114 was obtained using Method B. $^1$H-NMR (300 MHz, $CDCl_3$): δ 7.85 (d, 2H); 7.55-7.21 (m, 10H); 6.93 (s, 1H); 6.73 (s, 1H); 6.70-6.50 (m, 2H); 6.56 (s, 1H); 6.09 (s, 1H); 5.99 (s, 1H); 5.03 (d, 1H); 4.53 (s, 1H); 4.39 (s, 1H); 4.21 (d, 1H); 4.11 (dd 1H); 3.91 (d, 1H); 3.61 (s, 3H); 3.45 (s, 3H); 3.20-3.11 (m, 1H); 2.99 (d, 2H); 2.74-2.65 (m, 1H); 2.53-2.47 (m, 1H); 2.28 (s, 3H); 2.17 (s, 3H); 2.11 (s, 3H); 1.52 (s, 9H).
$^{13}$C-NMR (75 MHz, $CDCl_3$): δ 172.1, 164.7, 164.3, 151.8, 148.8, 148.4, 147.5, 147.4, 145.9, 143.5, 141.5, 140.6, 139.1, 134.3, 133.9, 132.4, 131.7, 131.2, 131.0, 130.9, 129.2, 129.1, 128.9, 128.5, 128.3, 127.3, 124.5, 122.5, 121.3, 118.0, 116.6, 116.2, 114.3, 112.0, 102.2, 83.7, 65.4, 61.4, 60.2, 59.7, 59.2, 55.7, 55.3, 54.6, 42.7, 41.8, 39.9, 32.1, 31.8, 29.9, 29.6, 28.8, 27.8, 22.8, 16.0, 14.3, 10.1.
ESI-MS m/z: Calcd. for $C_{61}H_{60}N_4O_{13}S$: 1088.3 Found ($M+H^+$): 1089.4.
Example 100
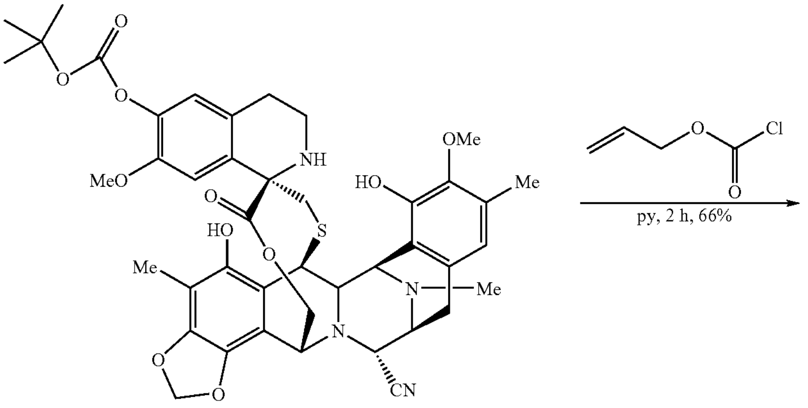
106
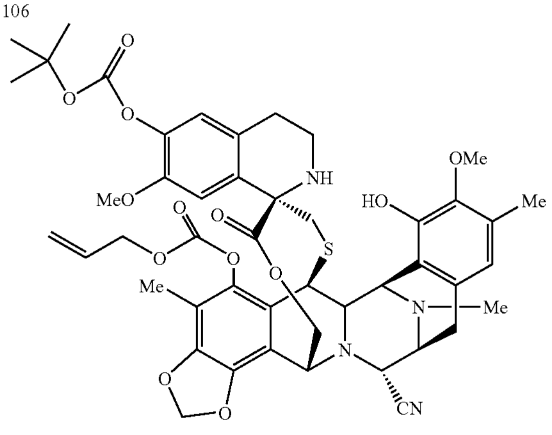
115

115 was obtained using Method B. $^1$H-NMR (300 MHz, $CDCl_3$): δ 6.69 (s, 1H); 6.58 (s, 2H); 6.04 (d, 1H); 5.99 (d, 1H); 5.96-5.85 (m, 1H); 5.71 (s, 1H); 5.38 (dd, 1H); 5.27 (dd, 1H); 5.00 (d, 1H); 4.67 (s, 1H); 4.64-4.61 (m, 2H); 4.30 (s, 1H); 4.28 (dd, 1H); 4.17 (d, 1H); 4.11 (dd, 1H); 3.77 (s, 3H); 3.58 (s, 3H); 3.50 (d, 1H); 3.41 (s, 1H); 3.16-3.08 (m, 1H); 2.93 (d, 2H); 2.81-2.74 (m, 1H); 2.69-2.59 (m, 1H); 2.51-2.45 (m, 1H); 2.39 (d, 1H); 2.31 (s, 3H); 2.21-2.16 (m, 1H); 2.19 (s, 3H); 2.09 (s, 3H); 1.50 (s, 9H).
$^{13}$C-NMR (75 MHz, $CDCl_3$): δ 172.3, 15.5, 151.8, 148.7, 148.1, 145.6, 143.2, 141.4, 140.5, 139.1, 132.7, 131.4, 130.9,
129.5, 128.8, 122.5, 121.5, 120.7, 119.1, 118.3, 118.2, 114.2, 113.5, 112.0, 102.2, 83.7, 69.4, 64.9, 61.3, 60.5, 60.2, 59.8, 55.4, 54.9, 54.8, 42.6, 41.8, 41.7, 39.7, 29.9, 28.8, 27.8, 24.3, 16.0, 9.5.
ESI-MS m/z: Calcd. for $C_{47}H_{52}N_4O_{13}S$: 912.3 Found ($M+H^+$): 913.3.
Example 101
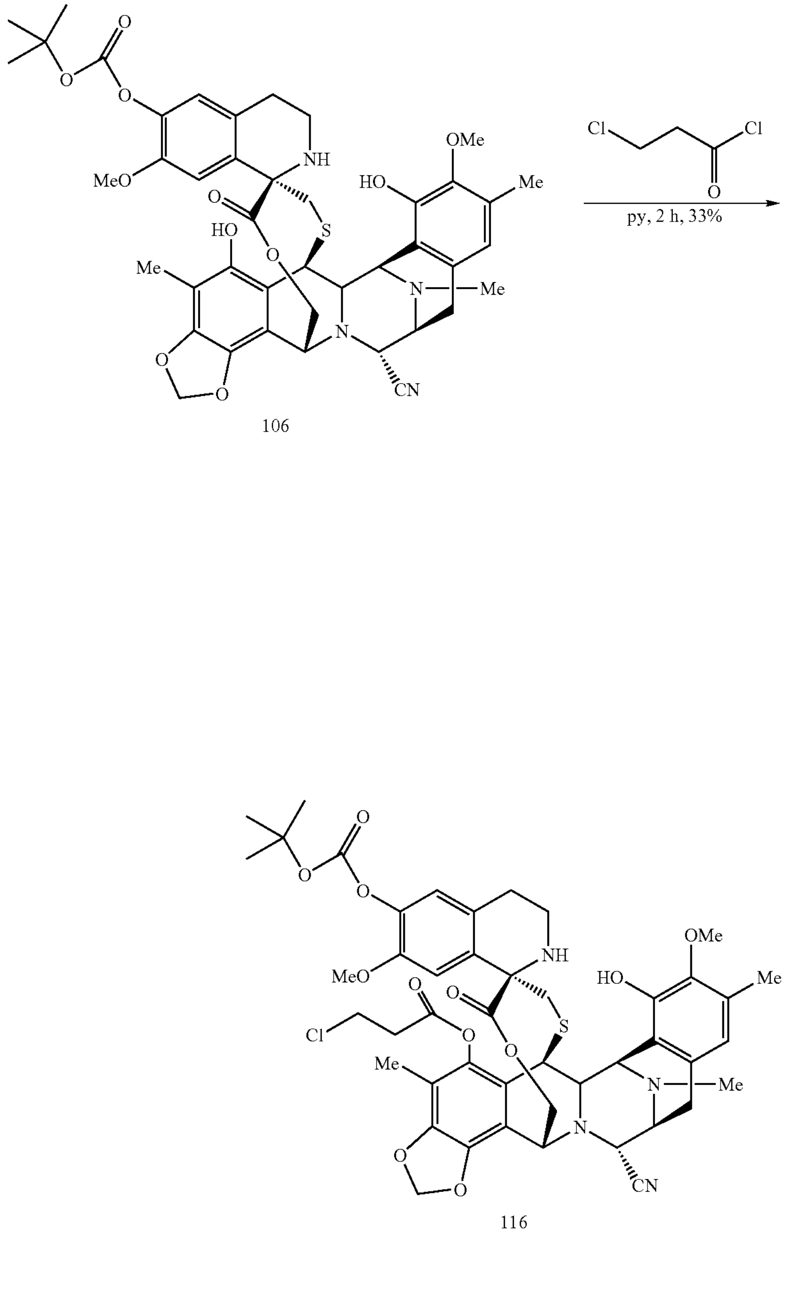
106
116

116 was obtained using Method B. $^1$H-NMR (300 MHz, $CDCl_3$): δ 6.69 (s, 1H); 6.58 (s, 1H); 6.56 (s, 1H); 6.05 (d, 1H); 5.98 (d, 1H); 5.74 (s, 1H); 5.00 (d, 1H); 4.52 (s, 1H); 4.32 (s, 1H); 4.27 (d, 1H); 4.17 (d, 1H); 4.09 (dd, 1H); 3.84 (ddd, 2H); 3.79 (s, 3H); 3.58 (s, 3H); 3.50 (d, 1H); 3.41 (s, 1H); 3.12-3.02 (m, 1H); 3.04 (t, 2H); 2.93 (d, 2H); 2.81-2.75 (m, 1H); 2.69-2.58 (m, 1H); 2.50-2.44 (m, 1H); 2.31 (s, 3H); 2.18 (s, 3H); 2.04 (s, 3H); 1.50 (s, 9H).
ESI-MS m/z: Calcd. for $C_{46}H_{51}ClN_4O_{12}S$: 918.3 Found ($M+H^+$): 919.7.
Example 102
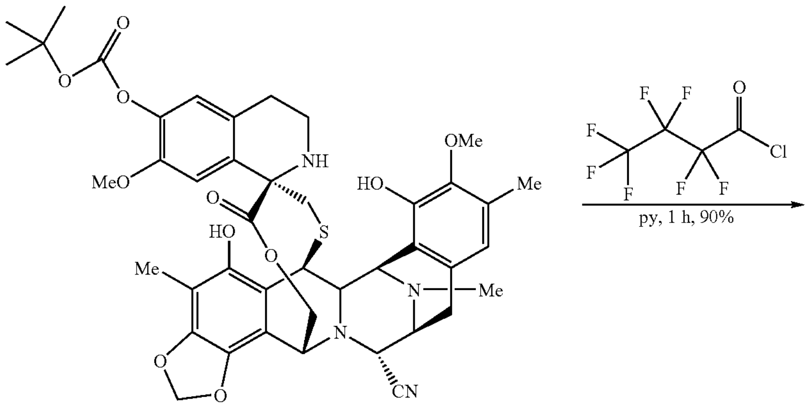
106
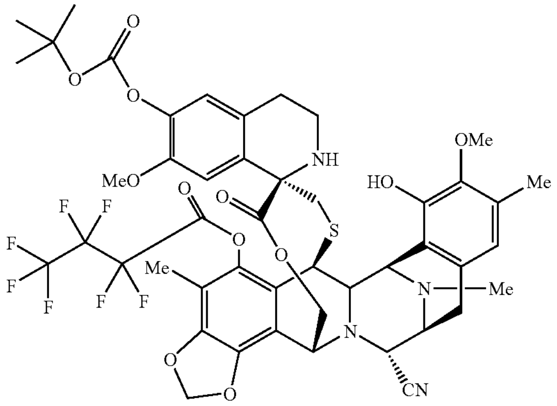
117

117 was obtained using Method B. $^1$H-NMR (300 MHz, $CDCl_3$): δ 6.70 (s, 1H); 6.58 (s, 1H); 6.54 (s, 1H); 6.11 (d, 1H); 6.04 (d, 1H); 5.67 (s, 1H); 5.02 (d, 1H); 4.46 (s, 1H); 4.33 (s, 2H); 4.29 (d, 1H); 4.20 (s, 1H); 4.11 (dd, 1H); 3.73 (s, 3H); 3.58 (s, 3H); 3.51 (d, 1H); 3.44 (s, 1H); 3.21-3.11 (m, 1H); 3.05-2.93 (m, 2H); 2.84-2.78 (m, 1H); 2.68-2.60 (m, 1H); 2.52-2.47 (m, 1H); 2.35 (s, 3H); 2.20 (s, 2H); 2.14 (s, 3H); 2.04 (s, 3H); 1.50 (s, 9H).

ESI-MS m/z: Calcd. for $C_{47}H_{47}F_7N_4O_{12}S$: 1024.3 Found $(M+H^+)$: 1025.2.

Example 103

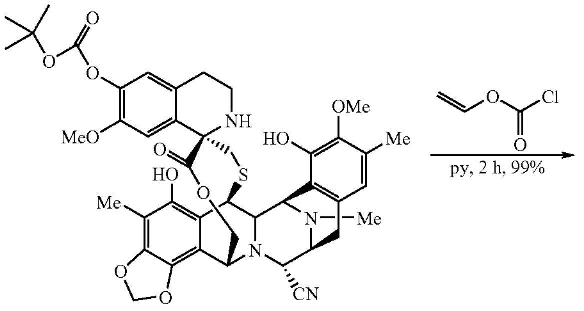

106

-continued

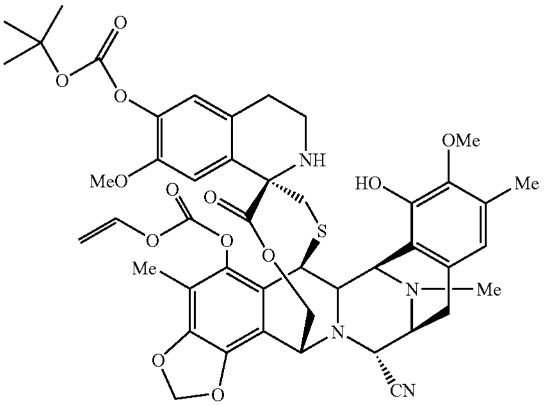

118

118 was obtained using Method B $^1$H-NMR (300 MHz, $CDCl_3$): δ 6.98 (dd, 1H); 6.70 (s, 1H); 6.59 (s, 1H); 6.58 (s, 1H); 6.06 (d, 1H); 5.99 (d, 1H); 5.74 (s, 1H); 5.01 (d, 1H); 4.98 (dd, 1H); 4.65 (s, 1H); 4.60 (dd, 1H); 4.31 (s, 2H); 4.28 (d, 1H); 4.18 (s, 1H); 4.12 (dd, 1H); 3.75 (s, 3H); 3.58 (s, 3H); 3.50 (d, 1H); 3.41 (s, 1H); 3.18-3.10 (m, 1H); 2.93 (d, 2H); 2.81-2.74 (m, 1H); 2.68-2.58 (m, 1H); 2.51-2.46 (m, 1H); 2.38 (d, 1H); 2.31 (s, 3H); 2.20 (s, 3H); 2.10 (s, 3H); 1.50 (s, 9H).

ESI-MS m/z: Calcd. for $C_{46}H_{51}N_4O_{13}S$: 898.3 Found $(M+H^+)$: 899.3.

Example 104

Method C: To a solution of 1 equiv. of compound 106 in $CH_2Cl_2$ (0.032M) under Argon were added 2 equiv. of acid, 2 equiv. of DMAP and 2 equiv. of EDC.HCl. The reaction was stirred at room temperature for 2 h. After this time was diluted with $CH_2Cl_2$, washed with brine and the organic layer dried with $Na_2SO_4$. Flash chromatography gives pure compounds.

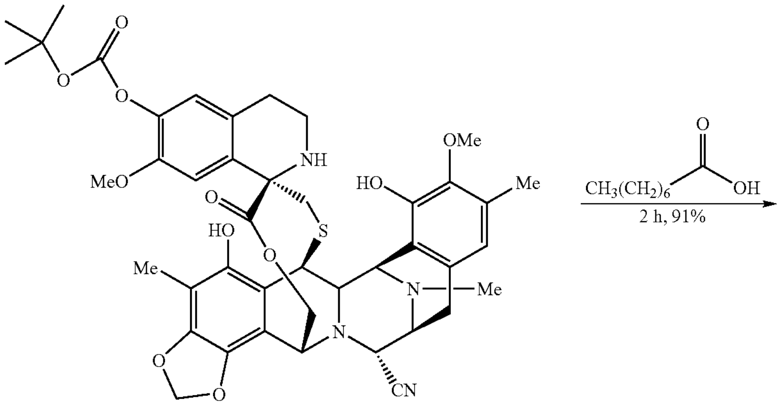

106

-continued
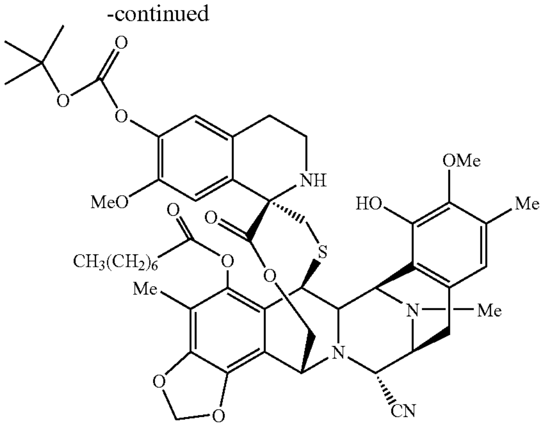
119
119 was obtained using Method C. $^{1}$H-NMR (300 MHz, $CDCl_3$): δ 6.68 (s, 1H); 6.58 (s, 1H); 6.56 (s, 1H); 6.00 (dd, 2H); 5.66 (s, 1H); 4.99 (d, 1H); 4.53 (s, 1H); 4.31 (s, 1H); 4.26 (dd, 1H); 4.16 (d, 1H); 4.09 (dd, 1H); 3.77 (s, 3H); 3.57 (s, 3H); 3.51 (d, 1H); 3.42-3.40 (m, 1H); 3.16-3.05 (m, 1H); 2.93 (d, 2H); 2.82-2.74 (m, 1H); 2.69-2.58 (m, 1H); 2.51-2.44 (m, 1H); 2.53 (t, 2H); 2.34-2.14 (m, 2H); 2.31(s, 3H); 2.18 (s, 3H); 2.01 (s, 3H); 1.75-1.70 (m, 2H); 1.50 (s, 9H); 1.35-1.25 (m, 11H).
$^{13}$C-NMR (75 MHz, $CDCl_3$): δ 172.0, 170.8, 151.5, 148.5, 147.7, 145.3, 143.0, 141.4, 141.3, 140.0, 138.9, 132.4, 130.8, 129.2, 128.6, 122.1, 121.0, 120.6, 118.2, 118.0, 113.9, 111.9, 101.9, 83.3, 64.8, 61.0, 60.2, 60.1, 59.7, 59.6, 55.2, 54.7, 54.6, 42.3, 41.8, 41.5, 39.6, 33.9, 31.6, 29.6, 29.3, 28.9, 28.6, 27.5, 24.8, 24.2, 22.5, 15.7, 14.0, 9.7.
ESI-MS m/z: Calcd. for $C_{51}H_{62}N_4O_{12}S$: 954.4 Found ($M+H^+$): 955.5.
Example 105
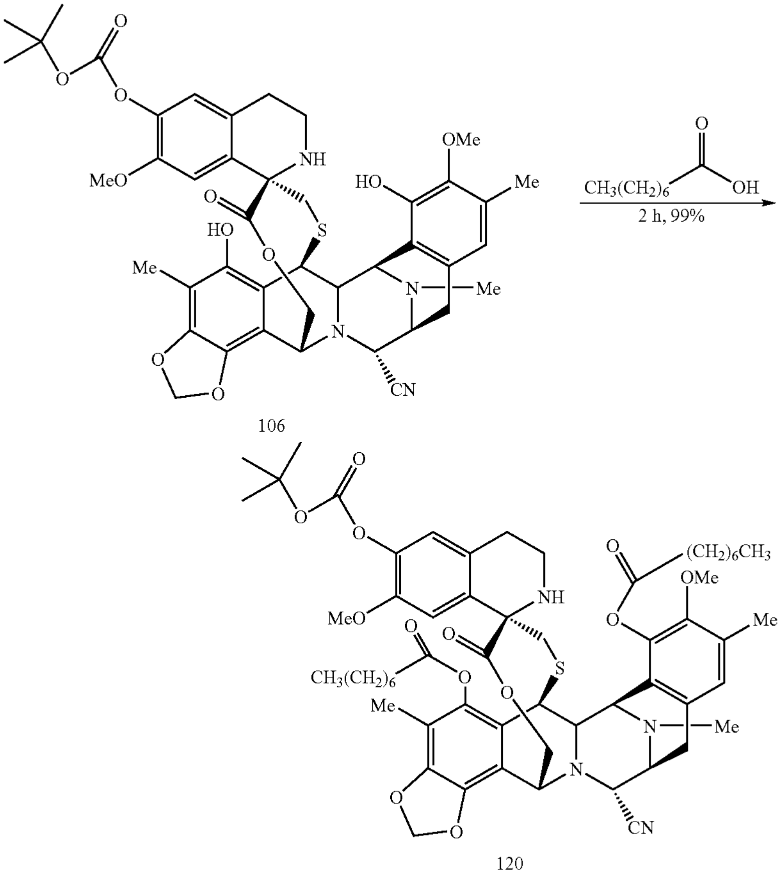
106
120

120 is obtained with 10 equiv. of each reagent (Method C).

$^1$H-NMR (300 MHz, $CDCl_3$): δ 6.93 (s, 1H); 6.69 (s, 1H); 6.54 (s, 1H); 6.00 (dd, 2H); 4.99 (d, 1H); 4.44 (s, 1H); 4.31 (s, 1H); 4.16 (d, 1H); 4.09 (dd, 1H); 3.86 (d, 1H); 3.73 (s, 3H); 3.57 (s, 3H); 3.50 (d, 1H); 3.44-3.42 (m, 1H); 3.16-3.05 (m, 1H); 2.97 (d, 2H); 2.84-2.79 (m, 1H); 2.64-2.44 (m, 6H); 2.35-2.15 (m, 2H); 2.31 (s, 3H); 2.14 (s, 3H); 2.02 (s, 3H); 1.94-1.58 (m, 8H); 1.50 (s, 9H); 1.38-1.18 (m, 18H).

$^{13}$C-NMR (75 MHz, $CDCl_3$): δ 172.2, 171.4 170.8, 151.8, 148.8, 148.2, 145.7, 143.9, 141.5, 140.4, 139.1, 132.5, 131.6, 130.8, 128.8, 127.4, 124.7, 122.4, 120.9 118.0, 114.1, 112.1, 102.2, 83.6, 65.1, 61.3, 60.3, 60.2, 59.9, 59.5, 56.1, 55.4, 54.6, 42.6, 42.2, 41.8, 39.8, 34.4, 34.1, 31.8, 29.6, 29.5, 29.2, 29.1, 29.0, 28.8, 27.8, 25.4, 24.9, 22.8, 16.0, 14.2, 9.9.

ESI-MS m/z: Calcd. for $C_{59}H_{76}N_4O_{13}S$: 1080.5 Found (M+H$^+$): 1081.3.

Example 106

2.69-2.44 (m, 2H); 2.53 (t, 2H); 2.35-2.15 (m, 2H); 2.31 (s, 3H); 2.18 (s, 3H); 2.01 (s, 3H); 1.74-1.69 (m, 2H); 1.50 (s, 9H); 1.38-1.10 (m, 27H).

$^{13}$C-NMR (75 MHz, $CDCl_3$): δ 172.0, 171.8, 148.4, 148.0, 145.5, 143.2, 141.6, 140.2, 139.1, 137.4, 132.6, 131.0, 129.5, 128.8, 122.4, 121.2, 120.9, 118.3, 114.2, 112.1, 102.0, 65.1, 61.3, 60.5, 60.3, 59.9, 59.8, 55.4, 54.9, 54.8, 42.5, 42.0, 41.8, 39.8, 34.2, 32.1, 29.9, 29.7, 29.6, 29.5, 28.8, 27.8, 25.1, 24.4, 22.8, 16.0, 14.3, 9.9.

ESI-MS m/z: Calcd. for $C_{59}H_{78}N_4O_{12}S$: 1066.5 Found (M+H$^+$): 1067.4.

122: $^1$H-NMR (300 MHz, $CDCl_3$): δ 6.94 (s, 1H); 6.70 (s, 1H); 6.55 (s, 1H); 6.02 (dd, 2H); 5.00 (d, 1H); 4.46 (s, 1H); 4.33 (s, 1H); 4.18 (d, 1H); 4.09 (dd, 1H); 3.79 (d, 1H); 3.74 (s, 3H); 3.58 (s, 3H); 3.52 (d, 1H); 3.46-3.43 (m, 1H); 3.15-3.05

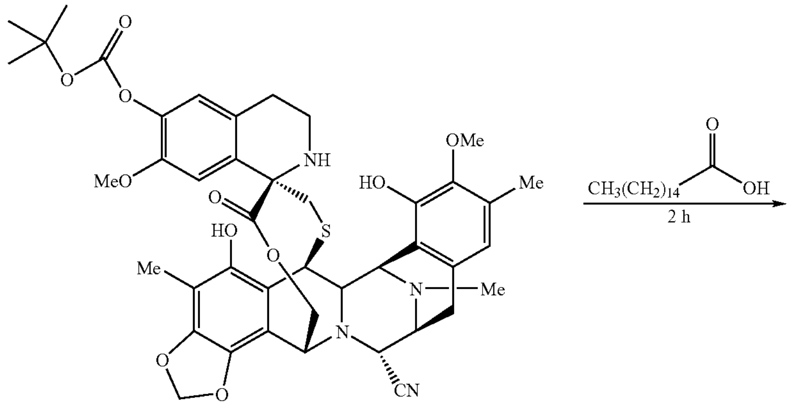

106

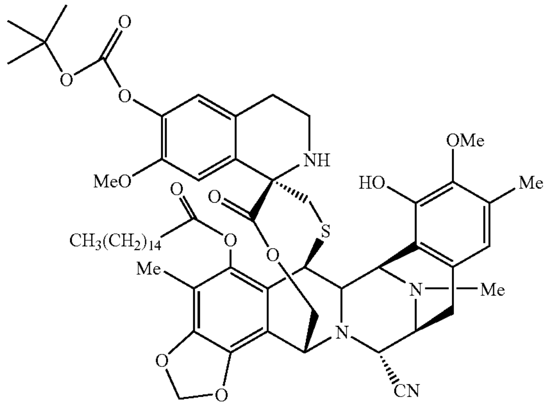

121
67%

+

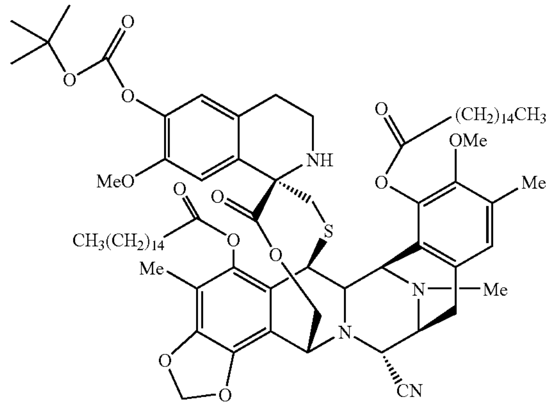

122
24%

It was used 1 equiv. of palmitic acid (Method C).

121: $^1$H-NMR (300 MHz, $CDCl_3$): δ 6.68 (s, 1H); 6.58 (s, 1H); 6.56 (s, 1H); 6.00 (dd, 2H); 5.66 (s, 1H); 4.99 (d, 1H); 4.53 (s, 1H); 4.31 (s, 1H); 4.26 (dd, 1H); 4.16 (d, 1H); 4.09 (dd, 1H); 3.77 (s, 3H); 3.58 (s, 3H); 3.51 (d, 1H); 3.42-3.40 (m, 1H); 3.16-3.08 (m, 1H); 2.93 (d, 2H); 2.84-2.76 (m, 1H); (m, 1H); 2.99-2.97 (m, 2H); 2.68-2.45 (m, 7H); 2.36-2.11 (m, 2H); 2.32 (s, 3H); 2.15 (s, 3H); 2.03 (s, 3H); 1.86-1.60 (m, 4H); 1.50 (s, 9H); 1.40-1.10 (m, 54H).

ESI-MS m/z: Calcd. for $C_{75}H_{108}N_4O_{13}S$: 1302.7 Found (M+H$^+$): 1303.6.

Example 107
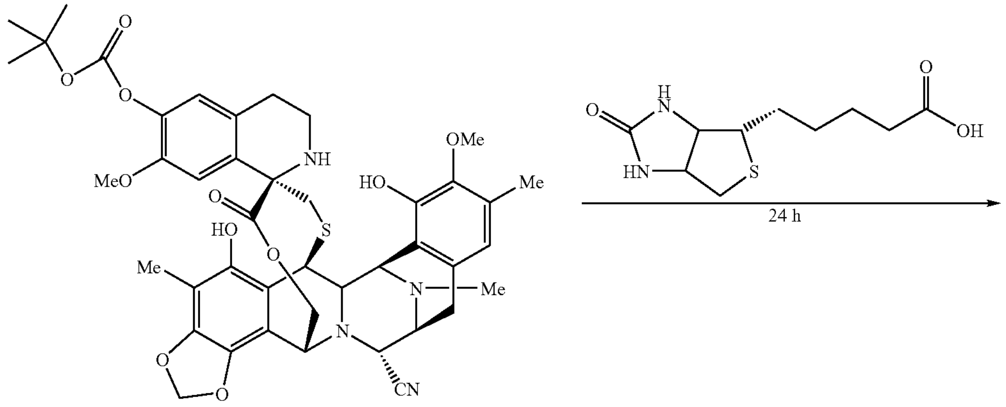
106
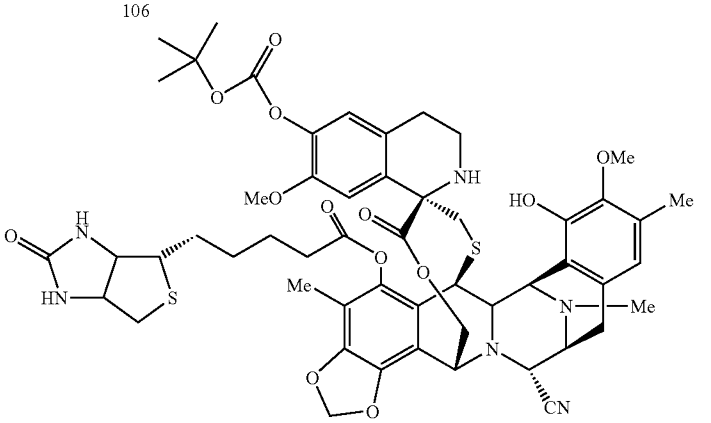
\+
123
51%
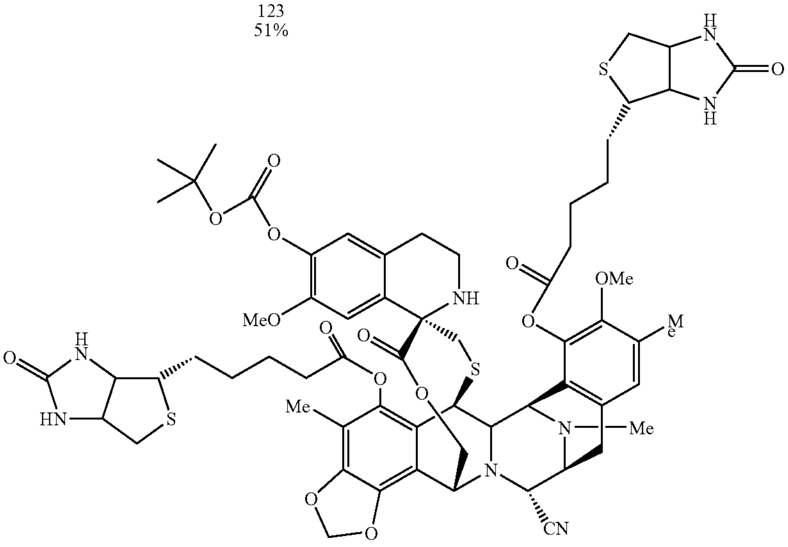
124
Compound 124 is isolated impurified with DMAP.
123 was obtained using Method C: $^{1}$H-NMR (300 MHz, $CDCl_3$): δ 7.74 (s, 1H); 6.96 (s, 1H); 6.69 (s, 1H); 6.54 (s, 2H); 6.04 (d, 1H); 5.96 (d, 1H); 5.09(s, 1H); 5.00 (d, 1H); 4.51-4.48 (m, 2H); 4.34 (s, 2H); 4.30 (d, 1H); 4.19 (d, 1H); 4.06 (dd, 1H); 3.75 (s, 3H); 3.57 (s, 3H); 3.52 (d, 1H); 3.41 (s, 1H); 3.19-3.08 (m, 2H); 2.92-2.80 (m, 3H); 2.75-2.44 (m, 5H); 2.29 (s, 3H); 2.17 (s, 3H); 2.01 (s, 3H); 2.82-1.66 (m, 6H); 1.50 (s, 9H).
ESI-MS m/z: Calcd. for $C_{53}H_{62}N_6O_{13}S_2$: 1055.2 Found $(M+H^+)$: 1056.3.
124 was obtained using Method C: ESI-MS m/z: Calcd. for $C_{63}H_{76}N_8O_{15}S_3$: 1281.5 Found $(M+H^+)$: 1282.4.

Example 108

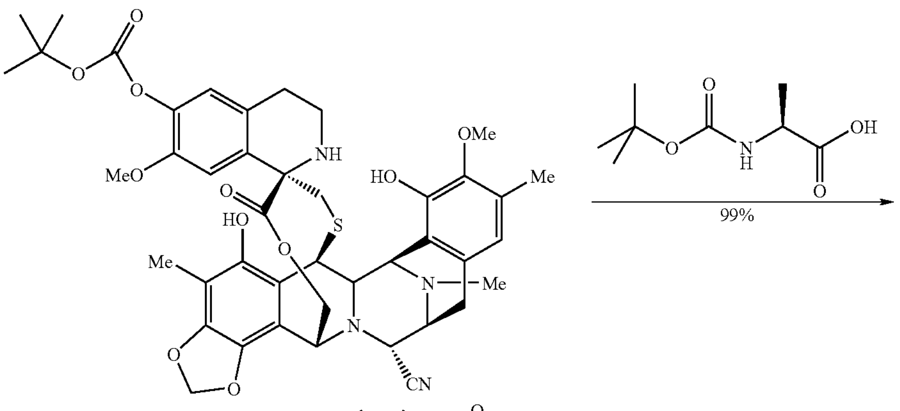

106

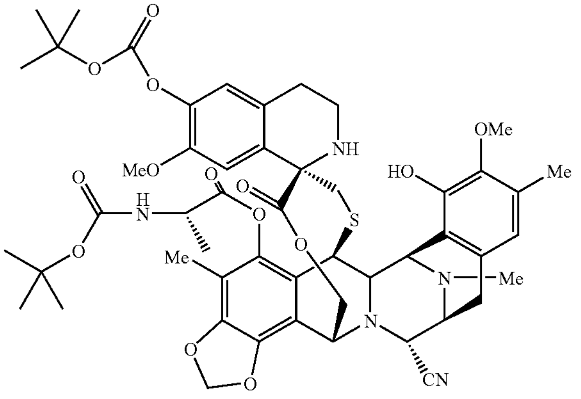

125

125 was obtained using Method C $^{1}$H-NMR (300 MHz, $CDCl_3$): δ 6.69 (s, 1H); 6.55 (s, 2H); 6.05 (d, 1H); 5.97 (d, 1H); 5.00 (d, 1H); 4.61 (t, 1H); 4.51 (s, 1H); 4.34 (s, 1H); 4.27 (d, 1H); 4.18 (d, 1H); 4.12-4.06 (m, 2H); 3.76 (s, 3H); 3.57 (s, 3H); 3.50 (d, 1H); 3.42 (s, 1H); 3.14-3.06 (m, 1H); 2.92 (d, 1H); 2.84-2.80 (m, 1H); 2.69-2.60 (m, 1H); 2.50-2.45 (m, 1H); 2.30 (s, 3H); 2.17 (s, 3H); 2.02 (s, 3H); 1.61 (d, 3H); 1.50 (s, 9H); 1.43 (s, 9H).

ESI-MS m/z: Calcd. for $C_{51}H_{61}N_5O_{14}S$: 999.4 Found ($M+H^+$): 1000.3.

Example 109

Method E: To a solution of 1 equiv. of compound 106 in DMF (0.032M) under Argon at room temperature were added 2 equiv. of $Cs_2CO_3$ and 2 equiv. of the alkyl bromide. The reaction was followed by TLC and quenched with $NaHCO_3$, extracted with $CH_2Cl_2$ and the organic layers dried with $Na_2SO_4$. Flash chromatography gives pure compounds.

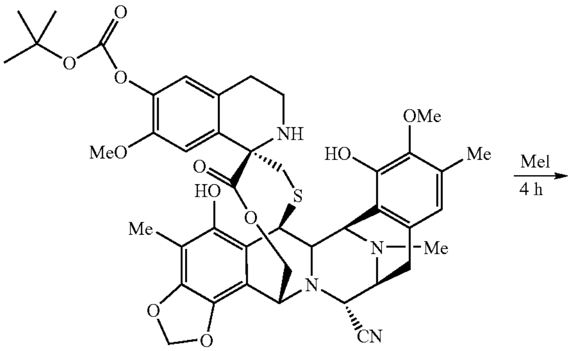

106

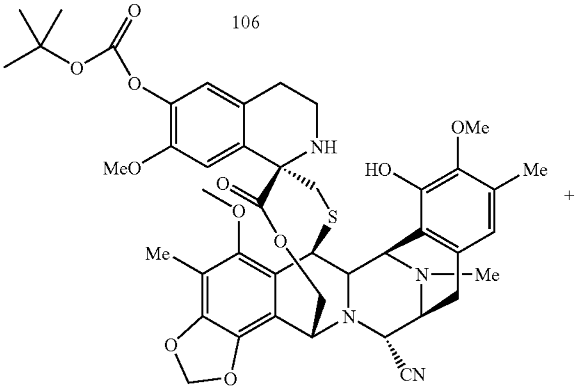

126

45%

-continued

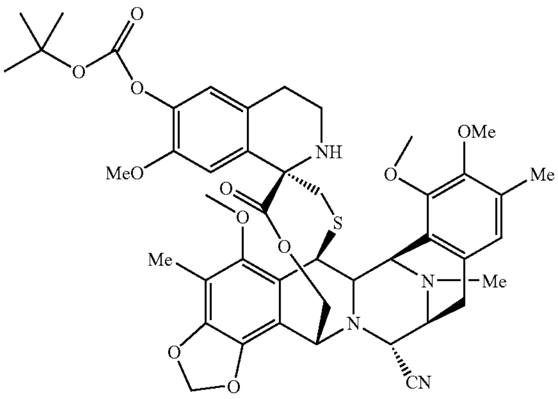

127
15%

126: was obtained using Method E $^1$H-NMR (300 MHz, $CDCl_3$): δ 6.70 (s, 1H); 6.58 (s, 2H); 5.97 (d, 1H); 5.90 (d, 1H); 5.79 (s, 1H); 5.00 (d, 1H); 4.88 (s, 1H); 4.30-4.29 (m, 3H); 4.15-4.11 (m, 2H); 3.85-3.82 (m, 2H); 3.80 (s, 3H); 3.58 (s, 3H); 3.51 (d, 1H); 3.40 (s, 1H); 3.12-3.00 (m, 1H); 2.92 (d, 2H); 2.83-2.79 (m, 1H); 2.67-2.60 (m, 1H); 2.50-2.44 (m, 1H); 2.31 (s, 3H); 2.28-2.37 (m, 1H); 2.20 (s, 3H); 2.18 (s, 3H); 1.50 (s, 9H).

ESI-MS m/z: Calcd. for $C_{44}H_{50}N_4O_{11}S$: 842.3 Found ($M+H^+$): 843.4.

127 was obtained using Method E: $^1$H-NMR (300 MHz, $CDCl_3$): δ 6.75 (s, 1H); 6.71 (s, 1H); 6.58 (s, 1H); 5.98 (s, 1H); 5.91 (s, 1H); 5.01 (d, 1H); 4.81 (s, 1H); 4.29 (s, 1H); 4.26 (dd, 1H); 4.15 (s, 1H); 4.13 (dd, 1H); 3.96 (s, 3H); 3.85-3.74 (m, 1H); 3.83 (s, 3H); 3.74 (s, 3H); 3.58 (s, 3H); 3.50 (d, 1H); 3.41 (s, 1H); 3.10-3.04 (m, 1H); 2.93 (d, 2H); 2.85-2.80 (m, 1H); 2.70-2.59 (m, 1H); 2.51-2.44 (m, 1H); 2.31-2.20 (m, 1H); 2.28 (s, 3H); 2.24 (s, 3H); 2.18 (s, 3H); 1.51 (s, 9H).

ESI-MS m/z: Calcd. for $C_{45}H_{52}N_4O_{11}S$: 856.3 Found ($M+H^+$): 857.3.

Example 110

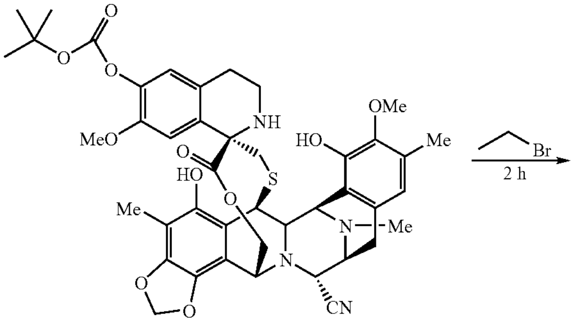

106

-continued

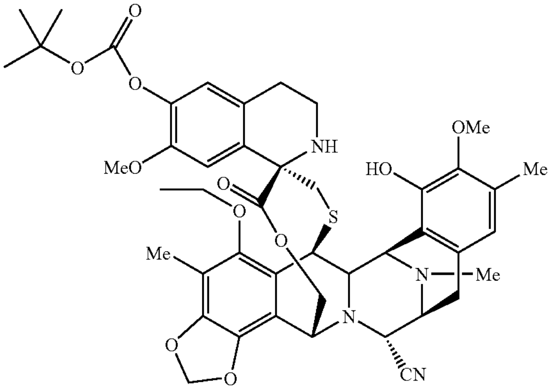

+

128
19%

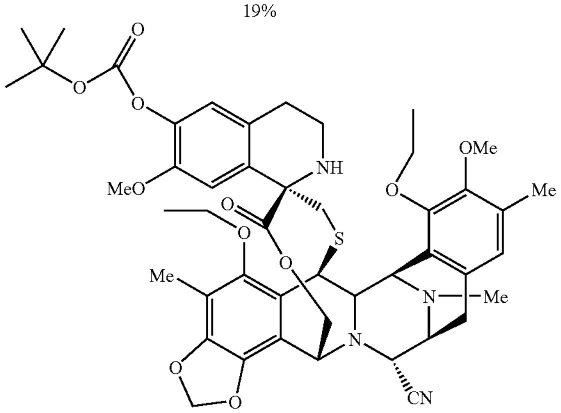

129
6%

Compound 106 (15%) is recovered after chromatographic purification.

128: was obtained using Method E. $^1$H-NMR (300 MHz, $CDCl_3$): δ 6.70 (s, 1H); 6.59 (s, 1H); 6.58 (s, 1H); 5.97 (s, 1H); 5.90 (s, 1H); 5.75 (s, 1H); 5.01 (d, 1H); 4.91 (s, 1H); 4.29 (s, 2H); 4.16 (s, 1H); 4.14 (dd, 1H); 3.82 (q, 2H); 3.80 (s, 3H); 3.58 (s, 3H); 3.50 (d, 1H); 3.41 (s, 1H); 3.11-3.03 (m, 1H); 2.92 (d, 2H); 2.84-2.80 (m, 1H); 2.70-2.60 (m, 1H); 2.50-2.45 (m, 1H); 2.31 (s, 3H); 2.23 (s, 2H); 2.20 (s, 3H); 2.17 (s, 3H); 1.50 (s, 9H); 1.39 (t, 3H).

ESI-MS m/z: Calcd. for $C_{45}H_{52}N_4O_{11}S$: 856.3 Found ($M+H^+$): 857.3.

129 was obtained using Method E: $^1$H-NMR (300 MHz, $CDCl_3$): δ 6.75 (s, 1H); 6.70 (s, 1H); 6.58 (s, 1H); 5.97 (d, 1H); 5.91 (d, 1H); 5.00 (d, 1H); 4.87 (s, 1H); 4.29-4.26 (m, 2H); 4.1-4.13 (m, 2H); 3.89-3.81 (m, 4H); 3.85 (s, 3H); 3.58 (s, 3H); 3.50 (d, 1H); 3.42 (s, 1H); 3.11-3.04 (m, 1H); 2.94 (d, 2H); 2.85-2.80 (m, 1H); 2.70-2.60 (m, 1H); 2.52-2.44 (m, 1H); 2.27 (s, 3H); 2.22 (s, 2H); 2.20 (s, 3H); 2.17 (s, 3H); 1.51 (s, 9H); 1.41 (t, 3H); 1.40 (t, 3H).

$^{13}$C-NMR (75 MHz, $CDCl_3$): δ 172.0, 151.8, 151.0, 149.6, 149.0, 148.7, 145.8, 139.0, 138.7, 132.6, 131.4, 130.5, 129.0, 124.7, 124.3, 122.5, 122.0, 118.3, 114.0, 113.2, 111.9, 101.7, 83.7, 69.2, 68.2, 65.6, 61.7, 60.6, 60.3, 59.7, 59.6, 55.3, 54.9, 42.9, 42.1, 41.9, 39.8, 29.9, 28.9, 27.8, 24.5, 16.4, 16.0, 15.6, 9.8.

ESI-MS m/z: Calcd. for $C_{47}H_{56}N_4O_{11}S$: 884.3 Found ($M+H^+$): 885.5.

Example 111

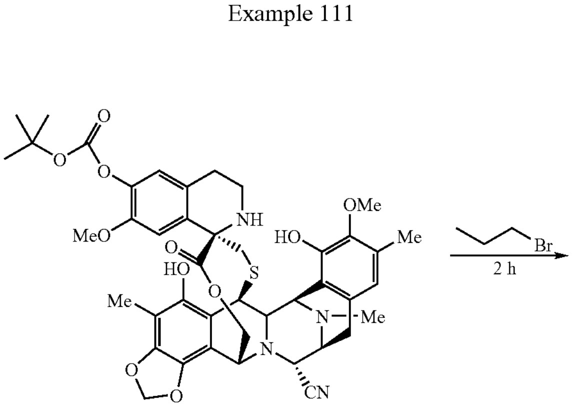

106

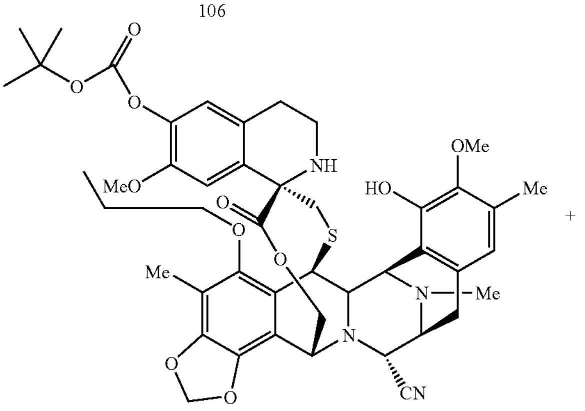

130

17%

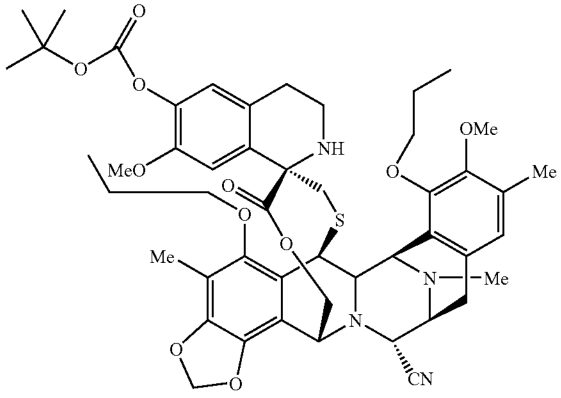

131

6%

Compound 106 (33%) is recovered after chromatographic purification.

130 was obtained using Method E: $^1$H-NMR (300 MHz, $CDCl_3$): δ 6.70 (s, 1H); 6.58 (s, 2H); 5.96 (s, 1H); 5.90 (s, 1H); 5.68 (s, 1H); 5.00 (d, 1H); 4.90 (s, 1H); 4.29 (s, 2H); 4.15 (s, 1H); 4.13 (dd, 1H); 3.85-3.78 (m, 2H); 3.79 (s, 3H); 3.58 (s, 3H); 3.50 (d, 1H); 3.40 (s, 1H); 3.12-3.04 (m, 1H); 2.92 (d, 2H); 2.86-2.80 (m, 1H); 2.71-2.60 (m, 1H); 2.50-2.43 (m, 1H); 2.30 (s, 3H); 2.23 (s, 2H); 2.19 (s, 3H); 2.16 (s, 3H); 1.83-1.76 (m, 2H); 1.50 (s, 9H); 1.06 (t, 3H).

ESI-MS m/z: Calcd. for $C_{46}H_{54}N_4O_{11}S$: 871.3 Found (M+H$^+$): 872.5.

131 was obtained using Method E: $^1$H-NMR (300 MHz, $CDCl_3$): δ 6.75 (s, 1H); 6.70 (s, 1H); 6.58 (s, 1H); 5.97 (d, 1H); 5.90 (d, 1H); 5.00 (d, 1H); 4.88 (s, 1H); 4.28-4.11 (m, 4H); 3.85 (s, 3H); 3.82-3.64 (m, 4H); 3.58 (s, 3H); 3.51 (d, 1H); 3.41 (s, 1H); 3.12-3.05 (m, 1H); 2.94 (d, 2H); 2.86-2.80 (m, 1H); 2.74-2.62 (m, 1H); 2.51-2.46 (m, 1H); 2.27 (s, 3H); 2.22 (s, 2H); 2.20 (s, 3H); 2.16 (s, 3H); 1.81-1.75 (m, 4H); 1.50 (s, 9H); 1.07 (t, 3H); 1.02 (t, 3H).

$^{13}$C-NMR (75 MHz, $CDCl_3$): δ 170.9, 150.6, 150.0, 148.3, 147.8, 147.4, 144.6, 137.8, 137.4, 131.4, 130.1, 129.3, 127.8, 123.4, 123.1, 121.3, 120.7, 117.1, 112.7, 112.0, 110.7, 100.4, 82.4, 73.6, 73.3, 64.4, 60.4, 59.5, 59.1, 58.6, 58.5, 54.1, 54.0, 53.6, 41.8, 40.8, 40.7, 38.6, 28.6, 27.7, 26.5, 23.3, 22.9, 22.4, 14.7, 9.9, 9.4, 8.5.

ESI-MS m/z: Calcd. for $C_{49}H_{60}N_4O_{11}S$: 912.4 Found (M+H$^+$): 913.5.

Example 112

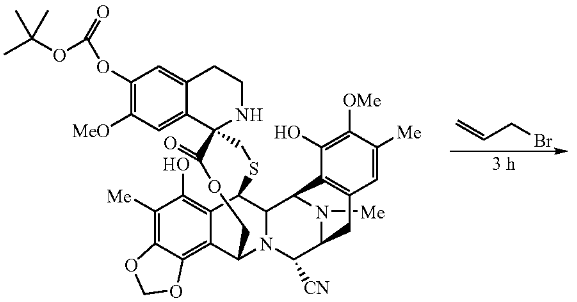

106

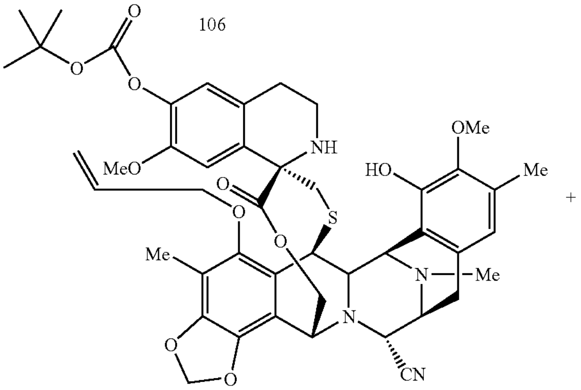

132

27%

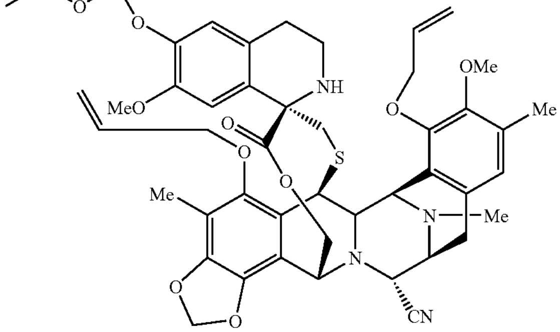

133

39%

With 1 equiv. of allyl bromide and 1 equiv. of cesium carbonate the reaction is complete and other fraction is isolated after chromatographic purification which is a mixture of compound 131 and compound 132 (Method E).

132: $^1$H-NMR (300 MHz, $CDCl_3$): δ 6.70 (s, 1H); 6.58 (s, 2H); 6.15-6.02 (m, 1H); 5.98 (d, 1H); 5.91 (d, 1H); 5.69 (s, 1H); 5.43 (dd, 1H); 5.26 (d, 1H); 5.01 (d, 1H); 4.91 (s, 1H);

4.48 (dd, 1H); 4.29-4.28 (m, 2H); 4.23-4.12 (m, 3H); 3.80 (s, 3H); 3.58 (s, 3H); 3.50 (d, 1H); 3.41 (s, 1H); 3.12-3.03 (m, 1H); 2.95-2.91 (m, 2H); 2.88-2.80 (m, 1H); 2.70-2.60 (m, 1H); 2.50-2.45 (m, 1H); 2.31 (s, 3H); 2.24 (s, 2H); 2.20 (s, 3H); 2.18 (s, 3H); 1.51 (s, 9H).

$^{13}$C-NMR (75 MHz, $CDCl_3$): δ 172.3, 168.5, 152.0, 149.7, 148.9, 148.2, 146.0, 143.5, 139.3, 139.0, 134.0, 132.8, 131.3, 129.7, 129.3, 129.2, 122.7, 122.2, 121.0, 118.5, 118.4, 117.9, 113.9, 113.2, 111.8, 101.7, 83.7, 74.2, 73.3, 65.6, 61.6, 60.5, 60.3, 59.8, 59.7, 55.3, 54.8, 43.0, 42.0, 41.9, 39.8, 38.9, 27.8, 24.5, 16.0, 9.9.

ESI-MS m/z: Calcd. for $C_{49}H_{56}N_4O_{11}S$: 909.1 Found ($M+H^+$): 910.3.

Example 113

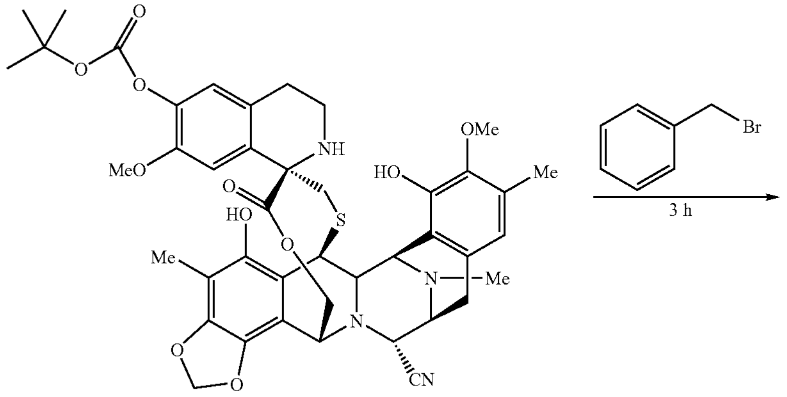

106

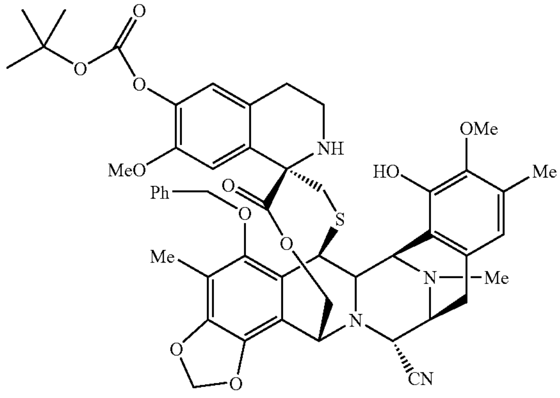

134

46%

+

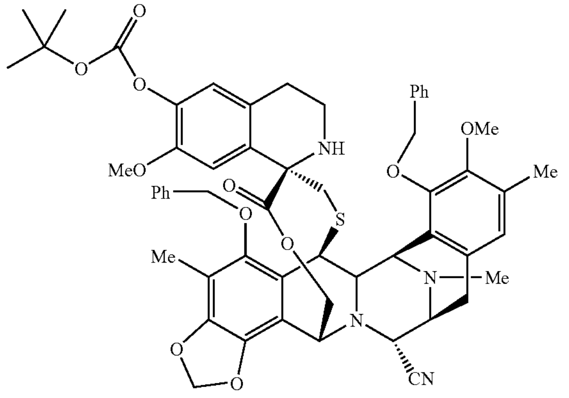

135

17%

114.2, 113.4, 112.1, 101.9, 83.9, 74.5, 65.8, 61.8, 60.8, 60.6, 60.0, 55.5, 55.1, 55.1, 43.1, 42.3, 42.0, 40.1, 30.1, 29.1, 28.0, 24.6, 16.2, 14.5, 10.1.

ESI-MS m/z: Calcd. for $C_{46}H_{52}N_4O_{11}S$: 868.3 Found ($M+H^+$): 869.3.

Compound 133: $^{1}$H-NMR (300 MHz, $CDCl_3$): δ 6.77 (s, 1H); 6.70 (s, 1H); 6.58 (s, 1H); 6.14-6.01 (m, 2H); 5.97 (s, 1H); 5.91 (s, 1H) 5.43 (dd, 1H); 5.37 (dd, 1H); 5.23 (dd, 1H); 5.19 (dd, 1H); 5.00 (d, 1H); 4.89 (s, 1H); 4.78 (dd, 1H); 4.71-4.36 (m, 2H); 4.28-4.12 (m, 4H); 3.84 (s, 3H); 3.58 (s, 3H); 3.50 (d, 1H); 3.41 (s, 1H); 3.12-3.03 (m, 1H); 2.93 (d, 2H); 2.86-2.80 (m, 1H); 2.72-2.60 (m, 1H); 2.51-2.46 (m, 1H); 2.28 (s, 3H); 2.23 (s, 2H); 2.18 (s, 3H); 2.17 (s, 3H); 1.50 (s, 9H).

$^{13}$C-NMR (75 MHz, $CDCl_3$): δ 172.1, 151.8, 150.8, 149.3, 149.0, 148.7, 145.8, 139.1, 138.8, 134.7, 133.6, 132.5, 131.4, 130.5, 129.0, 124.7, 124.5, 122.5, 122.0, 118.3, 118.0, 117.2, 134 was obtained using Method E: $^{1}$H-NMR (300 MHz, $CDCl_3$): δ 7.52-7.50 (m, 2H); 7.43-7.37 (m, 3H); 6.70 (s, 1H); 6.61 (s, 1H); 6.57 (s, 1H); 5.97 (dd, 2H); 5.56 (s, 1H); 5.01 (d, 1H); 4.99 (d, 1H); 4.87 (s, 1H); 4.74 (d, 1H); 4.30 (s, 1H); 4.20-4.14 (m, 3H); 3.76 (s, 3H); 3.60 (s, 3H); 3.41 (d, 2H); 3.13-3.02 (m, 1H); 2.90-2.88 (m, 2H); 2.88-2.78 (m, 1H); 2.64-2.58 (m, 1H); 2.51-2.44 (m, 1H); 2.34-2.10 (m, 2H); 2.30 (s, 3H); 2.24 (s, 3H); 2.17 (s, 3H); 1.50 (s, 9H).

$^{13}$C-NMR (75 MHz, $CDCl_3$): δ 172.1, 149.0, 148.7, 148.0, 145.9, 139.0, 137.4, 132.6, 131.1, 129.5, 129.1, 128.7, 128.6, 128.3, 128.2, 122.5, 120.8, 118.3, 118.2, 114.1, 113.4, 112.0, 101.8, 83.7, 74.8, 65.6, 61.8, 60.6, 60.4, 59.7, 55.4, 54.8, 43.0, 42.2, 41.8, 39.9, 29.9, 29.0, 27.8, 24.4, 16.0, 9.9.

ESI-MS m/z: Calcd. for $C_{50}H_{54}N_4O_{11}S$: 918.3 Found ($M+H^+$): 919.3.

135 was obtained using Method E: $^{1}$H-NMR (300 MHz, $CDCl_3$): δ 7.47-7.43 (m, 2H); 7.32-7.20 (m, 8H); 6.79 (s, 1H); 6.71 (s, 1H); 6.62 (s, 1H); 5.96 (dd, 2H); 5.24 (d, 1H); 5.03-4.93 (m, 4H); 4.68 (d, 1H); 4.28 (s, 1H); 4.18-4.08 (m, 3H); 3.87 (s, 3H); 3.60 (s, 3H); 3.43 (d, 1H); 3.35-3.32 (m, 1H);

3.15-3.08 (m, 1H); 2.92-2.91 (m, 2H); 2.88-2.80 (m, 1H); 2.72-2.60 (m, 1H); 2.54-2.46 (m, 1H); 2.32 (s, 3H); 2.23 (s, 3H); 2.22 (d, 1H); 2.05 (d, 1H); 1.84 (s, 3H); 1.51 (s, 9H).

ESI-MS m/z: Calcd. for $C_{57}H_{60}N_4O_{11}S$: 1008.4 Found ($M+H^+$): 1009.3.

Example 114

Method F: To a solution of 1 equiv. of starting material in $CH_2Cl_2/H_2O/TFA$ 2:1:3.3 (0.013M) was stirred at room temperature for 15 min. The reaction was followed by TLC and neutralised with $NaHCO_3$, extracted with $CH_2Cl_2$ and the organic layers dried over $Na_2SO_4$. Flash chromatography gives pure compounds.

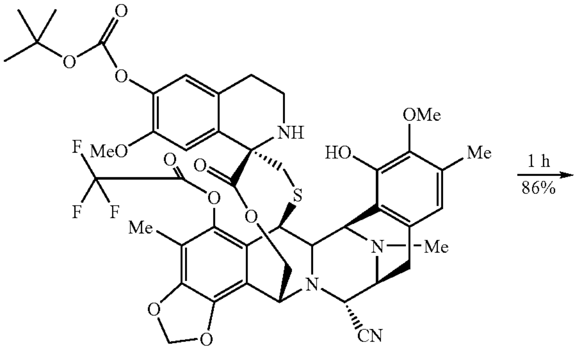

107

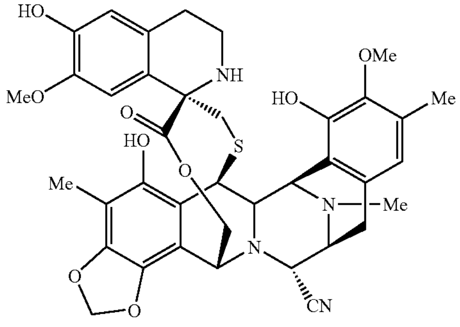

136

136 was obtained using Method F. $^1$H-NMR (300 MHz, $CDCl_3$): δ 6.61 (s, 1H); 6.49 (s, 1H); 6.39 (s, 1H); 5.92 (dd, 2H); 5.69 (s, 1H); 4.90 (d, 1H); 4.48 (s, 1H); 4.34 (s, 1H); 4.31 (dd, 1H); 4.16 (d, 1H); 4.03 (dd, 1H); 3.79 (s, 3H); 3.63-3-59 (m, 1H); 3.60 (s, 3H); 3.44-3.40 (m, 1H); 3.16-3.08 (m, 1H); 2.94 (d, 2H); 2.82-2.73 (m, 1H); 2.69-2.54 (m, 1H); 2.51-2.46 (m, 1H); 2.41-2.24 (m, 2H); 2.39 (s, 3H); 2.19 (s, 3H); 2.16 (s, 3H).

$^{13}$C-NMR (75 MHz, $CDCl_3$): δ 172.0, 148.2, 146.4, 144.5, 136.3, 130.8, 129.6, 125.9, 120.9, 118.3, 114.5, 113.4, 109.7, 101.4, 64.2, 61.1, 60.7, 60.0, 59.3, 55.4, 54.9, 54.8, 43.3, 41.7, 41.5, 39.8, 29.9, 29.5, 28.9, 24.4, 16.1, 14.3, 8.9.

ESI-MS m/z: Calcd. for $C_{38}H_{40}N_4O_9S$: 728.2 Found ($M+H^+$): 729.3.

Example 115

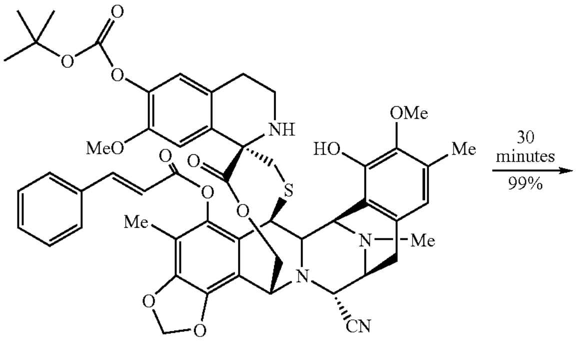

113

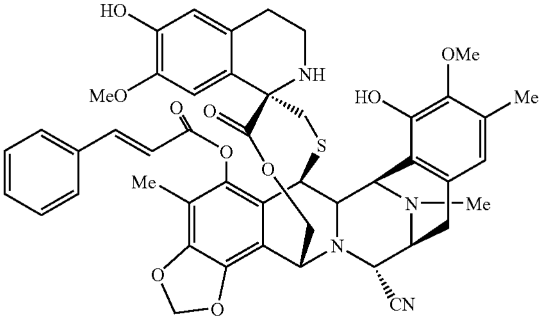

137

137 was obtained using Method F. $^1$H-NMR (300 MHz, $CDCl_3$): δ 7.87 (d, 1H); 7.60-7.57 (m, 2H); 7.46-7.44 (m, 3H); 6.58 (d, 1H); 6.54 (s, 1H); 6.49 (s, 1H); 6.45 (s, 1H); 6.03 (dd, 2H); 5.42 (s, 1H); 5.02 (d, 1H); 4.60 (s, 1H); 4.36 (s, 1H); 4.26 (dd, 1H); 4.19 (d, 1H); 4.13 (dd, 1H); 3.64 (s, 3H); 3.55 (d, 1H); 3.44 (s, 3H); 3.44-3.40 (m, 1H); 3.16-3.08 (m, 1H); 2.92 (d, 2H); 2.84-2.78 (m, 1H); 2.69-2.58 (m, 1H); 2.49-2.42 (m, 1H); 2.38-2.29 (m, 2H); 2.24 (s, 3H); 2.17 (s, 3H); 2.09 (s, 3H).

$^{13}$C-NMR (75 MHz, $CDCl_3$): δ 172.2, 147.9, 146.7, 145.6, 144.7, 144.5, 143.2, 141.6, 134.4, 131.0, 129.5, 129.3, 128.4, 125.9, 121.7, 120.8, 118.3, 118.1, 116.9, 114.4, 114.2, 110.0, 102.0, 65.0, 61.4, 60.2, 60.1, 59.9, 59.5, 55.3, 54.9, 54.8, 42.5, 42.3, 41.8, 39.9, 32.1, 31.7, 30.6, 29.9, 29.0, 24.3, 22.8, 15.9, 14.3, 10.0.

ESI-MS m/z: Calcd. for $C_{47}H_{46}N_4O_{10}$: 858.2 Found ($M+H^+$): 859.3.

Example 116
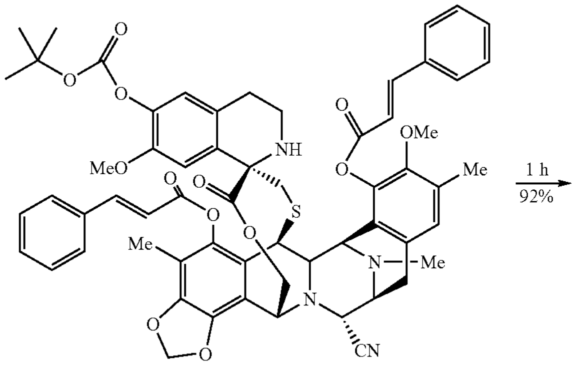
114
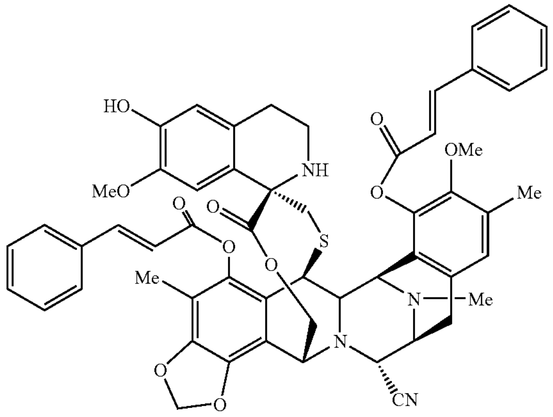
138
138 was obtained using Method F $^1$H-NMR (300 MHz, $CDCl_3$): δ 7.87 (d, 1H); 7.82 (d, 1H); 7.56-7.53 (m, 4H); 7.46-7.31 (m, 6H); 6.93 (s, 1H); 6.64 (d, 1H); 6.52 (d, 1H); 6.51 (s, 1H); 6.43 (s, 1H); 6.10 (s, 1H); 6.00 (s, 1H); 5.43 (s, 1H); 5.04 (d, 1H); 4.55 (s, 1H); 4.40 (s, 1H); 4.23 (d, 1H); 4.13 (dd, 1H); 3.92 (d, 1H); 3.65 (s, 3H); 3.59 (d, 1H); 3.51-3.46 (m, 1H); 3.44 (s, 3H); 3.19-3.11 (m, 1H); 3.00 (d, 2H); 2.93-2.86 (m, 1H); 2.74-2.63 (m, 1H); 2.50-2.45 (m, 1H); 2.36-2.24 (m, 2H); 2.28 (s, 3H); 2.17 (s, 3H); 2.13 (s, 3H).
ESI-MS m/z: Calcd. for $C_{56}H_{52}N_4O_{11}S$: 989.1 Found ($M+H^+$): 990.2.
Example 117
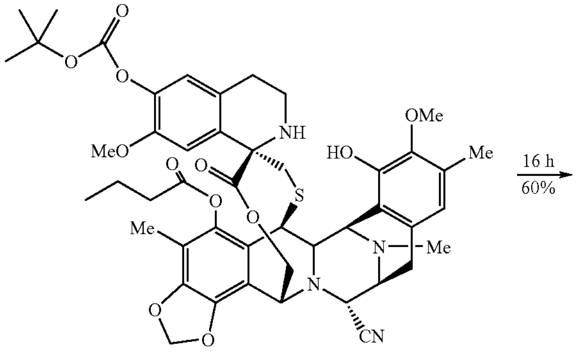
111
-continued
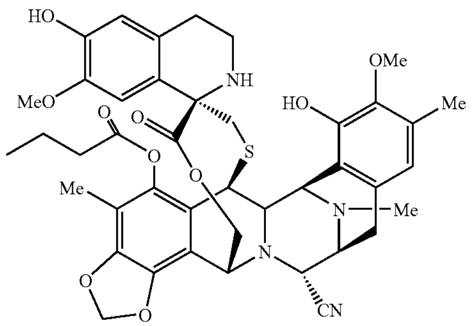
139
139 was obtained using Method F $^1$H-NMR (300 MHz, $CDCl_3$): δ 6.58 (s, 1H); 6.47 (s, 1H); 6.43 (s, 1H); 6.04 (d, 1H); 5.97 (d, 1H); 5.67 (s, 1H); 5.41 (s, 1H); 5.01 (d, 1H); 4.55 (s, 1H); 4.32 (s, 1H); 4.26 (d, 1H); 4.18 (d, 1H); 4.11 (dd, 1H); 3.78 (s, 3H); 3.61 (s, 3H); 3.51 (d, 1H); 3.41 (s, 1H); 3.15-3.08 (m, 1H); 2.93 (d, 2H); 2.82-2.76 (m, 1H); 2.61-2.42 (m, 2H); 2.53 (t, 2H); 2.31 (s, 3H); 2.18 (s, 3H); 2.02 (s, 3H); 1.79-1.72 (m, 2H); 1.02 (t, 3H).
ESI-MS m/z: Calcd. for $C_{42}H_{46}H_{46}N_4O_{10}S$: 798.3 Found ($M+H^+$): 799.3.
Example 118
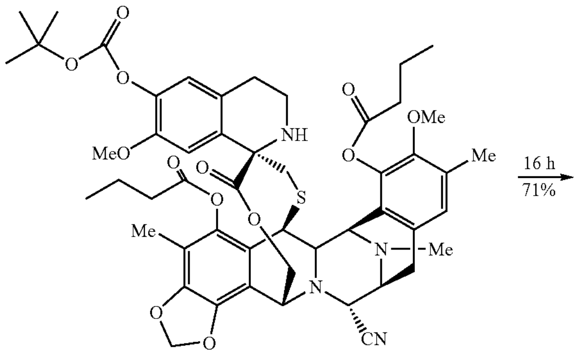
112
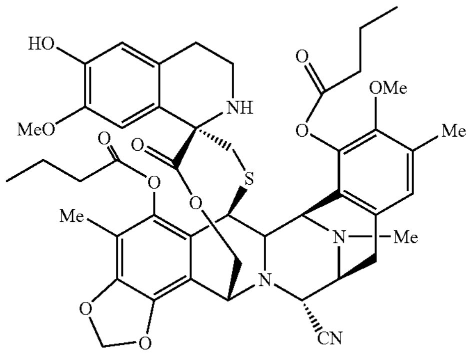
140

140 was obtained using Method F $^1$H-NMR (300 MHz, $CDCl_3$): δ 6.94 (s, 1H); 6.48 (s, 1H); 6.41 (s, 1H); 6.06 (d, 1H); 5.98 (d, 1H); 5.42 (s, 1H); 5.01 (d, 1H); 4.47 (s, 1H); 4.32 (s, 1H); 4.18 (d, 1H); 4.11 (dd, 1H); 3.81-3.66 (m, 2H); 3.74 (s, 3H); 3.61 (s, 3H); 3.51 (d, 1H); 3.44 (s, 1H); 3.16-3.06 (m, 1H); 2.98 (d, 2H); 2.83-2.79 (m, 1H); 2.64-2.48 (m, 2H); 2.60 (t, 2H); 2.55 (t, 2H); 2.32 (s, 3H); 2.15 (s, 3H); 2.03 (s, 3H); 1.93-1.73 (m, 4H); 1.09 (t, 3H); 1.01 (t, 3H).

$^{13}$C-NMR (75 MHz, $CDCl_3$): δ 171.4, 170.0, 147.0, 144.4, 143.5, 143.2, 142.6, 140.3, 139.1, 130.4, 129.6, 128.1, 126.2, 124.4, 123.4, 119.8, 116.8, 113.0, 112.9, 108.7, 100.7, 63.7, 60.1, 59.0, 58.9, 58.7, 58.3, 54.9, 54.0, 53.4, 41.4, 40.9, 40.6, 38.7, 35.0, 34.8, 28.6, 27.7, 23.0, 17.6, 17.2, 14.8, 12.9, 12.8, 8.7.

ESI-MS m/z: Calcd. for $C_{46}H_{52}N_4O_{11}S$: 868.3 Found ($M+H^+$): 869.3.

Example 119

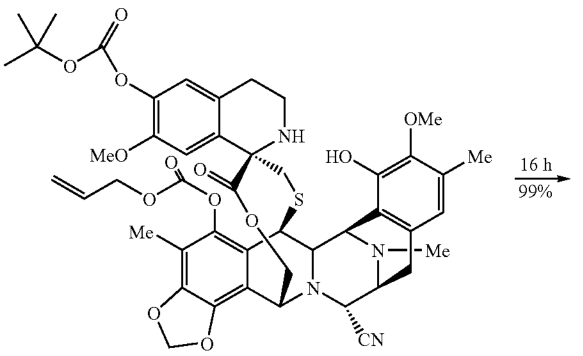

115

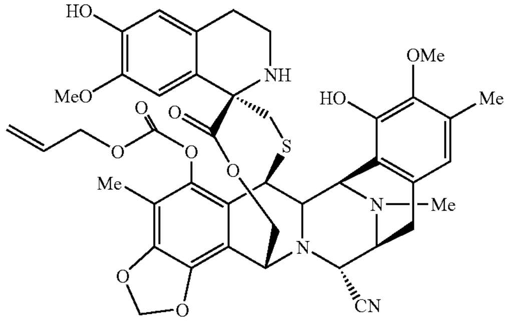

141

141 was obtained using Method F $^1$H-NMR (300 MHz, $CDCl_3$): δ 6.58 (s, 1H); 6.47 (s, 1H); 6.45 (s, 1H); 6.05 (d, 1H); 5.98 (d, 1H); 5.72 (s, 1H); 5.37 (dd, 1H); 5.26 (dd, 1H); 5.01 (d, 1H); 4.67 (s, 1H); 4.62 (d, 1H); 4.31 (s, 1H); 4.26 (d, 1H); 4.18 (d, 1H); 4.13 (dd, 1H); 3.77 (s, 3H); 3.61 (s, 3H); 3.50 (d, 1H); 3.41 (s, 1H); 3.16-3.08 (m, 1H); 2.93 (d, 2H); 2.80-2.74 (m, 1H); 2.68-2.56 (m, 1H); 2.48-2.36 (m, 2H); 2.31 (s, 3H); 2.19 (s, 3H); 2.18-2.14 (m, 2H); 2.09 (s, 3H).

ESI-MS m/z: Calcd. for $C_{42}H_{44}N_4O_{11}S$: 812.3 Found ($M+H^+$): 813.3.

Example 120

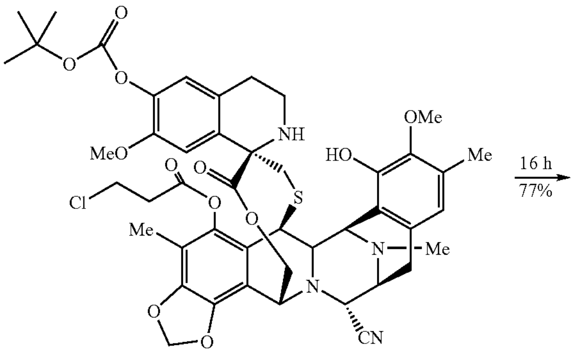

116

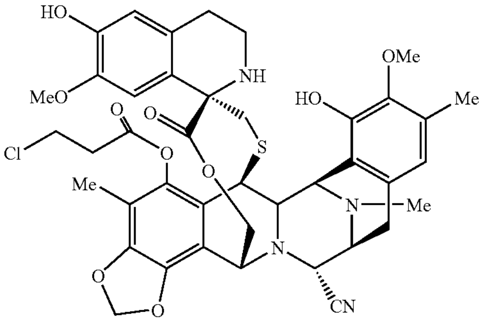

142

$^1$H-NMR (300 MHz, $CDCl_3$): δ 6.59 (s, 1H); 6.47 (s, 1H); 6.43 (s, 1H); 6.06 (d, 1H); 5.99 (d, 1H); 5.75 (s, 1H); 5.41 (s, 1H); 5.01 (d, 1H); 4.53 (s, 1H); 4.33 (s, 1H); 4.27 (d, 1H); 4.18 (d, 1H); 4.11 (dd, 1H); 3.83 (ddd, 2H); 3.78 (s, 3H); 3.62 (s, 3H); 3.51 (d, 1H); 3.42 (s, 1H); 3.16-3.08 (m, 1H); 3.04 (t, 2H); 2.93 (d, 2H); 2.82-2.76 (m, 1H); 2.68-2.58 (m, 1H); 2.48.2.42 (m, 1H); 2.31 (s, 3H); 2.18 (s, 3H); 2.05 (s, 3H).

ESI-MS m/z: Calcd. for $C_{41}H_{43}ClN_4O_{10}S$: 818.2 Found ($M+H^+$): 819.2.

Example 121

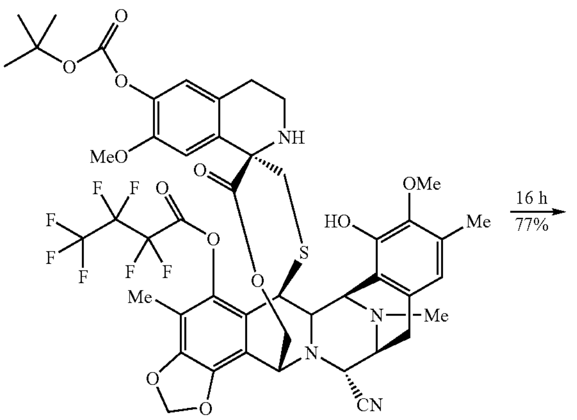

117

-continued

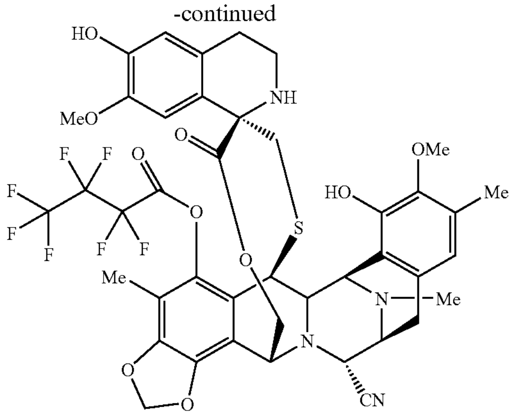

143

143 was obtained using Method F. $^1$H-NMR (300 MHz, $CDCl_3$): δ 6.59 (s, 1H); 6.49 (s, 1H); 6.45 (s, 1H); 6.10 (d, 1H); 6.03 (d, 1H); 5.68 (s, 1H); 5.47 (s, 1H); 5.04 (d, 1H); 4.57 (s, 1H); 4.34 (s, 1H); 4.29 (d, 1H); 4.21 (d, 1H); 4.14 (dd, 1H); 3.75 (s, 3H); 3.62 (s, 3H); 3.50 (d, 1H); 3.43 (s, 1H); 3.18-3.09 (m, 1H); 2.94 (d, 2H); 2.80-2.72 (m, 1H); 2.68-2.56 (m, 1H); 2.52-2.45 (m, 1H); 2.35-2.04 (m, 2H); 2.31 (s, 3H); 2.20 (s, 3H); 2.04 (s, 3H).

ESI-MS m/z: Calcd. for $C_{42}H_{39}F_7N_4O_{10}S$: 924.2 Found (M+H$^+$): 925.2.

Example 122

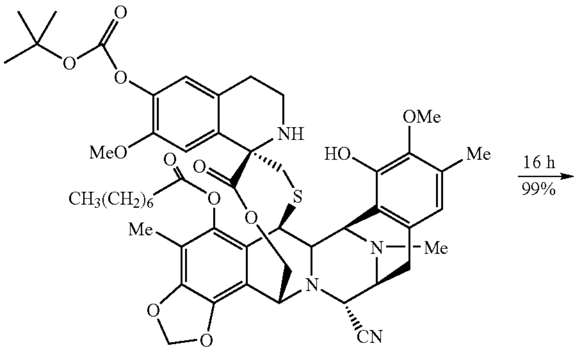

119

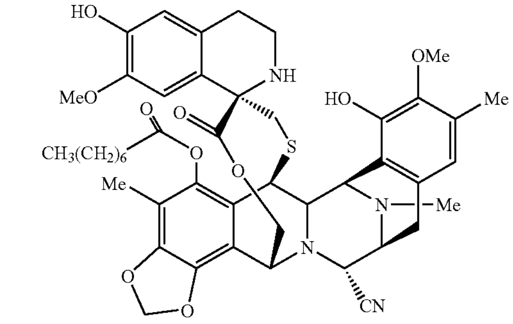

144

144 was obtained using Method F. $^1$H-NMR (300 MHz, $CDCl_3$): δ 6.59 (s, 1H); 6.47 (s, 1H); 6.43 (s, 1H); 6.01 (dd, 2H); 5.68 (s, 1H); 5.01 (d, 1H); 4.56 (s, 1H); 4.32 (s, 1H); 4.27 (dd, 1H); 4.18 (d, 1H); 4.12 (dd, 1H); 3.78 (s, 3H); 3.62 (s, 3H); 3.51 (d, 1H); 3.43-3.40 (m, 1H); 3.18-3.06 (m, 1H); 2.93 (d, 2H); 2.82-2.76 (m, 1H); 2.63-2.44 (m, 2H); 2.53 (t, 2H); 2.36-2.15 (m, 2H); 2.32 (s, 3H); 2.19 (s, 3H); 2.02 (s, 3H); 1.75-1.70 (m, 2H); 1.40-1.21 (m, 11H).

$^{13}$C-NMR (75 MHz, $CDCl_3$): δ 172.5, 170.9, 147.7, 145.2, 144.5, 144.2, 143.0, 141.3, 140.0, 130.7, 129.2, 129.1, 127.1, 125.7, 121.1, 120.7, 118.1, 114.0, 113.2, 109.8, 101.7, 64.6, 61.1, 60.3, 60.0, 59.7, 59.6, 55.1, 54.7, 54.6, 42.2, 41.7, 41.5, 39.7, 34.0, 31.6, 29.6, 29.3, 28.9, 28.7, 24.8, 24.2, 22.5, 15.7, 14.0, 9.7.

ESI-MS m/z: Calcd. for $C_{46}H_{54}N_4O_{10}S$: 854.3 Found (M+H$^+$): 855.3.

Example 123

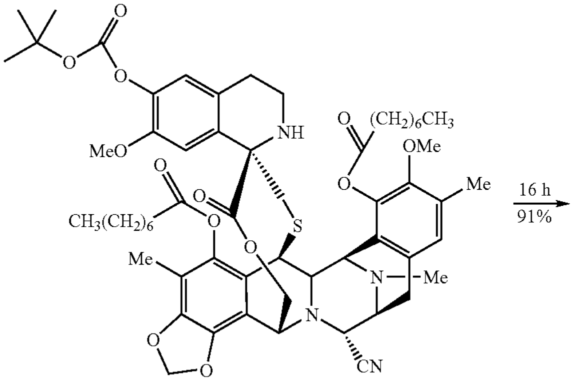

120

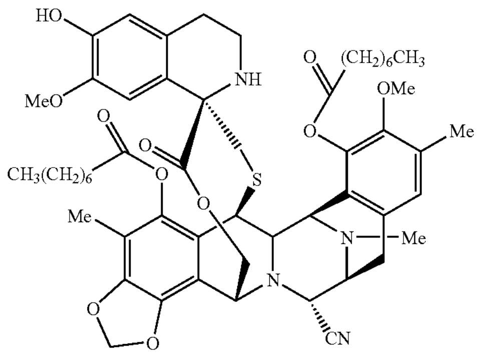

145

145 was obtained using Method F. $^1$H-NMR (300 MHz, $CDCl_3$): δ 6.94 (s, 1H); 6.47 (s, 1H); 6.41 (s, 1H); 6.01 (dd, 2H); 5.01 (d, 1H); 4.47 (s, 1H); 4.32 (s, 1H); 4.18 (d, 1H); 4.11 (dd, 1H); 3.79 (d, 1H); 3.73 (s, 3H); 3.61 (s, 3H); 3.50 (d, 1H); 3.45-3.42 (m, 1H); 3.16-3.04 (m, 1H); 2.99-2.97 (m, 2H); 2.82-2.78 (m, 1H); 2.64-2.54 (m, 5H); 2.48-2.42 (m, 1H); 2.36-2.09 (m, 2H); 2.31 (s, 3H); 2.14 (s, 3H); 2.03 (s, 3H); 1.85-1.77 (m, 2H); 1.73-1.66 (m, 2H); 1.44-1.18 (m, 22H).

$^{13}$C-NMR (75 MHz, $CDCl_3$): δ 172.6, 171.5, 148.2, 145.6, 144.8, 144.5, 143.9, 141.5, 140.3, 131.7, 130.8, 129.3, 127.4, 125.6, 124.6, 121.0, 118.1, 115.0, 114.9, 114.2, 114.1, 109.9, 102.1, 64.8, 61.1, 60.3, 60.1, 59.9, 59.5, 56.1, 55.2, 54.6, 42.6, 42.1, 41.8, 39.9, 34.5, 34.1, 32.0, 31.9, 29.9, 29.6, 29.5, 29.2, 29.1, 28.9, 25.4, 24.9, 24.2, 22.8, 16.0, 14.2, 9.9.
ESI-MS m/z: Calcd. for $C_{46}H_{54}N_4O_{10}S$: 980.5 Found (M+H$^+$): 981.5.
Example 124
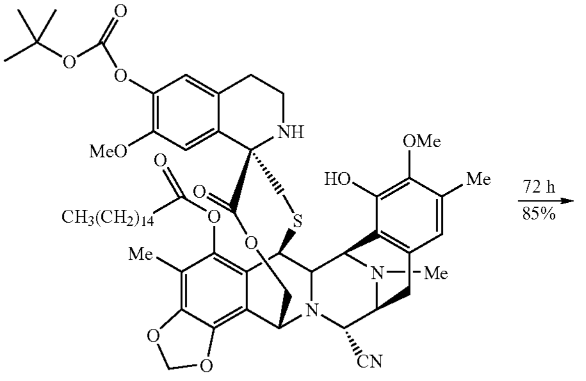
121
-continued
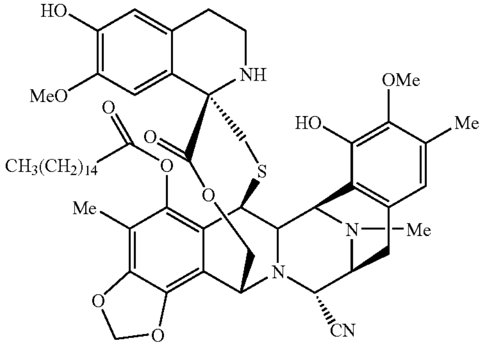
146
146 was obtained using Method F. $^1$H-NMR (300 MHz, $CDCl_3$): δ 6.59 (s, 1H); 6.47 (s, 1H); 6.43 (s, 1H); 6.01 (dd, 2H); 5.66 (s, 1H); 5.39 (s, 1H); 5.02 (d, 1H); 4.55 (s, 1H); 4.31 (s, 1H); 4.26 (dd, 1H); 4.17 (d, 1H); 4.11 (dd, 1H); 3.77 (s, 3H); 3.61 (s, 3H); 3.51 (d, 1H); 3.42-3.40 (m, 1H); 3.16-3.04 (m, 1H); 2.94-2-92 (m, 2H); 2.82-2.74 (m, 1H); 2.66-2.44 (m, 2H); 2.53 (t, 2H); 2.36-2.15 (m, 2H); 2.31 (s, 3H); 2.18 (s, 3H); 2.02 (s, 3H); 1.78-1.59 (m, 4H); 1.40-1.16 (m, 25H).
$^{13}$C-NMR (75 MHz, $CDCl_3$): δ 172.0, 148.0, 144.7, 144.5, 143.2, 141.5, 140.5, 138.7, 137.5, 131.0, 129.5, 129.3, 129.0, 125.9, 121.4, 120.9, 118.3, 114.2, 102.0, 64.8, 61.3, 60.5, 60.2, 59.9, 59.8, 55.3, 54.9, 54.8, 42.5, 42.0, 41.8, 39.9, 34.2, 32.1, 31.7, 29.9, 29.7, 29.6, 29.5, 29.4, 29.0, 25.0, 24.4, 22.8, 16.0, 14.2, 9.9.
ESI-MS m/z: Calcd. for $C_{54}H_{70}N_4O_{10}S$: 966.4 Found (M+H$^+$): 967.5.
Example 125
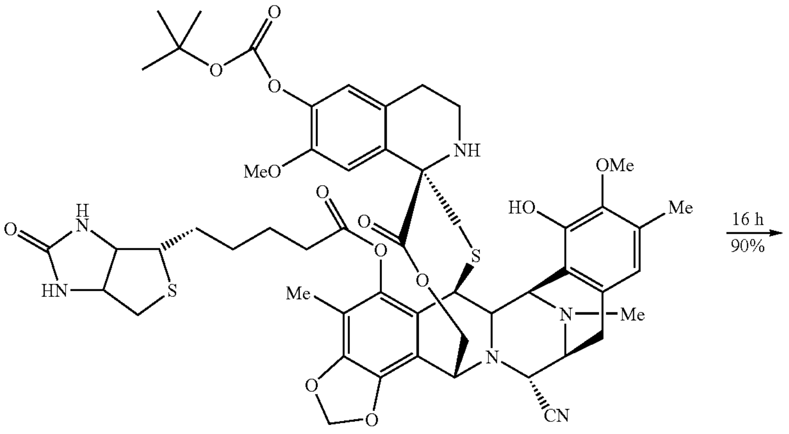
123
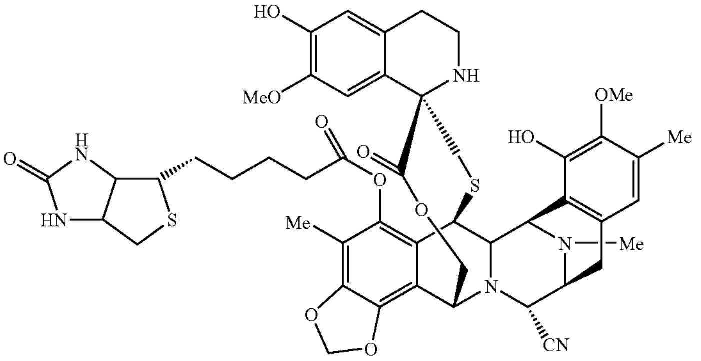
147

147 was obtained using Method F. $^1$H-NMR (300 MHz, $CDCl_3$): δ 7.58 (s, 1H); 6.91 (s, 1H); 6.54 (s, 1H); 6.46 (s, 1H); 6.40 (s, 1H); 6.04 (d, 1H); 5.96 (d, 1H); 5.66 (s, 1H); 5.26 (s, 1H); 5.01 (d, 1H); 4.50-4.46 (m, 2H); 4.34 (s, 1H); 4.31-4.26 (m, 2H); 4.18 (d, 1H); 4.08 (dd, 1H); 3.74 (s, 3H); 3.60 (s, 3H); 3.51 (d, 1H); 3.40 (s, 1H); 3.17-3.08 (m, 2H); 2.92-2.80 (m, 4H); 2.74-2.35 (m, 5H); 2.28 (s, 3H); 2.17 (s, 3H); 2.02 (s, 3H); 1.80-1.70 (m, 6H).
ESI-MS m/z: Calcd. for $C_{45}H_{54}N_6O_{11}S_2$: 954.4 Found ($M+H^+$): 955.4.
Example 126
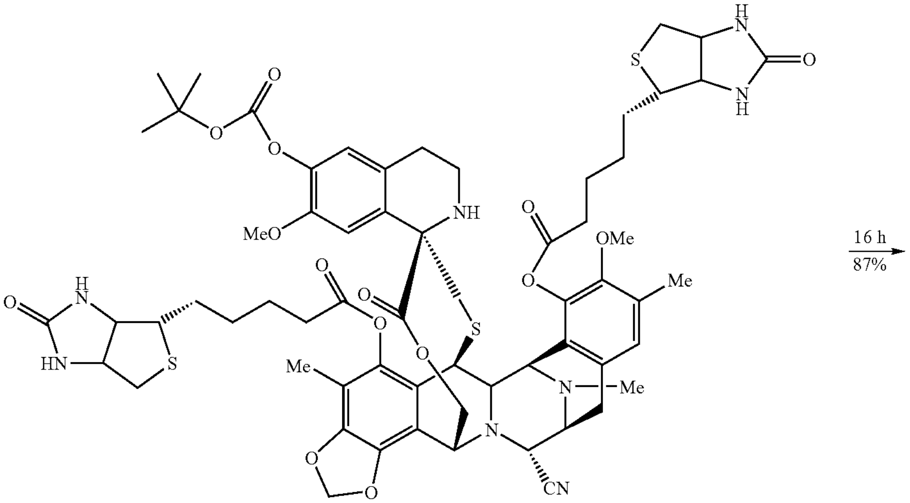
124
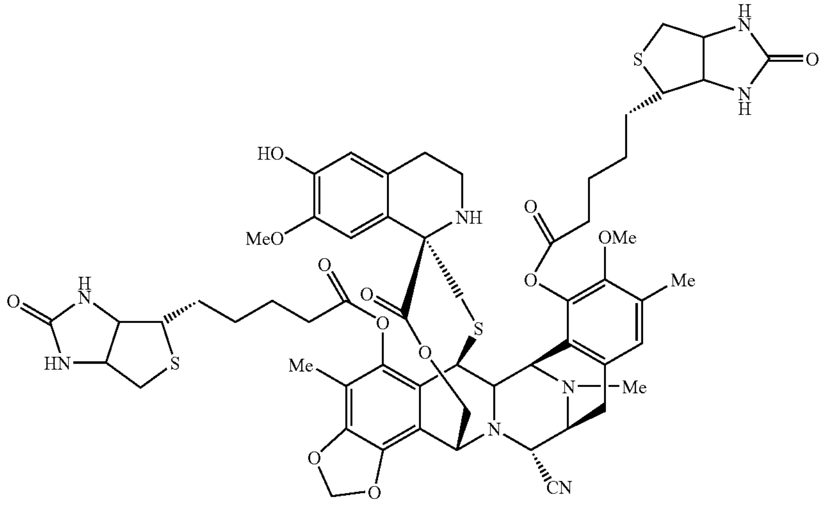
148

ESI-MS m/z: Calcd. for $C_{58}H_{68}N_8O_{13}S_3$: 1180.4 Found (M+H$^+$): 1181.3.

Example 127

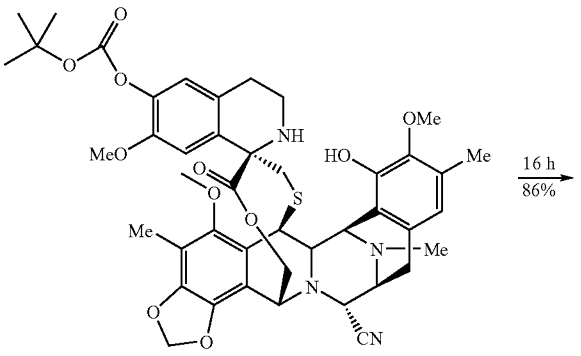

126

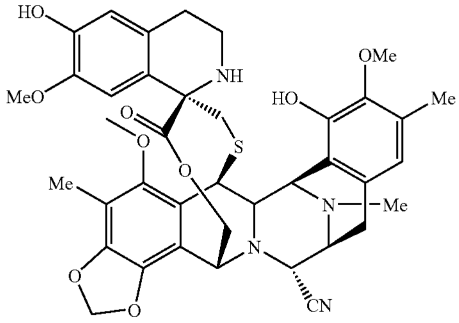

149

149 was obtained using Method F. $^1$H-NMR (300 MHz, $CDCl_3$): δ 6.58 (s, 1H); 6.49 (s, 1H); 6.44 (s, 1H); 5.99 (s, 1H); 5.91 (s, 1H); 5.78 (s, 1H); 5.41 (s, 1H); 5.00 (d, 1H); 4.87 (s, 1H); 4.30-4.29 (m, 2H); 4.15-4.13 (m, 2H); 3.80 (s, 3H); 3.65 (s, 3H); 3.62 (s, 3H); 3.51 (d, 1H); 3.40 (s, 1H); 3.12-3.02 (m, 1H); 2.93 (d, 2H); 2.82-2.78 (m, 1H); 2.66-2.58 (m, 1H); 2.48-2.43 (m, 1H); 2.32 (s, 3H); 2.20 (s, 3H); 2.18 (s, 3H).

ESI-MS m/z: Calcd. for $C_{39}H_{42}N_4O_9S$: 742.3 Found (M+H$^+$): 743.3.

Example 128

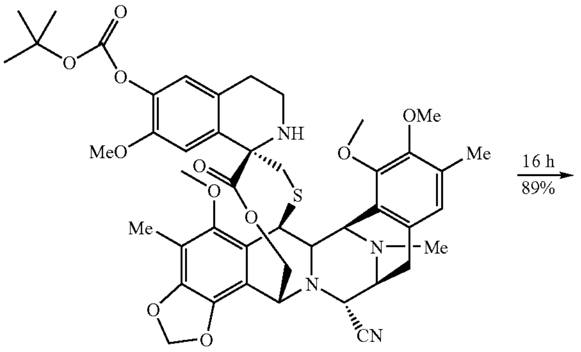

127

-continued

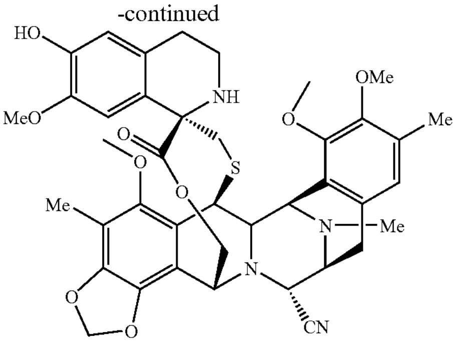

150

150 was obtained using Method F. $^1$H-NMR (300 MHz, $CDCl_3$): δ 6.75 (s, 1H); 6.50 (s, 1H); 6.44 (s, 1H); 6.00 (s, 1H); 5.92 (s, 1H); 5.39 (s, 1H); 5.01 (d, 1H); 4.81 (s, 1H); 4.30-4.25 (m, 2H); 4.16-4.13 (m, 2H); 3.95 (s, 3H); 3.83 (s, 3H); 3.74 (s, 3H); 3.62 (s, 3H); 3.51 (d, 1H); 3.41 (s, 1H); 3.12-3.02 (m, 1H); 2.93 (d, 2H); 2.87-2.80 (m, 1H); 2.66-2.58 (m, 1H); 2.49-2.43 (m, 1H); 2.28 (s, 3H); 2.23 (s, 3H); 2.18 (s, 3H).

ESI-MS m/z: Calcd. for $C_{40}H_{44}N_4O_9S$: 756.3 Found (M+H$^+$): 757.3.

Example 129

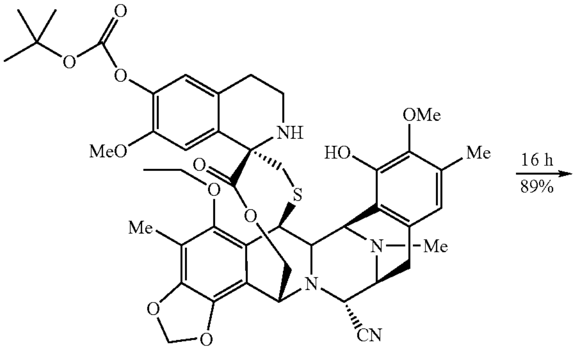

128

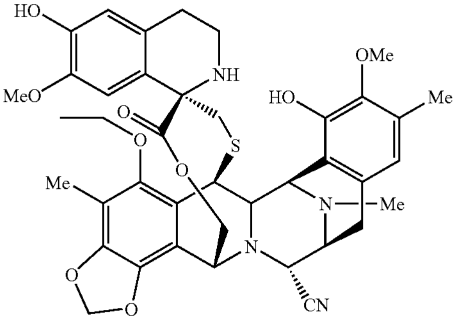

151

151 was obtained using Method F. $^1$H-NMR (300 MHz, $CDCl_3$): δ 6.58 (s, 1H); 6.49 (s, 1H); 6.44 (s, 1H); 5.99 (s, 1H); 5.91 (s, 1H); 5.75 (s, 1H); 5.00 (d, 1H); 4.90 (s, 1H); 4.30 (d, 2H); 4.17 (s, 1H); 4.15 (dd, 1H); 3.88 (q, 2H); 3.80 (s, 3H); 3.62 (s, 3H); 3.51 (d, 1H); 3.40 (s, 1H); 3.12-3.02 (m, 1H); 2.93 (d, 2H); 2.86-2.80 (m, 1H); 2.68-2.56 (m, 1H); 2.48-2.42 (m, 1H); 2.31 (s, 3H); 2.23-2.21 (m, 2H); 2.20 (s, 3H); 2.17 (s, 3H); 1.39 (t, 3H).

ESI-MS m/z: Calcd. for $C_{40}H_{44}N_4O_9S$: 756.3 Found (M+H$^+$): 757.5

Example 130

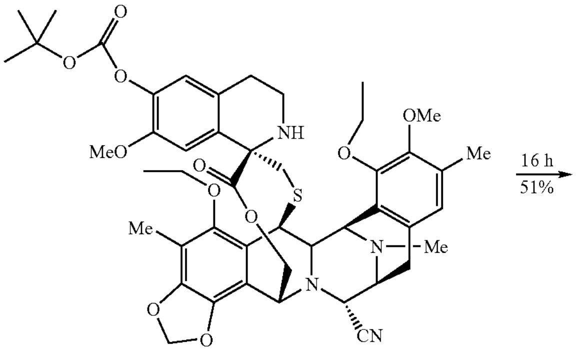

129

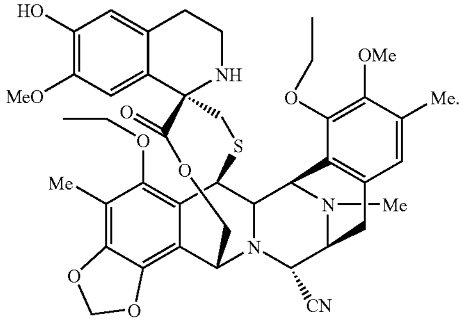

152

152 was obtained using Method F $^1$H-NMR (300 MHz, $CDCl_3$): δ 6.76 (s, 1H); 6.50 (s, 1H); 6.44 (s, 1H); 5.99 (d, 1H); 5.92 (d, 1H); 5.42 (s, 1H); 5.001 (d, 1H); 4.87 (s, 1H); 4.35-4.27 (m, 3H); 4.18 (s, 1H); 4.16 (dd, 1H); 3.97-3.80 (m, 4H); 3.85 (s, 3H); 3.63 (s, 3H); 3.51 (d, 1H); 3.43 (s, 1H); 3.14-3.06 (m, 1H); 2.95 (d, 2H); 2.88-2.80 (m, 1H); 2.70-2.58 (m, 1H); 2.50-2.45 (m, 1H); 2.28 (s, 3H); 2.21 (s, 3H); 2.18 (s, 3H); 1.41 (t, 3H); 1.40 (t, 3H).

ESI-MS m/z: Calcd. for $C_{42}H_{48}N_4O_9S$: 784.3 Found (M+H$^+$): 785.3.

Example 131

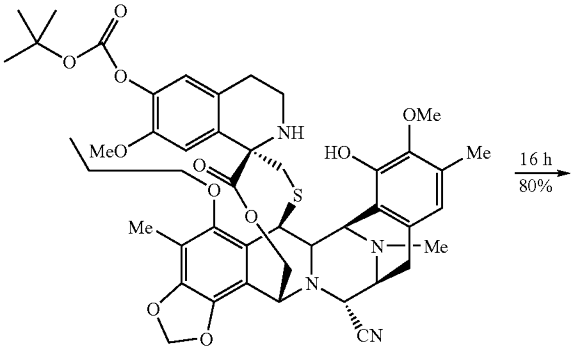

130

-continued

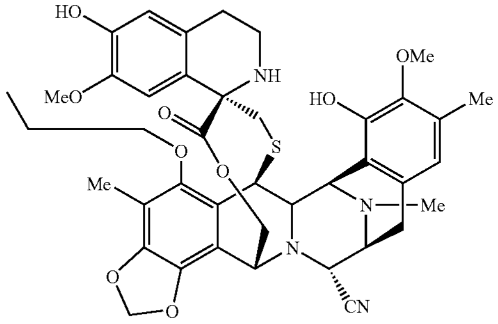

153

153 was obtained using Method F. $^1$H-NMR (300 MHz, $CDCl_3$): δ 6.58 (s, 1H); 6.49 (s, 1H); 6.43 (s, 1H); 5.98 (s, 1H); 5.91 (s, 1H); 5.70 (s, 1H); 5.40 (s, 1H); 5.01 (d, 1H); 4.90 (s, 1H); 4.30 (s, 2H); 4.17 (s, 1H); 4.15 (dd, 1H); 3.85-3.73 (m, 2H); 3.79 (s, 3H); 3.62 (s, 3H); 3.51 (d, 1H); 3.41 (s, 1H); 3.14-3.04 (m, 1H); 2.93 (d, 2H); 2.86-2.82 (m, 1H); 2.70-2.60 (m, 1H); 2.48-2.42 (m, 1H); 2.31 (s, 3H); 2.23 (s, 2H); 2.19 (s, 3H); 2.17 (s, 3H); 1.82-1.76 (m, 2H); 1.06 (t, 3H).

ESI-MS m/z: Calcd. for $C_{41}H_{46}N_4O_9S$: 770.3 Found (M+H$^+$): 771.3.

Example 132

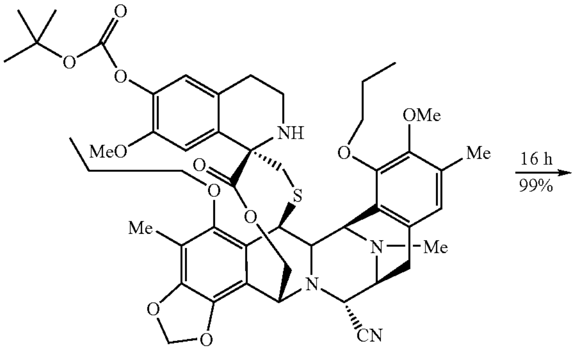

131

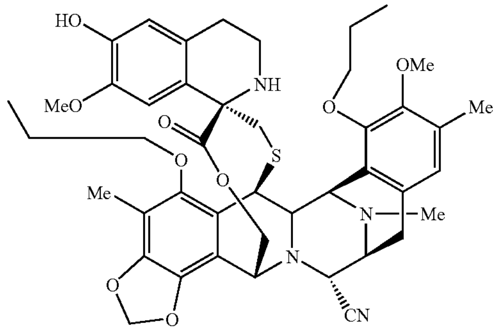

154

154 was obtained using Method F. $^1$H-NMR (300 MHz, $CDCl_3$): δ 6.76 (s, 1H); 6.50 (s, 1H); 6.43 (s, 1H); 5.98 (d, 1H); 5.91 (d, 1H); 5.40 (s, 1H); 5.01 (d, 1H); 4.88 (s, 1H); 44.32-4.12 (m, 5H); 3.85 (s, 3H); 3.82-3.59 (m, 4H); 3.62 (s, 3H); 3.51 (d, 1H); 3.43 (s, 1H); 3.14-3.06 (m, 1H); 2.94 (d, 2H); 2.87-2.80 (m, 1H); 2.71-2.60 (m, 1H); 2.49-2.44 (m, 1H); 2.27 (s, 3H); 2.21 (s, 3H); 2.17 (s, 3H); 1.82-1.67 (m, 4H); 1.07 (t, 3H); 1.02 (t, 3H).

ESI-MS m/z: Calcd. for $C_{44}H_{52}N_4O_9S$: 812.3 Found ($M+H^+$): 813.3.

Example 133

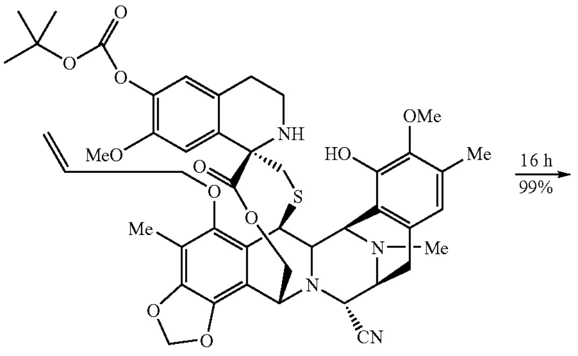

132

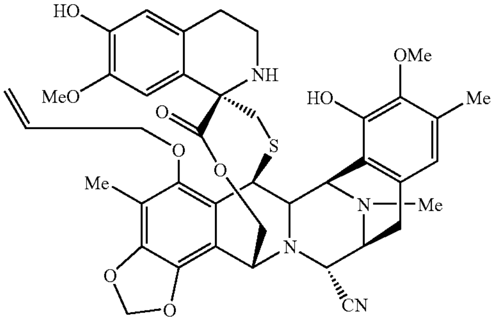

155

155 was obtained using Method F. $^1$H-NMR (300 MHz, $CDCl_3$): δ 6.58 (s, 1H); 6.49 (s, 1H); 6.44 (s, 1H); 6.15-6.02 (m, 1H); 5.99 (s, 1H); 5.92 (s, 1H); 5.70 (s, 1H); 5.43 (dd, 1H); 5.26 (dd, 1H); 5.01 (d, 1H); 4.91 (s, 1H); 4.49 (dd, 1H); 4.32-4.28 (m, 2H); 4.21-4.13 (m, 3H); 3.79 (s, 3H); 3.62 (s, 3H); 3.50 (d, 1H); 3.41 (s, 1H); 3.12-3.04 (m, 1H); 2.93 (d, 2H); 2.86-2.82 (m, 1H); 2.67-2.58 (m, 1H); 2.48-2.43 (m, 1H); 2.31 (s, 3H); 2.24 (s, 2H); 2.20 (s, 3H); 2.18 (s, 3H).

ESI-MS m/z: Calcd. for $C_{41}H_{44}N_4O_9S$: 768.3 Found ($M+H^+$): 769.2

Example 134

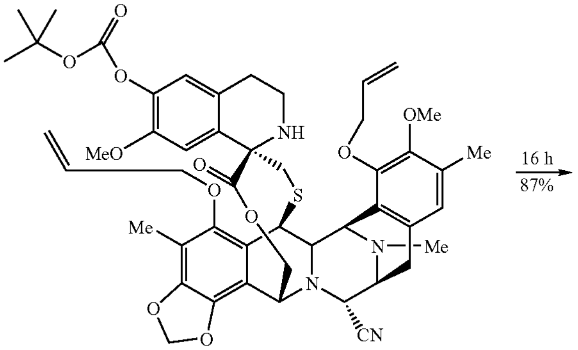

133

-continued

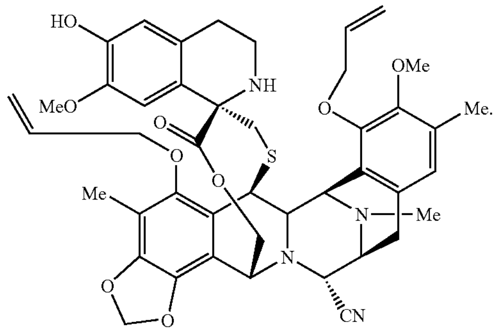

156

156 was obtained using Method F. $^1$H-NMR (300 MHz, $CDCl_3$): δ 6.77 (s, 1H); 6.49 (s, 1H); 6.43 (s, 1H); 6.15-6.01 (m, 2H); 5.99 (d, 1H); 5.92 (d, 1H); 5.43 (dd, 1H); 5.37 (dd, 1H); 5.24-5.18 (m, 2H); (dd, 1H); 5.01 (d, 1H); 4.89 (s, 1H); 4.78 (dd, 1H); 4.48-4.35 (m, 2H); 4.29-4.26 (m, 2H); 4.23-4.13 (m, 3H); 3.84 (s, 3H); 3.62 (s, 3H); 3.50 (d, 1H); 3.41 (s, 1H); 3.14-3.05 (m, 1H); 2.94 (d, 2H); 2.86-2.82 (m, 1H); 2.70-2.60 (m, 1H); 2.49-2.43 (m, 1H); 2.28 (s, 3H); 2.23 (s, 2H); 2.19 (s, 3H); 2.18 (s, 3H).

$^{13}$C-NMR (75 MHz, $CDCl_3$): δ 172.2, 150.8, 149.4, 149.0, 145.8, 144.7, 144.4, 138.8, 134.7, 133.6, 131.4, 130.5, 129.5, 124.7, 124.5, 122.2, 118.3, 118.0, 117.2, 114.4, 114.0, 113.2, 109.7, 101.7, 74.2, 73.3, 65.4, 61.6, 60.5, 60.3, 59.8, 59.7, 55.3, 55.2, 54.8, 42.9, 42.0, 41.9, 40.0, 29.9, 29.0, 24.5, 16.0, 9.8.

ESI-MS m/z: Calcd. for $C_{44}H_{48}N_4O_9S$: 808.3 Found ($M+H^+$): 809.5.

Example 135

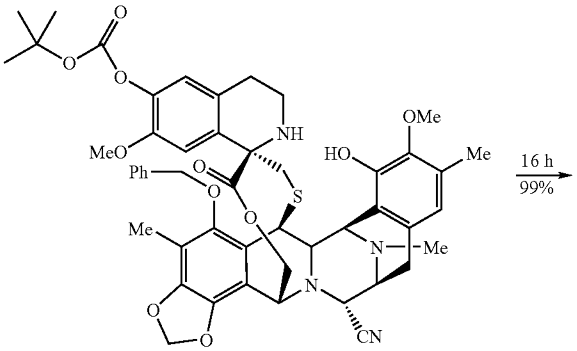

134

-continued

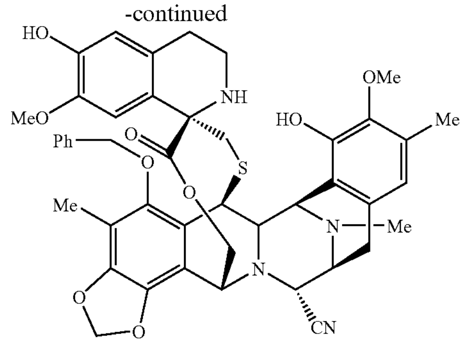

157

157 was obtained using Method F. $^1$H-NMR (300 MHz, $CDCl_3$): δ 7.53-7.50(m, 2H); 7.44-7.37 (m, 3H); 6.57 (s, 1H); 6.49 (s, 1H); 6.47 (s, 1H); 5.97 (dd, 2H); 5.56 (s, 1H); 5.02 (d, 1H); 5.00 (d, 1H); 4.87 (s, 1H); 4.76 (d, 1H); 4.31 (s, 1H); 4.20-4.14 (m, 3H); 3.76 (s, 3H); 3.64 (s, 3H); 3.41 (d, 2H); 3.13-3.05 (m, 1H); 2.92 (d, 2H); 2.84-2.78 (m, 1H); 2.69-2.58 (m, 1H); 2.49-2.42 (m, 1H); 2.35-2.04 (m, 2H); 2.31 (s, 3H); 2.25 (s, 3H); 2.17 (s, 3H).

$^{13}$C-NMR (75 MHz, $CDCl_3$): δ 72.5, 148.9, 148.0, 145.9, 144.4, 143.3, 139.0, 137.3, 131.0, 129.6, 128.6, 128.4, 128.2, 120.8, 118.4, 118.2, 114.9, 114.4, 114.2, 113.3, 109.8, 101.8, 92.6, 65.4, 61.6, 60.6, 60.4, 59.7, 55.2, 54.8, 42.9, 42.02, 41.8, 40.0, 31.8, 29.9, 24.4, 22.8, 16.0, 14.3, 9.9.

ESI-MS m/z: Calcd. for $C_{45}H_{46}N_4O_9S$: 818.3 Found ($M+H^+$): 819.2.

Example 136

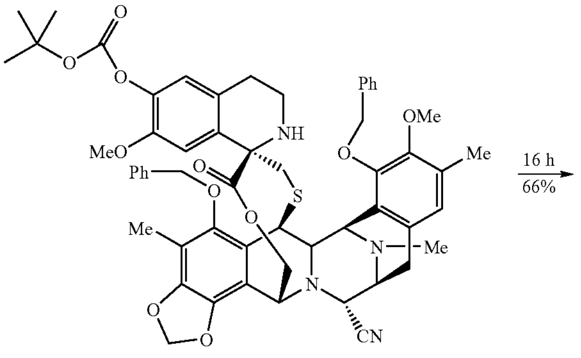

135

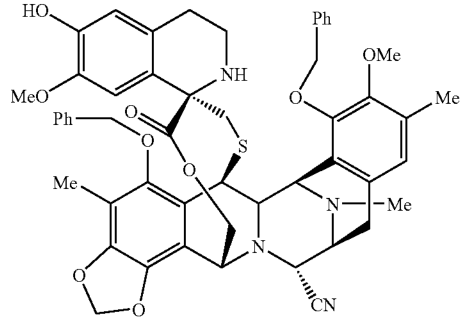

158

158 was obtained using Method F $^1$H-NMR (300 MHz, $CDCl_3$): δ 7.51-7.47 (m, 2H); 7.30-7.25 (m, 5H); 7.22-7.18 (m, 3H); 6.79 (s, 1H); 6.50 (s, 1H); 6.47 (s, 1H); 6.01 (d, 1H); 5.93 (d, 1H); 5.43 (s, 1H); 5.24 (d, 1H); 5.02 (d, 1H); 5.01 (s, 2H); 4.95 (d, 1H); 4.66 (d, 1H); 4.28 (s, 1H); 4.18-4.09 (m, 3H); 3.88 (s, 3H); 3.64 (s, 3H); 3.43 (d, 2H); 3.36-3.34 (m, 1H); 3.16-3.07 (m, 1H); 2.91 (d, 2H); 2.88-2.80 (m, 1H); 2.69-2.59 (m, 1H); 2.50-2.45 (m, 1H); 2.37-2.29 (m, 2H); 2.32 (s, 6H); 2.23 (s, 3H).

$^{13}$C-NMR (75 MHz, $CDCl_3$): δ 172.7, 150.8, 149.3, 148.9, 146.1, 144.9, 144.6, 139.2, 138.0, 137.3, 131.6, 131.2, 130.8, 128.7, 128.6, 128.5, 128.4, 128.3, 126.0, 125.1, 124.8, 122.6, 118.6, 114.6, 114.4, 113.6, 110.0, 101.9, 74.8, 74.6, 65.5, 61.9, 60.7, 60.1, 59.9, 55.4, 55.0, 53.8, 43.3, 42.2, 41.7, 40.1, 29.3, 24.7, 16.2, 10.0.

ESI-MS m/z: Calcd. for $C_{52}H_{52}N_4O_9S$: 908.3 Found ($M+H^+$): 909.3.

Example 137

Method J: To a solution of 1 equiv. of starting material in $CH_3CN/CH_2Cl_2$ 1.2:1 were added NaI (6 equiv.) and TMSCl (6 equiv.). After 1 h the reaction was quenched with brine, the aqueous phase was extracted with $CH_2Cl_2$. The organic layer was dried over $Na_2SO_4$. Chromatography gives pure compounds.

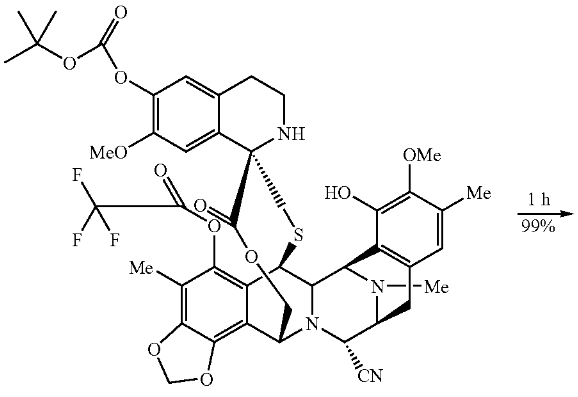

107

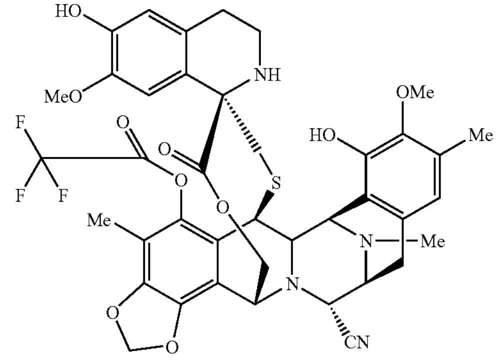

159

159 was obtained using Method J. $^1$H-NMR (300 MHz, $CDCl_3$): δ 6.59 (s, 1H); 6.49 (s, 1H); 6.46 (s, 1H); 6.10 (d, 1H); 6.03 (d, 1H); 5.69 (s, 1H); 5.04 (d, 1H); 4.58 (s, 1H); 4.34 (s, 1H); 4.29 (d, 1H); 4.21 (d, 1H); 4.14 (dd, 1H); 3.76 (s, 3H); 3.63 (s, 3H); 3.50 (d, 1H); 3.43 (s, 1H); 3.20-3.08 (m, 1H); 2.95 (d, 2H); 2.90-2.84 (m, 1H); 2.78-2.72 (m, 1H); 2.91-2.48 (m, 1H); 2.34-2.03 (m, 2H); 2.31 (s, 3H); 2.20 (s, 3H); 2.06 (s, 3H).

ESI-MS m/z: Calcd. for $C_{40}H_{39}F_3N_4O_{10}S$: 824.2 Found $(M+H^+)$: 825.2.

Example 138

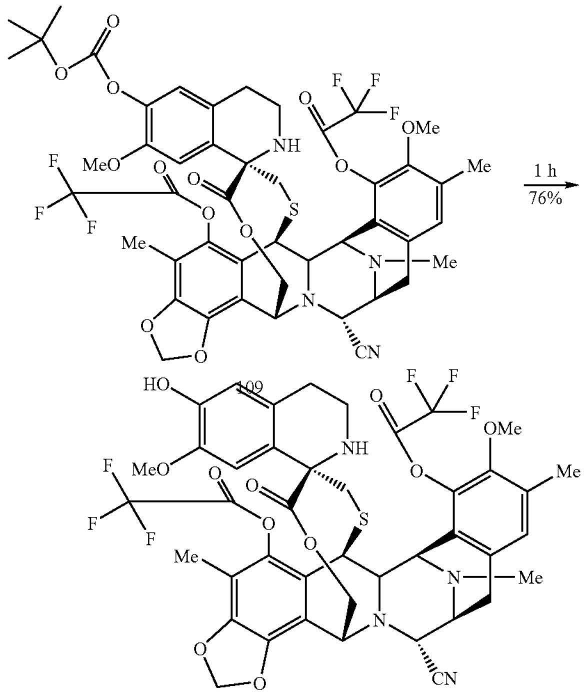

160

160 was obtained using Method J. $^1H$-NMR (300 MHz, $CDCl_3$): δ 6.89(s, 1H); 6.50 (s, 1H); 6.13 (d, 1H); 6.04 (d, 1H); 6.01 (s, 1H); 5.50 (s, 1H); 4.80 (d, 1H); 4.56 (s, 1H); 4.21 (s, 1H); 4.14-4.10 (m, 2H); 3.79-3.65 (m, 2H); 3.77 (s, 3H); 3.59 (s, 3H); 3.47 (s, 1H); 3.20 (d, 1H); 2.98 (d, 2H); 2.67 (t, 3H); 2.51 (d, 1H); 2.26 (s, 3H); 2.08 (s, 3H); 2.06 (s, 3H).

ESI-MS m/z: Calcd. for $C_{42}H_{38}F_6N_4O_{11}S$: 920.2 Found $(M+H^+)$: 921.3.

Example 139

Method H: To a solution of 1 equiv. of starting material in $CH_3CN/H_2O$ 3:2 (0.009M) were added 30 equiv. of $AgNO_3$. After 24 h the reaction was quenched with a mixture 1:1 of saturated solutions of brine and $NaHCO_3$, stirred for 10 min and diluted and extracted with $CH_2Cl_2$. The organic layer was dried over $Na_2SO_4$. Chromatography gives pure compounds.

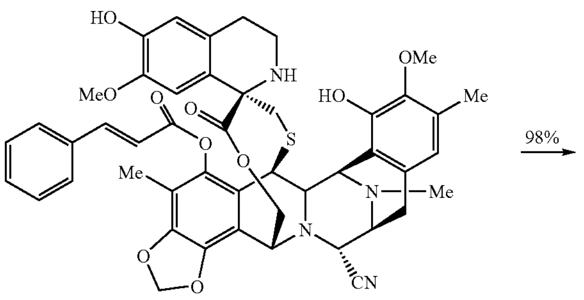

137

-continued

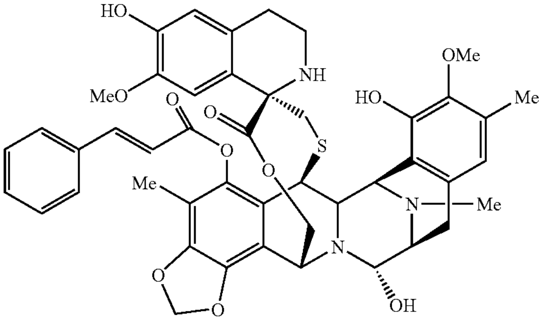

161

161 was obtained using Method H. $^1H$-NMR (300 MHz, $CDCl_3$): δ 7.89 (d, 1H); 7.60-7.56 (m, 2H); 7.46-7.44 (m, 3H); 6.57 (d, 1H); 6.56 (s, 1H); 6.48 (s, 1H); 6.44 (s, 1H); 5.99 (dd, 2H); 5.43 (s, 1H); 5.14 (d, 1H); 4.86 (s, 1H); 4.52-4.50 (m, 2H); 4.19 (d, 1H); 4.06 (dd, 1H); 3.63 (s, 3H); 3.46 (s, 3H); 3.25-3.02 (m, 3H); 2.88-2.85 (m, 3H); 2.73-2.59 (m, 1H); 2.50-2.24 (m, 3H); 2.25 (s, 3H); 2.17 (s, 3H); 2.07 (s, 3H).

ESI-MS m/z: Calcd. for $C_{46}H_{47}N_3O_{11}S$: 849.3 Found $(M+H^+)$: 850.3.

Example 140

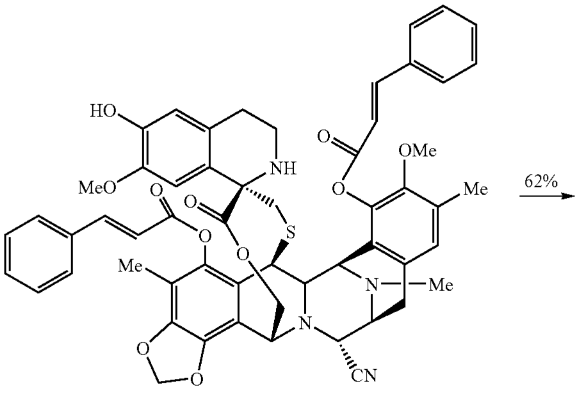

138

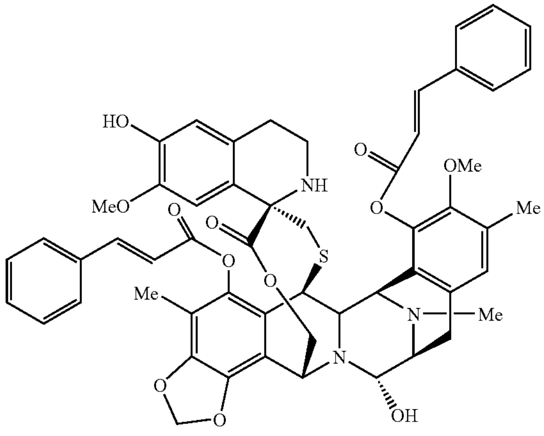

162

162 was obtained using Method H. $^{1}$H-NMR (300 MHz, $CDCl_3$): δ 7.88 (d, 1H); 7.85 (d, 1H); 7.45-7.31 (m, 10H); 6.94 (s, 1H); 6.63 (d, 1H); 6.52 (d, 1H); 6.51 (s, 1H); 6.43 (s, 1H); 6.07 (s, 1H); 5.97 (s, 1H); 5.42 (s, 1H); 5.16 (d, 1H); 4.88 (s, 1H); 4.54 (s, 1H); 4.45 (s, 1H); 4.06 (d, 1H); 3.80-3.78 (m, 1H); 3.64 (s, 3H); 3.46 (s, 3H); 3.28-3.15 (m, 2H); 3.00-2.88 (m, 3H); 2.76-2.66 (m, 1H); 2.50-2.17 (m, 4H); 2.28 (s, 3H); 2.14 (s, 3H); 2.11 (s, 3H).

$^{13}$C-NMR (75 MHz, $CDCl_3$): δ 172.3, 164.5, 164.2, 148.0, 147.2, 146.9, 145.4, 144.5, 144.2, 143.1, 141.2, 140.7, 134.1, 133.7, 131.3, 130.9, 130.7, 129.1, 129.0, 128.9, 128.2, 128.1, 127.3, 125.6, 124.1, 121.8, 116.6, 116.1, 116.0, 114.0, 112.5, 109.7, 101.7, 81.6, 64.9, 61.1, 59.9, 57.7, 57.6, 56.1, 55.8, 54.9, 42.7, 42.5, 41.4, 39.8, 29.6, 28.7, 23.9, 22.6, 15.8, 9.7.

ESI-MS m/z: Calcd. for $C_{55}H_{53}N_3O_{12}S$: 979.3 Found (M+H$^+$): 980.3.

Example 141

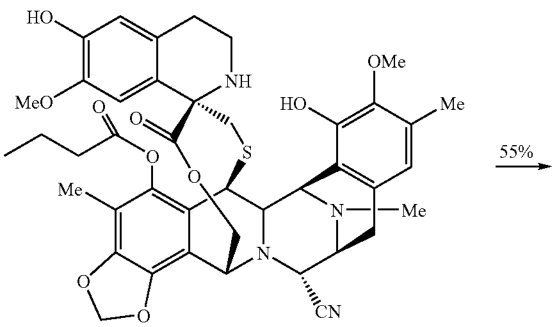

139

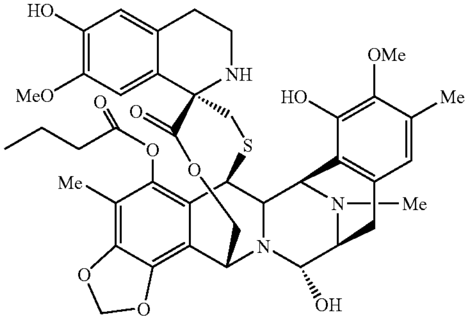

163

163 was obtained using Method H. $^{1}$H-NMR (300 MHz, $CDCl_3$): δ 6.59 (s, 1H); 6.47 (s, 1H); 6.43 (s, 1H); 6.02 (d, 1H); 5.93 (d, 1H); 5.64 (s, 1H); 5.12 (d, 1H); 4.81 (s, 1H); 4.47 (s, 1H); 4.15 (d, 1H); 4.03 (dd, 1H); 3.78 (s, 3H); 3.60 (s, 3H); 3.60-3.59 (m, 1H); 3.58 (d, 1H); 3.21-3.10 (m, 2H); 2.87-2.79 (m, 3H); 2.68-2.58 (m, 2H); 2.54-2.38 (m, 2H); 2.52 (t, 2H); 2.31 (s, 3H); 2.16 (s, 3H); 2.01 (s, 3H); 1.81-1.73 (m, 2H); 1.02 (t, 3H).

ESI-MS m/z: Calcd. for $C_{41}H_{47}N_3O_{11}S$: 789.3 Found (M+H$^+$): 790.1.

Example 142

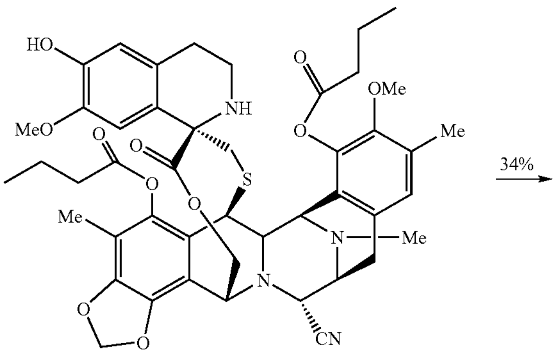

140

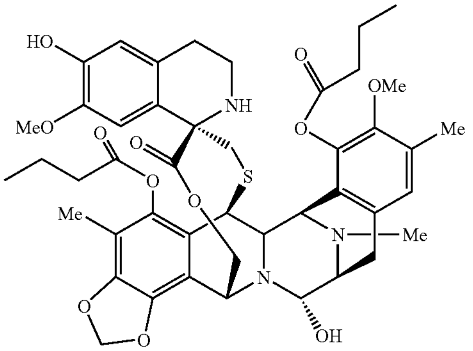

164

164 was obtained using Method H $^{1}$H-NMR (300 MHz, $CDCl_3$): δ 7.96 (s, 1H); 6.47 (s, 1H); 6.42 (s, 1H); 6.02 (d, 1H); 5.93 (d, 1H); 5.40 (s, 1H); 5.12 (d, 1H); 4.81 (s, 1H); 4.47 (s, 1H); 4.18-4.16 (m, 1H); 4.03 (d, 1H); 3.78 (s, 3H); 3.71-3.70 (m, 2H); 3.61 (s, 3H); 3.23-3.10 (m, 2H); 2.87-2.79 (m, 3H); 2.68-2.40 (m, 3H); 2.60 (t, 2H); 2.60 (t, 2H); 2.31 (s, 3H); 2.16 (s, 3H); 2.01 (s, 3H); 1.84-1.73 (m, 4H); 1-09 (t, 3H); 1.03 (t, 3H).

ESI-MS m/z: Calcd. for $C_{45}H_{53}N_3O_{12}S$: 859.3 Found (M+H$^+$): 860.3.

Example 143

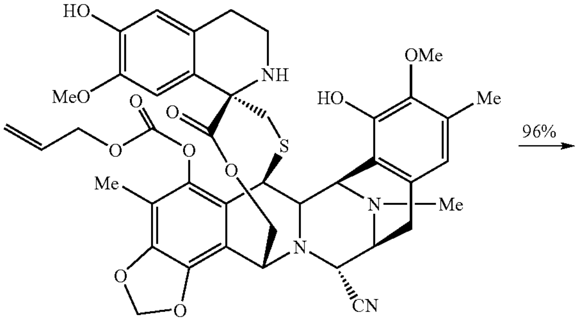

141

-continued

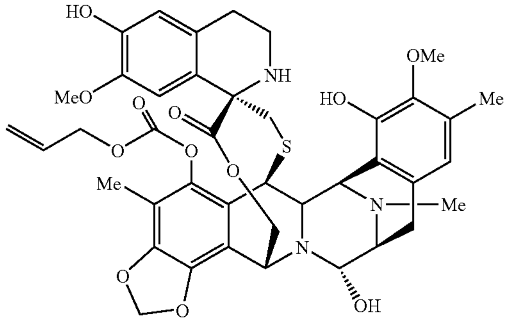

165

165 was obtained using Method H $^1$H-NMR (300 MHz, $CDCl_3$): δ 6.59 (s, 1H); 6.47 (s, 1H); 6.45 (s, 1H); 6.03 (d, 1H); 5.98-5.85 (m, 1); 5.95 (d, 1H); 5.70 (s, 1H); 5.37 (dd, 1H); 5.26 (dd, 1H); 5.12 (d, 1H); 4.80 (s, 1H); 4.64-4.62 (m, 2H); 4.58 (s, 1H); 4.48 (d, 1H); 4.17 (d, 1H); 4.05 (dd, 1H); 3.77 (s, 3H); 3.60 (s, 3H); 3.57 (d, 1H); 3.22-3.10 (m, 2H); 2.87-2.78 (m, 3H); 2.68-2.58 (m, 1H); 2.49-2.20 (m, 2H); 2.31 (s, 3H); 2.17 (s, 3H); 2.08 (s, 3H).

$^{13}$C-NMR (75 MHz, $CDCl_3$): δ 172.7, 152.7, 147.9, 145.3, 144.6, 144.4, 143.1, 141.3, 140.9, 131.5, 129.4, 129.2, 126.2, 122.3, 121.0, 119.0, 116.1, 114.2, 112.6, 109.9, 101.9, 82.3, 69.3, 64.7, 61.4, 60.5, 57.9, 57.8, 56.2, 55.3, 55.0, 42.5, 42.0, 41.6, 39.8, 29.9, 28.9, 24.2, 16.0, 9.5.

ESI-MS m/z: Calcd. for $C_{41}H_{45}N_3O_{12}S$: 803.3 Found ($M+H^+$): 804.3.

Example 144

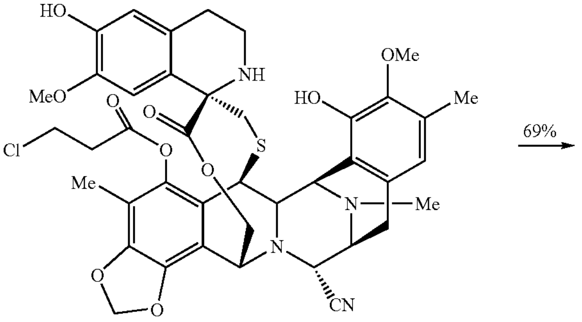

142

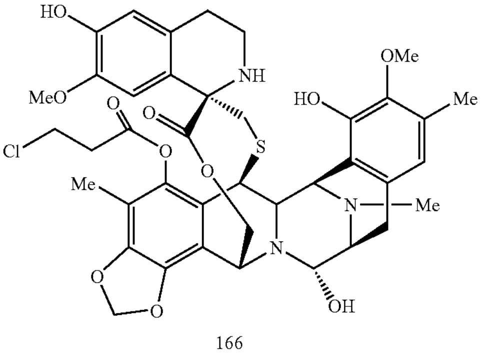

166

166 was obtained using Method H. $^1$H-NMR (300 MHz, $CDCl_3$): δ 6.60 (s, 1H); 6.47 (s, 1H); 6.32 (s, 1H); 6.03 (d, 1H); 5.95 (d, 1H); 5.72 (s, 1H); 5.12 (d, 1H); 4.82 (s, 1H); 4.48 (d, 1H); 4.43 (s, 1H); 4.17-4.14 (m, 1H); 4.04 (dd, 1H); 3.85 (ddd, 2H); 3.79 (s, 3H); 3.61 (s, 3H); 3.60-3.57 (m, 1H); 3.24-3.10 (m, 2H); 3.03 (t, 2H); 2.88-2.78 (m, 3H); 2.68-2.56 (m, 1H); 2.49-2.43 (m, 1H); 2.38-2.13 (m, 2H); 2.31 (s, 3H); 2.17 (s, 3H); 2.04 (s, 3H).

$^{13}$C-NMR (75 MHz, $CDCl_3$): δ 172.6, 167.8, 147.8, 145.4, 144.6, 144.4, 143.2, 141.1, 140.9, 131.6, 129.3, 126.1, 121.8, 114.2, 109.9, 101.9, 82.2, 64.7, 61.5, 60.6, 58.0, 57.8, 56.1, 55.3, 55.1, 42.5, 42.3, 41.6, 39.9, 38.8, 37.7, 29.9, 29.5, 29.0, 24.3, 22.9, 16.0, 14.3, 9.9.

ESI-MS m/z: Calcd. for $C_{40}H_{44}ClN_3O_{11}S$: 809.2 Found ($M+H^+$): 810.3.

Example 145

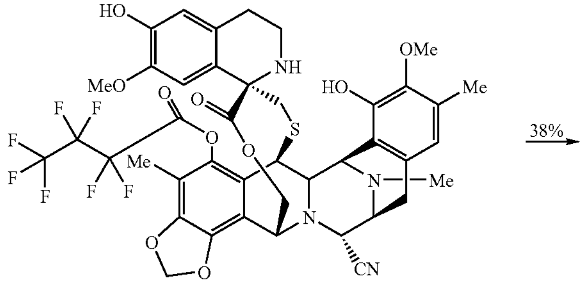

143

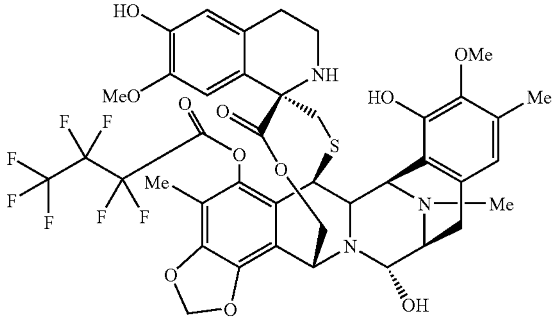

167

167 was obtained using Method H $^1$H-NMR (300 MHz, $CDCl_3$): δ 6.60 (s, 1H); 6.49 (s, 1H); 6.46 (s, 1H); 6.07 (s, 1H); 6.00 (s, 1H); 5.64 (s, 1H); 5.39 (s, 1H); 5.16 (d, 1H); 4.83 (s, 1H); 4.49 (s, 1H); 4.19-4.18 (m, 1H); 4.06 (dd, 1H); 3.76 (d, 1H); 3.62 (s, 3H); 3.57-3.56 (m, 1H); 3.24-3.12 (m, 2H); 2.89-2.85 (m, 2H); 2.79-2.73 (m, 1H); 2.68-2.58 (m, 1H); 2.52-2.45 (m, 1H); 2.37-2.10 (m, 2H); 2.31 (s, 3H); 2.18 (s, 3H); 2.03 (s, 3H).

ESI-MS m/z: Calcd. for $C_{41}H_{40}F_7N_3O_{11}S$: 915.2 Found (M+H$^+$): 916.2.

Example 146

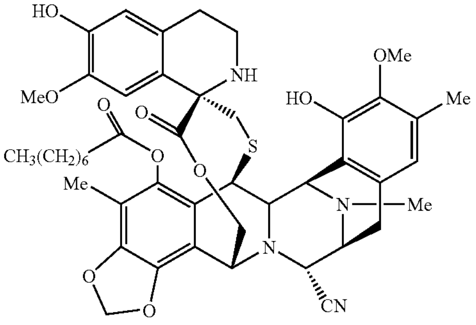

144

86%

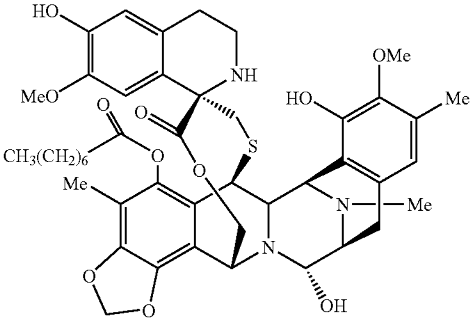

168

168 was obtained using Method H. $^1$H-NMR (300 MHz, $CDCl_3$): δ 6.60 (s, 1H); 6.47 (s, 1H); 6.43 (s, 1H); 5.97 (dd, 2H); 5.64 (s, 1H); 5.32 (s, 1H); 5.12 (d, 1H); 4.81 (s, 1H); 4.48 (s, 1H); 4.48-4.45 (m, 1H); 4.16 (d, 1H); 4.03 (dd, 1H); 3.78 (s, 3H); 3.60 (s, 3H); 3.58 (d, 1H); 3.24-3.08 (m, 2H); 2.94-2.78 (m, 3H); 2.66-2.42 (m, 2H); 2.53 (t, 2H); 2.38-2.12 (m, 2H); 2.31 (s, 3H); 2.16 (s, 3H); 2.01 (s, 3H); 1.80-1.68 (m, 2H); 1.42-1.23 (m, 11H).

$^{13}$C-NMR (75 MHz, $CDCl_3$): δ 172.6, 171.3, 147.8, 145.3, 144.6, 144.4, 143.1, 141.5, 140.6, 131.6, 129.3, 129.2, 121.9, 121.1, 114.2, 110.0, 101.8, 82.3, 64.9, 61.6, 60.5, 58.0, 57.9, 56.1, 55.2, 55.1, 42.3, 41.6, 39.9, 34.2, 31.9, 29.9, 29.6, 29.2, 25.1, 24.3, 22.8, 16.0, 14.3, 9.9.

ESI-MS m/z: Calcd. for $C_{45}H_{55}N_3O_{11}S$: 845.4 Found (M+H$^+$): 846.7.

Example 147

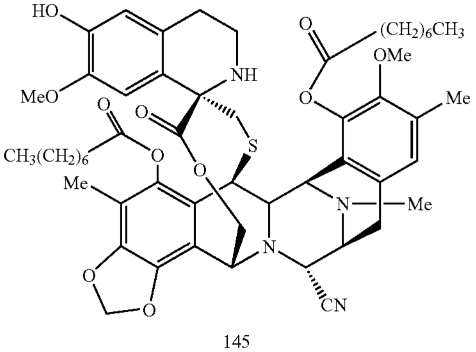

145

47%

-continued

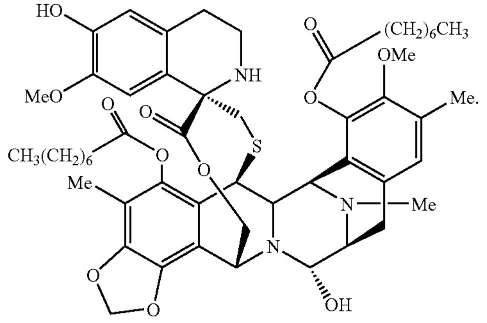

169

169 was obtained using Method H. $^1$H-NMR (300 MHz, $CDCl_3$): δ 6.94 (s, 1H); 6.47 (s, 1H); 6.41 (s, 1H); 6.03 (s, 1H); 5.94 (s, 1H); 5.12 (d, 1H); 4.81 (s, 1H); 4.49 (s, 1H); 4.37 (s, 1H); 4.03 (d, 1H); 3.74 (s, 3H); 3.67-3.57 (m, 2H); 3.60 (s, 3H); 3.24-3.10 (m, 2H); 2.92-2.80 (m, 3H); 2.68-2.44 (m, 2H); 2.61 (t, 2H); 2.56 (t, 2H); 2.38-2.18 (m, 2H); 2.31 (s, 3H); 2.12 (s, 3H); 2.02 (s, 3H); 1.84-1.68 (m, 4H); 1.42-1.20 (m, 22H).

ESI-MS m/z: Calcd. for $C_{53}H_{69}N_3O_{12}S$: 971.5 Found (M+H$^+$): 972.7.

Example 148

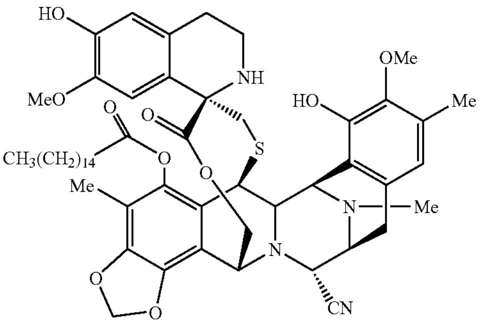

146

71%

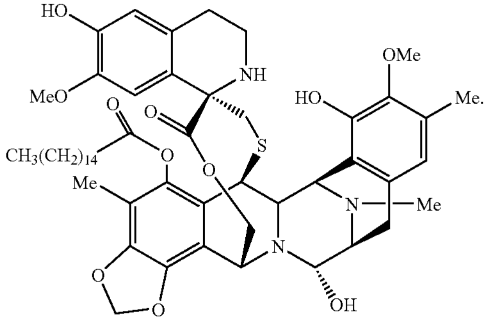

170

170 was obtained using Method H. $^1$H-NMR (300 MHz, $CDCl_3$): δ 6.59 (s, 1H); 6.47 (s, 1H); 6.43 (s, 1H); 6.01 (dd, 2H); 5.66 (s, 1H); 5.39 (s, 1H); 5.02 (d, 1H); 4.55 (s, 1H); 4.31 (s, 1H); 4.26 (dd, 1H); 4.17 (d, 1H); 4.11 (dd, 1H); 3.77 (s, 3H); 3.61 (s, 3H); 3.51 (d, 1H); 3.42-3.40 (m, 1H); 3.16-3.04 (m, 1H); 2.94-2.92 (m, 2H); 2.82-2.74 (m, 1H); 2.66-2.44 (m, 2H); 2.53 (t, 2H); 2.36-2.15 (m, 2H); 2.31 (s, 3H); 2.18 (s, 3H); 2.02 (s, 3H); 1.78-1.59 (m, 2H); 1.40-1.16 (m, 27H).

ESI-MS m/z: Calcd. for $C_{53}H_{71}N_3O_{11}S$: 957.5 Found (M+H$^+$): 958.4.

Example 149
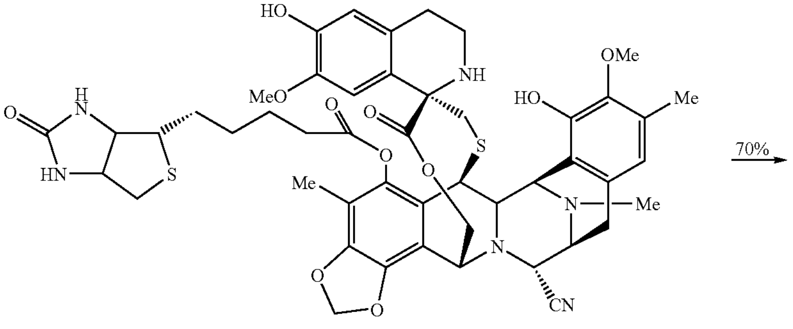
147
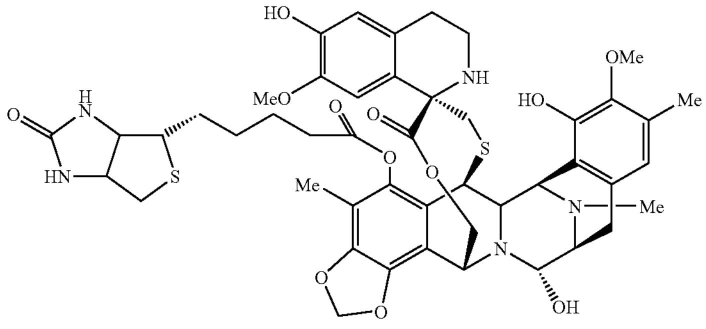
171
Compound 147 was recovered (19%) after chromatographic purification.
171 was obtained using Method H. $^{1}$H-NMR (300 MHz, $CDCl_3$): δ 7.50 (s, 1H); 6.81 (s, 1H); 6.56 (s, 1H); 6.45 (s, 1H); 6.40 (s, 1H); 6.02 (d, 1H); 5.93 (d, 1H); 5.21 (s, 1H); 5.12 (d, 1H); 4.84 (s, 1H); 4.51-4.46 (m, 2H); 4.41 (s, 1H); 4.32-4.21 (m, 3H); 4.01 (dd, 1H); 3.75 (s, 3H); 3.75-3.71 (m, 1H); 3.65 (s, 3H); 3.59 (s, 3H); 3.23 (s, 1H); 3.17-3.10 (m, 2H); 2.89-2.80 (m, 3H); 2.74-2.37 (m, 4H); 2.29 (s, 3H); 2.17 (s, 3H); 2.00 (s, 3H); 1.80-1.68 (m, 4H); 1.55-1.39(m, 2H).
$^{13}$C-NMR (75 MHz, $CDCl_3$): δ 172.6, 171.4, 164.5, 148.4, 145.4, 144.7, 144.6, 143.4, 141.5, 140.7, 131.1, 129.2, 129.0, 122.0, 120.6, 116.2, 114.3, 110.1, 101.9, 82.1, 70.7, 65.0, 62.4, 61.8, 60.5, 60.3, 58.1, 57.9, 56.1, 55.2, 55.0, 42.5, 41.6, 40.8, 40.1, 33.7, 32.1, 29.9, 29.5, 28.7, 28.2, 24.7, 24.3, 16.1, 14.3, 9.9.
ESI-MS m/z: Calcd. for $C_{47}H_{55}N_5O_{12}S_2$: 945.3 Found ($M-H_2O+H^+$): 928.3.
Example 150
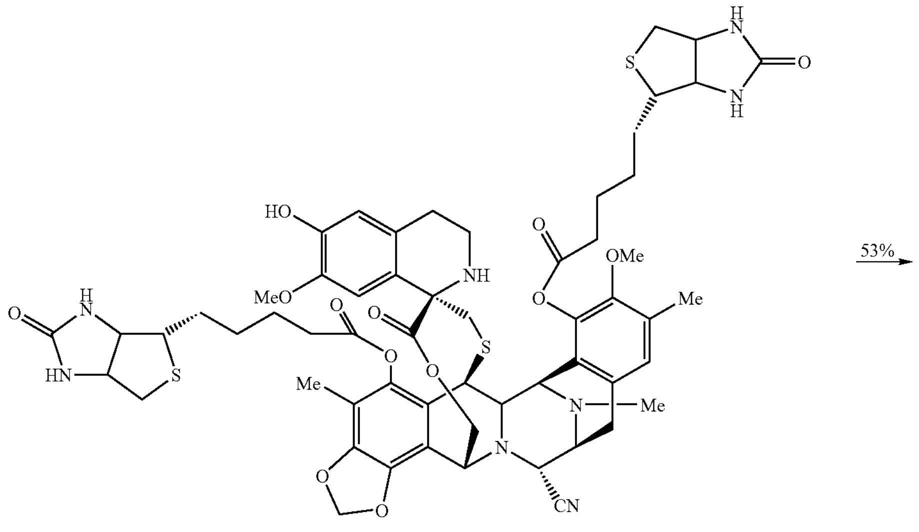
148

-continued
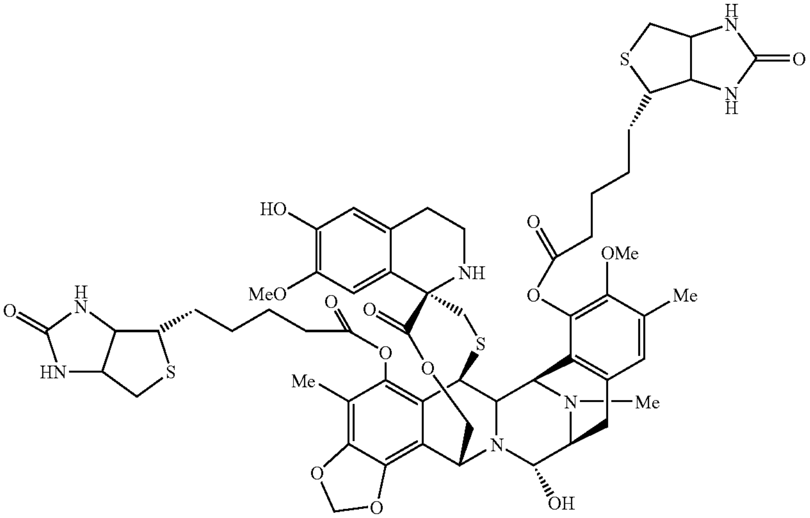
172
172 was obtained using Method H. $^{1}H$-NMR (300 MHz, $CDCl_3$): δ 6.94 (s, 1H); 6.46 (s, 1H); 6.39 (s, 1H); 6.26 (s, 1H); 6.02 (d, 1H); 5.94 (d, 1H); 5.57-5.55 (m, 2H); 5.11 (d, 1H); 4.82 (s, 1H); 4.48-4.45 (m, 3H); 4.32-4.22 (m, 3H); 4.01 (dd, 1H); 3.75 (s, 3H); 3.75-3.71 (m, 1H); 3.67-3.64 (m, 6H); 3.59 (s, 3H); 3.25-3.24 (m, 1H); 3.19-3.10 (m, 3H); 2.92-2.83 (m, 4H); 2.74-2.60 (m, 6H); 2.46-2.14 (m, 2H); 2.31 (s, 3H); 2.11 (s, 3H); 2.03 (s, 3H); 1.91-1.66 (m, 8H); 1.59-1.44 (m, 4H).
ESI-MS m/z: Calcd. for $C_{47}H_{55}N_3O_{12}S_2$: 1171.4 Found ($M-H_2O+H^+$): 1154.3.
Example 151
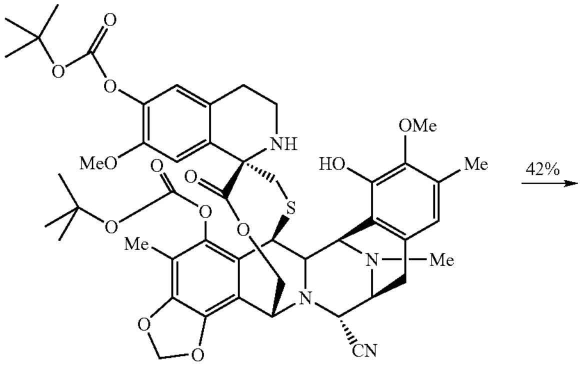
108
-continued
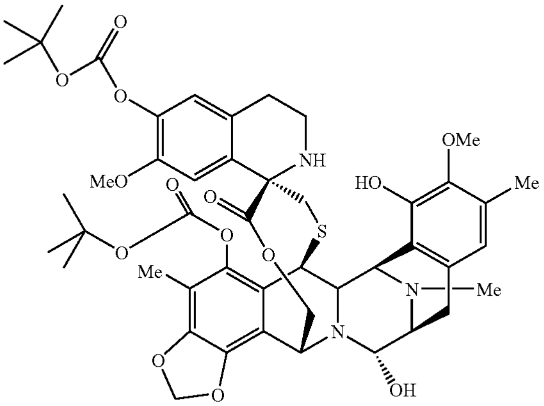
173
173 was obtained using Method H. $^{1}H$-NMR (300 MHz, $CDCl_3$): δ 6.69 (s, 1H); 6.60 (s, 1H); 6.59 (s, 1H); 6.00 (s, 1H); 5.92 (s, 1H); 5.66 (s, 1H); 5.11 (d, 1H); 4.78 (s, 1H); 4.59 (s, 1H); 4.46 (d, 1H); 4.15 (d, 1H); 4.04 (dd, 1H); 3.79 (s, 3H); 3.57 (s, 3H); 3.56-3.52 (m, 1H); 3.21-3.09 (m, 2H); 2.87-2.75 (m, 3H); 2.69-2.38 (m, 3H); 2.31 (s, 3H); 2.30-2.10 (m, 2H); 2.16 (s, 3H); 2.06 (s, 3H); 1.50 (s, 9H); 1.48 (s, 9H).
$^{13}C$-NMR (75 MHz, $CDCl_3$): δ 172.2, 151.8, 150.9, 148.6, 147.9, 145.3, 143.1, 141.3, 140.6, 138.9, 133.1, 131.7, 129.3, 128.8, 122.3, 121.0, 118.1, 115.9, 112.7, 112.1, 101.8, 83.6, 83.3, 82.3, 65.1, 61.6, 60.4, 57.9, 56.2, 55.4, 55.1, 42.5, 42.0, 41.6, 39.7, 29.9, 28.8, 27.9, 27.8, 24.3, 16.0, 9.5.
ESI-MS m/z: Calcd. for $C_{47}H_{57}N_3O_{14}S$: 919.4 Found ($M+H^+$): 920.3

Example 152
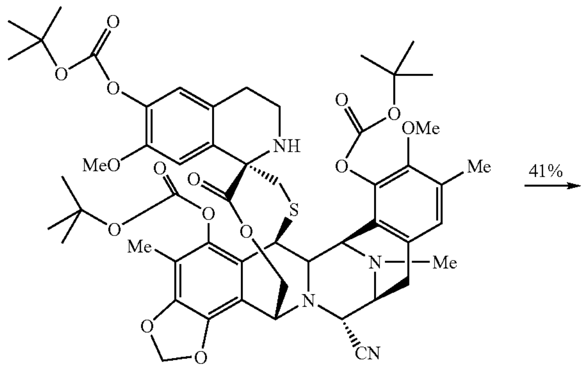
110
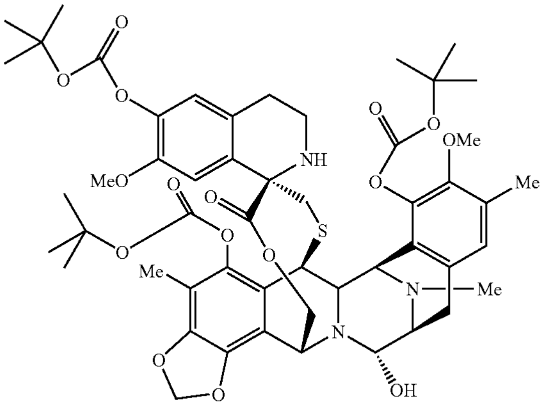
174
174 was obtained using Method H. $^1$H-NMR (300 MHz, $CDCl_3$): δ 6.92 (s, 1H); 6.69 (s, 1H); 6.58 (s, 1H); 6.01 (s, 1H); 5.93 (s, 1H); 5.10 (d, 1H); 4.76 (s, 1H); 4.55 (s, 1H); 4.46 (d, 1H); 4.04 (dd, 1H); 3.84 (d, 1H); 3.81 (s, 3H); 3.61-3.58 (m, 1H); 3.58 (s, 3H); 3.24-3.10 (m, 2H); 2.99-2.77 (m, 3H); 2.70-2.60 (m, 1H); 2.51-2.17 (m, 3H); 2.30 (s, 3H); 2.14 (s, 3H); 2.07 (s, 3H); 1.55 (s, 9H); 1.51 (s, 9H); 1.49 (s, 9H).
ESI-MS m/z: Calcd. for $C_{52}H_{65}N_3O_{16}S$: 1019.4 Found ($M+H^+$): 1020.4
Example 153
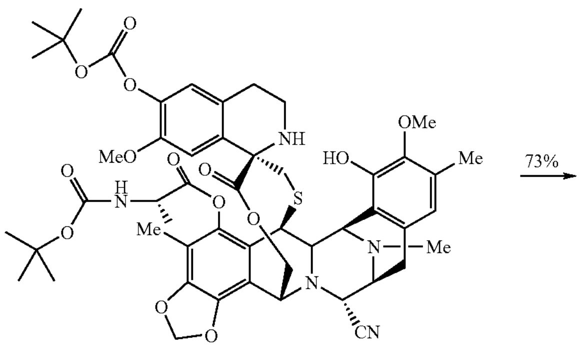
125
-continued
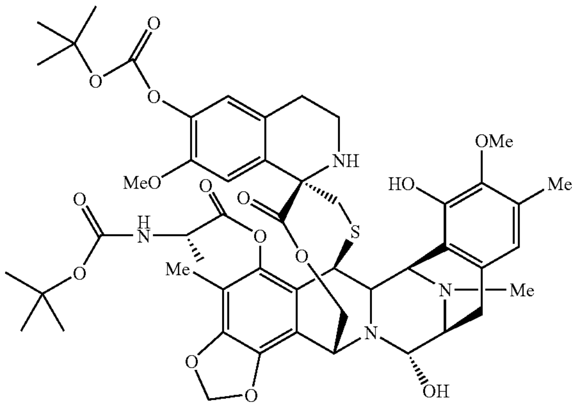
175
175 was obtained using Method H. $^1$H-NMR (300 MHz, $CDCl_3$): δ 6.69 (s, 1H); 6.57 (s, 1H); 6.55 (s, 1H); 6.02 (d, 1H); 5.94 (d, 1H); 5.12 (d, 1H); 5.02 (d, 1H); 4.82 (s, 1H); 4.61 (t, 1H); 4.49 (d, 1H); 4.41 (s, 1H); 4.17 (d, 1H); 4.00 (dd, 1H); 3.77 (s, 3H); 3.57-3.55 (m, 1H); 3.56 (s, 3H); 3.22-3.09 (m, 2H); 2.86-2.80 (m, 3H); 2.69-2.60 (m, 1H); 2.50-2.36 (m, 2H); 2.30 (s, 3H); 2.15 (s, 3H); 2.01 (s, 3H); 1.61 (d, 3H); 1.50 (s, 9H); 1.43 (s, 9H).
$^{13}$C-NMR (75 MHz, $CDCl_3$): δ 172.2, 171.3, 155.5, 151.8, 148.7, 147.9, 145.5, 143.3, 140.9, 139.0, 132.8, 131.7, 129.6, 128.8, 122.4, 122.0, 120.9, 118.1, 116.2, 112.1, 102.0, 83.6, 82.1, 65.3, 61.5, 60.6, 58.0, 56.2, 55.4, 54.9, 49.3, 42.4, 41.6, 39.9, 29.9, 28.9, 28.5, 27.8, 24.2, 18.6, 16.0, 9.8.
ESI-MS m/z: Calcd. for $C_{50}H_{62}N_4O_{15}S$: 990.4 Found ($M+H^+$): 991.4.
Example 154
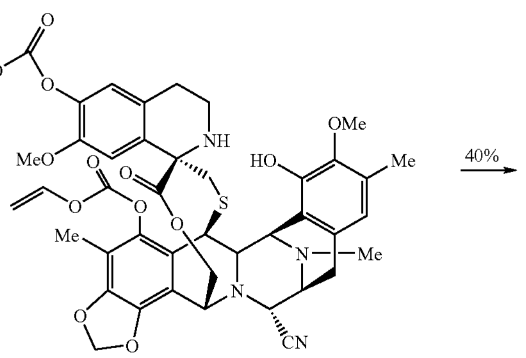
118

-continued

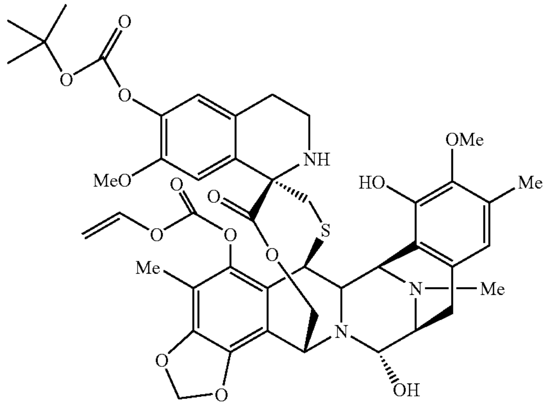

176

176 was obtained using Method H. $^{1}$H-NMR (300 MHz, $CDCl_3$): δ 6.99 (dd, 1H); 6.69 (s, 1H); 6.60 (s, 1H); 6.59 (s, 1H); 6.03 (d, 1H); 5.95 (d, 1H); 5.70 (s, 1H); 5.12 (d, 1H); 4.97 (dd, 1H); 4.80 (s, 1H); 4.60 (dd, 1H); 4.56 (s, 1H); 4.48 (d, 1H); 4.18 (d, 1H); 4.04 (dd, 1H); 3.76 (s, 3H); 3.58 (s, 3H); 3.58-3.56 (m, 1H); 3.47 (d, 1H); 3.24-3.12 (m, 2H); 2.87-2.78 (m, 3H); 2.68-2.58 (m, 1H); 2.52-2.47 (m, 1H); 2.43-2.20 (m, 2H); 2.31 (s, 3H); 2.18 (s, 3H); 2.08 (s, 3H); 1.50 (s, 9H).

$^{13}$C-NMR (75 MHz, $CDCl_3$): δ 172.3, 151.8, 150.5, 148.7, 148.0, 145.4, 143.1, 141.1, 140.9, 139.0, 133.1, 131.6, 129.4, 128.8, 122.4, 122.3, 120.9, 116.1, 112.6, 112.0, 102.0, 98.6, 86.6, 82.2, 64.8, 61.4, 60.5, 57.9, 57.7, 56.2, 55.5, 55.0, 42.5, 42.0, 41.6, 39.7, 29.9, 28.8, 27.8, 24.1, 16.0, 9.5.

ESI-MS m/z: Calcd. for $C_{45}H_{51}N_3O_{14}S$: 889.3 Found ($M+H^+$): 890.2

Example 155

Method I: To a solution of 1 equiv. of starting material in $THF/H_2O$ 4:1 (0.009M) were added 5 equiv. of BrCu. After 24 h the reaction was quenched with $NH_4Cl$, diluted with $CH_2Cl_2$, washed with brine and $NaHCO_3$ and extracted with $CH_2Cl_2$. The organic layer was dried over $Na_2SO_4$. Chromatography gives pure compounds.

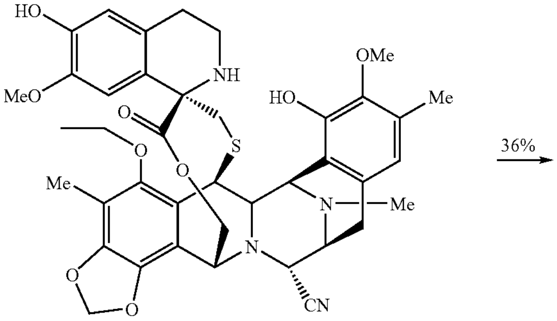

151

-continued

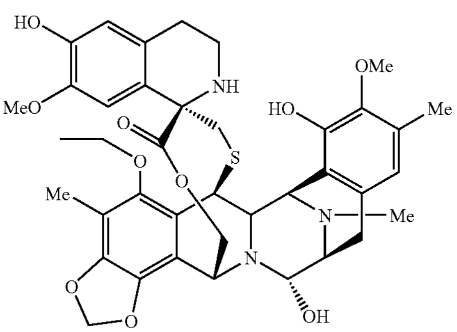

177

177 was obtained using Method I. ESI-MS m/z: Calcd. for $C_{39}H_{45}N_3O_{10}S$: 747.3 Found ($M+H^+$): 748.1.

Example 156

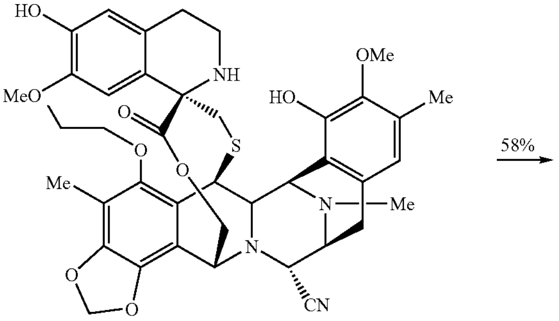

153

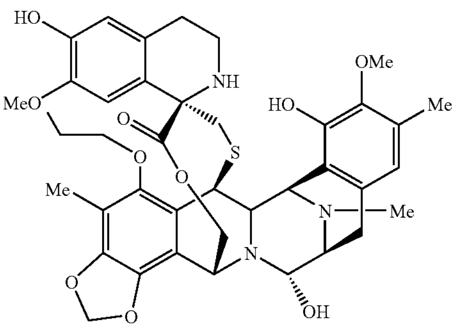

178

178 was obtained using Method I. $^{1}$H-NMR (300 MHz, $CDCl_3$): δ 6.59 (s, 1H); 6.49 (s, 1H); 6.44 (s, 1H); 5.96 (s, 1H); 5.87 (s, 1H); 5.67 (s, 1H); 5.12 (d, 1H); 4.85 (s, 1H); 4.78 (s, 1H); 4.49 (s, 1H); 4.20-4.18 (m, 1H); 4.08 (dd, 1H); 3.79 (s, 3H); 3.61 (s, 3H); 3.23-3.10 (m, 2H); 2.87-2.80 (m, 2H); 2.70-2.58 (m, 1H); 2.49-2.42 (m, 1H); 2.31 (s, 3H); 2.26-2.22 (m, 2H); 2.18 (s, 3H); 2.15 (s, 3H).

ESI-MS m/z: Calcd. for $C_{40}H_{47}N_3O_{10}S$: 761.3 Found (M+H$^+$): 762.3.

Example 157

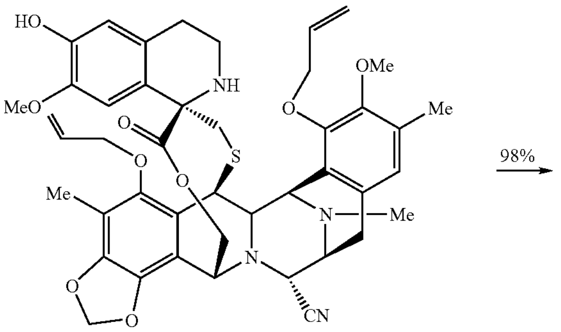

156

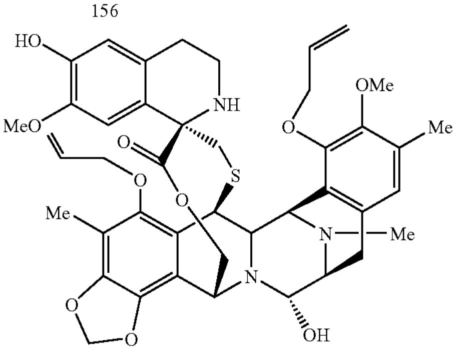

179

179 was obtained using Method I. $^1$H-NMR (300 MHz, $CDCl_3$): δ 6.79 (s, 1H); 6.50 (s, 1H); 6.45 (s, 1H); 6.15-6.02 (m, 2H); 5.97 (d, 1H); 5.88 (d, 1H); 5.46-5.35 (m, 3H); 5.20 (dd, 2H); 5.13 (d, 1H); 4.84 (s, 1H); 4.78-4.74 (m, 2H); 4.49-4.38 (m, 3H); 4.21-4.08 (m, 3H); 3.84 (s, 3H); 3.62 (s, 3H); 3.57 (d, 1H); 3.49 (s, 1H); 3.22-3.08 (m, 2H); 2.92-2.82 (m, 3H); 2.72-2.60 (m, 1H); 2.52-2.46 (m, 1H); 2.28 (s, 3H); 2.26-2.23 (m, 2H); 2.17 (s, 6H).

ESI-MS m/z: Calcd. for $C_{43}H_{49}N_3O_{10}S$: 799.3 Found (M+H$^+$): 800.2.

Example 158

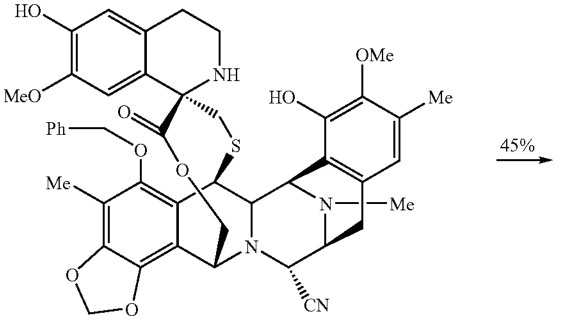

157

-continued

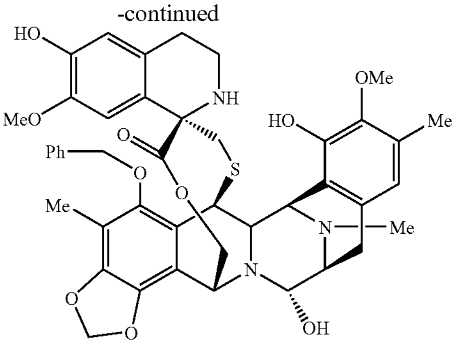

180

180 was obtained using Method I. $^1$H-NMR (300 MHz, $CDCl_3$): δ 7.54-7.51 (m, 2H); 7.40-7.29 (m, 3H); 6.58 (s, 1H); 6.49 (s, 1H); 6.48 (s, 1H); 5.99 (d, 1H); 5.91 (d, 1H); 5.34 (s, 1H); 5.14 (d, 1H); 5.01 (d, 1H); 4.84 (s, 1H); 4.79 (s, 1H); 4.72 (d, 1H); 4.49 (d, 1H); 4.12-4.07 (m, 2H); 3.77 (s, 3H); 3.64 (s, 3H); 3.50 (d, 1H); 3.22-3.10 (m, 2H); 2.87-2.82 (m, 2H); 2.70-2.60 (m, 1H); 2.49-2.43 (m, 1H); 2.34-2.10 (m, 2H); 2.31 (s, 3H); 2.24 (s, 3H); 2.15 (s, 3H).

ESI-MS m/z: Calcd. for $C_{44}H_{47}N_3O_{10}S$: 809.3 Found (M+H$^+$): 810.3.

Example 159

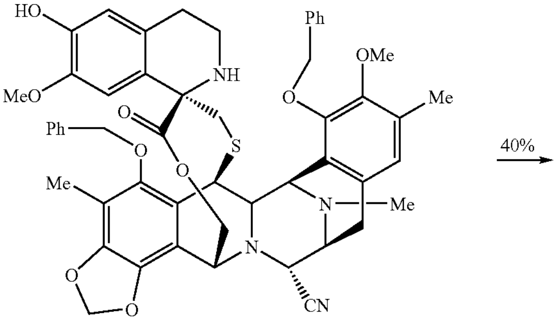

158

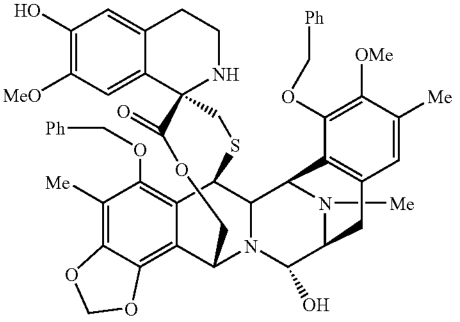

181

181 was obtained using Method I. ESI-MS m/z: Calcd. for $C_{51}H_{53}N_3O_{10}S$: 899.4 Found (M+H$^+$): 900.3.

Example 160

Method K: To a solution of 1 equiv. of starting material in $THF/H_2O$ 4:1 (0.009M) were added 5 equiv. of ClCu. After 24 h the reaction was quenched with $NH_4Cl$, diluted with $CH_2Cl_2$, washed with brine and $NaHCO_3$ and extracted with $CH_2Cl_2$. The organic layer was dried over $Na_2SO_4$. Chromatography gives pure compounds.

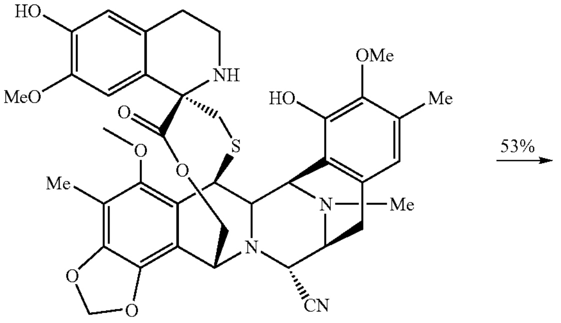

149

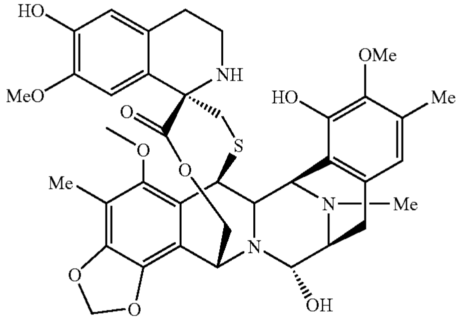

182

182 was obtained using Method I. $^{1}$H-NMR (300 MHz, $CDCl_3$): δ 6.60 (s, 1H); 6.49 (s, 1H); 6.45 (s, 1H); 5.97 (s, 1H); 5.88 (s, 1H); 5.76 (s, 1H); 5.11 (d, 1H); 4.80 (s, 1H); 4.48-4.46 (m, 1H); 4.20-4.18 (m, 1H); 4.07 (dd, 1H); 3.80 (s, 3H); 3.74 (s, 3H); 3.74-3.60 (m, 2H); 3.61 (s, 3H); 3.22-3.08 (m, 2H); 2.87-2.78 (m, 3H); 2.66-2.58 (m, 1H); 2.49-2.44 (m, 1H); 2.32 (s, 3H); 2.31-2.24 (m, 2H); 2.18 (s, 3H); 2.17 (s, 3H).

ESI-MS m/z: Calcd. for $C_{38}H_{43}N_3O_{10}S$: 733.3 Found ($M+H^+$): 734.2.

Example 161

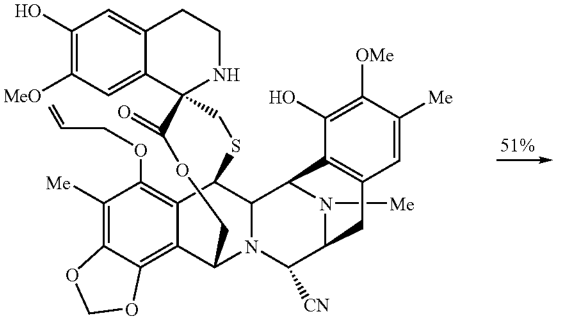

155

-continued

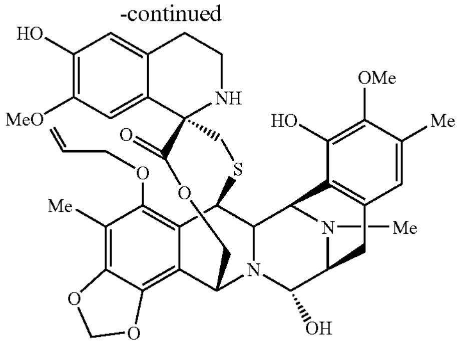

183

183 was obtained using Method I. $^{1}$H-NMR (300 MHz, $CDCl_3$): δ 6.59 (s, 1H); 6.49 (s, 1H); 6.45 (s, 1H); 6.15-6.02 (m, 1H); 5.97 (d, 1H); 5.88 (d, 1H); 5.69 (s, 1H); 5.43 (dd, 1H); 5.24 (dd, 1H); 5.12 (d, 1H); 4.85 (s, 1H); 4.78 (s, 1H); 4.52-4.47 (m, 2H); 4.21-4.15 (m, 2H); 4.08 (dd, 1H); 3.80 (s, 3H); 3.64-3.57 (m, 2H); 3.61 (s, 3H); 3.22-3.20 (m, 1H); 3.16-3.08 (m, 1H); 2.87-2.80 (m, 3H); 2.68-2.58 (m, 1H); 2.49-2.43 (m, 1H); 2.31 (s, 3H); 2.26 (d, 2H); 2.18 (s, 3H); 2.17 (s, 3H).

$^{13}$C-NMR (75 MHz, $CDCl_3$): δ 172.5, 149.4, 147.9, 145.6, 144.6, 144.4, 143.2, 139.2, 134.0, 129.5, 122.9, 121.0, 117.5, 115.9, 114.3, 112.4, 109.8, 101.8, 82.3, 74.1, 65.4, 61.7, 60.6, 58.4, 58.0, 56.5, 55.2, 55.1, 43.1, 42.3, 41.6, 40.0, 29.9, 29.5, 29.1, 24.4, 22.9, 16.0, 14.3, 9.8.

ESI-MS m/z: Calcd. for $C_{40}H_{45}N_3O_{10}S$: 759.3 Found ($M+H^+$): 760.3.

Example 162

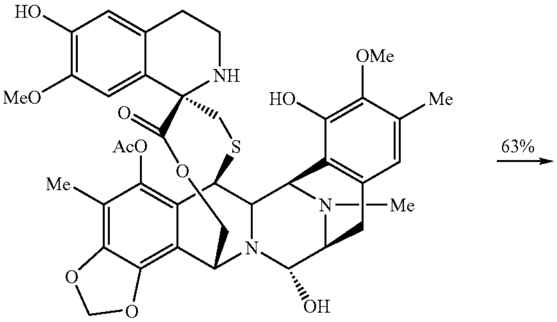

Et-743

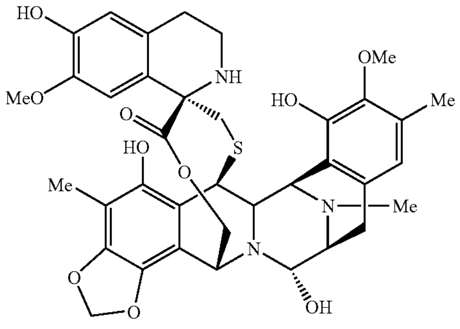

Et-701

To a solution of Et-743 in MeOH (0.19M) were added 15 equiv. of KOH. The reaction mixture was stirred at room temperature for 1 h 30 minutes. After this time the reaction was quenched with $NH_4Cl$, diluted and extracted with $CH_2Cl_2$. The organic layer was dried over $Na_2SO_4$. Chromatography gives pure Et-701.

Et-701 $^1$H-NMR (300 MHz, $CDCl_3$): δ 6.60 (s, 1H); 6.47 (s, 1H); 6.40 (s, 1H); 5.93 (d, 2H); 5.84 (d, 1H); 5.08 (d, 1H); 4.82 (s, 1H); 4.46 (d, 1H); 4.43 (d, 1H); 4.18 (d, 1H); 3.97 (dd, 1H); 3.70 (s, 3H); 3.65 (d, 1H); 3.57 (s, 3H); 3.23-3.08 (m, 2H); 2.88-2.78 (m, 3H); 2.65-2.55 (m, 1H); 2.49-2.36 (m, 2H); 2.30 (s, 3H); 2.14 (s, 3H); 2.13 (s, 3H).

ESI-MS m/z: Calcd. for $C_{37}H_{41}N_3O_{10}S$: 719.3 Found ($M-H_2O+H^+$): 702.2.

Example 163

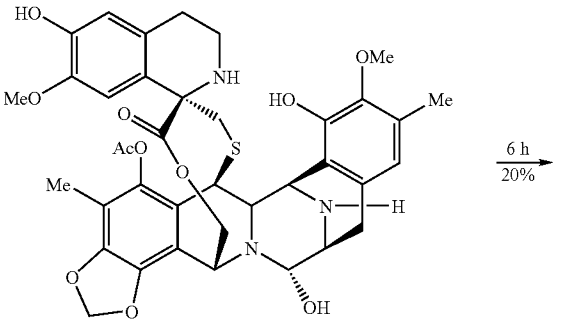

Et-729

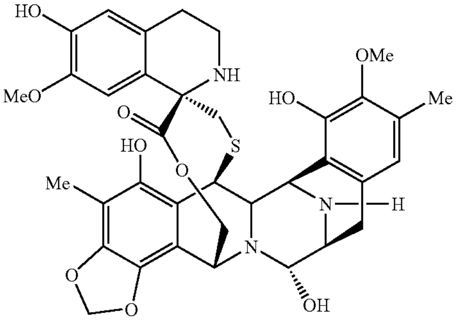

184

To a solution of ET-729 in MeOH (0.005M) at room temperature under Argon, were added 30 equiv. of KCN. The reaction mixture was stirred for 6 h. After this time the reaction was diluted with $CH_2Cl_2$, washed with NaCl, extracted with $CH_2Cl_2$. The organic layers were dried over $Na_2SO_4$. Flash chromatography gives pure compound 184 (20%).

184. $^1$H-NMR (300 MHz, $CDCl_3$): δ 6.64 (s, 1H), 6.50 (s, 1H), 6.39 (s, 1H), 5.94 (d, 2H), 5.42 (bs, 1H), 5.00 (d, 1H), 4.54 (d, 1H), 4.48 (s, 1H), 4.36 (s, 1H), 4.19 (d, 1H), 4.04 (dd 1H), 3.88-3.83 (m, 1H), 3.78 (s, 3H), 3.60 (bs, 4H), 3.17-3.06 (m, 2H), 2.99 (dd, 1H), 2.82-2.74 (m, 1H), 2.66-2.55 (m, 1H), 2.54-2.04 (m, 3H), 2.34 (s, 3H), 2.16 (s, 3H).

ESI-MS m/z: Calcd. for $C_{37}H_{38}N_4O_9S$: 714.2. Found ($M+H^+$): 715.2.

Example 164

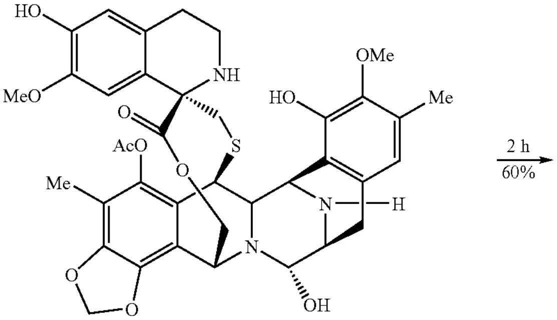

Et-729

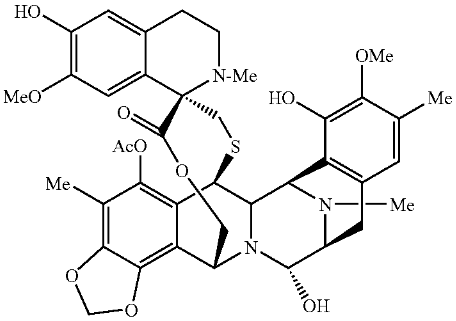

185

To a solution of ET-729 in acetonitrile (0.016M) at room temperature under Argon, were added 200 equiv. of formalin and 10 equiv. of $NaBH_3CN$. The reaction mixture was stirred for 1 h, then acetic acid (40 equiv.) was added and the reaction was left for 1 hour more. After this time the reaction was diluted with $CH_2Cl_2$, a saturated aqueous solution of $NaHCO_3$ was added and the aqueous phase was extracted with $CH_2Cl_2$. The organic layers were dried over $Na_2SO_4$. Flash chromatography gives pure compound 185 (60%).

185. $^1$H-NMR (300 MHz, $CD_3OD$): δ 6.40 (s, 1H), 6.35 (s, 1H), 6.23 (s, 1H), 6.06 (d, 2H), 5.01 (d, 1H), 4.63 (bs, 1H), 4.26 (d, 1H), 3.88-3.85 (m, 2H), 3.74 (s, 3H), 3.52 (s, 3H), 3.32-3.11 (m, 4H), 3.00-2.79 (m, 3H), 2.66-2.51 (m, 3H), 2.50-2.20 (m, 2H), 2.33 (s, 3H), 2.24 (s, 3H), 2.20 (s, 3H), 2.12 (s, 3H), 2.03 (s, 3H).

ESI-MS m/z: Calcd. for $C_{40}H_{45}N_3O_{10}S$: 759.3. Found ($M+H^+$): 760.2.

Example 165

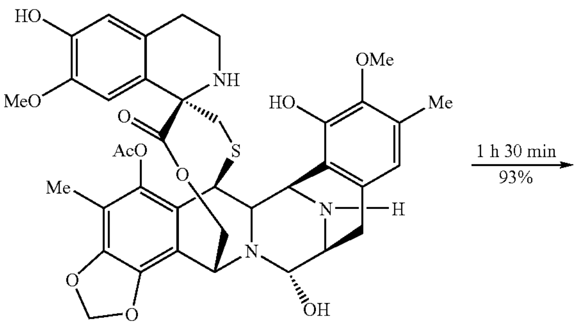

Et-729

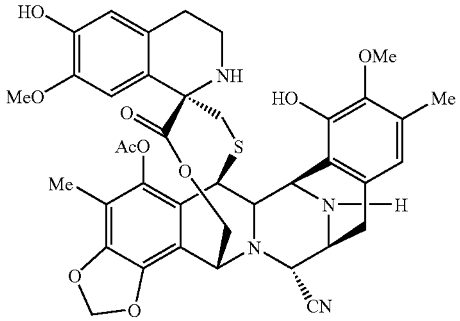

186

To a solution of ET-729 in MeOH (0.005M) at room temperature under Argon, were added 4.2 equiv. of KCN and 4.2 equiv. of acetic acid. The reaction mixture was stirred for 1 h 30 min. After this time the reaction was diluted with $CH_2Cl_2$, quenched with $NaHCO_3$, extracted with $CH_2Cl_2$. The organic layers were dried over $Na_2SO_4$. Flash chromatography gives pure compound 186 (93%).

186. $^1$H-NMR (300 MHz, $CDCl_3$): δ 6.60 (s, 1H), 6.43 (s, 1H), 6.42 (s, 1H), 6.00 (d, 2H), 5.96 (bs, 1H), 5.01 (d, 1H), 4.55 (bs, 1H), 4.49 (d, 1H), 4.32 (s, 1H), 4.18 (d, 1H), 4.10 (dd 1H), 3.82 (bd, 1H), 3.74 (s, 3H), 3.57 (s, 3H), 3.50 (d, 1H), 3.12-2.92 (m, 3H), 2.79-2.75 (m, 1H), 2.61-2.53 (m, 1H), 2.46-2.41 (m, 1H), 2.37-2.03 (m, 2H), 2.30 (s, 3H), 2.24 (s, 3H), 2.03 (s, 3H).

$^{13}$C-NMR (75 MHz, $CDCl_3$): δ 172.5, 168.1, 145.7, 145.2, 144.5, 144.3, 142.7, 141.2, 140.0, 131.2, 129.4, 129.0, 125.5, 124.3, 121.2, 121.0, 118.0, 114.1, 113.8, 113.3, 109.8, 101.8, 64.5, 61.1, 60.2, 59.8, 58.9, 58.7, 55.0, 48.5, 47.5, 42.0, 41.8, 39.6, 28.7, 28.0, 20.3, 15.6, 9.6.

ESI-MS m/z: Calcd. for $C_{39}H_{40}N_4O_{10}S$: 756.2. Found ($M+H^+$): 757.2.

Example 166

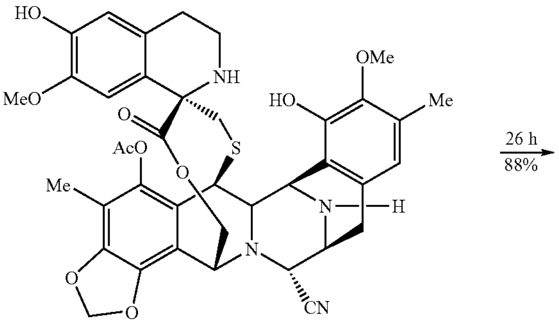

186

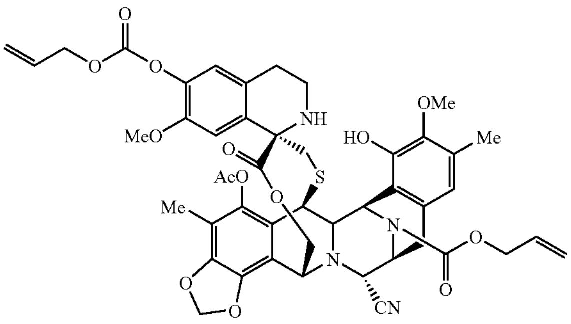

187

To a solution of 1 equiv. of compound 186 in $CH_2Cl_2$ (0.036M) under Argon at room temperature, were added 40 equiv. of Pyr, 20 equiv. of Allyl chloroformate and a catalityc amount of DMAP in small portions during 26 h. Then the reaction was quenched with water/ice. The aqueous layer was extracted with $CH_2Cl_2$ and the organic layer was dried over $Na_2SO_4$. Flash cromatography gives pure compound 187 (88%).

187. $^1$H-NMR (300 MHz, $CDCl_3$): δ 6.72 (s, 1H), 6.60 (s, 1H), 6.56 (bs, 1H), 6.02 (d, 2H), 6.04-5.76 (m, 2H), 5.69-5.57 (m, 1H), 5.42-4.97 (m, 6H), 4.69-4.49 (m, 5H), 4.34-4.29 (m, 1H), 4.22-4.09 (m, 2H), 3.78 (s, 3H), 3.57 (s, 3H), 3.78-3.48 (m, 2H), 3.22-3.05 (m, 3H), 2.89-2.43 (m, 3H), 2.36-2.16 (m, 2H), 2.31 (s, 3H), 2.29 (s, 3H), 2.05, 2.04 (2s, 3H).

ESI-MS m/z: Calcd. for $C_{47}H_{48}N_4O_{14}S$: 924.3. Found ($M+H^+$): 925.3.

Example 167

Method A: To a solution of 1 equiv. of starting material in $CH_2Cl_2$ (0.032M) under Argon were added 2 equiv. of the anhydride and 2 equiv. of base. The reaction was followed by TLC and quenched with $NaHCO_3$, extracted with $CH_2Cl_2$ and the organic layers dried over $Na_2SO_4$. Flash chromatography gives pure compounds.

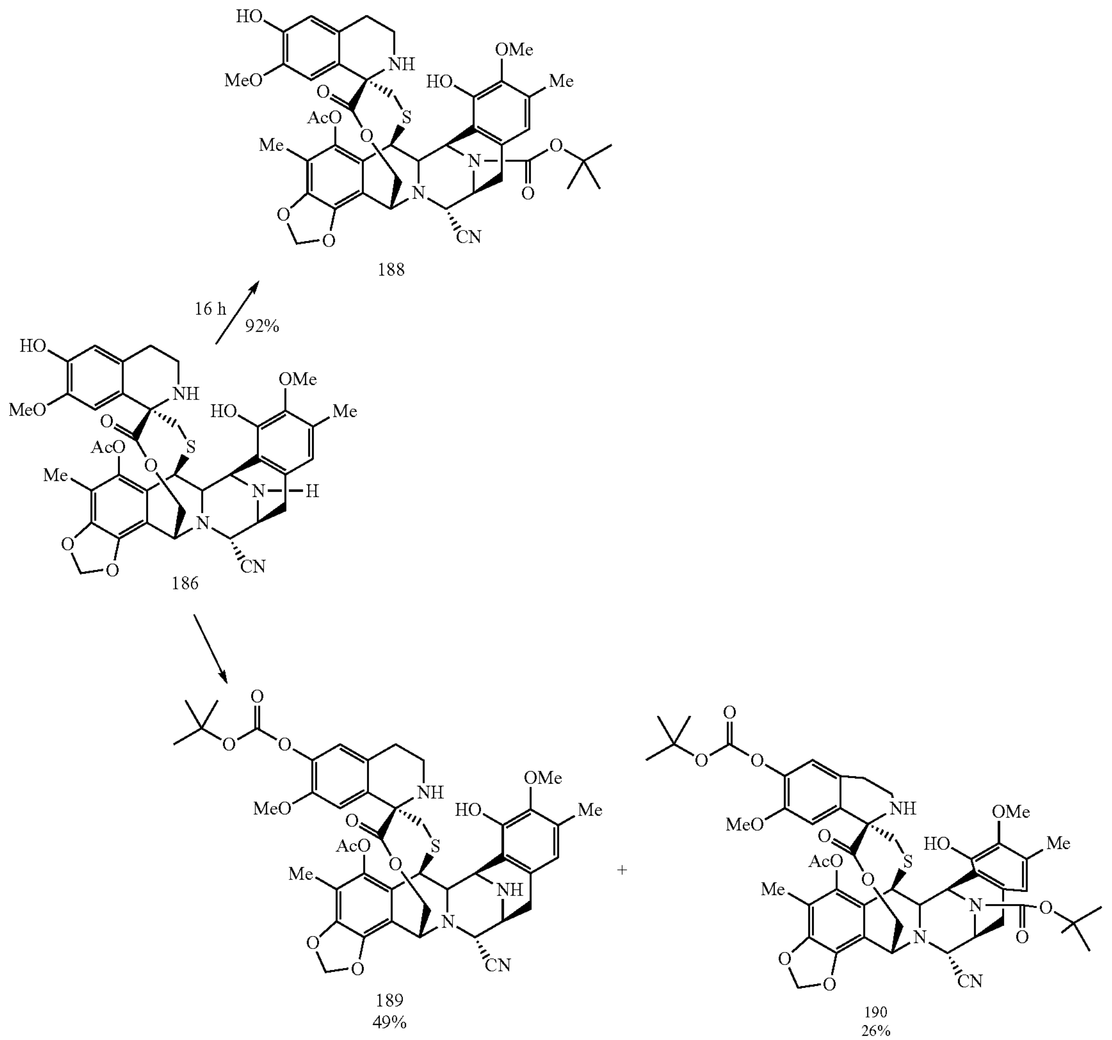

188

186

189
49%

190
26%

Compound 188 is obtained with 1.5 equiv. of $((CH_3)_3COCO)_2O$ without base in $CH_3CN$). Compounds 189 and 190 are obtained with 1 equiv. of $((CH_3)_3COCO)_2O$ and 4 equiv. of $^iPr_2NEt$ in $CH_3CN$. The ratio of these two compounds can be modified using other experimental conditions (reaction time and equiv. of reagents); even compound 190 can be obtained (78%) after 5 days when the reaction is performed with 7 equiv. of $(CH_3)_3COCO)_2O$ and 21 equiv. of $^iPr_2NEt$.

188: $^1$H-NMR (300 MHz, $CDCl_3$): δ 6.58 (s, 1H), 6.46 (s, 1H), 6.45, 6.43 (2s, 1H), 6.36, 5.80 (bs, s, 1H), 6.05-5.97 (m, 2H), 5.79, 5.44 (2d, 1H), 5.48 (bs, 1H), 5.05-4.94 (m, 2H), 4.67, 4.61 (2bs, 1H), 4.31 (s, 1H), 4.23-4.10 (m, 2H), 3.76, 3.75 (2s, 3H), 3.61 (s, 3H), 3.52-3.46 (m, 1H), 3.18-3.05 (m, 3H), 2.78-2.04 (m, 5H), 2.29 (s, 3H), 2.27 (s, 3H), 2.04, 1.98 (2s, 3H), 1.46, 1.32 (2s, 9H).

$^{13}$C-NMR (75 MHz, $CDCl_3$): δ 172.8, 172.4, 168.1, 154.5, 152.9, 146.9, 145.9, 145.3, 144.9, 144.5, 144.3, 143.2, 142.7, 141.2, 141.1, 140.0, 139.6, 131.0, 130.4, 130.1, 129.7, 129.0, 128.9, 125.5, 125.3, 121.6, 121.3, 121.1, 121.0, 120.6, 120.0, 116.8, 116.4, 114.1, 113.6, 113.3, 109.8, 101.7, 81.1, 80.7, 64.3, 61.2, 60.8, 60.2, 60.1, 59.9, 59.3, 58.3, 58.2, 58.1, 57.4, 55.0, 48.4, 48.2, 47.2, 45.8, 42.0, 41.7, 41.4, 39.6, 39.4, 28.6, 28.0, 27.9, 27.2, 20.7, 20.2, 15.7, 14.0, 9.6, 9.4.

ESI-MS m/z: Calcd. for $C_{44}H_{48}N_4O_{12}S$: 856.3. Found $(M+H^+)$: 857.2.

189: $^1$H-NMR (300 MHz, $CDCl_3$): δ 6.68 (s, 1H), 6.61 (s, 1H), 6.57 (s, 1H), 6.01 (dd, 2H), 5.78 (bs, 1H), 5.02 (d, 1H), 4.54 (bs, 1H), 4.50 (d, 1H), 4.35 (s, 1H), 4.18 (d 1H), 4.09 (dd, 1H), 3.87-3.82 (m, 1H), 3.77 (s, 3H), 3.58 (s, 3H), 3.53 (bd, 1H), 3.13-3.07 (m, 2H), 2.98 (dd, 1H), 2.83-2.75 (m, 1H), 2.68-2.57 (m, 1H), 2.52-2.43 (m, 1H), 2.37-2.16 (m, 2H), 2.30 (s, 3H), 2.27 (s, 3H), 2.03 (s, 3H), 1.50 (s, 9H).

ESI-MS m/z: Calcd. for $C_{44}H_{48}N_4O_{12}S$: 856.3. Found $(M+H^+)$: 857.3.

190: $^1$H-NMR (300 MHz, $CDCl_3$): δ 6.69 (s, 1H), 6.59-6.56 (m, 2H), 6.05-5.97 (m, 2H), 5.93, 5.77 (2s, 1H), 5.68, 5.43 (2d, 1H), 5.04-4.99 (m, 2H), 4.64-4.58 (m, 1H), 4.32-4.08 (m, 3H), 3.77 (s, 3H), 3.59 (s, 3H), 3.47-3.44 (m, 1H), 3.11-3.06 (m, 3H), 2.83-2.02 (m, 11H), 2.04, 2.02 (2s, 3H), 1.50, 1.45, 1.33 (3s, 18H).

ESI-MS m/z: Calcd. for $C_{49}H_{56}N_4O_{14}S$: 956.3. Found ($M+H^+$): 957.2.

Example 168

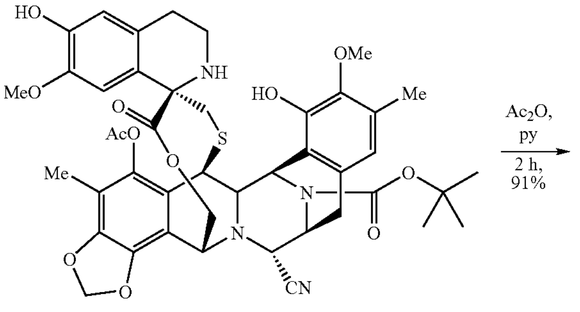

188

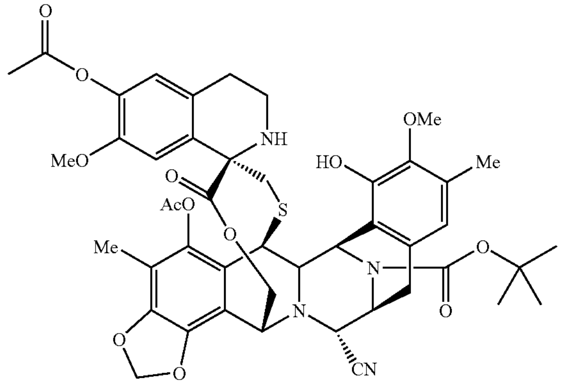

191

Compound 191 is obtained using 3 equiv. of acetic anhydride as the anhydride and 5 equiv. of pyr as base (Method A).

191. $^1$H-NMR (300 MHz, $CDCl_3$): δ 6.61, 6.60 (2s, 1H), 6.57, 6.56 (2s, 2H), 6.40, 5.81 (bs, s, 1H), 6.04-5.97 (m, 2H), 5.79, 5.44 (2d, 1H), 5.05-5.00 (m, 1H).4.94-4.90 (m, 1H), 4.67, 4.60 (2bs, 1H), 4.31 (s, 1H), 4.22-4.08 (m, 2H), 3.77, 3.76 (2s, 3H), 3.55 (s, 3H), 3.51-3.46 (m, 1H), 3.18-3.10 (m, 3H), 2.79-2.72 (m, 1H), 2.66-2.56 (m, 1H), 2.51-2.45 (m, 1H), 2.39-2.03 (m, 2H), 2.29 (s, 3H), 2.28, 2.27 (2s, 3H), 2.24 (s, 3H), 2.03, 1.97 (2s, 3H), 1.46, 1.32 (2s, 9H).

$^{13}$C-NMR (75 MHz, $CDCl_3$): δ 172.3, 172.1, 169.0, 168.1, 156.6, 152.9, 148.4, 146.6, 145.9, 145.2, 143.2, 142.8, 141.4, 138.6, 132.5, 131.2, 130.7, 130.0, 129.8, 128.7, 122.5, 121.7, 121.3, 120.8, 120.5, 116.6, 116.4, 113.4, 111.8, 101.9, 81.2, 80.9, 64.7, 61.2, 60.9, 60.3, 60.1, 59.8, 58.4, 58.2, 57.9, 55.1, 48.5, 48.2, 47.3, 45.9, 42.3, 41.5, 39.6, 39.5, 28.6, 28.3, 28.2, 28.1, 27.4, 20.6, 20.4, 15.8, 9.7.

ESI-MS m/z: Calcd. for $C_{46}H_{50}N_4O_{13}S$: 898.3. Found ($M+H^+$): 899.3.

Example 169

Method B: To a solution of 1 equiv. of starting material in $CH_2Cl_2$ (0.032M) under Argon at room temperature were added 2 equiv. of base and 2 equiv. of the acid chloride. The reaction was followed by TLC and quenched with $NaHCO_3$, extracted with $CH_2Cl_2$ and the organic layers dried over $Na_2SO_4$. Flash chromatography gives pure compounds.

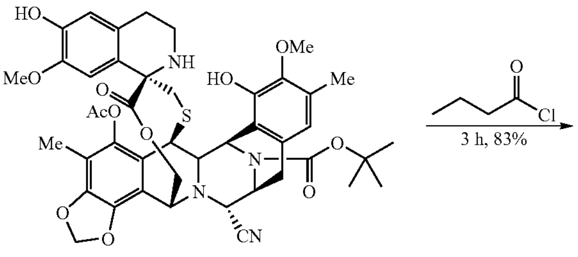

188

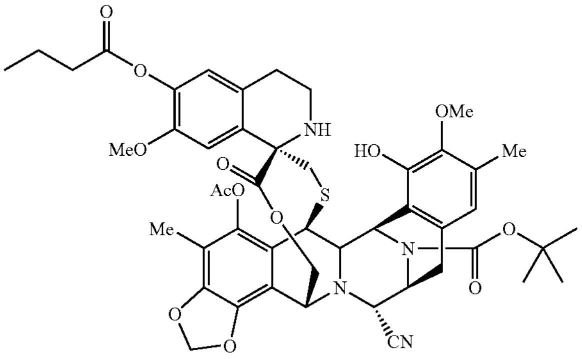

192

Compound 192 is obtained with 2.5 equiv. of butyryl chloride and 3.5 equiv. of pyridine. Some starting material (11%) was recovered after chromatographic purification (Method B).

192. $^1$H-NMR (300 MHz, $CDCl_3$): δ 6.60-6.55 (m, 3H), 6.47, 5.82 (2bs, 1H), 6.04-5.97 (m, 2H), 5.81, 5.44 (2d, 1H), 5.05-5.00 (m, 1H), 4.95-4.93 (m, 1H), 4.67, 4.59 (2bs, 1H), 4.31 (s, 1H), 4.21 (s, 1H), 4.15-4.08 (m, 1H), 3.77, 3.76 (2s, 3H), 3.54 (s, 3H), 3.52-3.46 (m, 1H), 3.18-3.10 (m, 3H), 2.79-2.75 (m, 1H), 2.65-2.55 (m, 1H), 2.50-2.45 (m, 1H), 2.48 (t, 2H), 2.38-2.03 (m, 2H), 2.29 (s, 3H), 2.28, 2.27 (2s, 3H), 2.04, 1.96 (2s, 3H), 1.79-1.67 (m, 2H), 1.47, 1.32 (2s, 9H), 1.00 (t, 3H).

$^{13}$C-NMR (75 MHz, $CDCl_3$): δ 172.3, 172.1, 171.6, 168.0, 154.6, 152.9, 148.5, 146.7, 145.9, 145.2, 143.2, 142.8, 141.4, 138.7, 132.3, 131.2, 130.7, 130.0, 129.8, 128.6, 122.5, 121.7, 121.3, 120.8, 120.5, 116.7, 116.4, 113.7, 113.4, 111.8, 101.9, 81.2, 80.9, 64.7, 61.2, 60.9, 60.3, 60.3, 60.1, 59.8, 58.4, 58.2, 57.9, 55.1, 48.5, 48.2, 47.3, 45.9, 42.3, 41.5, 39.6, 39.5, 35.8, 28.6, 28.3, 28.2, 28.1, 27.4, 20.6, 20.4, 18.5, 15.8, 13.5, 9.7, 9.6.

ESI-MS m/z: Calcd. for $C_{48}H_{54}N_4O_{13}S$: 926.3. Found ($M+H^+$): 927.3.

Example 170

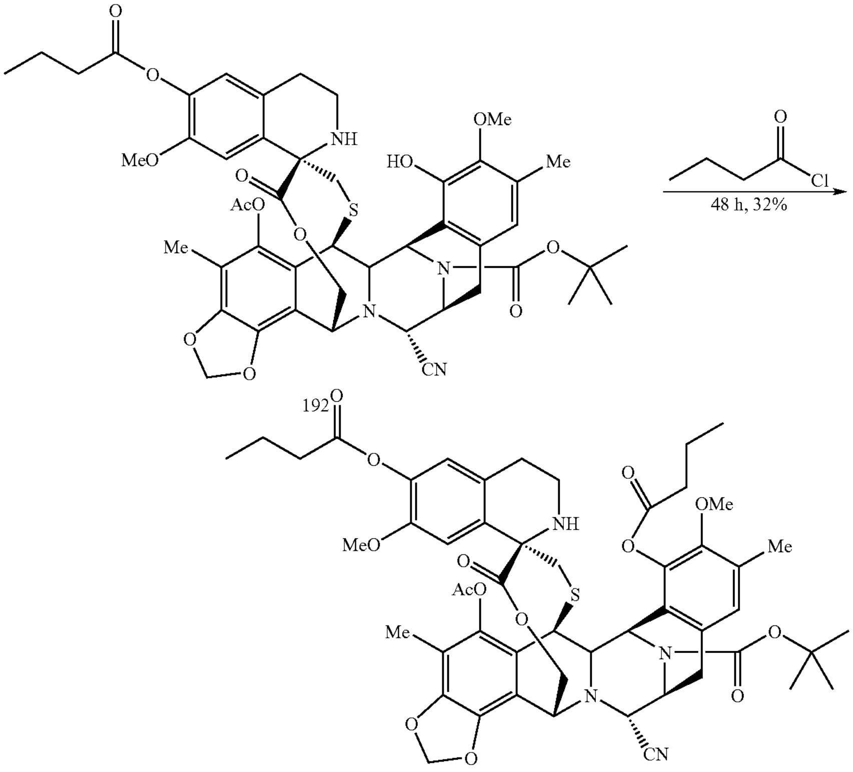

192

193

Compound 193 is obtained using 10 equiv. of butyryl chloride as the acid chloride and 10 equiv of $Et_3N$ as base (Method B). Compound 192 (13%) is recovered after chromatographic purification.

193. $^1$H-NMR (300 MHz, $CDCl_3$): δ 6.94 (s, 1H), 6.61 (s, 1H), 6.55 (s, 1H), 6.01 (d, 2H), 5.34-5.32 (m, 0.4H), 5.11-4.93 (m, 2.6H), 4.52-4.50 (m, 1H), 4.32-4.30 (m, 1H), 4.21 (d, 1H), 4.13-4.09 (m, 1H), 3.75, 3.74 (2s, 3H), 3.55 (s, 3H), 3.48-3.46 (m, 1H), 3.22-3.08 (m, 3H), 2.82-2.78 (m, 1H), 2.66-2.59 (m, 1H), 2.62 (t, 2H), 2.51-2.46 (m, 1H), 2.49 (t, 2H), 2.35-2.17 (m, 2H), 2.32, 2.31 (2s, 6H), 2.04 (s, 3H), 2.01-1.85 (m, 2H), 1.80-1.67 (m, 2H), 1.44, 1.37 (2s, 9H), 1.12 (t, 3H), 1.00 (t, 3H).

ESI-MS m/z: Calcd. for $C_{52}H_{60}N_4O_{14}S$: 996.4. Found ($M+H^+$): 997.3.

Example 171

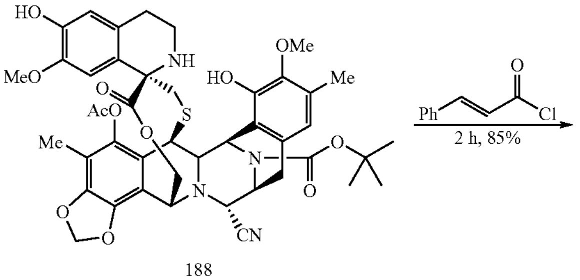

188

-continued

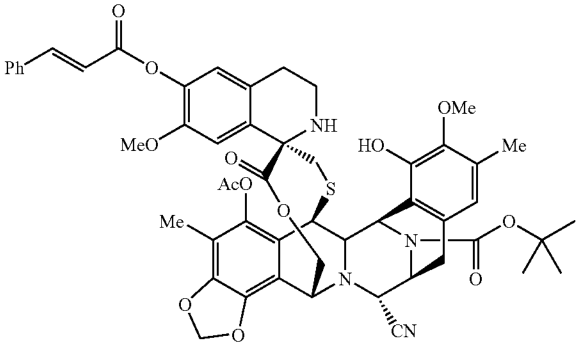

194

Compound 194 is obtained using 2.5 equiv. of cinnamoyl chloride as the acid chloride and 3.5 equiv. of pyr as base (Method B). Compound 188 (8%) is recovered after chromatographic purification.

194 $^1$H-NMR (300 MHz, $CDCl_3$): δ 7.80 (d, 1H), 7.68-7.54 (m, 2H), 7.50-7.38 (m, 3H), 6.69-6.57 (m, 4H), 6.47, 5.84 (2bs, 1H), 6.04-5.97 (m, 2H), 5.81, 5.45 (2d, 1H), 5.06-5.01 (m, 1H), 4.95-4.93 (m, 1H), 4.68, 4.61 (2bs, 1H), 4.32 (s, 1H), 4.23-4.10 (m, 2H), 3.77, 3.76 (2s, 3H), 3.57 (s, 3H), 3.52-3.47 (m, 1H), 3.19-3.09 (m, 3H), 2.82-2.78 (m, 1H), 2.69-2.62 (m, 1H), 2.54-2.47 (m, 1H), 2.41-2.20 (m, 2H), 2.30, 2.28 (2s, 6H), 2.04, 1.97 (2s, 3H), 1.47, 1.33 (2s, 9H).

$^{13}C$-NMR (75 MHz, $CDCl_3$): δ 172.3, 172.1, 168.1, 164.9, 152.9, 148.6, 146.7, 146.5, 145.9, 145.5, 143.2, 142.8, 138.6, 134.2, 132.3, 131.2, 130.7, 130.6, 130.3, 130.0, 129.8, 128.9, 128.7, 128.2, 128.1, 122.6, 121.3, 120.8, 120.5, 116.9, 116.7, 116.5, 113.7, 113.4, 111.8, 101.9, 81.2, 64.8, 61.2, 60.9, 60.3, 60.3, 60.2, 59.8, 58.4, 58.2, 57.9, 55.2, 48.5, 48.2, 47.3, 45.9, 42.3, 41.5, 39.6, 39.5, 28.6, 28.3, 28.2, 28.1, 27.4, 20.6, 20.4, 15.8, 9.7, 9.6.

ESI-MS m/z: Calcd. for $C_{53}H_{54}N_4O_{13}S$: 986.3. Found ($M+H^+$): 987.3.

Example 172

Method C: To a solution of 1 equiv. of starting material in $CH_2Cl_2$ (0.032M) under Argon were added 2 equiv. of acid, 2 equiv. of DMAP and 2 equiv. of EDC.HCl. The reaction was stirred at room temperature for 2 h. After this time was diluted with $CH_2Cl_2$, washed with brine and the organic layer dried over $Na_2SO_4$. Flash chromatography gives pure compounds.

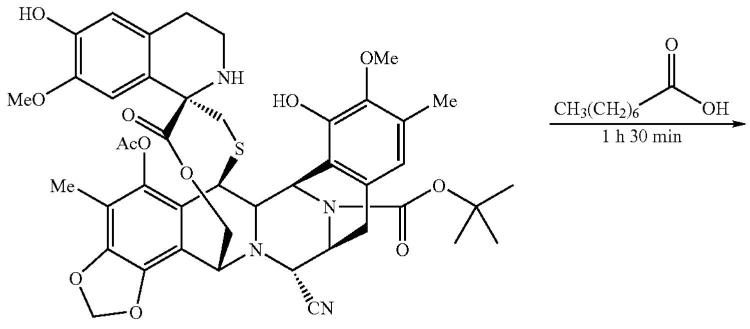

188

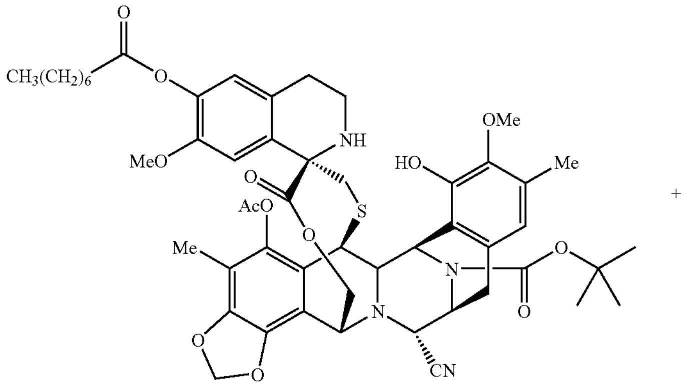

195

63%

+

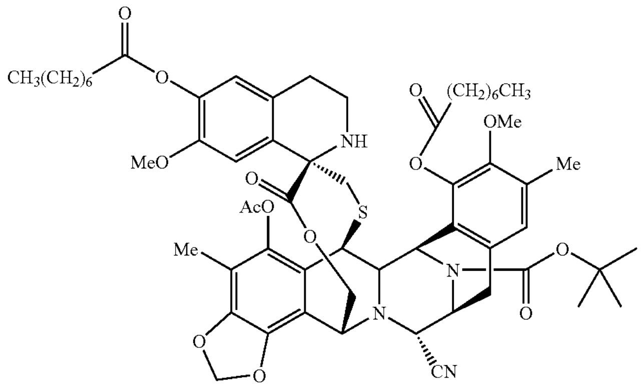

196

27%

Using 1.5 equiv. of octanoic acid as the acid, we obtain a mixture of compounds 195 and 196.

195: $^1H$-NMR (300 MHz, $CDCl_3$): δ 6.59-6.55 (m, 3H), 6.08, 5.78 (bs, s, 1H), 6.04-5.97 (m, 2H), 5.72, 5.44 (2d, 1H), 5.05-4.99 (m, 1H), 4.95-4.92 (m, 1H), 4.65, 4.60 (2bs, 1H), 4.31, 4.30 (2s, 1H), 4.22-4.18 (m, 1H), 4.14-4.09 (m, 1H), 3.77 (1s, 3H), 3.54 (s, 3H), 3.47 (d, 1H), 3.18-3.06 (m, 3H), 2.79-2.75 (m, 1H), 2.65-2.55 (m, 1H), 2.52-2.44 (m, 1H), 2.49 (t, 2H), 2.37-2.14 (m, 2H), 2.30 (s, 3H), 2.28, 2.27 (2s, 3H), 2.04, 2.00 (2s, 3H), 1.74-1.64 (m, 2H), 1.46, 1.33 (2s, 9H), 1.37-1.28 (m, 8H), 0.87 (t, 3H).

$^{13}C$-NMR (75 MHz, $CDCl_3$): δ 172.3, 172.1, 171.8, 168.1, 154.6, 152.9, 148.5, 146.6, 145.9, 145.5, 145.3, 143.1, 142.8, 141.4, 140.1, 139.9, 138.7, 132.3, 132.1, 131.2, 130.8, 129.9, 129.8, 128.7, 122.5, 121.7, 121.3, 120.7, 120.6, 116.6, 116.5, 114.7, 113.7, 113.4, 111.8, 102.0, 81.2, 80.9, 64.8, 61.2, 60.9, 60.4, 60.1, 59.9, 58.4, 58.2, 58.0, 55.1, 48.5, 48.2, 47.3, 45.9, 42.3, 41.6, 41.5, 39.6, 39.5, 34.0, 31.6, 28.9, 28.9, 28.6, 28.4, 28.2, 28.1, 27.4, 25.0, 22.6, 20.5, 20.4, 15.8, 14.0, 9.7.
ESI-MS m/z: Calcd. for $C_{52}H_{62}N_4O_{13}S$: 982.4. Found $(M+H^+)$: 983.3.
196: $^1$H-NMR (300 MHz, $CDCl_3$): δ 6.94 (s, 1H), 6.60 (s, 1H), 6.55 (s, 1H), 6.01 (d, 2H), 5.34-5.30, 5.11-4.93 (2m, 3H), 4.52-4.49 (m, 1H), 4.34-4.32 (m, 1H), 4.22-4.09 (m, 2H), 3.74, 3.73 (2s, 3H), 3.55 (s, 3H), 3.48-3.45 (m, 1H), 3.22-3.07 (m, 3H), 2.82-2.79 (m, 1H), 2.65-2.60 (m, 1H), 2.62 (t, 2H), 2.52-2.45 (m, 1H), 2.50 (t, 2H), 2.37-2.17 (m, 2H), 2.31, 2.30 (2s, 6H), 2.04 (s, 3H), 1.89-1.82 (m, 2H), 1.75-1.65 (m, 2H), 1.59-1.23 (m, 16H), 1.44, 1.37 (2s, 9H), 0.90-0.85 (m, 6H).
$^{13}$C-NMR (75 MHz, $CDCl_3$): δ 172.2, 171.8, 170.1, 167.7, 153.1, 148.5, 147.8, 145.6, 141.3, 140.2, 138.8, 132.1, 131.9, 131.3, 128.8, 127.7, 126.6, 125.1, 122.5, 120.5, 116.2, 114.7, 113.7, 113.6, 111.7, 102.0, 81.5, 64.8, 61.2, 60.0, 59.9, 58.6, 58.4, 58.0, 55.1, 48.5, 47.8, 46.4, 42.5, 41.6, 39.6, 34.3, 34.0, 31.7, 29.3, 29.2, 28.9, 28.9, 28.6, 28.1, 28.0, 27.5, 25.2, 25.0, 22.6, 20.3, 15.9, 14.0, 9.7.
ESI-MS m/z: Calcd. for $C_{60}H_{76}N_4O_{14}S$: 1108.5. Found $(M+H^+)$: 1109.4.
Example 173
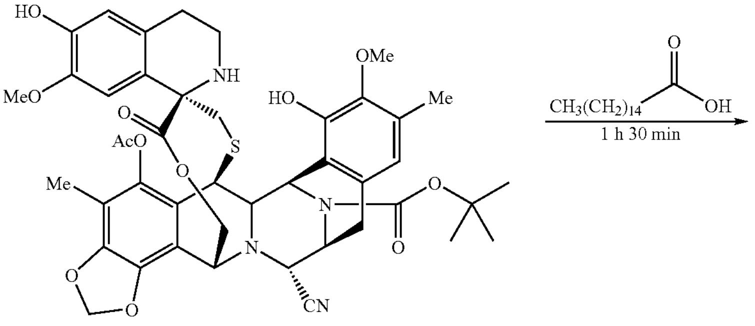
188
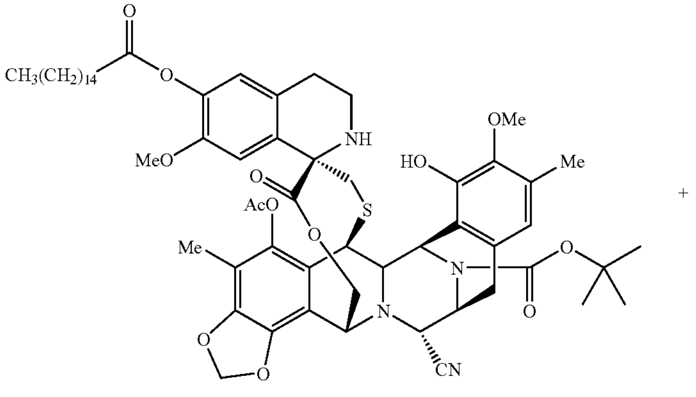
197
56%
+
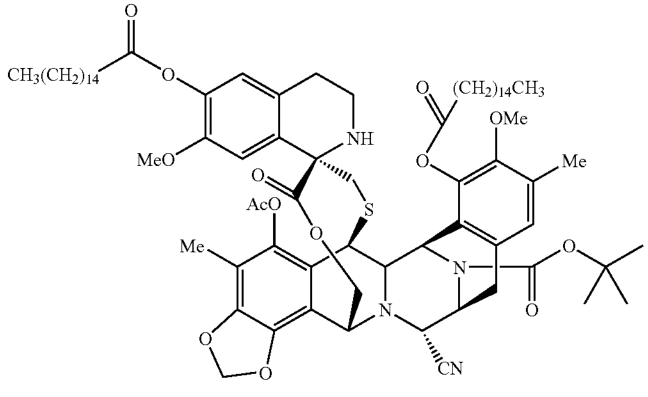
198
26%

Using 1.5 equiv. of palmitic acid as the acid, we obtain a mixture of compounds 197 and 198 (Method C).

197: [1]-NMR (300 MHz, $CDCl_3$): δ 6.59-6.55 (m, 3H), 6.25, 5.78 (bs, s, 1H), 6.04-5.97 (m, 2H), 5.77, 5.44 (2bd, 1H), 5.05-5.00 (m, 1H), 4.96-4.93 (m, 1H), 4.66, 4.60 (2bs, 1H), 4.31 (bs, 1H), 4.23-4.19 (m, 1H), 4.15-4.09 (m, 1H), 3.77, 3.76 (2s, 3H), 3.54 (s, 3H), 3.50-3.47 (m, 1H), 3.18-3.07 (m, 3H), 2.79-2.75 (m, 1H), 2.66-2.57 (m, 1H), 2.52-2.47 (m, 1H), 2.49 (t, 2H), 2.39-2.13 (m, 2H), 2.30, 2.28, 2.27 (3s, 6H), 2.04, 1.98 (2s, 3H), 1.71-1.64 (m, 2H), 1.46, 1.33 (2s, 9H), 1.46-1.25 (m, 24H), 0.88 (t, 3H).

$^{13}C$-NMR (75 MHz, $CDCl_3$): δ 172.3, 172.1, 171.8, 168.1, 154.6, 152.9, 148.5, 146.6, 145.9, 145.5, 143.1, 142.7, 141.4, 140.1, 138.7, 132.3, 131.2, 130.8, 129.8, 128.6, 122.5, 121.7, 121.3, 120.6, 116.6, 116.5, 113.7, 113.4, 111.8, 102.0, 81.2, 80.9, 64.8, 61.2, 60.9, 60.4, 60.1, 59.9, 58.4, 58.2, 58.0, 55.1, 53.4, 48.5, 48.2, 47.3, 45.9, 42.3, 41.6, 41.5, 39.6, 39.5, 34.0, 31.6, 29.7, 29.6, 29.6, 29.5, 29.3, 29.3, 29.0, 28.6, 28.2, 28.1, 27.4, 25.0, 22.7, 20.5, 20.4, 15.8, 14.1, 9.7.

ESI-MS m/z: Calcd. for $C_{60}H_{78}N_4O_{13}S$: 1094.5. Found ($M+H^+$): 1095.4.

198: $^1H$-NMR (300 MHz, $CDCl_3$): δ 6.94 (s, 1H), 6.60 (s, 1H), 6.54 (s, 1H), 6.01 (d, 2H), 5.34-5.33, 5.11-4.93 (2m, 3H), 4.53-4.52 (m, 1H), 4.32-4.29 (m, 1H), 4.22-4.09 (m, 2H), 3.74, 3.73 (2s, 3H), 3.55 (s, 3H), 3.48-3.46 (m, 1H), 3.22-3.09 (m, 3H), 2.82-2.78 (m, 1H), 2.65-2.60 (m, 1H), 2.62 (t, 2H), 2.52-2.47 (m, 1H), 2.50 (t, 2H), 2.37-2.17 (m, 2H), 2.31 (s, 3H), 2.30 (s, 3H), 2.04 (s, 3H), 1.89-1.81 (m, 2H), 1.72-1.64 (m, 2H), 1.44-1.25 (m, 48H), 1.44, 1.37 (2s, 9H), 0.90-0.85 (m, 6H).

$^{13}C$-NMR (75 MHz, $CDCl_3$): δ 172.1, 171.8, 170.4, 170.1, 167.7, 153.1, 148.5, 147.9, 145.6, 141.3, 140.2, 138.8, 132.1, 131.9, 131.3, 128.8, 127.7, 126.6, 125.1, 122.5, 120.5, 116.2, 114.7, 113.6, 111.7, 102.0, 81.5, 64.8, 61.2, 60.0, 58.6, 58.1, 55.1, 48.5, 47.8, 46.4, 42.5, 41.6, 39.6, 34.3, 34.0, 31.9, 29.7, 29.7, 29.5, 29.5, 29.3, 29.3, 29.0, 28.6, 28.1, 28.0, 27.4, 25.2, 25.0, 22.7, 20.3, 15.9, 14.1, 9.7.

ESI-MS m/z: Calcd. for $C_{76}H_{108}N_4O_{14}S$: 1332.8. Found ($M+H^+$): 1333.6.

Example 174

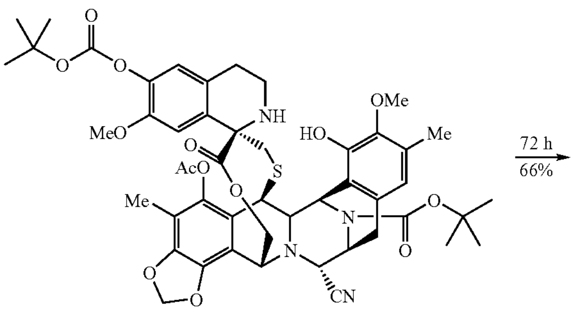

190

-continued

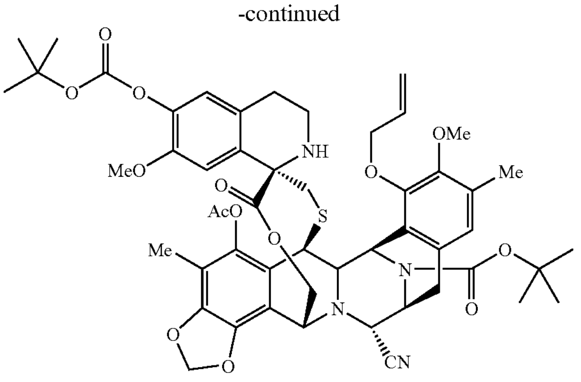

199

To a solution of 1 equiv. of compound 190 in DMF (0.02M) under Argon at room temperature, were added 0.7 equiv. of $Cs_2CO_3$ and 2 equiv. of allyl bromide. The reaction was stirred for 72 h and then quenched with AcOH. The crude was diluted with Hex/EtOAc 1:3, washed with a saturated solution of NaCl, the aqueous layers extracted with Hex/EtOAc 1:3, and the organic layers dried over $Na_2SO_4$. Flash cromatography gives pure compound 199 (66%).

199. $^1H$-NMR (300 MHz, $CDCl_3$): δ 6.79 (s, 1H), 6.69 (s, 1H), 6.57, 6.56 (2s, 1H), 6.28-6.01 (m, 1H), 6.01 (d, 1H), 5.56-5.24 (m, 3H), 5.07-4.43 (m, 5H), 4.31-4.29 (m, 1H), 4.20-4.08 (m, 2H), 3.84, 3.81 (2s, 3H), 3.58 (s, 3H), 3.48-3.45 (m, 1H), 3.17-3.06 (m, 3H), 2.83-2.77 (m, 1H), 2.69-2.59 (m, 1H), 2.55-2.47 (m, 1H), 2.36-2.17 (m, 2H), 2.28 (s, 3H), 2.24 (s, 3H), 2.04 (s, 3H), 1.50, 1.43, 1.40 (3s, 18H).

ESI-MS m/z: Calcd. for $C_{52}H_{60}N_4O_{14}S$: 996.4. Found ($M+H^+$): 997.2.

Example 175

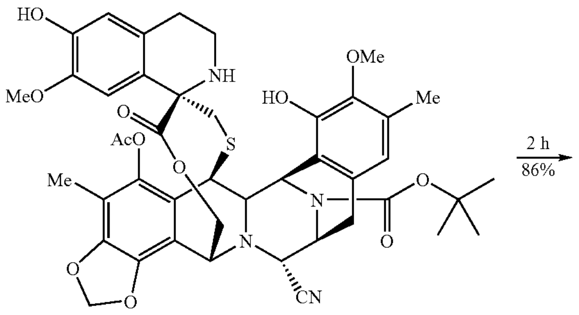

188

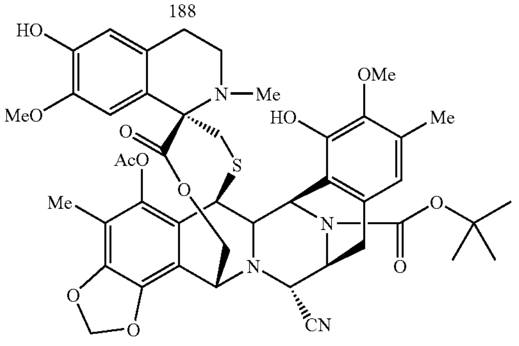

200

To a solution of compound 188 in $CH^3CN$ (0.016M) at room temperature under Argon, were added 100 equiv. of formaline (37 wt. % in water) and 5 equiv. of $NaCNBH_3$. After 1 h 20 equiv. of acetic acid were added. The reaction mixture was stirred for 2 h more. After this time, it was diluted with $CH_2Cl_2$, neutralise with $NaHCO_3$ and extracted with $CH_2Cl_2$. The organic layers were dried over $Na_2SO_4$. Flash chromatography gives pure compound (86%).

200 $^1$H-NMR (300 MHz, $CDCl_3$): δ 6.47-6.45 (m, 2H), 6.18 (s, 1H), 6.09-5.96 (m, 2H), 5.77, 5.42 (2s, 1H), 5.66, 5.43 (2d, 1H), 4.99-4.87 (m, 2H), 4.66, 4.62 (2bs, 1H), 4.35-4.32 (m, 1H), 4.13, 4.05 (2d, 1H), 3.90-3.83 (m, 1H), 3.77 (s, 3H), 3.55 (s, 3H), 3.49-3.44 (m, 1H), 3.23-3.13 (m, 2H), 3.04-2.93 (m, 1H), 2.71-2.56 (m, 3H), 2.47-2.17 (m, 2H), 2.32, 2.30 (2s, 3H), 2.2.20, 2.17 (2s, 6H), 2.02, 2.01 (2s, 3H), 1.46, 1.32 (2s, 9H).

ESI-MS m/z: Calcd. for $C_{45}H_{50}N_4O_{12}S$: 870.3. Found ($M+H^+$): 871.2.

Example 176

Method F: To a solution of 1 equiv. of starting material in $CH_2Cl_2/H_2O/TFA$ 2:1:3.3 (0.013M) was stirred at room temperature for 15 min. The reaction was followed by TLC and neutralised with $NaHCO_3$, extracted with $CH_2Cl_2$ and the organic layers dried with $Na_2SO_4$. Flash chromatography gives pure compounds.

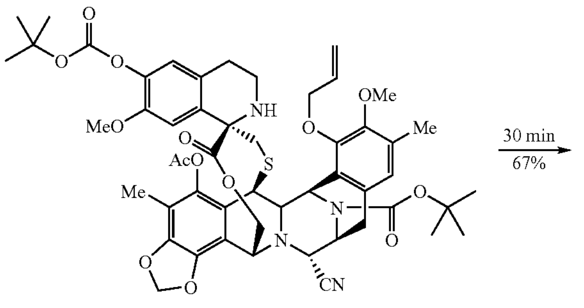

199

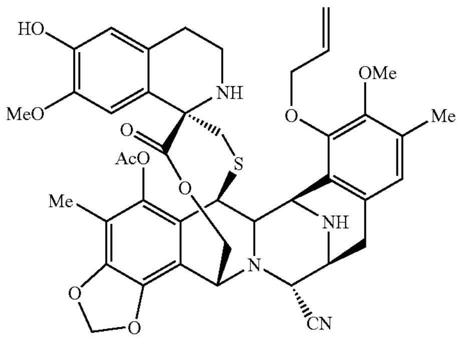

201

201 was obtained using Method F. $^1$H-NMR (300 MHz, $CDCl_3$): δ 6.82 (s, 1H), 6.49 (s, 1H), 6.41 (bs, 1H), 6.16-5.98 (m, 1H), 6.03 (d, 2H), 5.46-5.23 (m, 2H), 5.03 (d, 1H), 4.86-4.79 (m, 1H), 4.56-3.81 (m, 7H), 3.63 (s, 3H), 3.55-3.52 (m, 1H), 3.49 (s, 3H), 3.14-2.96 (m, 3H), 2.86-2.17 (m, 8H), 2.25 (bs, 3H), 2.04 (1s, 3H).

ESI-MS m/z: Calcd. for $C_{42}H_{44}N_4O_{10}S$: 796.3. Found ($M+H^+$): 797.3.

Example 177

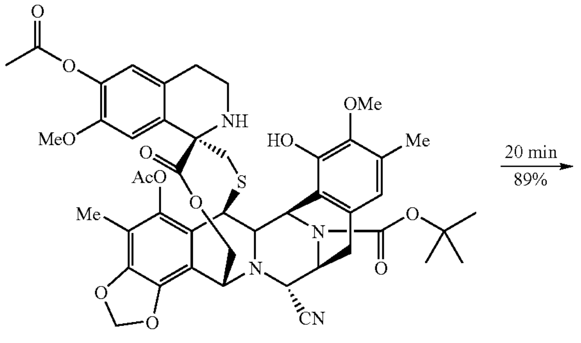

191

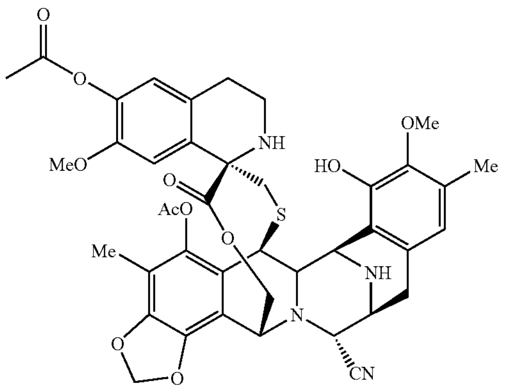

202

202 was obtained using Method F. $^1$H-NMR (300 MHz, $CDCl_3$): δ 6.62 (s, 1H), 6.61 (s, 1H), 6.56 (s, 1H), 6.00 (dd, 2H), 5.78 (bs, 1H), 5.02 (d, 1H), 4.56 (bs, 1H), 4.50 (d, 1H), 4.34 (s, 1H), 4.19 (d 1H), 4.11 (dd, 1H), 3.86-3.83 (m, 1H), 3.78 (s, 3H), 3.56 (s, 3H), 3.53 (bd, 1H), 3.14-3.09 (m, 2H), 2.99 (dd, 1H), 2.83-2.73 (m, 1H), 2.68-2.59 (m, 1H), 2.51-2.45 (m, 1H), 2.38-2.17 (m, 2H), 2.31 (s, 3H), 2.27 (s, 3H), 2.24 (s, 3H), 2.03 (s, 3H).

$^{13}$C-NMR (75 MHz, $CDCl_3$): δ 172.0, 169.0, 168.2, 148.4, 145.7, 145.4, 142.7, 141.3, 140.1, 138.5, 132.4, 131.3, 129.5, 128.6, 124.3, 122.5, 121.3, 120.9, 118.1, 113.9, 111.7, 101.9, 64.8, 61.2, 60.4, 60.0, 59.0, 58.8, 55.1, 48.6, 47.6, 41.9, 39.6, 28.6, 28.1, 20.6, 20.4, 15.8, 9.7.

ESI-MS m/z: Calcd. for $C_{41}H_{42}N_4O_{11}S$: 798.3. Found $(M+H^+)$: 799.3.
Example 178
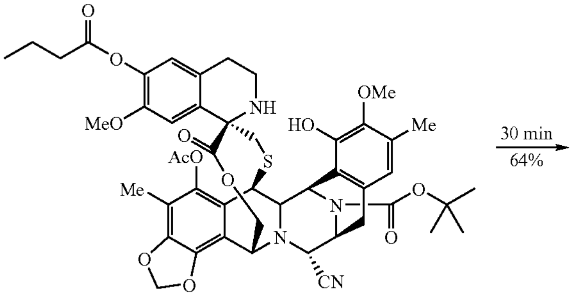
192
-continued
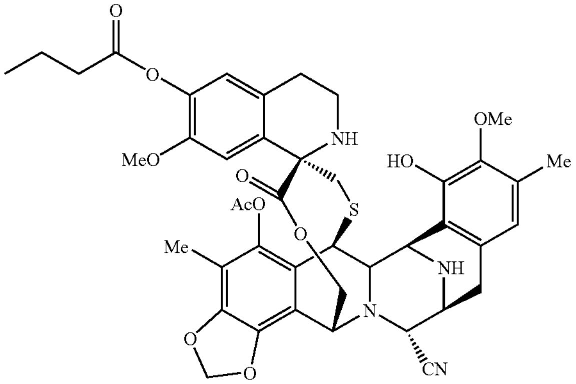
203
203 was obtained using Method F. $^1$H-NMR (300 MHz, $CDCl_3$): δ 6.62 (s, 1H), 6.60 (s, 1H), 6.57 (s, 1H), 5.97 (dd, 2H), 5.78 (bs, 1H), 5.02 (d, 1H), 4.56 (bs, 1H), 4.50 (d, 1H), 4.34 (s, 1H), 4.19 (d 1H), 4.10 (dd, 1H), 3.86-3.83 (m, 1H), 3.78 (s, 3H), 3.55 (s, 3H), 3.53 (bd, 1H), 3.14-3.09 (m, 2H), 2.99 (dd, 1H), 2.82-2.75 (m, 1H), 2.63-2.55 (m, 1H), 2.52-2.46 (m, 1H), 2.48 (t, 2H), 2.38-2.17 (m, 2H), 2.31 (s, 3H), 2.27 (s, 3H), 2.03 (s, 3H), 1.79-1.67 (m, 2H), 1.00 (t, 3H).
ESI-MS m/z: Calcd. for $C_{43}H_{46}N_4O_{11}S$: 826.3. Found $(M+H^+)$: 827.3.
Example 179
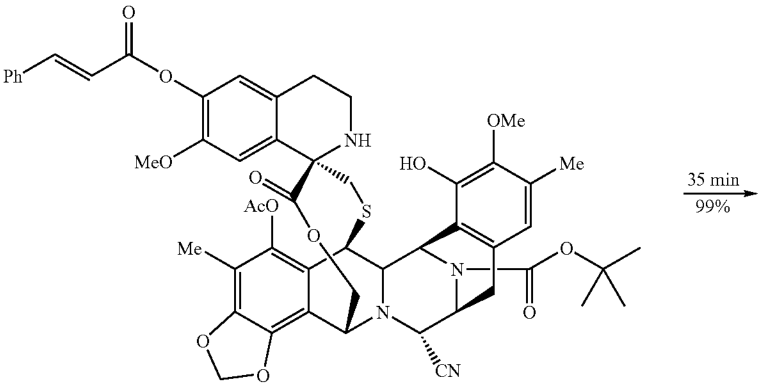
194
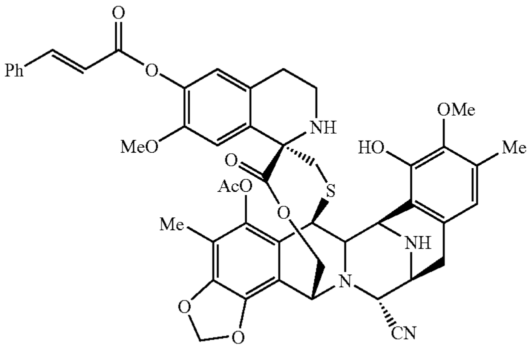
204

204 was obtained using Method F $^1$H-NMR (300 MHz, $CDCl_3$): δ 7.81 (d, 1H), 7.58-7.54 (m, 2H), 7.41-7.39 (m, 3H), 6.66 (d, 1H), 6.63 (s, 1H), 6.60 (s, 1H), 6.57 (s, 1H), 6.01 (d, 2H), 5.79 (bs, 1H), 5.04 (d, 1H), 4.57 (bs, 1H), 4.51 (d, 1H), 4.34 (s, 1H), 4.20 (d 1H), 4.12 (dd, 1H), 3.87-3.84 (m, 1H), 3.79 (s, 3H), 3.57 (s, 3H), 3.54 (bd, 1H), 3.15-3.09 (m, 2H), 3.00 (dd, 1H), 2.83-2.78 (m, 1H), 2.75-2.62 (m, 1H), 2.54-2.48 (m, 1H), 2.41-2.19 (m, 2H), 2.32 (s, 3H), 2.28 (s, 3H), 2.03 (s, 3H).

$^{13}$C-NMR (300 MHz, $CDCl_3$): δ 172.2, 168.2, 164.9, 148.6, 146.5, 145.8, 145.4, 142.8, 141.4, 140.1, 138.6, 134.2, 132.5, 131.3, 130.6, 129.6, 128.9, 128.7, 128.3, 124.4, 122.6, 121.0, 118.1, 116.9, 113.9, 113.4, 111.8, 101.9, 64.9, 61.2, 60.4, 60.0, 59.1, 58.8, 55.2, 48.6, 47.6, 42.2, 42.0, 39.6, 28.7, 28.2, 20.4, 15.8, 9.7.

ESI-MS m/z: Calcd. for $C_{48}H_{46}N_4O_{11}S$: 886.3. Found ($M+H^+$): 887.2.

Example 180

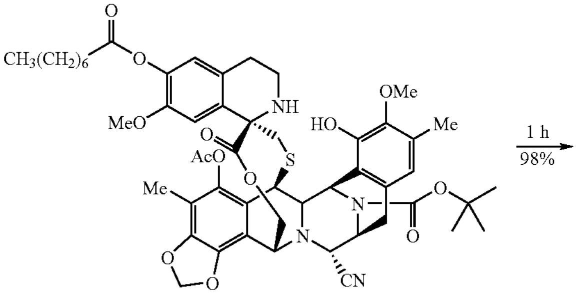

195

-continued

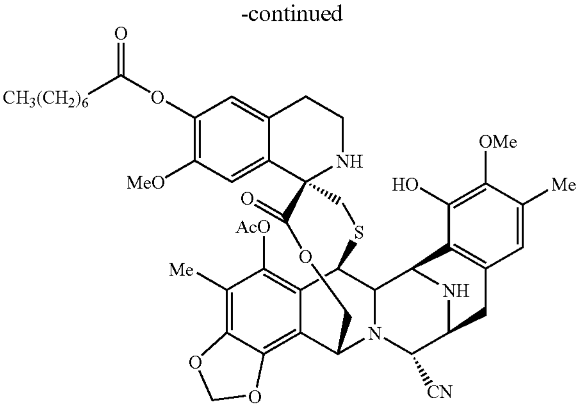

205

205 was obtained using Method F $^1$H-NMR (300 MHz, $CDCl_3$): δ 6.62 (s, 1H), 6.60 (s, 1H), 6.56 (s, 1H), 6.02 (d, 2H), 5.79 (bs, 1H), 5.03 (d, 1H), 4.57 (bs, 1H), 4.51 (d, 1H), 4.34 (s, 1H), 4.20 (d 1H), 4.12 (dd, 1H), 3.87-3.84 (m, 1H), 3.79 (s, 3H), 3.55 (s, 3H), 3.54 (bd, 1H), 3.15-3.09 (m, 2H), 3.00 (dd, 1H), 2.82-2.78 (m, 1H), 2.68-2.60 (m, 1H), 2.53-2.46 (m, 1H), 2.50 (t, 2H), 2.39-2.18 (m, 2H), 2.32 (s, 3H), 2.28 (s, 3H), 2.04 (s, 3H), 1.73-1.65 (m, 2H), 1.39-1.24 (m, 8H), 0.88 (t, 3H).

ESI-MS m/z: Calcd. for $C_{47}H_{54}N_4O_{11}S$: 882.3. Found ($M+H^+$): 883.3.

Example 181

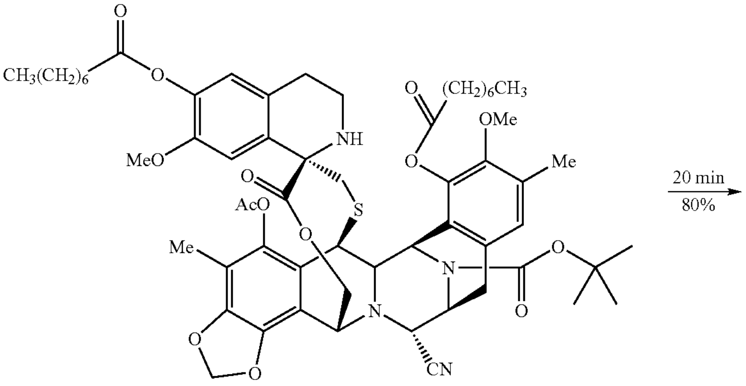

196

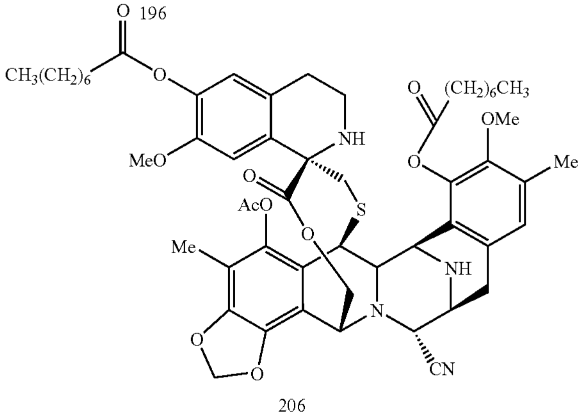

206

206 was obtained using Method F. $^1$-NMR (300 MHz, $CDCl_3$): δ 6.95 (s, 1H), 6.60 (s, 1H), 6.53 (s, 1H), 6.02 (dd, 2H), 5.02 (d, 1H), 4.45 (bs, 1H), 4.35 (s, 1H), 4.20 (d, 1H), 4.11 (dd, 1H), 4.04 (d, 1H), 3.88-3.85 (m, 1H), 3.74 (s, 3H), 3.54 (bs, 4H), 3.17-3.08 (m, 2H), 3.01 (dd, 1H), 2.83-2.78 (m, 1H), 2.64-2.59 (m, 1H), 2.62 (t, 2H), 2.52-2.47 (m, 1H), 2.50 (t, 2H), 2.38-2.17 (m, 2H), 2.31 (s, 3H), 2.29 (s, 3H), 2.04 (s, 3H), 1.87-1.77 (m, 2H), 1.72-1.64 (m, 2H), 1.49-1.23 (m, 16H), 0.89-0.85 (m, 6H).
ESI-MS m/z: Calcd. for $C_{55}H_{68}N_4O_{12}S$: 1008.5. Found ($M+H^+$): 1009.4.
Example 182
207 was obtained using Method F. $^1$-NMR (300 MHz, $CDCl_3$): δ 6.62 (s, 1H), 6.59 (s, 1H), 6.55 (s, 1H), 6.01 (dd, 2H), 5.78 (bs, 1H), 5.02 (d, 1H), 4.56 (bs, 1H), 4.50 (d, 1H), 4.33 (s, 1H), 4.19 (d 1H), 4.10 (dd, 1H), 3.86-3.83 (m, 1H), 3.78 (s, 3H), 3.54 (s, 3H), 3.53 (bd, 1H), 3.14-3.08 (m, 2H), 2.99 (dd, 1H), 2.81-2.78 (m, 1H), 2.68-2.55 (m, 1H), 2.52-2.45 (m, 1H), 2.49 (t, 2H), 2.38-2.17 (m, 2H), 2.31 (s, 3H), 2.27 (s, 3H), 2.03 (s, 3H), 1.72-1.64 (m, 2H), 1.38-1.25 (m, 24H), 0.87 (t, 3H).
ESI-MS m/z: Calcd. for $C_{55}H_{70}N_4O_{11}S$: 994.5. Found ($M+H^+$): 995.5.
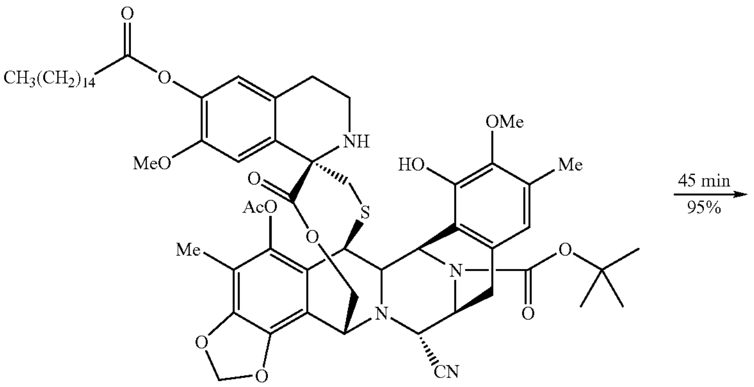
197
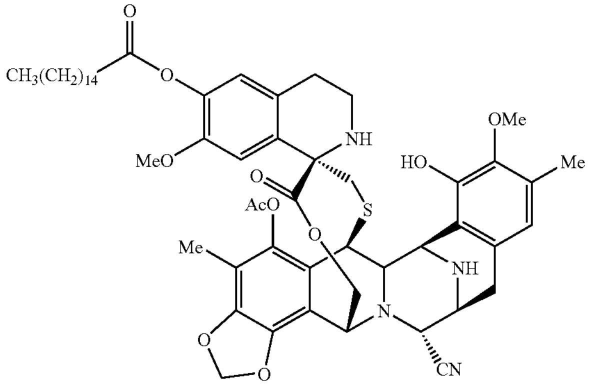
207

Example 183

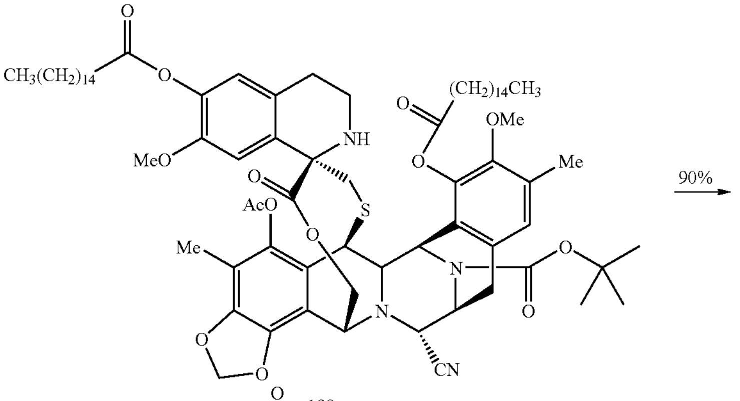

198

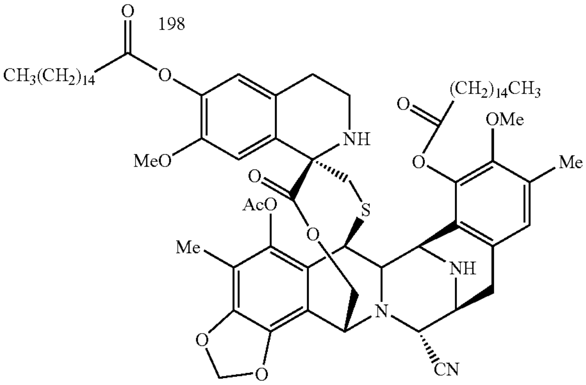

208

208 was obtained using Method F. $^1$H-NMR (300 MHz, $CDCl_3$): δ 6.96 (s, 1H), 6.60 (s, 1H), 6.53 (s, 1H), 6.02 (dd, 2H), 5.02 (d, 1H), 4.45 (bs, 1H), 4.35 (s, 1H), 4.20 (d, 1H), 4.10 (dd, 1H), 4.05 (d, 1H), 3.88-3.85 (m, 1H), 3.74 (s, 3H), 3.55 (bs, 4H), 3.17-3.07 (m, 2H), 3.01 (dd, 1H), 2.84-2.80 (m, 1H), 2.69-2.59 (m, 1H), 2.62 (t, 2H), 2.52-2.47 (m, 1H), 2.50 (t, 2H), 2.37-2.19 (m, 2H), 2.32 (s, 3H), 2.29 (s, 3H), 2.04 (s, 3H), 1.87-1.77 (m, 2H), 1.74-1.64 (m, 2H), 1.45-1.25 (m, 48H), 0.88 (t, 6H).

$^{13}$C-NMR (75 MHz, $CDCl_3$): δ 172.1, 171.9, 171.3, 167.6, 148.4, 147.6, 145.6, 141.4, 141.3, 140.2, 138.7, 132.1, 131.6, 131.3, 130.1, 128.6, 128.0, 122.5, 120.7, 117.8, 113.8, 111.7, 102.0, 72.5, 65.0, 64.9, 61.2, 60.2, 59.9, 58.9, 58.4, 55.1, 48.7, 48.4, 42.3, 42.2, 39.6, 34.2, 34.0, 31.9, 29.7, 29.6, 29.5, 29.3, 29.2, 29.0, 28.6, 27.7, 25.2, 25.0, 22.7, 20.3, 15.8, 14.1, 9.7.

ESI-MS m/z: Calcd. for $C_{71}H_{100}N_4O_{12}S$: 1232.7. Found ($M+H^+$): 1233.6.

Example 184

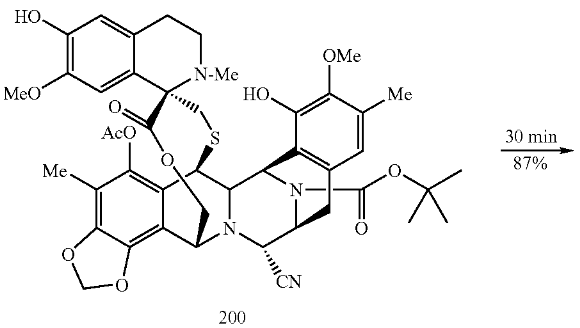

200

-continued

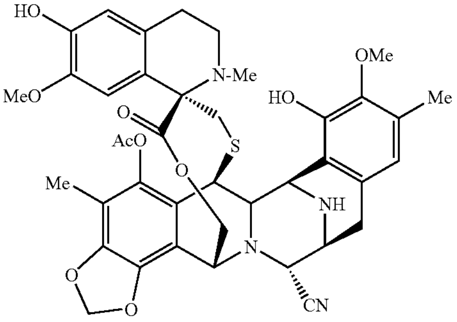

209

209 was obtained using Method F. $^1$H-NMR (300 MHz, $CDCl_3$): δ 6.50 (s, 1H), 6.44 (s, 1H), 6.19 (s, 1H), 6.02 (d, 2H), 5.77 (bp 1H), 5.46 (bp, 1H), 4.96 (d, 1H), 4.59 (bp, 1H), 4.50 (d, 1H), 4.35 (s, 1H), 4.10 (d, 1H), 3.87-3.82 (m, 2H), 3.78 (s, 3H), 3.54 (s, 3H), 3.53 (d, 1H), 3.30-3.15 (m, 1H), 3.07-2.91 (m, 2H), 2.69-2.55 (m, 3H), 2.46-2.39 (m, 2H), 2.30 (s, 3H), 2.23 (s, 3H), 2.19 (s, 3H), 2.02 (s, 3H).

ESI-MS m/z: Calcd. for $C_{40}H_{42}N_4O_{10}S$: 770.3. Found ($M+H^+$): 771.3.

Example 185

Method H: To a solution of 1 equiv. of starting material in $CH_3CN/H_2O$ 3:2 (0.009M) were added 30 equiv. of $AgNO_3$. After 24 h the reaction was quenched with a mixture 1:1 of saturated solutions of brine and $NaHCO_3$, stirred for 10 min and diluted and extracted with $CH_2Cl_2$. The organic layer was dried over $Na_2SO_4$. Chromatography gives pure compounds.

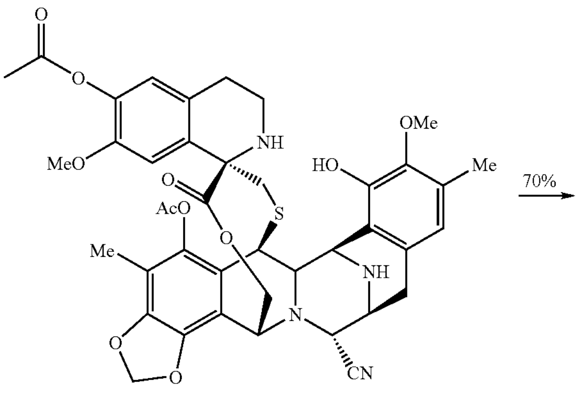

202

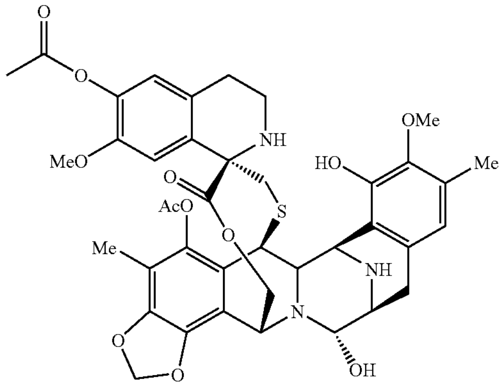

210

210 was obtained using Method H. $^1$H-NMR (300 MHz, $CDCl_3$): δ 6.62 (s, 1H), 6.60 (s, 1H), 6.56 (s, 1H), 5.99, 5.97 (2d, 2H), 5.13 (d, 1H), 4.84, 4.74 (2s, 1H), 4.52 (d, 1H), 4.45 (bs, 1H), 4.38 (d 1H), 4.02 (dd, 1H), 3.78 (s, 3H), 3.64-3.54 (m, 2H), 3.54 (s, 3H), 3.17-3.00 (m, 2H), 2.92-2.80 (m, 2H), 2.69-2.46 (m, 2H), 2.40-2.17 (m, 2H), 2.31 (s, 3H), 2.27 (s, 3H), 2.24 (s, 3H), 2.02 (s, 3H).

ESI-MS m/z: Calcd. for $C_{40}H_{43}N_3O_{12}S$: 789.3. Found ($M-H_2O+H^+$): 772.3.

Example 186

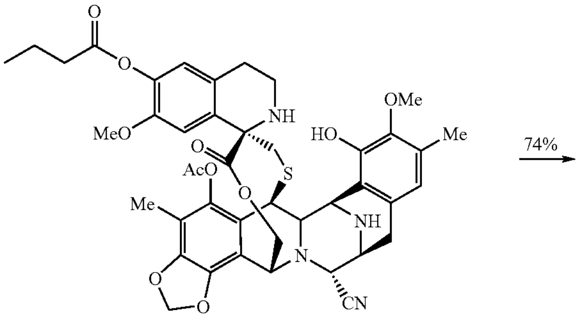

203

-continued

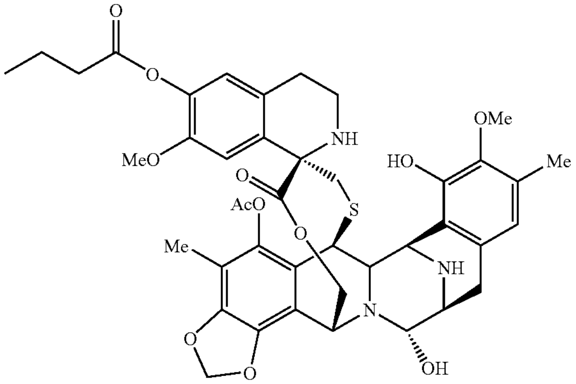

211

211 was obtained using Method F. $^1$H-NMR (300 MHz, $CDCl_3$): δ 6.62 (s, 1H), 6.59 (s, 1H), 6.56 (s, 1H), 5.99, 5.98 (d, dd, 2H), 5.76 (bp, 1H), 5.14 (d, 1H), 4.84, 4.74 (2s, 1H), 4.52-4.37 (m, 3H), 1.06-4.00 (m, 1H), 3.78 (s, 3H), 3.67-3.54 (m, 2H), 3.54 (s, 3H), 3.12-3.00 (m, 2H), 2.92-2.80 (m, 2H), 2.68-2.60 (m, 1H), 2.51-2.46 (m, 1H), 2.48 (t, 2H), 2.40-1.99 (m, 2H), 2.31 (s, 3H), 2.27 (s, 3H), 2.02 (s, 3H), 1.80-1.67 (m, 2H), 1.00 (t, 3H).

ESI-MS m/z: Calcd. for $C_{42}H_{47}N_3O_{12}S$: 817.3. Found ($M-H_2O+H^+$): 800.2.

Example 187

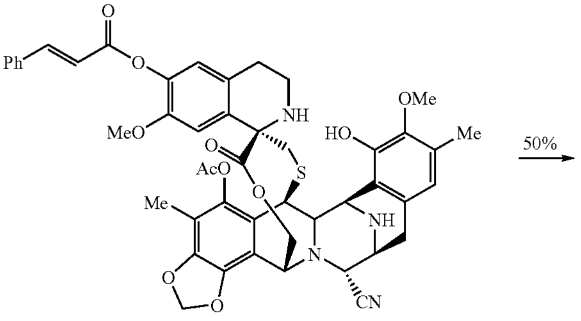

204

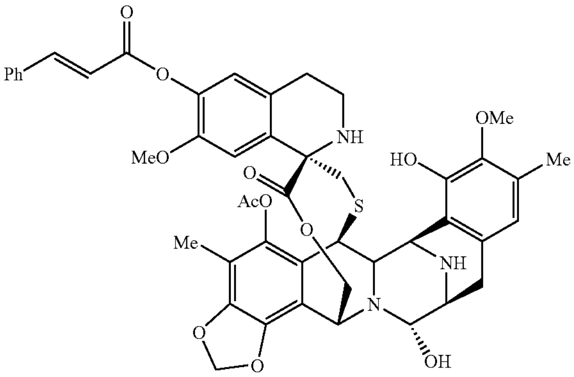

212

212 was obtained using Method F. $^1$H-NMR (300 MHz, $CDCl_3$): δ 7.81 (d, 1H), 7.57-7.54 (m, 2H), 7.41-7.39 (m, 3H), 6.66 (d, 1H), 6.63 (s, 1H), 6.60 (s, 1H), 6.58 (s, 1H), 5.99, 5.98 (2d, 2H), 5.75 (bp, 1H), 5.15 (d, 1H), 4.85, 4.75 (2s, 1H), 4.54-4.38 (m, 3H), 4.06-4.03 (m, 1H), 3.79 (s, 3H), 3.65-3.56 (m, 2H), 3.56 (s, 3H), 3.18-3.02 (m, 2H), 2.93-2.80 (m, 2H), 2.66-2.62 (m, 1H), 2.54-2.49 (m, 1H), 2.42-2.20 (m, 2H), 2.32 (s, 3H), 2.28 (s, 3H), 2.02 (s, 3H).

ESI-MS m/z: Calcd. for $C_{47}H_{47}N_3O_{12}S$: 877.3. Found ($M-H_2O+H^+$): 860.3.

Example 188

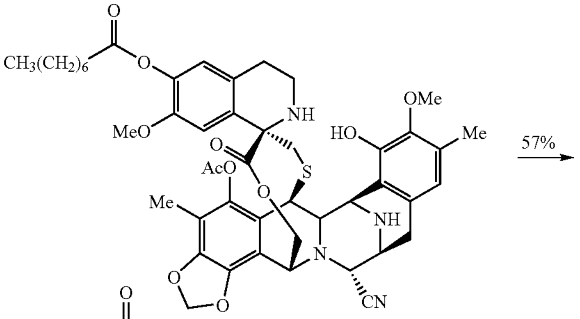

205

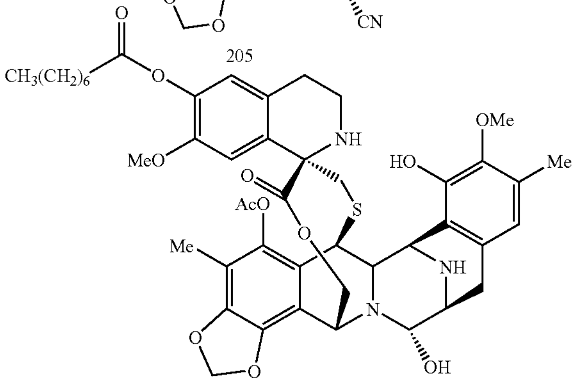

213

213 was obtained using Method F. $^1$H-NMR (300 MHz, $CDCl_3$): δ 6.62 (s, 1H), 6.59 (s, 1H), 6.56 (s, 1H), 5.99, 5.98 (2d, 2H), 5.72 (bs, 1H), 5.14 (d, 1H), 4.84, 4.74 (2s, 1H), 4.51-4.37 (m, 3H), 4.06-4.04 (m, 1H), 7.78, 3.76 (2s, 3H), 3.64-3.54 (m, 2H), 3.54, 3.53 (2s, 3H), 3.15-3.00 (m, 2H), 2.92-2.83 (m, 2H), 2.68-2.47 (m, 2H), 2.49 (t, 2H), 2.40-2.27 (m, 2H), 2.31 (s, 3H), 2.27 (s, 3H), 2.02 (s, 3H), 1.72-1.65 (m, 2H), 1.39-1.24 (m, 8H), 0.88 (t, 3H).

ESI-MS m/z: Calcd. for $C_{46}H_{55}N_3O_{12}S$: 873.4. Found ($M-H_2O+H^+$): 856.3.

Example 189

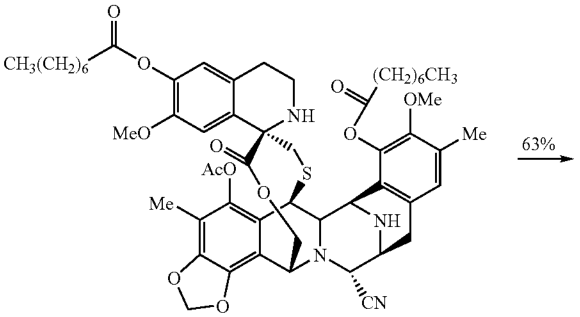

206

-continued

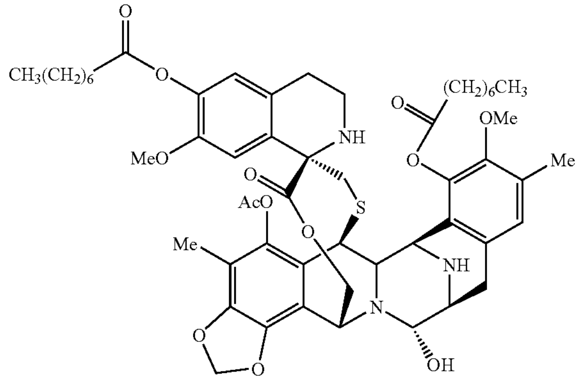

214

214 was obtained using Method F. $^1$H-NMR (300 MHz, $CDCl_3$): δ 6.96 (s, 1H), 6.60 (s, 1H), 6.54 (s, 1H), 5.99 (d, 2H), 5.14 (d, 1H), 4.84, 4.77 (2s, 1H), 4.54 (bp, 1H), 4.36 (bp, 1H), 4.02 (dd, 1H), 3.90 (d, 1H), 3.75 (s, 3H), 3.62-3.49 (m, 2H), 3.54 (s, 3H), 3.15-2.86 (m, 4H), 2.64-2.47 (m, 2H), 2.62 (t, 2H), 2.50 (t, 2H), 2.41-2.17 (m, 2H), 2.32 (s, 3H), 2.29 (s, 3H), 2.03 (s, 3H), 1.85-1.67 (m, 4H), 1.50-1.25 (m, 16H), 0.90-0.85 (m, 6H).

ESI-MS m/z: Calcd. for $C_{54}H_{69}N_3O_{13}S$: 999.5. Found ($M-H_2O+H^+$): 982.4.

Example 190

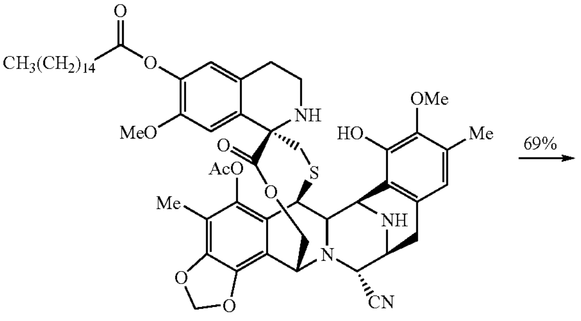

207

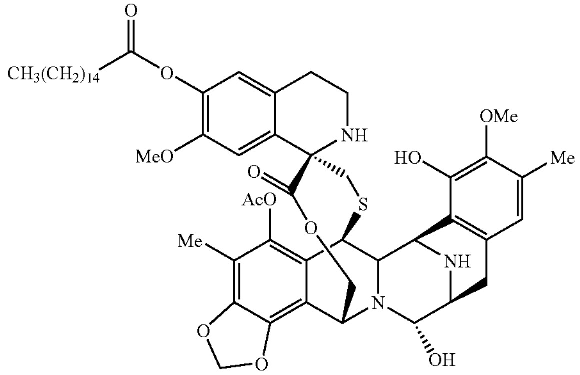

215

215 was obtained using Method F. $^1$H-NMR (300 MHz, $CDCl_3$): δ 6.62 (s, 1H), 6.59 (s, 1H), 6.55 (s, 1H), 5.99, 5.98 (2d, 2H), 5.13 (d, 1H), 4.84, 4.74 (2s, 1H), 4.52 (d, 1H), 4.45 (bs, 1H), 4.38 (d 1H), 4.02 (dd, 1H), 3.78 (s, 3H), 3.76-3.53

(m, 2H), 3.53 (s, 3H), 3.16-3.00 (m, 2H), 292-2.80 (m, 2H), 2.63-2.58 (m, 1H), 2.52-2.47 (m, 3H), 2.40-2.19 (m, 2H), 2.31 (s, 3H), 2.27 (s, 3H), 2.02 (s, 3H), 1.72-1.67 (m, 2H), 1.38-1.25 (m, 24H), 0.87 (t, 3H).

ESI-MS m/z: Calcd. for $C_{54}H_{71}N_3O_{12}S$: 986.2. Found ($M-H_2O^+$): 968.5.

Example 191

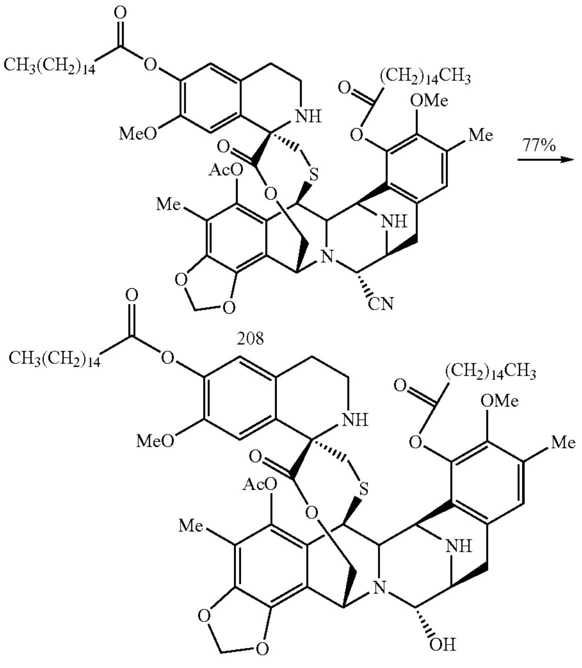

208

216

216 was obtained using Method F. $^1$H-NMR (300 MHz, $CDCl_3$): δ 6.96 (s, 1H), 6.60 (s, 1H), 6.54 (s, 1H), 6.00, 5.99 (d, dd, 2H), 5.14 (d, 1H), 4.85, 4.78 (2s, 1H), 4.54 (bp, 1H), 4.35 (bp, 1H), 4.02 (dd, 1H), 3.90 (d, 1H), 3.75 (s, 3H), 3.62-3.49 (m, 2H), 3.54 (s, 3H), 3.17-2.86 (m, 4H), 2.70-2.59 (m, 3H), 2.52-2.47 (m, 3H), 2.40-2.17 (m, 2H), 2.32 (s, 3H), 2.29 (s, 3H), 2.03 (s, 3H), 1.85-1.67 (m, 4H), 1.45-1.25 (m, 48H), 0.88 (t, 6H).

ESI-MS m/z: Calcd. for $C_{70}H_{101}N_3O_{13}S$: 1224.6. Found ($M-H_2O^+$): 1206.6.

Example 192

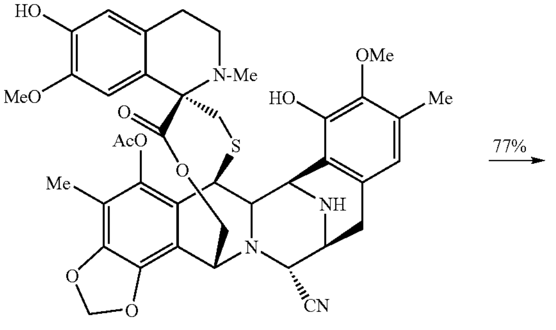

209

-continued

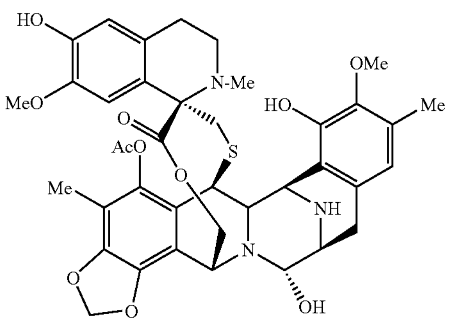

217

217 was obtained using Method F. $^1$H-NMR (300 MHz, CD3OD): δ 6.43 (s, 1H), 6.36 (s, 1H), 6.20 (s, 1H), 6.06 (d, 2H), 5.04 (d, 1H), 4.75 (d, 1H), 4.60 (bp, 1H), 4.42 (d 1H), 4.10 (d, 1H), 3.81 (dd, 1H), 3.72 (s, 3H), 3.65-3.60 (m, 2H), 3.51 (s, 3H), 3.13-3.01 (m, 2H), 2.86 (d, 1H), 2.65-2.32 (m, 5H), 2.32 (s, 3H), 2.21 (s, 3H), 2.19 (s, 3H), 2.01 (s, 3H).

ESI-MS m/z: Calcd. for $C_{39}H_{43}N_3O_{11}S$: 761.3 Found ($M+H^+$): 762.3.

Example 193

A solution of N-methyl pyridine-4-carboxaldehyde iodide in anhydrous DMF (0.26M) was treated with anhydrous toluene (2×5 mL). A solution of compound 218 (118.7 mg, 1 equiv) (previously treated with anhydrous toluene 2×5mL) in anhydrous $CH_2Cl_2$ (0.03M) was added, via cannula, at 23° C. to the solution of N-methyl pyridine-4-carboxaldehyde iodide. The reaction mixture was stirred at 23° C. for 4 hours. After this time DBU (1.0 equiv) was dropwise added at 23° C. and was stirred for 15 minutes at 23° C. A freshly aqueous saturated solution of oxalic acid (5.4 mL) was added to the reaction mixture and was stirred for 30 minutes at 23° C. Then the reaction mixture was cooled to 0° C. and $NaHCO_3$ was portionwise added followed by addition of aqueous saturated solution of $NaHCO_3$. The mixture was extracted with $Et_2O$. The combined organic layers were dried over $Na_2SO_4$, filtered and the solvent was removed under reduced pressure. Flash chromatography gives pure compound 219 (54%).

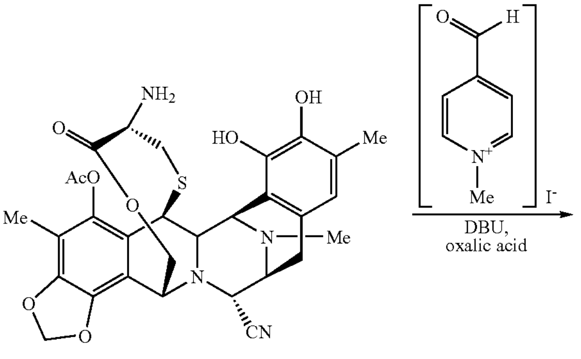

218

-continued

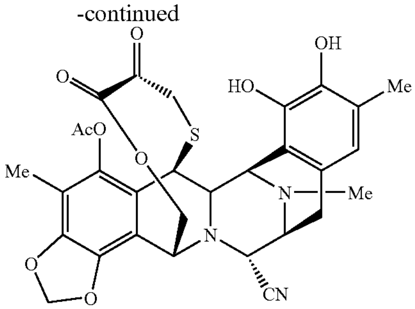

219

219. $^{1}$H-NMR (300 MHz, $CDCl_3$): δ 6.46 (s, 1H), 6.06 (dd, 2H), 5.59 (s, 1H), 5.08 (d, 1H), 4.66 (bs, 1H), 4.54 (bs, 1H), 4.38 (s, 1H), 4.28 (dd, 1H), 4.20 (dd, 1H), 4.14 (d, 1H), 3.54 (d, 1H), 3.43-3.40 (m, 1H), 2.93-2.82 (m, 2H), 2.71-2.55 (m, 2H), 2.34 (s, 3H), 2.19 (s, 3H), 2.13 (s, 3H), 2.04 (s, 3H).

$^{13}$C-NMR (75 MHz, $CDCl_3$): δ 186.5, 168.7, 160.5, 146.4, 143.5, 141.6, 140.6, 138.2, 127.2, 123.3, 121.0, 120.0, 118.0, 117.5, 113.4, 113.3, 102.2, 61.8, 61.3, 59.8, 59.0, 54.6, 54.5, 43.1, 41.6, 36.9, 23.9, 20.4, 15.7, 9.7.

ESI-MS m/z: Calcd. for $C_{30}H_{29}N_3O_9S$: 607.3 Found $(M+H^+)$: 608.2.

Example 194

To a solution of 1 equiv. of compound 219 in EtOH (0.03M) were added 5 equiv. of AcOH and 3.5 equiv. of 2-[3-hydroxy-4-methoxyphenyl]ethylamine. The reaction was stirred overnight. Then the solvent was eliminated under reduced pressure. Flash chromatography gives pure compound (62%).

220. $^{1}$H-NMR (300 MHz, $CDCl_3$): δ 6.54 (s, 1H), 6.44 (s, 1H), 6.41 (s, 1H), 6.01 (d, 2H), 4.98 (d, 1H), 4.58-4.40 (bm, 4H), 4.29 (s, 1H), 4.26 (d, 1H), 4.13-4.09 (m, 2H), 3.61 (s, 3H), 3.51-3.49 (m, 1H), 3.41-3.38 (m, 1H), 3.21 (dt, 1H), 3.00-2.85 (m, 3H), 2.71-2.60 (m, 1H), 2.42-1.97 (m, 3H), 2.28 (s, 6H), 2.21 (s, 3H), 2.04 (s, 3H).

$^{13}$C-NMR (75 MHz, $CDCl_3$): δ 172.1, 145.6, 145.3, 144.7, 144.5, 141.4, 140.0, 138.5, 128.7, 127.8, 124.9, 120.8, 119.8, 118.1, 118.0, 114.0, 113.8, 109.8, 101.8, 64.3, 60.9, 60.6, 60.2, 59.6, 55.2, 54.9, 54.6, 42.2, 41.7, 41.6, 28.3, 24.2, 20.5, 15.9, 9.7.???

ESI-MS m/z: Calcd. for $C_{39}H_{40}N_4O_{10}S$: 756.3 Found $(M+H^+)$: 757.2.

Example 195

To a solution of 1 equiv. of compound 220 in $CH_3CN/H_2O$ 3:2 (0.015M) were added 30 equiv. of $AgNO_3$. The reaction was stirred for 24 h protected from the light. After this time, 2 mL of a saturated solution of NaCl and 2 mL of a saturated solution of $NaHCO_3$ were added and the crude was stirred for 10 min. Then it was diluted with $CH_2Cl_2$, washed with 15 mL of brine and extracted with $CH_2Cl_2$. The organic layer was dried over $Na_2SO_4$, filtered and the solvent was eliminated under reduced pressure. Preparative chromatography gives pure compound (11%).

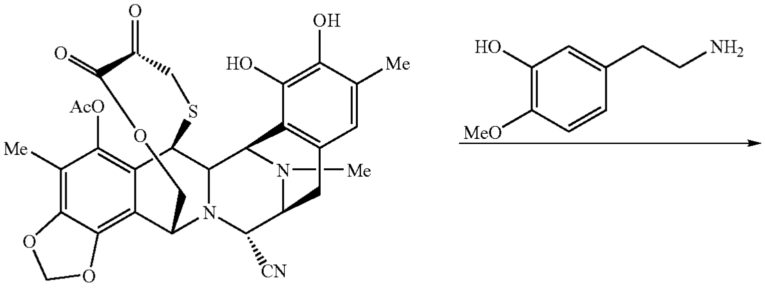

219

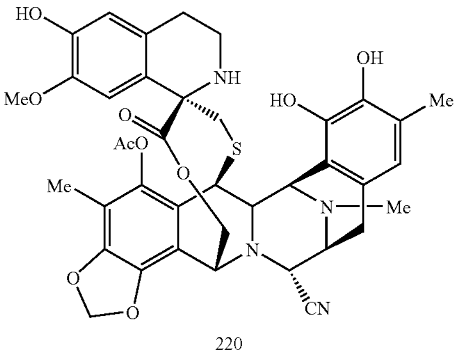

220

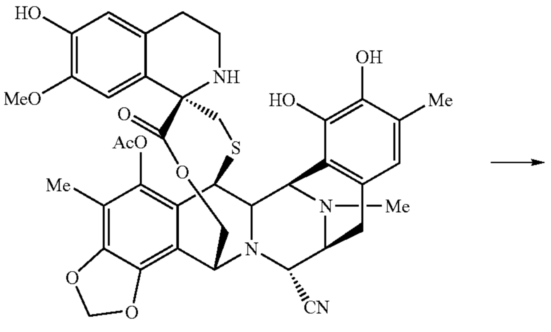

220

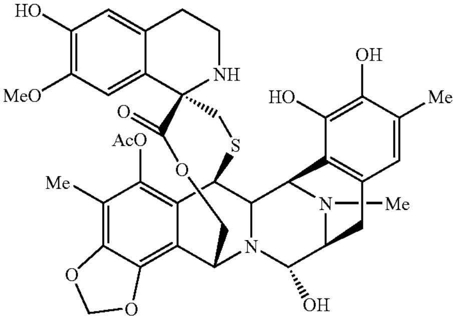

221

221 $^1$H-NMR (300 MHz, $CDCl_3$): δ 6.57 (s, 1H), 6.49 (s, 1H), 6.44 (s, 1H), 5.99 (d, 2H), 5.10 (d, 1H), 4.80 (s, 1H), 4.50-4.46 (m, 2H), 4.16 (d, 1H), 4.07 (m, 1H), 3.62 (s, 3H), 3.58-3.57 (m, 1H), 3.23-3.19 (m, 1H), 3.00-2.83 (m, 3H), 2.71-2.60 (m, 1H), 2.48-1.97 (m, 4H), 2.32 (s, 3H), 2.29 (s, 3H), 2.20 (s, 3H), 2.03 (s, 3H).

ESI-MS m/z: Calcd. for $C_{38}H_{41}N_3O_{11}S$: 747.3 Found $(M-H_2O+H^+)$: 730.2.

Example 196

To a solution of 1 equiv. of compound 222 in EtOH (0.064M) under Argon at room temperature were added 3.5 equiv. of a-ethyl-3-hydroxy-4-methylphenethylamine chlorhydrate and 2 equiv. of $K_2CO_3$ and silica gel. The reaction was stirred at room temperature for 7 hours. Then the solvent was eliminated under reduced pressure. Flash chromatography gives pure compound (68%). Compound 223 is isolated as a mixture of two isomers. These compounds can also be obtained when the reaction is performed with acetic acid as solvent and heating at 50° C. for 24 hours (99%).

-continued

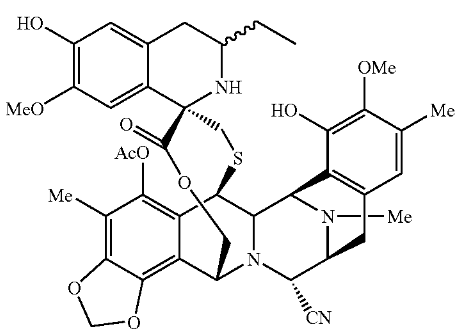

223

223. $^1$H-NMR (300 MHz, $CDCl_3$): δ 6.79 (s, 1H), 6.57 (s, 1H), 6.54 (s, 1H), 6.51 (s, 1H), 6.19 (s, 1H), 6.13-6.08 (m, 3H), 6.03-6.02 (m, 2H), 5.74 (s, 1H), 5.71 (d, 1H); 5.03 (d, 1H); 4.94 (d, 1H), 4.56 (s, 2H), 4.34-4.08 (m, 10H); 3.77 (s, 3H), 3.76 (s, 3H), 3.51-3-49 (m, 2H), 3.41 (s, 2H), 2.96-2.87 (m, 4H), 2.51-2.37 (m, 2H), 2.29 (s, 3H), 2.28 (s, 3H), 2.26 (s, 3H), 2.24 (s, 3H), 2.15 (s, 3H), 2.09 (s, 3H), 2.06 (s, 3H), 2.04 (s, 3H), 2.00 (s, 3H), 1.47-1.34 (m, 4H); 0.98 (t, 6H).

ESI-MS m/z: Calcd. for $C_{42}H_{46}N_4O_9S$: 782.3 Found $(M+H^+)$: 783.3.

Example 197

To a solution of 1 equiv. of compound 223 in $CH_3CN/H_2O$ 3:2 (0.01M) were added 30 equiv. of $AgNO_3$. The reaction was stirred at room temperature for 24 h protected from the light. After this time, the reaction was quenched with a mixture 1:1 of an aqueous saturated solutions of NaCl and $NaHCO_3$, stirred for 10 min and diluted and extracted with $CH_2Cl_2$. The organic layer was dried over $Na_2SO_4$, filtered and the solvent was eliminated under reduced pressure. Chromatography gives a mixture of the two isomers compound 224 (72%).

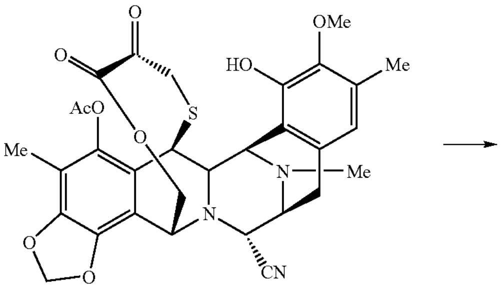

222

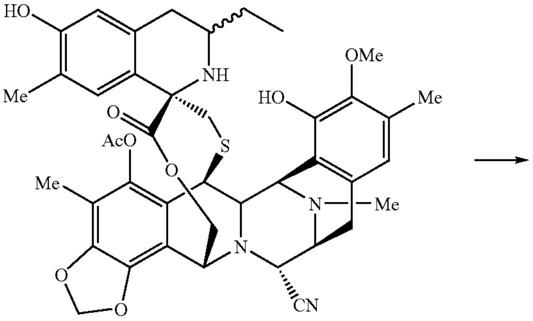

223

-continued

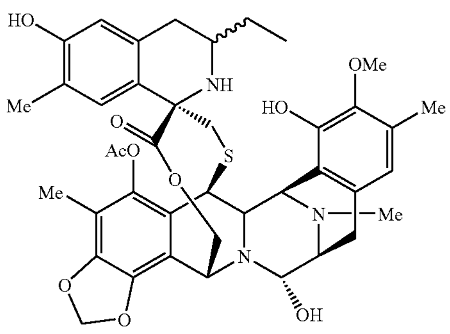

224

224A First isomer: $^1$H-NMR (300 MHz, $CDCl_3$): δ 6.59(s, 1H); 6.52 (s, 1H); 6.29 (s, 1H); 6.06 (d, 1H); 6.01 (d, 1H); 5.68

(s, 1H); 5.06 (d, 1H); 4.80 (s, 1H); 4.48 (m, 2H); 4.16 (d, 1H); 4.07 (dd, 1H); 3.78 (s, 3H); 3.59 (d, 3H); 3.23-3.21 (m, 1H); 3.05-3.01 (m, 1H); 2.87-2.84 (m, 2H); 2.44-2.20 (m, 2H); 2.28 (s, 3H); 2.25 (s, 3H); 2.14 (s, 3H); 2.06 (s, 3H), 2.01 (s, 3H), 1.45 (m, 2H), 1.01 (t, 3H).

ESI-MS m/z: Calcd. for $C_{41}H_{47}N_3O_{10}S$: 773.3 Found $(M-H_2O+H^+)$: 756.2.

224B Second isomer: $^1$H-NMR (300 MHz, $CDCl_3$): δ 6.80 (s, 1H); 6.55 (s, 1H); 6.26 (s, 1H); 6.09 (d, 1H); 6.00 (d, 1H); 5.66 (s, 1H); 5.12 (d, 1H); 4.82 (s, 1H); 4.48 (m, 2H); 4.20-4.13 (m, 3H); 3.77 (s, 3H); 3.57 (d, 1H); 3.21 (s, 1H); 2.83-2.80 (m, 2H); 2.55-2.50 (m, 1H); 2.33-2.06 (m, 2H), 2.30 (s, 3H); 2.27 (s, 3H); 2.08 (s, 3H), 2.03 (s, 6H), 1.45-1.37 (m, 2H), 1.01 (t, 3H).

ESI-MS m/z: Calcd. for $C_{41}H_{47}N_3O_{10}S$: 773.3 Found $(M-H_2O+H^+)$: 756.3.

Bioassays for Antitumor Screening

The finality of these assays is to interrupt the growth of a "in vitro" tumor cell culture by means a continued exhibition of the cells to the sample to be testing.

| Cell Lines | | | | |
|---|---|---|---|---|
| Name | N° ATCC | Species | Tissue ascites | Characteristics |
| P-388 | CCL-46 | mouse | fluid | lymphoid neoplasm |
| K-562 | CCL-243 | human | leukemia | erythroleukemia (pleural effusion) |
| A-549 | CCL-185 | human | lung | lung carcinoma "NSCL" |
| SK-MEL-28 | HTB-72 | human | melanoma | malignant melanoma |
| HT-29 | HTB-38 | human | colon | colon adenocarcinoma |
| LoVo | CCL-229 | human | colon | colon adenocarcinoma |
| LoVo-Dox | | human | colon | colon adenocarcinoma (MDR) |
| SW620 | CCL-228 | human | colon | colon adenocarcinoma (lymph node metastasis) |
| DU-145 | HTB-81 | human | prostate | prostate carcinoma, not androgen receptors |
| LNCaP | CRL-1740 | human | prostate | prostate adenocarcinoma, with androgen receptors |
| SK-BR-3 | HTB-30 | human | breast | breast adenocarcinoma, Her2/neu+, (pleural effusion) |
| MCF-7 | HTB-22 | human | breast | breast adenocarcinoma, (pleural effusion) |
| MDA-MB-231 | HTB-26 | human | breast | breast adenocarcinoma, Her2/neu+, (pleural effusion) |
| IGROV-1 | | human | ovary | ovary adenocarcinoma |
| IGROV-ET | | human | ovary | ovary adenocarcinoma, characterized as ET-743 resistant cells |
| SK-OV-3 | HTB-77 | human | ovary | ovary adenocarcinoma (malignant ascites) |
| OVCAR-3 | HTB-161 | human | ovary | ovary adenocarcinoma |
| HeLa | CCL-2 | human | cervix | cervix epitheloid carcinoma |
| HeLa-APL | CCL-3 | human | cervix | cervix epitheloid carcinoma, characterized as aplidine resistant cells |
| A-498 | HTB-44 | human | kidney | kidney carcinoma |
| PANC-1 | CRL-1469 | human | pancreas | pancreatic epitheloid carcinoma |
| HMEC1 | | human | endo-thelium | |

1°. Inhibition of Cell Growth by Counting Cells.

This form of the assay employs 24 well multidishes of 16 mm diameter (Bergeron, 1984; Schroeder, 1981). The tumor cell lines employed are: P-388 (ATCC CCL 46), suspension culture of a lymphoid neoplasm from a DBA/2 mouse; A-549 (ATCC CCL 185), monolayer culture of a human lung carcinoma; HT-29 (ATCC HTB-38), monolayer culture of a human colon carcinoma; MEL-28 (ATCC HTB-72), monolayer culture of a human melanoma and DU-145 (ATCC HTB-81), monolayer culture of a human prostate carcinoma.

Cells were maintained, in logarithmic phase of growth in Eagle's Minimum Essential Medium, with Earle's Balanced Salts, with non-essential amino acids, with 2.0 mM L-Glutamine, without sodium bicarbonate (EMEM/neaa), supplemented with 10% Fetal Calf Serum (FCS), $10^{-2}$ M. sodium bicarbonate and 0.1 U/l penicillin G+0.1 g/l streptomycin sulfate. For the experiments, cells are harvested from subconfluent cultures using trypsin and resuspended in fresh medium before plating.

P-388 cells were seeded into 16 mm diameter wells at $1\times10^4$ cells per well in 1 ml aliquots of EMEM 5% FCS containing different concentrations of the sample to be tested. A separate set of cultures without drug was seeded as control of growth, to ensure that cells remained in exponential phase of growth. All determinations are carrying out in duplicate. After three days of incubation at 37° C., 5% $CO_2$ in a 98% humid atmosphere, an approximately IC50 was determined by comparing the growth in wells with drug to the growth in wells control.

A-549, HT-29, MEL-28 and DU-145 cells were seeded into 16 mm diameter wells at $1\times10^4$ cells per well in 1 ml aliquots of EMEM 5% FCS containing different concentrations of the sample to be tested. A separate set of cultures without drug was seeded as control of growth, to ensure that cells remained in exponential phase of growth. All determinations are carrying out in duplicate. After three days of incubation at 37° C., 5% $CO_2$ in a 98% humid atmosphere cells were stained with 0.1% crystal violet. An approximately IC50 was determined by comparing the growth in wells with drug to the growth in wells control.

For quantifying the activity, after the incubation time, cells are trypsinized and counted in a Coulter Counter ZM. All counts (net cells per well), represent the average of duplicate wells. % G, percent of growth relative to cultures without drug. The results of these assays are used to generate dose-response curves from which more precise IC50 values are determined (sample concentration which produces 50% cell growth inhibition).

Obtained results may predict the usefulness of a certain drug as a potential cancer treatment. For this technique, compounds which show IC50 values smaller than 1 μg/ml are selected to continue with further studies. IC50's data allow to predict that not only could a drug be cystostatic, but also it could have a potential in terms of tumor reduction.

2°. Inhibition of Cells Growth by Colorimetric Assay.

A colorimetric type of assay, using sulforhodamine B (SRB) reaction has been adapted for a quantitative measurement of cell growth and viability [following the technique described by Philip Skehan, et al. (1990), New colorimetric cytotoxicity assay for anticancer drug screening, *J. Natl. Cancer Inst.,* 82:1107-1112]

This form of the assay employs 96 well cell culture microplates of 9 mm diameter (Faircloth, 1988; Mosmann, 1983). Most of the cell lines are obtained from American Type Culture Collection (ATCC) derived from different human cancer types.

Cells are maintained in RPMI 1640 10% FBS, supplemented with 0.1 g/l penicillin and 0.1 g/l streptomycin sulfate and then incubated at 37° C., 5% $CO_2$ and 98% humidity. For the experiments, cells were harvested from subconfluent cultures using trypsin and resuspended in fresh medium before plating.

Cells are seeded in 96 well microtiter plates, at $5\times10^3$ cells per well in aliquots of 195 μl medium, and they are allowed to attach to the plate surface by growing in drug free medium for 18 hours. Afterward, samples are added in aliquots of 5 μl in a ranging from 10 to $10^{-8}$ μg/ml, dissolved in DMSO/EtOH/PBS (0.5:0.5:99). After 48 hours exposure, the antitumor effect are measured by the SRB methodology: cells are fixed by adding 50 μl of cold 50% (wt/vol) trichloroacetic acid (TCA) and incubating for 60 minutes at 4° C. Plates are washed with deionized water and dried. One hundred μl of SRB solution (0.4% wt/vol in 1% acetic acid) is added to each microtiter well and incubated for 10 minutes at room temperature. Unbound SRB is removed by washing with 1% acetic acid. Plates are air dried and bound stain is solubilized with Tris buffer. Optical densities are read on a automated spectrophotometric plate reader at a single wavelength of 490 nm.

The values for mean+/−SD of data from triplicate wells are calculated. Some parameters for cellular responses can be calculated: GI═growth inhibition, TGI═total growth inhibition (cytostatic effect) and LC═cell killing (cytotoxic effect).

Obtained results may predict the usefulness of a certain drug as a potential cancer treatment. For this technique, compounds which show GI50 values smaller than 10 μg/ml are selected to continue with further studies. GI50's data allow to predict that not only could a drug be cystostatic, but also it could have a potential in terms of tumor reduction.

Activity Data

| | $IC_{50}$ (molar) | | | | |
|---|---|---|---|---|---|
| Compound | P-388 | A-549 | HT-29 | MEL-28 | DU-145 |
| 2 | 1.48E−10 | 1.48E−10 | 1.48E−10 | 1.48E−10 | |
| 3 | 1.15E−09 | 1.15E−09 | 1.15E−09 | 1.15E−09 | 1.15E−09 |
| 4 | 1.15E−10 | 1.15E−10 | 1.15E−10 | 1.15E−10 | 1.15E−10 |
| 5 | 5.15E−10 | 5.15E−10 | 5.15E−10 | 5.15E−10 | 5.15E−10 |
| 6 | 1.41E−09 | 2.93E−09 | 2.93E−09 | 2.93E−09 | |
| 7 | 1.19E−10 | 1.19E−10 | 5.95E−10 | 1.19E−10 | 5.95E−10 |
| 8 | 1.11E−10 | 1.11E−10 | 5.56E−10 | 1.11E−10 | 5.56E−10 |
| 9 | 1.10E−10 | 1.10E−10 | 1.10E−10 | 1.10E−10 | 1.10E−10 |
| 10 | 9.70E−09 | 9.70E−09 | 9.70E−09 | 9.70E−09 | 9.70E−09 |
| 11 | | 5.54E−10 | 5.54E−10 | | |
| 12 | | 1.16E−10 | 1.16E−10 | | |
| 14 | 1.11E−09 | 1.11E−09 | 1.11E−09 | 1.11E−09 | 1.11E−09 |
| 15 | 9.78E−08 | 9.78E−08 | 9.78E−08 | 9.78E−08 | 9.78E−08 |
| 16 | 9.91E−09 | 9.91E−09 | 9.91E−09 | 9.91E−09 | 9.91E−09 |
| 17 | 8.02E−08 | 8.02E−08 | 8.02E−08 | 8.02E−08 | 8.02E−08 |
| 18 | 4.41E−10 | 4.41E−10 | 4.41E−10 | 4.41E−10 | 4.41E−10 |
| 19 | 5.02E−10 | 5.02E−10 | 5.02E−10 | 5.02E−10 | 5.02E−10 |
| 20 | 8.18E−09 | 8.18E−09 | 8.18E−09 | 8.18E−09 | 8.18E−09 |
| 24 | | 5.31E−10 | 5.31E−10 | | |
| 25 | 1.41E−10 | 1.41E−10 | 1.41E−10 | 1.41E−10 | |
| 26 | 5.33E−09 | 5.33E−09 | 5.33E−09 | 5.33E−09 | |
| 27 | 1.11E−10 | 1.11E−10 | 1.11E−10 | 1.11E−10 | 1.11E−10 |
| 28 | 9.62E−09 | 9.62E−09 | 9.62E−09 | 9.62E−09 | 9.62E−09 |
| 37 | 1.25E−10 | 1.25E−10 | 1.25E−10 | 1.25E−10 | |
| 38 | 1.21E−08 | 1.21E−08 | 1.21E−08 | 1.21E−08 | 1.21E−08 |
| 39 | 6.16E−10 | 6.16E−10 | 6.16E−10 | 6.16E−10 | |
| 40 | 1.17E−06 | 1.17E−06 | 1.17E−06 | 1.17E−06 | 1.17E−06 |
| 41 | 1.23E−09 | 1.23E−09 | 1.23E−09 | 1.23E−09 | 1.23E−09 |
| 42 | 1.18E−08 | 1.18E−08 | 1.18E−08 | 1.18E−08 | 1.18E−08 |
| 43 | 1.16E−09 | 1.16E−09 | 1.16E−09 | 1.16E−09 | 1.16E−09 |

-continued

| Activity Data | | | | | |
|---|---|---|---|---|---|
| 44 | 1.05E−07 | 1.05E−07 | 1.05E−07 | 1.05E−07 | 1.05E−07 |
| 45 | | 1.13E−10 | 1.13E−10 | | |
| 47 | 1.15E−09 | 1.15E−09 | 1.15E−09 | 1.15E−09 | 1.15E−09 |
| 49 | 9.99E−10 | 9.99E−10 | 9.99E−10 | 9.99E−10 | 9.99E−10 |
| 50 | 1.24E−07 | 1.24E−07 | 1.24E−07 | 1.24E−07 | 1.24E−07 |
| 51 | 6.16E−10 | 1.23E−09 | 1.23E−09 | 1.23E−09 | |
| 52 | | 1.27E−09 | 1.27E−09 | | |
| 53 | 4.85E−09 | 9.71E−09 | 9.71E−09 | 9.71E−09 | |
| 54 | 1.28E−10 | 1.28E−10 | 1.28E−10 | 1.28E−10 | |
| 55 | 3.13E−09 | 3.13E−09 | 3.13E−09 | 6.26E−09 | |
| 56 | 1.23E−10 | 1.23E−10 | 1.23E−10 | 1.23E−10 | |
| 57 | 1.49E−10 | 1.49E−10 | 1.49E−10 | 1.49E−10 | |
| 58 | 1.20E−10 | 1.20E−10 | 1.20E−10 | 1.20E−10 | 1.20E−10 |
| 59 | 1.13E−10 | 1.13E−10 | 1.13E−10 | 1.13E−10 | 1.13E−10 |
| 60 | 1.00E−08 | 5.00E−09 | 5.00E−09 | 5.00E−09 | 5.00E−09 |
| 61 | 1.12E−10 | 1.12E−10 | 1.12E−10 | 1.12E−10 | 1.12E−10 |
| 62 | 8.88E−10 | 8.88E−10 | 8.88E−10 | 8.88E−10 | 8.88E−10 |
| 63 | 5.06E−10 | 5.06E−10 | 5.06E−10 | 5.06E−10 | 5.06E−10 |
| 64 | 1.18E−10 | 5.92E−10 | 5.92E−10 | 5.92E−10 | |
| 65 | 1.12E−10 | 1.12E−10 | 1.12E−10 | 1.12E−10 | 1.12E−10 |
| 66 | 1.16E−10 | 1.16E−10 | 1.16E−10 | 1.16E−10 | 1.16E−10 |
| 68 | | 6.33E−10 | 6.33E−10 | | |
| 69 | 1.25E−10 | 6.23E−10 | 6.23E−10 | 6.23E−10 | 6.23E−10 |
| 70 | 1.25E−10 | 1.25E−10 | 1.25E−10 | 1.25E−10 | 1.25E−10 |
| 71 | 5.88E−10 | 5.88E−10 | 5.88E−10 | 5.88E−10 | 5.88E−10 |
| 79 | | 1.07E−10 | 1.07E−10 | | |
| 80 | 2.96E−09 | 5.92E−09 | 5.92E−09 | 5.92E−09 | |
| 81 | | 5.54E−09 | 5.54E−09 | | |
| 82 | | 9.86E−08 | 9.86E−08 | | |
| 83 | 8.08E−08 | 8.08E−08 | 8.08E−08 | 8.08E−08 | 8.08E−08 |
| 84 | | 4.89E−08 | 4.89E−08 | | |
| 85 | | 9.71E−09 | 9.71E−09 | | |
| 86 | 5.20E−10 | 5.20E−10 | 5.20E−10 | 5.20E−10 | 5.20E−10 |
| 88 | 1.22E−08 | 1.22E−08 | 1.22E−08 | 1.22E−08 | 1.22E−08 |
| 89 | 5.91E−07 | 5.91E−07 | 5.91E−07 | 5.91E−07 | 5.91E−07 |
| 90 | 1.19E−08 | 1.19E−08 | 1.19E−08 | 1.19E−08 | 1.19E−08 |
| 91 | 1.06E−07 | 1.06E−07 | 1.06E−07 | 1.06E−07 | 1.06E−07 |
| 94 | 1.52E−10 | 1.52E−10 | 1.52E−10 | 1.52E−10 | |
| 96 | 1.25E−09 | 1.25E−09 | 1.25E−09 | 1.25E−09 | |
| 98 | | 1.29E−10 | 1.29E−10 | | |
| 104 | 1.17E−10 | 5.83E−10 | 5.83E−10 | 5.83E−10 | 5.83E−10 |
| 106 | 1.21E−09 | 1.21E−09 | 1.21E−09 | 1.21E−09 | 1.21E−09 |
| 107 | 1.08E−09 | 1.08E−09 | 1.08E−09 | 1.08E−09 | 1.08E−09 |
| 108 | | 1.08E−10 | 1.08E−10 | | |
| 109 | | 9.80E−10 | 9.80E−10 | | |
| 110 | | 9.72E−11 | 9.72E−11 | | |
| 111 | 1.11E−09 | 1.11E−09 | 1.11E−09 | 1.11E−09 | 1.11E−09 |
| 112 | | 1.03E−08 | 1.03E−08 | | |
| 113 | 1.04E−08 | 1.04E−08 | 1.04E−08 | 1.04E−08 | 1.04E−08 |
| 114 | | 9.18E−09 | 9.18E−09 | | |
| 115 | | 1.10E−10 | 1.10E−10 | | |
| 116 | | 1.09E−10 | 1.09E−10 | | |
| 119 | 1.05E−08 | 1.05E−08 | 1.05E−08 | 1.05E−08 | 1.05E−08 |
| 120 | 4.63E−07 | 4.63E−07 | 4.63E−07 | 4.63E−07 | 4.63E−07 |
| 121 | 4.69E−07 | 4.69E−07 | 4.69E−07 | 4.69E−07 | 4.69E−07 |
| 122 | 8.30E−07 | 8.30E−07 | 8.30E−07 | 8.30E−07 | 8.30E−07 |
| 126 | | 1.19E−10 | 1.19E−10 | | |
| 127 | | 1.17E−10 | 1.17E−10 | | |
| 128 | | 1.17E−09 | 1.17E−09 | | |
| 129 | | 1.13E−08 | 1.13E−08 | | |
| 130 | | 1.15E−09 | 1.15E−09 | | |
| 131 | | 1.10E−07 | 1.10E−07 | | |
| 132 | | 1.15E−09 | 1.15E−09 | | |
| 133 | | 1.10E−07 | 1.10E−07 | | |
| 134 | 5.44E−10 | 5.44E−10 | 5.44E−10 | 5.44E−10 | 5.44E−10 |
| 135 | 4.96E−09 | 4.96E−09 | 4.96E−09 | 4.96E−09 | 4.96E−09 |
| 136 | 1.37E−10 | 1.37E−10 | 1.37E−10 | 1.37E−10 | 1.37E−10 |
| 137 | 1.17E−10 | 1.17E−10 | 1.17E−10 | 1.17E−10 | 1.17E−10 |
| 138 | | 1.01E−09 | 1.01E−09 | | |
| 139 | | 1.25E−09 | 1.25E−09 | | |
| 140 | | 1.15E−09 | 1.15E−09 | | |
| 141 | | 1.23E−10 | 1.23E−10 | | |
| 142 | | 1.22E−09 | 1.22E−09 | | |
| 144 | 1.17E−09 | 1.17E−09 | 1.17E−09 | 1.17E−09 | 1.17E−09 |
| 145 | | 1.02E−07 | 1.02E−07 | | |
| 146 | 1.03E−07 | 1.03E−07 | 1.03E−07 | 1.03E−07 | 1.03E−07 |
| 149 | | 1.35E−10 | 1.35E−10 | | |
| 150 | | 1.32E−09 | 1.32E−09 | | |
| 151 | | 1.32E−10 | 1.32E−10 | | |
| 152 | | 1.28E−08 | 1.28E−08 | | |
| 153 | | 1.30E−10 | 1.30E−10 | | |
| 154 | | 1.23E−08 | 1.23E−08 | | |
| 155 | | 1.30E−09 | 1.30E−09 | | |
| 156 | | 1.24E−08 | 1.24E−08 | | |
| 157 | | 1.22E−10 | 1.22E−10 | | |
| 158 | | 1.10E−09 | 1.10E−09 | | |
| 159 | 1.37E−09 | 1.37E−09 | 1.37E−09 | 1.37E−09 | 1.37E−09 |
| 160 | | 1.09E−09 | 1.09E−09 | | |
| 161 | 1.18E−10 | 1.18E−10 | 1.18E−10 | 1.18E−10 | 1.18E−10 |
| 162 | | 5.10E−09 | 5.10E−09 | | |
| 164 | | 1.16E−08 | 1.16E−08 | | |
| 168 | 5.91E−10 | 5.91E−10 | 5.91E−10 | 5.91E−10 | 5.91E−10 |
| 169 | | 1.03E−09 | 1.03E−09 | | |
| 170 | 5.22E−08 | 5.22E−08 | 5.22E−08 | 5.22E−08 | 5.22E−08 |
| 177 | | 1.34E−10 | 1.34E−10 | | |
| 178 | | 1.31E−09 | 1.31E−09 | | |
| 179 | | 1.25E−08 | 1.25E−08 | | |
| 180 | | 6.18E−10 | 6.18E−10 | | |
| 181 | | 1.11E−08 | 1.11E−08 | | |
| 183 | | 1.32E−10 | 1.32E−10 | | |
| 184 | 6.99E−10 | 6.99E−10 | 6.99E−10 | 6.99E−10 | |
| 185 | 1.32E−08 | 1.32E−08 | 1.32E−08 | 1.32E−08 | |
| 186 | 1.59E−10 | 1.59E−10 | 1.59E−10 | 1.59E−10 | |
| 187 | 1.08E−09 | 1.08E−09 | 1.08E−09 | 1.08E−09 | |
| 188 | 5.83E−10 | 5.83E−10 | 5.83E−10 | 5.83E−10 | |
| 189 | 5.83E−10 | 5.83E−10 | 5.83E−10 | 5.83E−10 | |
| 190 | 5.22E−09 | 5.22E−09 | 5.22E−09 | 5.22E−09 | |
| 191 | 1.11E−09 | 1.11E−09 | 1.11E−09 | 1.11E−09 | 1.11E−09 |
| 192 | 5.39E−09 | 5.39E−09 | 5.39E−09 | 5.39E−09 | 5.39E−09 |
| 194 | 5.07E−08 | 5.07E−08 | 5.07E−08 | 5.07E−08 | 5.07E−08 |
| 195 | 1.02E−08 | 1.02E−08 | 1.02E−08 | 1.02E−08 | 1.02E−08 |
| 196 | 9.02E−06 | 9.02E−06 | 9.02E−06 | 9.02E−06 | 9.02E−06 |
| 197 | 9.13E−06 | 9.13E−06 | 9.13E−06 | 9.13E−06 | 9.13E−06 |
| 198 | 7.50E−06 | 7.50E−06 | 7.50E−06 | 7.50E−06 | 7.50E−06 |
| 201 | 1.26E−08 | 1.57E−08 | 1.57E−08 | 1.57E−08 | |
| 202 | 1.25E−10 | 1.25E−10 | 1.25E−10 | 6.25E−11 | 6.25E−11 |
| 203 | 1.21E−10 | 1.21E−10 | 1.21E−10 | 1.21E−10 | 1.21E−10 |
| 204 | 1.13E−10 | 1.13E−10 | 1.13E−10 | 1.13E−10 | 1.13E−10 |
| 205 | 1.13E−10 | 1.13E−10 | 1.13E−10 | 1.13E−10 | 1.13E−10 |
| 206 | 4.96E−08 | 4.96E−08 | 4.96E−08 | 4.96E−08 | 4.96E−08 |
| 207 | 5.03E−09 | 5.03E−09 | 5.03E−09 | 5.03E−09 | 5.03E−09 |
| 208 | 8.11E−06 | 8.11E−06 | 8.11E−06 | 8.11E−06 | 8.11E−06 |
| 213 | | 1.14E−10 | 1.14E−10 | | |
| 214 | | 5.00E−09 | 5.00E−09 | | |
| 216 | | 8.16E−08 | 8.16E−08 | | |
| 221 | | 1.34E−09 | 1.34E−09 | | |

| | | Compound 13 | Compound 21 | Compound 29 |
|---|---|---|---|---|
| A-549 | $GI_{50}$ | 1.08E−09 | 3.34E−09 | 2.16E−09 |
| | TGI | 3.24E−09 | 1.06E−08 | 4.32E−09 |
| | $LC_{50}$ | 8.65E−09 | 1.06E−05 | 1.08E−08 |
| H-T29 | $GI_{50}$ | 3.24E−10 | 5.31E−09 | 2.16E−09 |
| | TGI | 3.24E−10 | 1.06E−07 | 2.16E−09 |
| | $LC_{50}$ | 1.08E−08 | 1.06E−05 | 1.08E−06 |
| SW-620 | $GI_{50}$ | | | |
| | TGI | | | |
| | $LC_{50}$ | | | |
| MEL-28 | $GI_{50}$ | | | |
| | TGI | | | |
| | $LC_{50}$ | | | |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | | | |
| | TGI | | | |
| | $LC_{50}$ | | | |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |

-continued

| Activity Data | | | | |
|---|---|---|---|---|
| HMEC-1 | $GI_{50}$ | | | |
| | TGI | | | |
| | $LC_{50}$ | | | |
| LNCAP | $GI_{50}$ | | | |
| | TGI | | | |
| | $LC_{50}$ | | | |
| SK-OV3 | $GI_{50}$ | | | |
| | TGI | | | |
| | $LC_{50}$ | | | |
| IGROV | $GI_{50}$ | | | |
| | TGI | | | |
| | $LC_{50}$ | | | |
| IGROV-ET | $GI_{50}$ | | | |
| | TGI | | | |
| | $LC_{50}$ | | | |
| SK-BR3 | $GI_{50}$ | | | |
| | TGI | | | |
| | $LC_{50}$ | | | |
| K-562 | $GI_{50}$ | | | |
| | TGI | | | |
| | $LC_{50}$ | | | |
| PANC-1 | $GI_{50}$ | | | |
| | TGI | | | |
| | $LC_{50}$ | | | |
| LOVO | $GI_{50}$ | | | |
| | TGI | | | |
| | $LC_{50}$ | | | |
| LOVO-DOX | $GI_{50}$ | | | |
| | TGI | | | |
| | $LC_{50}$ | | | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |
| | | Compound 30 | Compound 31 | Compound 32 |
| A-549 | $GI_{50}$ | 3.29E−08 | 4.08E−08 | 2.20E−09 |
| | TGI | 5.49E−08 | 9.17E−08 | 6.59E−09 |
| | $LC_{50}$ | 3.29E−06 | 1.02E−06 | 1.10E−08 |
| H-T29 | $GI_{50}$ | 8.78E−08 | 8.15E−08 | 1.10E−09 |
| | TGI | 8.78E−08 | 8.15E−08 | 6.60E−09 |
| | $LC_{50}$ | 1.10E−05 | 1.02E−05 | 9.88E−09 |
| SW-620 | $GI_{50}$ | | | |
| | TGI | | | |
| | $LC_{50}$ | | | |
| MEL-28 | $GI_{50}$ | | | |
| | TGI | | | |
| | $LC_{50}$ | | | |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | | | |
| | TGI | | | |
| | $LC_{50}$ | | | |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | | | |
| | TGI | | | |
| | $LC_{50}$ | | | |
| LNCAP | $GI_{50}$ | | | |
| | TGI | | | |
| | $LC_{50}$ | | | |
| SK-OV3 | $GI_{50}$ | | | |
| | TGI | | | |
| | $LC_{50}$ | | | |
| IGROV | $GI_{50}$ | | | |
| | TGI | | | |
| | $LC_{50}$ | | | |

-continued

| Activity Data | | | | |
|---|---|---|---|---|
| IGROV-ET | $GI_{50}$ | | | |
| | TGI | | | |
| | $LC_{50}$ | | | |
| SK-BR3 | $GI_{50}$ | | | |
| | TGI | | | |
| | $LC_{50}$ | | | |
| K-562 | $GI_{50}$ | | | |
| | TGI | | | |
| | $LC_{50}$ | | | |
| PANC-1 | $GI_{50}$ | | | |
| | TGI | | | |
| | $LC_{50}$ | | | |
| LOVO | $GI_{50}$ | | | |
| | TGI | | | |
| | $LC_{50}$ | | | |
| LOVO-DOX | $GI_{50}$ | | | |
| | TGI | | | |
| | $LC_{50}$ | | | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |
| | | Compound 33 | Compound 34 | Compound 35 |
| A-549 | $GI_{50}$ | 4.37E−09 | 7.64E−10 | 5.68E−09 |
| | TGI | 2.50E−08 | 2.84E−09 | 7.22E−08 |
| | $LC_{50}$ | 1.27E−05 | 9.06E−09 | 2.15E−06 |
| H-T29 | $GI_{50}$ | 3.42E−08 | 8.09E−10 | 5.41E−09 |
| | TGI | 1.25E−07 | 1.29E−08 | 1.25E−08 |
| | $LC_{50}$ | 1.25E−05 | 1.27E−05 | 1.25E−05 |
| SW-620 | $GI_{50}$ | | | |
| | TGI | | | |
| | $LC_{50}$ | | | |
| MEL-28 | $GI_{50}$ | | | |
| | TGI | | | |
| | $LC_{50}$ | | | |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | | | |
| | TGI | | | |
| | $LC_{50}$ | | | |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | | | |
| | TGI | | | |
| | $LC_{50}$ | | | |
| LNCAP | $GI_{50}$ | | | |
| | TGI | | | |
| | $LC_{50}$ | | | |
| SK-OV3 | $GI_{50}$ | | | |
| | TGI | | | |
| | $LC_{50}$ | | | |
| IGROV | $GI_{50}$ | | | |
| | TGI | | | |
| | $LC_{50}$ | | | |
| IGROV-ET | $GI_{50}$ | | | |
| | TGI | | | |
| | $LC_{50}$ | | | |
| SK-BR3 | $GI_{50}$ | | | |
| | TGI | | | |
| | $LC_{50}$ | | | |
| K-562 | $GI_{50}$ | | | |
| | TGI | | | |
| | $LC_{50}$ | | | |
| PANC-1 | $GI_{50}$ | | | |
| | TGI | | | |
| | $LC_{50}$ | | | |

-continued

| Activity Data | | | | |
|---|---|---|---|---|
| LOVO | $GI_{50}$ | | | |
| | TGI | | | |
| | $LC_{50}$ | | | |
| LOVO-DOX | $GI_{50}$ | | | |
| | TGI | | | |
| | $LC_{50}$ | | | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |
| | | Compound 36 | Compound 46 | Compound 48 |
| A-549 | $GI_{50}$ | 6.26E−09 | 1.79E−07 | 2.72E−07 |
| | TGI | 1.03E−07 | 4.06E−07 | 7.50E−07 |
| | $LC_{50}$ | 4.14E−06 | 9.27E−07 | 3.89E−06 |
| H-T29 | $GI_{50}$ | 5.67E−09 | 3.98E−07 | 1.97E−06 |
| | TGI | 2.55E−08 | 1.95E−06 | 1.23E−05 |
| | $LC_{50}$ | 1.27E−05 | 1.10E−05 | 1.23E−05 |
| SW-620 | $GI_{50}$ | | | |
| | TGI | | | |
| | $LC_{50}$ | | | |
| MEL-28 | $GI_{50}$ | | | 1.10E−06 |
| | TGI | | | 2.87E−06 |
| | $LC_{50}$ | | | 7.06E−06 |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | | | 6.14E−07 |
| | TGI | | | 3.20E−06 |
| | $LC_{50}$ | | | 1.23E−05 |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | | 1.52E−07 | |
| | TGI | | 5.18E−07 | |
| | $LC_{50}$ | | 1.10E−05 | |
| LNCAP | $GI_{50}$ | | | |
| | TGI | | | |
| | $LC_{50}$ | | | |
| SK-OV3 | $GI_{50}$ | | | 6.14E−07 |
| | TGI | | | 3.40E−06 |
| | $LC_{50}$ | | | 1.23E−05 |
| IGROV | $GI_{50}$ | | | 4.39E−07 |
| | TGI | | | 1.78E−06 |
| | $LC_{50}$ | | | 7.98E−06 |
| IGROV-ET | $GI_{50}$ | | | 6.78E−07 |
| | TGI | | | 2.93E−06 |
| | $LC_{50}$ | | | 1.23E−05 |
| SK-BR3 | $GI_{50}$ | | | 4.43E−07 |
| | TGI | | | 1.54E−06 |
| | $LC_{50}$ | | | 6.97E−06 |
| K-562 | $GI_{50}$ | | | 2.23E−07 |
| | TGI | | | 5.47E−07 |
| | $LC_{50}$ | | | 1.23E−06 |
| PANC-1 | $GI_{50}$ | | | 9.10E−07 |
| | TGI | | | 5.10E−06 |
| | $LC_{50}$ | | | 1.23E−05 |
| LOVO | $GI_{50}$ | | | 7.13E−07 |
| | TGI | | | 2.95E−06 |
| | $LC_{50}$ | | | 1.23E−05 |
| LOVO-DOX | $GI_{50}$ | | | 7.90E−07 |
| | TGI | | | 4.18E−06 |
| | $LC_{50}$ | | | 1.23E−05 |
| HELA | $GI_{50}$ | | | |
| | TGI | | | |
| | $LC_{50}$ | | | |

-continued

| Activity Data | | | | |
|---|---|---|---|---|
| HELA-APL | $GI_{50}$ | | | |
| | TGI | | | |
| | $LC_{50}$ | | | |
| | | Compound 67 | Compound 72 | Compound 73 |
| A-549 | $GI_{50}$ | 1.31E−09 | 1.12E−09 | 3.52E−10 |
| | TGI | 3.63E−09 | 3.36E−09 | 2.35E−09 |
| | $LC_{50}$ | 1.01E−08 | 7.83E−09 | 5.87E−09 |
| HT-29 | $GI_{50}$ | 7.41E−10 | 2.24E−09 | 9.39E−10 |
| | TGI | 5.59E−09 | 7.83E−09 | 7.04E−09 |
| | $LC_{50}$ | 1.29E−05 | 1.12E−08 | 1.06E−08 |
| SW-620 | $GI_{50}$ | | 2.24E−09 | 3.52E−10 |
| | TGI | | 3.36E−09 | 1.17E−09 |
| | $LC_{50}$ | | 1.12E−08 | 9.39E−09 |
| MEL-28 | $GI_{50}$ | 4.11E−10 | 2.24E−09 | 8.22E−10 |
| | TGI | 9.90E−10 | 3.36E−09 | 9.39E−10 |
| | $LC_{50}$ | 6.24E−09 | 7.83E−09 | 3.52E−09 |
| OVCAR | $GI_{50}$ | | | |
| | TGI | | | |
| | $LC_{50}$ | | | |
| A-498 | $GI_{50}$ | | 2.24E−09 | 3.52E−10 |
| | TGI | | 4.47E−09 | 7.04E−10 |
| | $LC_{50}$ | | 1.12E−08 | 3.52E−09 |
| DU-145 | $GI_{50}$ | 4.33E−10 | 2.24E−09 | 2.35E−10 |
| | TGI | 8.61E−10 | 3.36E−09 | 3.52E−10 |
| | $LC_{50}$ | 4.47E−06 | 8.95E−09 | 9.39E−10 |
| MCF | $GI_{50}$ | | 2.24E−09 | 7.04E−10 |
| | TGI | | 4.47E−09 | 3.52E−09 |
| | $LC_{50}$ | | 1.12E−08 | 1.17E−08 |
| MB-231 | $GI_{50}$ | | 2.24E−09 | 2.35E−10 |
| | TGI | | 3.36E−09 | 4.69E−11 |
| | $LC_{50}$ | | 1.12E−08 | 1.17E−09 |
| HMEC-1 | $GI_{50}$ | 1.02E−09 | | |
| | TGI | 8.49E−09 | | |
| | $LC_{50}$ | 5.05E−06 | | |
| LNCAP | $GI_{50}$ | 3.07E−10 | | |
| | TGI | 5.09E−10 | | |
| | $LC_{50}$ | 8.44E−10 | | |
| SK-OV3 | $GI_{50}$ | 3.85E−10 | | |
| | TGI | 8.52E−10 | | |
| | $LC_{50}$ | 7.94E−06 | | |
| IGROV | $GI_{50}$ | 2.66E−10 | | |
| | TGI | 5.67E−10 | | |
| | $LC_{50}$ | 1.21E−09 | | |
| IGROV-ET | $GI_{50}$ | 1.88E−09 | | |
| | TGI | 7.02E−09 | | |
| | $LC_{50}$ | 4.96E−06 | | |
| SK-BR3 | $GI_{50}$ | 3.94E−10 | | |
| | TGI | 1.11E−09 | | |
| | $LC_{50}$ | 7.48E−09 | | |
| K-562 | $GI_{50}$ | 1.18E−10 | | |
| | TGI | 2.85E−10 | | |
| | $LC_{50}$ | 8.00E−10 | | |
| PANC-1 | $GI_{50}$ | 4.43E−10 | | |
| | TGI | 1.09E−09 | | |
| | $LC_{50}$ | 2.67E−06 | | |
| LOVO | $GI_{50}$ | 6.02E−10 | | |
| | TGI | 3.34E−09 | | |
| | $LC_{50}$ | 1.77E−08 | | |
| LOVO-DOX | $GI_{50}$ | 4.21E−09 | | |
| | TGI | 3.65E−08 | | |
| | $LC_{50}$ | 1.28E−05 | | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |
| | | Compound 74 | Compound 75 | Compound 76 |
| A-549 | $GI_{50}$ | 3.99E−10 | 4.26E−09 | 2.06E−09 |
| | TGI | 9.04E−10 | 8.23E−09 | 4.31E−09 |
| | $LC_{50}$ | 6.38E−09 | 4.90E−08 | 9.07E−09 |
| HT-29 | $GI_{50}$ | 3.54E−10 | 3.89E−09 | 1.28E−09 |
| | TGI | 8.35E−10 | 1.18E−08 | 6.18E−09 |
| | $LC_{50}$ | 1.04E−05 | 1.20E−07 | 4.52E−06 |

-continued

| Activity Data | | | | |
|---|---|---|---|---|
| SW-620 | $GI_{50}$ | | | |
| | TGI | | | |
| | $LC_{50}$ | | | |
| MEL-28 | $GI_{50}$ | 2.75E−10 | 2.00E−09 | 6.22E−10 |
| | TGI | 5.22E−10 | 4.82E−09 | 2.51E−09 |
| | $LC_{50}$ | 9.94E−10 | 1.17E−08 | 8.28E−09 |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | 3.66E−10 | 5.63E−10 | 2.49E−10 |
| | TGI | 7.61E−10 | 9.47E−10 | 6.16E−10 |
| | $LC_{50}$ | 2.79E−06 | 8.33E−06 | 2.14E−06 |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | 5.98E−10 | 6.97E−09 | 1.83E−09 |
| | TGI | 1.45E−08 | 5.77E−08 | 6.55E−09 |
| | $LC_{50}$ | 4.70E−06 | 1.20E−05 | 1.86E−07 |
| LNCAP | $GI_{50}$ | 1.29E−10 | 5.79E−10 | 2.17E−10 |
| | TGI | 2.69E−10 | 8.31E−10 | 4.40E−10 |
| | $LC_{50}$ | 5.64E−10 | 1.19E−09 | 8.91E−10 |
| SK-OV3 | $GI_{50}$ | 2.48E−10 | 2.19E−09 | 2.93E−10 |
| | TGI | 4.76E−10 | 1.04E−08 | 8.93E−10 |
| | $LC_{50}$ | 1.11E−09 | 1.20E−05 | 4.81E−06 |
| IGROV | $GI_{50}$ | 2.37E−10 | 5.20E−10 | 1.92E−10 |
| | TGI | 4.65E−10 | 1.63E−09 | 4.56E−10 |
| | $LC_{50}$ | 9.11E−10 | 1.00E−08 | 1.66E−09 |
| IGROV-ET | $GI_{50}$ | 1.76E−09 | 3.38E−09 | 1.52E−09 |
| | TGI | 4.69E−09 | 6.58E−09 | 3.92E−09 |
| | $LC_{50}$ | 1.97E−08 | 1.20E−08 | 2.10E−08 |
| SK-BR3 | $GI_{50}$ | 2.75E−10 | 1.20E−09 | 3.37E−10 |
| | TGI | 7.64E−10 | 3.21E−09 | 1.24E−09 |
| | $LC_{50}$ | 4.18E−09 | 8.58E−09 | 6.17E−09 |
| K-562 | $GI_{50}$ | 5.26E−11 | 3.64E−10 | 2.78E−12 |
| | TGI | 2.10E−10 | 7.42E−10 | 3.78E−11 |
| | $LC_{50}$ | 6.61E−10 | 4.16E−09 | 3.51E−10 |
| PANC-1 | $GI_{50}$ | 3.13E−10 | 3.04E−09 | 1.22E−09 |
| | TGI | 6.77E−10 | 8.45E−09 | 4.68E−09 |
| | $LC_{50}$ | 2.55E−09 | 3.59E−08 | 4.41E−08 |
| LOVO | $GI_{50}$ | 3.69E−10 | 2.25E−09 | 1.03E−09 |
| | TGI | 1.16E−09 | 4.82E−09 | 3.30E−09 |
| | $LC_{50}$ | 1.10E−08 | 1.20E−08 | 1.08E−08 |
| LOVO-DOX | $GI_{50}$ | 6.31E−09 | 4.26E−08 | 1.39E−08 |
| | TGI | 6.33E−08 | 1.23E−07 | 4.70E−08 |
| | $LC_{50}$ | 3.59E−07 | 1.20E−05 | 1.07E−07 |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 77 | Compound 78 | Compound 87 |
|---|---|---|---|---|
| A-549 | $GI_{50}$ | 2.11E−09 | 9.59E−09 | 2.38E−08 |
| | TGI | 3.64E−09 | 1.99E−08 | 4.77E−08 |
| | $LC_{50}$ | 6.29E−09 | 4.11E−08 | 9.58E−08 |
| HT-29 | $GI_{50}$ | 2.96E−09 | 1.71E−08 | 2.44E−08 |
| | TGI | 9.52E−09 | 1.10E−07 | 1.12E−07 |
| | $LC_{50}$ | 1.01E−05 | 8.19E−06 | 3.80E−07 |
| SW-620 | $GI_{50}$ | | | |
| | TGI | | | |
| | $LC_{50}$ | | | |
| MEL-28 | $GI_{50}$ | 2.66E−10 | 2.15E−09 | 1.92E−08 |
| | TGI | 5.06E−10 | 4.48E−09 | 4.57E−08 |
| | $LC_{50}$ | 9.62E−10 | 1.69E−08 | 1.09E−07 |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | 4.88E−10 | 3.21E−09 | 1.35E−08 |
| | TGI | 1.45E−09 | 8.52E−09 | 5.22E−08 |
| | $LC_{50}$ | 1.01E−05 | 8.19E−06 | 1.80E−07 |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | 5.28E−09 | 2.83E−08 | 1.67E−08 |
| | TGI | 5.28E−08 | 2.35E−07 | 9.65E−08 |
| | $LC_{50}$ | 1.01E−05 | 8.19E−06 | 1.27E−05 |
| LNCAP | $GI_{50}$ | 3.28E−10 | 2.74E−09 | 4.73E−09 |
| | TGI | 6.12E−10 | 4.05E−09 | 1.12E−08 |
| | $LC_{50}$ | 1.58E−09 | 5.99E−09 | 4.05E−08 |
| SK-OV3 | $GI_{50}$ | 2.55E−09 | 3.79E−09 | 2.16E−08 |
| | TGI | 7.76E−09 | 6.27E−08 | 6.56E−08 |
| | $LC_{50}$ | 1.01E−05 | 8.19E−06 | 8.99E−06 |
| IGROV | $GI_{50}$ | 4.54E−10 | 2.38E−09 | 4.80E−09 |
| | TGI | 1.53E−09 | 6.27E−09 | 1.63E−08 |
| | $LC_{50}$ | 8.82E−09 | 5.39E−08 | 8.04E−08 |
| IGROV-ET | $GI_{50}$ | 4.22E−09 | 1.14E−07 | 2.84E−08 |
| | TGI | 9.57E−08 | 7.42E−07 | 7.77E−08 |
| | $LC_{50}$ | 3.03E−07 | 8.19E−06 | 5.84E−06 |
| SK-BR3 | $GI_{50}$ | 4.75E−10 | 4.31E−09 | 1.65E−08 |
| | TGI | 2.04E−09 | 1.70E−08 | 4.08E−08 |
| | $LC_{50}$ | 8.12E−09 | 6.33E−08 | 1.01E−07 |
| K-562 | $GI_{50}$ | 2.77E−10 | 1.24E−09 | 8.71E−10 |
| | TGI | 7.77E−10 | 2.56E−09 | 2.96E−09 |
| | $LC_{50}$ | 3.79E−08 | 7.50E−09 | 7.15E−09 |
| PANC-1 | $GI_{50}$ | 3.27E−09 | 5.42E−09 | 2.53E−08 |
| | TGI | 9.14E−09 | 3.24E−08 | 7.39E−08 |
| | $LC_{50}$ | 6.30E−06 | 4.90E−06 | 8.76E−07 |
| LOVO | $GI_{50}$ | 1.91E−09 | 1.07E−08 | 2.27E−08 |
| | TGI | 3.96E−09 | 2.83E−08 | 5.27E−08 |
| | $LC_{50}$ | 8.21E−09 | 7.43E−08 | 1.23E−07 |
| LOVO-DOX | $GI_{50}$ | 3.13E−08 | 8.85E−08 | 3.87E−08 |
| | TGI | 9.39E−08 | 8.77E−07 | 1.42E−07 |
| | $LC_{50}$ | 1.01E−05 | 8.19E−06 | 1.27E−05 |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 92 | Compound 93 | Compound 95 |
|---|---|---|---|---|
| A-549 | $GI_{50}$ | 3.33E−09 | 4.63E−10 | 2.68E−08 |
| | TGI | 7.77E−09 | 2.90E−09 | 5.55E−08 |
| | $LC_{50}$ | 3.33E−08 | 1.29E−08 | 1.47E−07 |
| HT-29 | $GI_{50}$ | 1.11E−09 | 6.35E−10 | 4.04E−08 |
| | TGI | 1.11E−09 | 1.29E−08 | 1.27E−07 |
| | $LC_{50}$ | 5.55E−08 | 1.29E−05 | 1.20E−05 |
| SW-620 | $GI_{50}$ | | | |
| | TGI | | | |
| | $LC_{50}$ | | | |
| MEL-28 | $GI_{50}$ | | 2.81E−10 | 2.52E−08 |
| | TGI | | 6.24E−10 | 4.58E−08 |
| | $LC_{50}$ | | 3.58E−09 | 8.32E−08 |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | | 3.31E−10 | 3.76E−08 |
| | TGI | | 6.30E−10 | 8.92E−08 |
| | $LC_{50}$ | | 1.29E−09 | 1.01E−06 |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | | 3.70E−11 | 9.36E−09 |
| | TGI | | 1.55E−10 | 2.80E−08 |
| | $LC_{50}$ | | 4.87E−10 | 7.56E−08 |

-continued

Activity Data

| | | | | |
|---|---|---|---|---|
| LNCAP | $GI_{50}$ | | 2.85E−09 | 1.77E−08 |
| | TGI | | 6.77E−09 | 3.41E−08 |
| | $LC_{50}$ | | 1.29E−07 | 6.60E−08 |
| SK-OV3 | $GI_{50}$ | | 4.09E−10 | 2.81E−08 |
| | TGI | | 1.29E−09 | 6.59E−08 |
| | $LC_{50}$ | | 1.29E−05 | 3.68E−07 |
| IGROV | $GI_{50}$ | | 2.14E−10 | 2.80E−08 |
| | TGI | | 6.46E−10 | 6.67E−08 |
| | $LC_{50}$ | | 1.29E−07 | 1.09E−06 |
| IGROV-ET | $GI_{50}$ | | 2.15E−08 | 5.05E−08 |
| | TGI | | 1.31E−07 | 1.16E−07 |
| | $LC_{50}$ | | 1.29E−05 | 1.20E−05 |
| SK-BR3 | $GI_{50}$ | | 4.45E−10 | 2.98E−08 |
| | TGI | | 1.96E−09 | 7.62E−08 |
| | $LC_{50}$ | | 9.50E−09 | 5.22E−07 |
| K-562 | $GI_{50}$ | | 6.11E−10 | 1.53E−08 |
| | TGI | | 1.29E−08 | 5.30E−08 |
| | $LC_{50}$ | | 9.54E−06 | 2.22E−06 |
| PANC-1 | $GI_{50}$ | | 3.14E−10 | 3.88E−08 |
| | TGI | | 1.29E−09 | 1.08E−07 |
| | $LC_{50}$ | | 1.29E−05 | 1.09E−06 |
| LOVO | $GI_{50}$ | | 7.68E−10 | 2.62E−08 |
| | TGI | | 4.58E−09 | 5.40E−08 |
| | $LC_{50}$ | | 1.29E−05 | 1.11E−07 |
| LOVO-DOX | $GI_{50}$ | | 7.71E−09 | 2.40E−07 |
| | TGI | | 9.87E−08 | 8.68E−07 |
| | $LC_{50}$ | | 1.29E−05 | 1.20E−05 |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 97 | Compound 99 | Compound 100 |
|---|---|---|---|---|
| A5-49 | $GI_{50}$ | 3.48E−10 | 4.35E−08 | 2.98E−08 |
| | TGI | 9.28E−10 | 9.96E−08 | 6.20E−08 |
| | $LC_{50}$ | 3.48E−09 | 1.03E−05 | 1.12E−07 |
| HT-29 | $GI_{50}$ | 9.28E−10 | 3.43E−08 | 3.50E−08 |
| | TGI | 2.32E−09 | 1.03E−07 | 8.07E−08 |
| | $LC_{50}$ | 9.28E−09 | 1.03E−05 | 1.11E−05 |
| SW-620 | $GI_{50}$ | 5.80E−10 | | |
| | TGI | 2.32E−09 | | |
| | $LC_{50}$ | 9.28E−09 | | |
| MEL-28 | $GI_{50}$ | 3.48E−10 | | 2.65E−08 |
| | TGI | 9.28E−10 | | 5.04E−08 |
| | $LC_{50}$ | 3.48E−09 | | 9.59E−08 |
| OVCAR | $GI_{50}$ | | | |
| | TGI | | | |
| | $LC_{50}$ | | | |
| A-498 | $GI_{50}$ | 5.80E−10 | | |
| | TGI | 2.32E−09 | | |
| | $LC_{50}$ | 9.28E−09 | | |
| DU-145 | $GI_{50}$ | 2.32E−10 | | 4.31E−08 |
| | TGI | 3.48E−10 | | 1.03E−07 |
| | $LC_{50}$ | 9.28E−10 | | 8.32E−06 |
| MCF | $GI_{50}$ | 1.16E−09 | | |
| | TGI | 3.48E−09 | | |
| | $LC_{50}$ | 1.16E−08 | | |
| MB-231 | $GI_{50}$ | 3.48E−10 | | |
| | TGI | 6.96E−10 | | |
| | $LC_{50}$ | 3.48E−08 | | |
| HMEC-1 | $GI_{50}$ | | | 2.75E−08 |
| | TGI | | | 5.14E−08 |
| | $LC_{50}$ | | | 9.61E−08 |
| LNCAP | $GI_{50}$ | | | 2.15E−08 |
| | TGI | | | 3.79E−08 |
| | $LC_{50}$ | | | 6.65E−08 |
| SK-OV3 | $GI_{50}$ | | | 2.82E−08 |
| | TGI | | | 5.74E−08 |
| | $LC_{50}$ | | | 1.11E−07 |
| IGROV | $GI_{50}$ | | | 3.51E−08 |
| | TGI | | | 6.54E−08 |
| | $LC_{50}$ | | | 9.15E−07 |
| IGROV-ET | $GI_{50}$ | | | 6.32E−08 |
| | TGI | | | 7.41E−07 |
| | $LC_{50}$ | | | 1.11E−05 |

-continued

Activity Data

| | | | | |
|---|---|---|---|---|
| SK-BR3 | $GI_{50}$ | | | 4.05E−08 |
| | TGI | | | 9.87E−08 |
| | $LC_{50}$ | | | 1.72E−06 |
| K-562 | $GI_{50}$ | | | 3.64E−08 |
| | TGI | | | 6.20E−08 |
| | $LC_{50}$ | | | 1.06E−07 |
| PANC-1 | $GI_{50}$ | | | 4.14E−08 |
| | TGI | | | 1.14E−08 |
| | $LC_{50}$ | | | 8.32E−06 |
| LOVO | $GI_{50}$ | | | 2.44E−08 |
| | TGI | | | 4.48E−08 |
| | $LC_{50}$ | | | 8.23E−08 |
| LOVO-DOX | $GI_{50}$ | | | 3.92E−07 |
| | TGI | | | 2.73E−06 |
| | $LC_{50}$ | | | 1.11E−05 |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 101 | Compound 102 | Compound 118 |
|---|---|---|---|---|
| A5-49 | $GI_{50}$ | 3.69E−09 | 1.52E−07 | 3.34E−09 |
| | TGI | 6.52E−09 | 4.24E−07 | 8.90E−08 |
| | $LC_{50}$ | 1.15E−08 | 1.19E−06 | 2.22E−06 |
| HT-29 | $GI_{50}$ | 3.57E−09 | 8.70E−08 | 7.79E−09 |
| | TGI | 1.03E−08 | 2.19E−06 | 7.79E−09 |
| | $LC_{50}$ | 1.29E−05 | 1.24E−05 | 1.11E−05 |
| SW-620 | $GI_{50}$ | | | |
| | TGI | | | |
| | $LC_{50}$ | | | |
| MEL-28 | $GI_{50}$ | 3.35E−09 | 3.79E−08 | |
| | TGI | 7.02E−09 | 6.89E−08 | |
| | $LC_{50}$ | 2.60E−08 | 1.28E−07 | |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | 3.74E−09 | 3.98E−08 | |
| | TGI | 7.46E−09 | 7.84E−08 | |
| | $LC_{50}$ | 1.79E−08 | 1.24E−07 | |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | 3.05E−09 | | |
| | TGI | 1.17E−08 | | |
| | $LC_{50}$ | 1.29E−05 | | |
| LNCAP | $GI_{50}$ | 2.50E−09 | 1.75E−08 | |
| | TGI | 4.40E−09 | 4.09E−08 | |
| | $LC_{50}$ | 7.71E−09 | 9.54E−08 | |
| SK-OV3 | $GI_{50}$ | 4.49E−09 | 4.13E−08 | |
| | TGI | 9.77E−09 | 1.10E−07 | |
| | $LC_{50}$ | 1.29E−05 | 1.24E−07 | |
| IGROV | $GI_{50}$ | 2.50E−09 | 3.53E−08 | |
| | TGI | 5.17E−09 | 7.63E−08 | |
| | $LC_{50}$ | 1.07E−08 | 1.34E−07 | |
| IGROV-ET | $GI_{50}$ | 3.05E−08 | 1.01E−07 | |
| | TGI | 6.88E−08 | 1.53E−06 | |
| | $LC_{50}$ | 2.46E−07 | 7.81E−06 | |
| SK-BR3 | $GI_{50}$ | 2.63E−09 | | |
| | TGI | 6.44E−09 | | |
| | $LC_{50}$ | 4.68E−08 | | |
| K-562 | $GI_{50}$ | 2.50E−10 | 1.02E−08 | |
| | TGI | 6.20E−10 | 4.35E−08 | |
| | $LC_{50}$ | 1.92E−08 | 1.26E−07 | |
| PANC-1 | $GI_{50}$ | 5.66E−09 | 5.54E−08 | |
| | TGI | 2.27E−08 | 1.39E−07 | |
| | $LC_{50}$ | 1.34E−06 | 1.24E−05 | |
| LOVO | $GI_{50}$ | 1.34E−08 | 6.98E−08 | |
| | TGI | 4.68E−08 | 4.58E−07 | |
| | $LC_{50}$ | 2.19E−07 | 1.24E−05 | |

-continued

Activity Data

| | | | | |
|---|---|---|---|---|
| LOVO-DOX | $GI_{50}$ | 2.51E−07 | 4.17E−07 | |
| | TGI | 9.29E−07 | 1.02E−06 | |
| | $LC_{50}$ | 1.29E−05 | 1.24E−05 | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 123 | Compound 124 | Compound 125 |
|---|---|---|---|---|
| A-549 | $GI_{50}$ | 7.33E−09 | 6.87E−09 | 1.00E−09 |
| | TGI | 2.09E−08 | 7.33E−07 | 3.00E−09 |
| | $LC_{50}$ | 7.33E−08 | 7.80E−06 | 8.00E−09 |
| HT-29 | $GI_{50}$ | 3.14E−09 | 3.56E−09 | 2.00E−10 |
| | TGI | 3.14E−09 | 7.80E−08 | 2.00E−10 |
| | $LC_{50}$ | 3.14E−08 | 7.80E−06 | 3.00E−09 |
| SW-620 | $GI_{50}$ | | | |
| | TGI | | | |
| | $LC_{50}$ | | | |
| MEL-28 | $GI_{50}$ | | | |
| | TGI | | | |
| | $LC_{50}$ | | | |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | | | |
| | TGI | | | |
| | $LC_{50}$ | | | |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | | | |
| | TGI | | | |
| | $LC_{50}$ | | | |
| LNCAP | $GI_{50}$ | | | |
| | TGI | | | |
| | $LC_{50}$ | | | |
| SK-OV3 | $GI_{50}$ | | | |
| | TGI | | | |
| | $LC_{50}$ | | | |
| IGROV | $GI_{50}$ | | | |
| | TGI | | | |
| | $LC_{50}$ | | | |
| IGROV-ET | $GI_{50}$ | | | |
| | TGI | | | |
| | $LC_{50}$ | | | |
| SK-BR3 | $GI_{50}$ | | | |
| | TGI | | | |
| | $LC_{50}$ | | | |
| K-562 | $GI_{50}$ | | | |
| | TGI | | | |
| | $LC_{50}$ | | | |
| PANC-1 | $GI_{50}$ | | | |
| | TGI | | | |
| | $LC_{50}$ | | | |
| LOVO | $GI_{50}$ | | | |
| | TGI | | | |
| | $LC_{50}$ | | | |
| LOVO-DOX | $GI_{50}$ | | | |
| | TGI | | | |
| | $LC_{50}$ | | | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

-continued

Activity Data

| | | Compound 143 | Compound 147 | Compound 148 |
|---|---|---|---|---|
| A-549 | $GI_{50}$ | 2.16E−08 | 3.26E−08 | 2.55E−07 |
| | TGI | 4.32E−08 | 6.84E−08 | 5.19E−07 |
| | $LC_{50}$ | 1.08E−07 | 1.05E−06 | 2.88E−06 |
| HT-29 | $GI_{50}$ | 1.08E−08 | 1.97E−08 | 1.40E−07 |
| | TGI | 1.08E−08 | 1.05E−07 | 3.32E−07 |
| | $LC_{50}$ | 1.08E−05 | 1.05E−05 | 7.86E−07 |
| SW-620 | $GI_{50}$ | | | |
| | TGI | | | |
| | $LC_{50}$ | | | |
| MEL-28 | $GI_{50}$ | | | |
| | TGI | | | |
| | $LC_{50}$ | | | |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | | | |
| | TGI | | | |
| | $LC_{50}$ | | | |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | | | |
| | TGI | | | |
| | $LC_{50}$ | | | |
| LNCAP | $GI_{50}$ | | | |
| | TGI | | | |
| | $LC_{50}$ | | | |
| SK-OV3 | $GI_{50}$ | | | |
| | TGI | | | |
| | $LC_{50}$ | | | |
| IGROV | $GI_{50}$ | | | |
| | TGI | | | |
| | $LC_{50}$ | | | |
| IGROV-ET | $GI_{50}$ | | | |
| | TGI | | | |
| | $LC_{50}$ | | | |
| SK-BR3 | $GI_{50}$ | | | |
| | TGI | | | |
| | $LC_{50}$ | | | |
| K-562 | $GI_{50}$ | | | |
| | TGI | | | |
| | $LC_{50}$ | | | |
| PANC-1 | $GI_{50}$ | | | |
| | TGI | | | |
| | $LC_{50}$ | | | |
| LOVO | $GI_{50}$ | | | |
| | TGI | | | |
| | $LC_{50}$ | | | |
| LOVO-DOX | $GI_{50}$ | | | |
| | TGI | | | |
| | $LC_{50}$ | | | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 163 | Compound 165 | Compound 166 |
|---|---|---|---|---|
| A-549 | $GI_{50}$ | 3.80E−10 | 1.24E−10 | 9.88E−10 |
| | TGI | 2.53E−09 | 3.73E−10 | 3.70E−09 |
| | $LC_{50}$ | 8.86E−09 | 1.24E−09 | 9.88E−09 |
| HT-29 | $GI_{50}$ | 3.80E−10 | 2.49E−10 | 1.23E−09 |
| | TGI | 1.14E−09 | 3.73E−10 | 3.70E−09 |
| | $LC_{50}$ | 3.80E−09 | 9.95E−10 | 9.88E−09 |
| SW-620 | $GI_{50}$ | 3.80E−10 | 1.24E−10 | 3.70E−10 |
| | TGI | 2.53E−09 | 4.98E−10 | 3.70E−09 |
| | $LC_{50}$ | 1.01E−08 | 6.22E−09 | 1.11E−08 |

-continued

| Activity Data | | | | |
|---|---|---|---|---|
| MEL-28 | $GI_{50}$ | 2.53E−10 | 1.24E−10 | 4.94E−10 |
| | TGI | 1.01E−09 | 3.73E−10 | 1.23E−09 |
| | $LC_{50}$ | 3.80E−09 | 9.95E−10 | 4.94E−09 |
| OVCAR | $GI_{50}$ | | | |
| | TGI | | | |
| | $LC_{50}$ | | | |
| A-498 | $GI_{50}$ | 3.80E−10 | 2.49E−10 | 1.23E−09 |
| | TGI | 1.27E−09 | 6.22E−10 | 4.94E−09 |
| | $LC_{50}$ | 1.27E−08 | 2.49E−09 | 1.11E−08 |
| DU-145 | $GI_{50}$ | 2.53E−10 | 2.49E−11 | 3.70E−10 |
| | TGI | 3.80E−10 | 6.22E−11 | 4.94E−10 |
| | $LC_{50}$ | 1.01E−09 | 2.49E−10 | 1.23E−09 |
| MCF | $GI_{50}$ | 2.53E−09 | 9.95E−10 | 2.47E−09 |
| | TGI | 5.06E−09 | 4.98E−09 | 8.64E−09 |
| | $LC_{50}$ | 1.27E−08 | 1.12E−08 | 1.11E−08 |
| MB-231 | $GI_{50}$ | 2.53E−10 | 2.49E−10 | 4.94E−10 |
| | TGI | 6.33E−10 | 1.24E−09 | 2.47E−09 |
| | $LC_{50}$ | 1.27E−08 | 1.12E−08 | 1.23E−08 |
| HMEC-1 | $GI_{50}$ | | | |
| | TGI | | | |
| | $LC_{50}$ | | | |
| LNCAP | $GI_{50}$ | | | |
| | TGI | | | |
| | $LC_{50}$ | | | |
| SK-OV3 | $GI_{50}$ | | | |
| | TGI | | | |
| | $LC_{50}$ | | | |
| IGROV | $GI_{50}$ | | | |
| | TGI | | | |
| | $LC_{50}$ | | | |
| IGROV-ET | $GI_{50}$ | | | |
| | TGI | | | |
| | $LC_{50}$ | | | |
| SK-BR3 | $GI_{50}$ | | | |
| | TGI | | | |
| | $LC_{50}$ | | | |
| K-562 | $GI_{50}$ | | | |
| | TGI | | | |
| | $LC_{50}$ | | | |
| PANC-1 | $GI_{50}$ | | | |
| | TGI | | | |
| | $LC_{50}$ | | | |
| LOVO | $GI_{50}$ | | | |
| | TGI | | | |
| | $LC_{50}$ | | | |
| LOVO-DOX | $GI_{50}$ | | | |
| | TGI | | | |
| | $LC_{50}$ | | | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 167 | Compound 171 | Compound 172 |
|---|---|---|---|---|
| A-549 | $GI_{50}$ | 2.83E−08 | 2.28E−08 | 2.41E−07 |
| | TGI | 6.54E−08 | 4.68E−08 | 4.59E−07 |
| | $LC_{50}$ | 4.82E−07 | 9.60E−08 | 8.53E−07 |
| HT-29 | $GI_{50}$ | 2.89E−08 | 3.91E−09 | 3.88E−08 |
| | TGI | 1.51E−07 | 3.24E−08 | 1.43E−07 |
| | $LC_{50}$ | 1.09E−05 | 1.06E−05 | 8.53E−06 |
| SW-620 | $GI_{50}$ | | | |
| | TGI | | | |
| | $LC_{50}$ | | | |
| MEL-28 | $GI_{50}$ | 2.38E−08 | 5.65E−09 | 1.31E−09 |
| | TGI | 5.06E−08 | 2.33E−08 | 3.22E−09 |
| | $LC_{50}$ | 1.07E−07 | 1.02E−07 | 7.97E−09 |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | 4.88E−08 | 5.05E−09 | 3.79E−08 |
| | TGI | 1.01E−07 | 2.96E−08 | 8.31E−08 |
| | $LC_{50}$ | 1.09E−05 | 1.06E−05 | 8.53E−06 |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | 5.15E−08 | 2.94E−09 | 4.32E−07 |
| | TGI | 3.49E−07 | 6.90E−09 | 8.53E−06 |
| | $LC_{50}$ | 1.09E−05 | 1.06E−05 | 8.53E−06 |
| LNCAP | $GI_{50}$ | 1.97E−08 | 1.66E−09 | 2.77E−08 |
| | TGI | 3.80E−08 | 3.14E−09 | 4.31E−08 |
| | $LC_{50}$ | 7.36E−08 | 5.94E−09 | 6.68E−08 |
| SK-OV3 | $GI_{50}$ | 4.02E−08 | 6.89E−09 | 2.19E−07 |
| | TGI | 1.48E−07 | 9.73E−08 | 5.09E−07 |
| | $LC_{50}$ | 1.09E−05 | 1.06E−05 | 8.53E−07 |
| IGROV | $GI_{50}$ | 6.46E−09 | 1.93E−09 | 1.42E−08 |
| | TGI | 2.49E−08 | 4.12E−09 | 3.01E−08 |
| | $LC_{50}$ | 8.92E−08 | 8.80E−09 | 6.36E−08 |
| IGROV-ET | $GI_{50}$ | 7.76E−08 | 2.25E−07 | 1.65E−07 |
| | TGI | 9.05E−07 | 7.08E−07 | 4.18E−07 |
| | $LC_{50}$ | 5.24E−06 | 1.06E−05 | 8.53E−07 |
| SK-BR3 | $GI_{50}$ | 1.76E−08 | 2.47E−09 | 5.02E−08 |
| | TGI | 5.19E−08 | 6.54E−09 | 2.00E−07 |
| | $LC_{50}$ | 2.38E−07 | 3.75E−08 | 7.85E−07 |
| K-562 | $GI_{50}$ | 7.00E−09 | 2.43E−10 | 6.03E−09 |
| | TGI | 9.64E−09 | 4.88E−10 | 9.98E−09 |
| | $LC_{50}$ | 7.17E−08 | 9.82E−10 | 3.53E−08 |
| PANC-1 | $GI_{50}$ | 4.65E−08 | 7.30E−09 | 3.26E−07 |
| | TGI | 1.09E−07 | 4.63E−08 | 8.34E−07 |
| | $LC_{50}$ | 1.09E−05 | 1.06E−06 | 8.53E−06 |
| LOVO | $GI_{50}$ | 3.36E−08 | 2.37E−08 | 2.26E−07 |
| | TGI | 6.74E−08 | 7.66E−08 | 4.61E−07 |
| | $LC_{50}$ | 1.90E−07 | 1.06E−05 | 8.53E−07 |
| LOVO-DOX | $GI_{50}$ | 4.16E−07 | 9.38E−07 | 2.88E−06 |
| | TGI | 1.58E−06 | 1.23E−06 | 7.23E−06 |
| | $LC_{50}$ | 1.09E−05 | 1.06E−05 | 8.53E−06 |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 173 | Compound 174 | Compound 175 |
|---|---|---|---|---|
| A-549 | $GI_{50}$ | 3.26E−09 | 9.80E−10 | 2.25E−09 |
| | TGI | 4.35E−09 | 2.94E−09 | 4.24E−09 |
| | $LC_{50}$ | 1.09E−08 | 9.80E−09 | 7.97E−09 |
| HT-29 | $GI_{50}$ | 2.17E−09 | 1.96E−09 | 4.15E−09 |
| | TGI | 6.52E−09 | 6.86E−09 | 1.54E−08 |
| | $LC_{50}$ | 9.78E−09 | 9.80E−09 | 1.01E−05 |
| SW-620 | $GI_{50}$ | 3.26E−09 | 9.80E−10 | |
| | TGI | 6.52E−09 | 6.86E−09 | |
| | $LC_{50}$ | 2.17E−08 | 6.86E−07 | |
| MEL-28 | $GI_{50}$ | 2.17E−09 | 1.96E−09 | 3.28E−09 |
| | TGI | 5.43E−09 | 4.90E−09 | 6.63E−09 |
| | $LC_{50}$ | 1.09E−08 | 9.80E−09 | 2.52E−08 |
| OVCAR | $GI_{50}$ | | | |
| | TGI | | | |
| | $LC_{50}$ | | | |
| A-498 | $GI_{50}$ | 2.17E−09 | 1.96E−09 | |
| | TGI | 4.35E−09 | 3.92E−09 | |
| | $LC_{50}$ | 2.17E−08 | 9.80E−09 | |
| DU-145 | $GI_{50}$ | 1.09E−09 | 2.94E−10 | 3.67E−09 |
| | TGI | 2.17E−09 | 9.80E−10 | 9.20E−09 |
| | $LC_{50}$ | 3.26E−09 | 3.92E−09 | 1.01E−05 |
| MCF | $GI_{50}$ | 3.26E−09 | 3.92E−09 | |
| | TGI | 9.78E−09 | 1.96E−08 | |
| | $LC_{50}$ | 1.09E−07 | 8.82E−08 | |
| MB-231 | $GI_{50}$ | 2.17E−09 | 9.80E−10 | |
| | TGI | 7.61E−09 | 5.88E−09 | |
| | $LC_{50}$ | 2.17E−08 | 9.80E−08 | |
| HMEC-1 | $GI_{50}$ | | | 3.54E−09 |
| | TGI | | | 1.29E−08 |
| | $LC_{50}$ | | | 1.01E−05 |
| LNCAP | $GI_{50}$ | | | 3.82E−10 |
| | TGI | | | 1.12E−09 |
| | $LC_{50}$ | | | 3.64E−09 |

-continued

Activity Data

| | | | | |
|---|---|---|---|---|
| SK-OV3 | $GI_{50}$ | | | 3.56E−09 |
| | TGI | | | 8.77E−09 |
| | $LC_{50}$ | | | 1.01E−05 |
| IGROV | $GI_{50}$ | | | 6.41E−10 |
| | TGI | | | 2.37E−09 |
| | $LC_{50}$ | | | 8.13E−09 |
| IGROV-ET | $GI_{50}$ | | | 3.97E−09 |
| | TGI | | | 9.56E−09 |
| | $LC_{50}$ | | | 1.72E−06 |
| SK-BR3 | $GI_{50}$ | | | 1.31E−09 |
| | TGI | | | 3.78E−09 |
| | $LC_{50}$ | | | 1.32E−08 |
| K-562 | $GI_{50}$ | | | 2.93E−10 |
| | TGI | | | 4.76E−10 |
| | $LC_{50}$ | | | 7.75E−10 |
| PANC-1 | $GI_{50}$ | | | 4.38E−09 |
| | TGI | | | 1.33E−08 |
| | $LC_{50}$ | | | 1.01E−05 |
| LOVO | $GI_{50}$ | | | 2.30E−09 |
| | TGI | | | 4.38E−09 |
| | $LC_{50}$ | | | 8.33E−09 |
| LOVO-DOX | $GI_{50}$ | | | 4.33E−08 |
| | TGI | | | 1.55E−07 |
| | $LC_{50}$ | | | 1.01E−05 |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 176 | Compound 182 | Et-701 |
|---|---|---|---|---|
| A-549 | $GI_{50}$ | 2.75E−09 | 4.09E−10 | 2.99E−09 |
| | TGI | 6.01E−09 | 1.36E−09 | 7.06E−09 |
| | $LC_{50}$ | 1.12E−08 | 6.81E−08 | 1.39E−08 |
| HT-29 | $GI_{50}$ | 3.83E−09 | 2.72E−10 | 4.24E−09 |
| | TGI | 7.96E−09 | 1.09E−09 | 3.72E−08 |
| | $LC_{50}$ | 1.12E−05 | 1.36E−09 | 9.56E−06 |
| SW-620 | $GI_{50}$ | | 1.09E−09 | |
| | TGI | | 4.09E−09 | |
| | $LC_{50}$ | | 1.36E−08 | |
| MEL-28 | $GI_{50}$ | 2.58E−08 | 4.09E−10 | 9.74E−09 |
| | TGI | 4.97E−08 | 1.36E−09 | 3.50E−08 |
| | $LC_{50}$ | 9.56E−08 | 5.45E−09 | 1.22E−07 |
| OVCAR | $GI_{50}$ | | | |
| | TGI | | | |
| | $LC_{50}$ | | | |
| A-498 | $GI_{50}$ | | 4.09E−10 | |
| | TGI | | 1.36E−09 | |
| | LC50 | | 5.45E−09 | |
| DU-145 | $GI_{50}$ | 5.24E−09 | 2.72E−10 | 4.04E−09 |
| | TGI | 1.10E−08 | 4.09E−10 | 9.70E−09 |
| | $LC_{50}$ | 8.36E−06 | 1.09E−09 | 2.97E−06 |
| MCF | $GI_{50}$ | | 2.72E−09 | |
| | TGI | | 5.45E−09 | |
| | $LC_{50}$ | | 1.36E−08 | |
| MB-231 | $GI_{50}$ | | 2.72E−10 | |
| | TGI | | 6.81E−10 | |
| | $LC_{50}$ | | 8.17E−09 | |
| HMEC-1 | $GI_{50}$ | 3.46E−09 | | 3.99E−09 |
| | TGI | 1.48E−07 | | 1.35E−08 |
| | $LC_{50}$ | 1.12E−05 | | 4.57E−06 |
| LNCAP | $GI_{50}$ | 1.62E−09 | | 3.24E−10 |
| | TGI | 3.25E−09 | | 1.56E−09 |
| | $LC_{50}$ | 6.49E−09 | | 5.28E−09 |
| SK-OV3 | $GI_{50}$ | 3.26E−09 | | 2.10E−09 |
| | TGI | 8.07E−09 | | 1.08E−08 |
| | $LC_{50}$ | 1.10E−08 | | 9.85E−06 |
| IGROV | $GI_{50}$ | 1.74E−09 | | 2.33E−09 |
| | TGI | 4.30E−09 | | 5.08E−09 |
| | $LC_{50}$ | 1.07E−08 | | 1.11E−08 |
| IGROV-ET | $GI_{50}$ | 4.88E−09 | | 1.64E−08 |
| | TGI | 3.38E−08 | | 7.78E−08 |
| | $LC_{50}$ | 3.45E−06 | | 3.75E−06 |
| SK-BR3 | $GI_{50}$ | 2.70E−09 | | 2.21E−09 |
| | TGI | 7.73E−09 | | 6.25E−09 |
| | $LC_{50}$ | 4.06E−08 | | 2.75E−08 |

-continued

Activity Data

| | | | | |
|---|---|---|---|---|
| K-562 | $GI_{50}$ | 7.37E−10 | | 1.33E−09 |
| | TGI | 1.52E−09 | | 3.50E−09 |
| | $LC_{50}$ | 6.89E−09 | | 1.13E−08 |
| PANC-1 | $GI_{50}$ | 5.31E−09 | | 4.61E−09 |
| | TGI | 1.97E−08 | | 1.19E−08 |
| | $LC_{50}$ | 3.20E−06 | | 2.06E−07 |
| LOVO | $GI_{50}$ | 1.11E−08 | | 4.56E−09 |
| | TGI | 5.12E−08 | | 1.18E−08 |
| | $LC_{50}$ | 1.12E−07 | | 3.75E−06 |
| LOVO-DOX | $GI_{50}$ | 4.73E−08 | | 5.06E−08 |
| | TGI | 1.15E−06 | | 5.46E−07 |
| | $LC_{50}$ | 1.12E−05 | | 1.39E−05 |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 193 | Compound 200 | Compound 209 |
|---|---|---|---|---|
| A-549 | $GI_{50}$ | 4.01E−10 | 2.30E−08 | 9.09E−11 |
| | TGI | 4.01E−09 | 3.45E−08 | 3.90E−10 |
| | $LC_{50}$ | 1.00E−07 | 1.15E−07 | 1.17E−09 |
| HT-29 | $GI_{50}$ | 1.00E−10 | 2.30E−08 | 7.79E−11 |
| | TGI | 2.01E−08 | 8.05E−09 | 3.90E−10 |
| | $LC_{50}$ | 2.01E−05 | 1.15E−06 | 1.17E−09 |
| SW-620 | $GI_{50}$ | | | 7.79E−11 |
| | TGI | | | 3.90E−10 |
| | $LC_{50}$ | | | 1.30E−09 |
| MEL-28 | $GI_{50}$ | | | 6.49E−11 |
| | TGI | | | 2.60E−10 |
| | $LC_{50}$ | | | 1.30E−09 |
| OVCAR | $GI_{50}$ | | | |
| | TGI | | | |
| | $LC_{50}$ | | | |
| A-498 | $GI_{50}$ | | | 1.30E−10 |
| | TGI | | | 3.90E−10 |
| | $LC_{50}$ | | | 1.30E−09 |
| DU-145 | $GI_{50}$ | | | 1.30E−11 |
| | TGI | | | 3.90E−11 |
| | $LC_{50}$ | | | 1.30E−10 |
| MCF | $GI_{50}$ | | | 2.60E−10 |
| | TGI | | | 7.79E−10 |
| | $LC_{50}$ | | | 5.19E−09 |
| MB-231 | $GI_{50}$ | | | 1.30E−11 |
| | TGI | | | 2.60E−10 |
| | $LC_{50}$ | | | 1.30E−09 |
| HMEC-1 | $GI_{50}$ | | | |
| | TGI | | | |
| | $LC_{50}$ | | | |
| LNCAP | $GI_{50}$ | | | |
| | TGI | | | |
| | $LC_{50}$ | | | |
| SK-OV3 | $GI_{50}$ | | | |
| | TGI | | | |
| | $LC_{50}$ | | | |
| IGROV | $GI_{50}$ | | | |
| | TGI | | | |
| | $LC_{50}$ | | | |
| IGROV-ET | $GI_{50}$ | | | |
| | TGI | | | |
| | $LC_{50}$ | | | |
| SK-BR3 | $GI_{50}$ | | | |
| | TGI | | | |
| | $LC_{50}$ | | | |
| K-562 | $GI_{50}$ | | | |
| | TGI | | | |
| | $LC_{50}$ | | | |
| PANC-1 | $GI_{50}$ | | | |
| | TGI | | | |
| | $LC_{50}$ | | | |
| LOVO | $GI_{50}$ | | | |
| | TGI | | | |
| | $LC_{50}$ | | | |
| LOVO-DOX | $GI_{50}$ | | | |
| | TGI | | | |
| | $LC_{50}$ | | | |

-continued

| Activity Data | | | | |
|---|---|---|---|---|
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 210 | Compound 211 | Compound 212 |
|---|---|---|---|---|
| A-549 | $GI_{50}$ | 6.33E−14 | 3.67E−12 | 9.11E−09 |
| | TGI | 5.06E−13 | 6.11E−09 | 2.28E−08 |
| | $LC_{50}$ | 3.80E−05 | 6.11E−05 | 1.14E−07 |
| HT-29 | $GI_{50}$ | 6.33E−14 | 1.22E−12 | 2.28E−09 |
| | TGI | 6.33E−08 | 1.22E−12 | 4.56E−09 |
| | $LC_{50}$ | 6.33E−05 | 6.11E−05 | 1.14E−08 |
| SW-620 | $GI_{50}$ | | | 2.28E−11 |
| | TGI | | | 1.14E−08 |
| | $LC_{50}$ | | | 2.28E−06 |
| MEL-28 | $GI_{50}$ | | | 1.14E−09 |
| | TGI | | | 3.42E−09 |
| | $LC_{50}$ | | | 9.11E−09 |
| OVCAR | $GI_{50}$ | | | 3.42E−10 |
| | TGI | | | 3.42E−09 |
| | $LC_{50}$ | | | 2.28E−06 |
| A-498 | $GI_{50}$ | | | 2.28E−09 |
| | TGI | | | 1.14E−08 |
| | $LC_{50}$ | | | 1.14E−06 |
| DU-145 | $GI_{50}$ | | | 1.14E−10 |
| | TGI | | | 6.83E−10 |
| | $LC_{50}$ | | | 1.14E−08 |
| MCF | $GI_{50}$ | | | 3.42E−10 |
| | TGI | | | 1.14E−08 |
| | $LC_{50}$ | | | 3.42E−07 |
| MB-231 | $GI_{50}$ | | | 2.28E−10 |
| | TGI | | | 5.69E−09 |
| | $LC_{50}$ | | | 1.14E−07 |
| HMEC-1 | $GI_{50}$ | | | |
| | TGI | | | |
| | $LC_{50}$ | | | |
| LNCAP | $GI_{50}$ | | | |
| | TGI | | | |
| | $LC_{50}$ | | | |
| SK-OV3 | $GI_{50}$ | | | |
| | TGI | | | |
| | $LC_{50}$ | | | |
| IGROV | $GI_{50}$ | | | |
| | TGI | | | |
| | $LC_{50}$ | | | |
| IGROV-ET | $GI_{50}$ | | | |
| | TGI | | | |
| | $LC_{50}$ | | | |
| SK-BR3 | $GI_{50}$ | | | |
| | TGI | | | |
| | $LC_{50}$ | | | |
| K-562 | $GI_{50}$ | | | |
| | TGI | | | |
| | $LC_{50}$ | | | |
| PANC-1 | $GI_{50}$ | | | |
| | TGI | | | |
| | $LC_{50}$ | | | |
| LOVO | $GI_{50}$ | | | |
| | TGI | | | |
| | $LC_{50}$ | | | |
| LOVO-DOX | $GI_{50}$ | | | |
| | TGI | | | |
| | $LC_{50}$ | | | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 215 | Compound 217 | Compound 219 |
|---|---|---|---|---|
| A-549 | $GI_{50}$ | 9.24E−08 | 2.10E−09 | 8.24E−09 |
| | TGI | 1.01E−05 | 6.16E−09 | 1.65E−06 |
| | $LC_{50}$ | 1.01E−05 | 4.57E−08 | 1.65E−05 |
| H-T29 | $GI_{50}$ | 8.68E−08 | 1.31E−08 | 8.24E−08 |
| | TGI | 1.01E−05 | 1.31E−05 | 1.65E−06 |
| | $LC_{50}$ | 1.01E−05 | 1.31E−05 | 1.65E−05 |
| SW-620 | $GI_{50}$ | | | |
| | TGI | | | |
| | $LC_{50}$ | | | |
| MEL-28 | $GI_{50}$ | 1.97E−08 | 5.37E−10 | |
| | TGI | 4.54E−08 | 1.48E−09 | |
| | $LC_{50}$ | 1.19E−07 | 9.39E−09 | |
| OVCAR | $GI_{50}$ | | | |
| | TGI | | | |
| | $LC_{50}$ | | | |
| A-498 | $GI_{50}$ | | | |
| | TGI | | | |
| | $LC_{50}$ | | | |
| DU-145 | $GI_{50}$ | 4.22E−08 | 5.03E−10 | |
| | TGI | 8.06E−08 | 8.77E−10 | |
| | $LC_{50}$ | 1.01E−05 | 1.31E−09 | |
| MCF | $GI_{50}$ | | | |
| | TGI | | | |
| | $LC_{50}$ | | | |
| MB-231 | $GI_{50}$ | | | |
| | TGI | | | |
| | $LC_{50}$ | | | |
| HMEC-1 | $GI_{50}$ | 6.76E−10 | 1.82E−10 | |
| | TGI | 7.95E−10 | 4.08E−10 | |
| | $LC_{50}$ | 1.01E−09 | 9.19E−10 | |
| LNCAP | $GI_{50}$ | 3.65E−08 | 3.44E−09 | |
| | TGI | 5.50E−08 | 9.78E−09 | |
| | $LC_{50}$ | 1.01E−07 | 6.60E−06 | |
| SK-OV3 | $GI_{50}$ | 3.45E−08 | 4.76E−10 | |
| | TGI | 1.29E−07 | 1.31E−09 | |
| | $LC_{50}$ | 1.01E−05 | 1.31E−05 | |
| IGROV | $GI_{50}$ | 2.68E−08 | 2.63E−08 | |
| | TGI | 5.82E−08 | 6.35E−08 | |
| | $LC_{50}$ | 1.01E−07 | 1.31E−07 | |
| IGROV-ET | $GI_{50}$ | 2.87E−07 | 2.44E−08 | |
| | TGI | 7.32E−07 | 1.31E−07 | |
| | $LC_{50}$ | 1.01E−05 | 1.31E−05 | |
| SK-BR3 | $GI_{50}$ | 1.62E−08 | 4.94E−10 | |
| | TGI | 4.85E−08 | 2.14E−09 | |
| | $LC_{50}$ | 3.88E−07 | 8.34E−09 | |
| K-562 | $GI_{50}$ | 3.39E−07 | 3.68E−10 | |
| | TGI | 2.79E−06 | 1.42E−09 | |
| | $LC_{50}$ | 1.01E−05 | 4.27E−06 | |
| PANC-1 | $GI_{50}$ | 2.92E−08 | 6.05E−10 | |
| | TGI | 1.74E−07 | 9.32E−09 | |
| | $LC_{50}$ | 1.01E−05 | 1.31E−05 | |
| LOVO | $GI_{50}$ | 2.35E−08 | 1.38E−09 | |
| | TGI | 5.19E−08 | 5.47E−09 | |
| | $LC_{50}$ | 1.01E−07 | 1.31E−08 | |
| LOVO-DOX | $GI_{50}$ | 6.07E−07 | 3.85E−08 | |
| | TGI | 1.01E−05 | 1.31E−07 | |
| | $LC_{50}$ | 1.01E−05 | 1.31E−05 | |
| HELA | $GI_{50}$ | | | |
| | TGI | | | |
| | $LC_{50}$ | | | |
| HELA-APL | $GI_{50}$ | | | |
| | TGI | | | |
| | $LC_{50}$ | | | |

| | | Compound 220 | Compound 223 | Compound 224 |
|---|---|---|---|---|
| A-549 | $GI_{50}$ | 1.32E−07 | 3.87E−09 | 5.32E−09 |
| | TGI | 3.96E−07 | 1.01E−08 | 1.10E−08 |
| | $LC_{50}$ | 6.61E−06 | 1.28E−05 | 1.29E−05 |
| H-T29 | $GI_{50}$ | 1.32E−07 | 6.54E−09 | 5.19E−09 |
| | TGI | 5.28E−07 | 1.28E−07 | 1.36E−08 |
| | $LC_{50}$ | 1.32E−06 | 1.28E−05 | 1.26E−05 |
| SW-620 | $GI_{50}$ | | | |
| | TGI | | | |
| | $LC_{50}$ | | | |
| MEL-28 | $GI_{50}$ | | | 2.79E−09 |
| | TGI | | | 5.35E−09 |
| | $LC_{50}$ | | | 1.02E−08 |
| OVCAR | $GI_{50}$ | | | |
| | TGI | | | |
| | $LC_{50}$ | | | |

-continued

| | Activity Data | |
|---|---|---|
| A-498 | $GI_{50}$ | |
| | TGI | |
| | $LC_{50}$ | |
| DU-145 | $GI_{50}$ | 5.07E−09 |
| | TGI | 1.08E−08 |
| | $LC_{50}$ | 3.32E−08 |
| MCF | $GI_{50}$ | |
| | TGI | |
| | $LC_{50}$ | |
| MB-231 | $GI_{50}$ | |
| | TGI | |
| | $LC_{50}$ | |
| HMEC-1 | $GI_{50}$ | 1.01E−09 |
| | TGI | 2.58E−09 |
| | $LC_{50}$ | 6.91E−09 |
| LNCAP | $GI_{50}$ | 1.83E−09 |
| | TGI | 3.62E−09 |
| | $LC_{50}$ | 7.16E−09 |
| SK-OV3 | $GI_{50}$ | 4.47E−09 |
| | TGI | 8.33E−09 |
| | $LC_{50}$ | 6.60E−06 |
| IGROV | $GI_{50}$ | 3.55E−09 |
| | TGI | 8.61E−09 |
| | $LC_{50}$ | 4.35E−06 |
| IGROV-ET | $GI_{50}$ | 4.16E−08 |
| | TGI | 1.11E−07 |
| | $LC_{50}$ | 1.29E−05 |
| SK-BR3 | $GI_{50}$ | 4.61E−09 |
| | TGI | 1.27E−06 |
| | $LC_{50}$ | 3.06E−07 |
| K-562 | $GI_{50}$ | 1.72E−09 |
| | TGI | 3.44E−09 |
| | $LC_{50}$ | 5.94E−08 |
| PANC-1 | $GI_{50}$ | 3.49E−09 |
| | TGI | 1.01E−08 |
| | $LC_{50}$ | 5.12E−07 |
| LOVO | $GI_{50}$ | 5.07E−09 |
| | TGI | 2.57E−08 |
| | $LC_{50}$ | 4.19E−06 |
| LOVO-DOX | $GI_{50}$ | 6.41E−08 |
| | TGI | 7.00E−07 |
| | $LC_{50}$ | 1.29E−05 |
| HELA | $GI_{50}$ | |
| | TGI | |
| | $LC_{50}$ | |
| HELA-APL | $GI_{50}$ | |
| | TGI | |
| | $LC_{50}$ | |

Toxicity Data

Toxicity was asssessed by the methods reported in Toxicology in Vitro, 15 (2001) 571-577, J. Luber Narod et al.: "Evaluation of the use of in vitro methodologies as tools for screening new compounds for potential in vivo toxicity".

| Compound | Liver | Heart | Myelo | Skeletal | Kidney |
|---|---|---|---|---|---|
| 57 | 4.66E−09 | 3.48E−09 | 1.85E−08 | REDO | 3.35E−09 |
| 59 | 2.53E−08 | 8.14E−08 | 4.18E−08 | 1.46E−07 | 2.87E−08 |
| 61 | 1.32E−08 | 2.76E−08 | 1.69E−08 | 1.47E−08 | 5.12E−09 |
| 63 | 1.44E−08 | 6.66E−08 | 1.52E−08 | 3.06E−09 | 1.58E−08 |
| 64 | 2.57E−08 | 5.50E−08 | 1.93E−08 | 1.66E−09 | 1.77E−08 |
| 65 | 5.30E−09 | 9.00E−09 | 1.70E−08 | 3.77E−09 | 3.15E−09 |
| 67 | 3.20E−08 | 4.54E−08 | 3.27E−08 | 2.37E−08 | 5.36E−08 |
| 68 | 1.76E−08 | 1.13E−08 | 1.89E−08 | 1.27E−08 | 5.10E−09 |
| 70 | 3.16E−08 | 2.20E−07 | 6.61E−08 | 3.67E−08 | 1.07E−07 |
| 72 | 1.55E−08 | 3.78E−08 | 2.15E−08 | 1.32E−08 | 1.85E−08 |
| 74 | 3.07E−08 | 2.86E−08 | 3.30E−08 | 8.30E−10 | 3.05E−08 |
| 75 | 4.11E−08 | 8.17E−08 | 5.85E−08 | 4.06E−09 | 3.86E−08 |
| 76 | 1.35E−08 | 1.62E−08 | 8.19E−09 | 2.15E−09 | 3.20E−09 |
| 77 | 9.53E−09 | 1.64E−08 | 8.52E−09 | 2.20E−09 | 3.22E−09 |
| 78 | 5.88E−08 | 8.19E−07 | NT | 1.96E−08 | 2.59E−07 |
| 79 | 2.28E−08 | 3.46E−08 | 1.35E−08 | 2.75E−09 | 1.74E−08 |

-continued

| Compound | Liver | Heart | Myelo | Skeletal | Kidney |
|---|---|---|---|---|---|
| 86 | 1.47E−08 | 8.16E−08 | 8.35E−08 | 3.88E−08 | 1.37E−08 |
| 87 | 6.18E−08 | 3.60E−08 | 2.44E−07 | 2.00E−07 | 8.09E−08 |
| 92 | 2.30E−08 | 2.80E−08 | 1.92E−08 | 1.21E−08 | 1.35E−08 |
| 93 | 1.13E−08 | 4.46E−08 | 3.35E−09 | 5.52E−10 | 6.32E−08 |
| 94 | 1.24E−08 | 6.66E−08 | 1.13E−08 | 1.44E−09 | 3.49E−09 |
| 97 | 1.57E−08 | 9.63E−08 | 1.77E−08 | 4.62E−09 | 1.43E−08 |
| 98 | 4.21E−08 | 4.98E−08 | 3.79E−08 | 1.24E−08 | 1.08E−06 |
| 99 | 4.80E−08 | 1.13E−07 | 1.45E−07 | 9.71E−08 | 2.56E−08 |
| 101 | 5.40E−08 | 7.67E−08 | 1.96E−08 | 3.40E−09 | 3.17E−08 |
| 104 | 4.16E−09 | 3.44E−09 | 1.93E−08 | 4.10E−07 | 2.67E−09 |
| 161 | 8.58E−09 | 1.13E−08 | 2.27E−08 | 1.65E−08 | 2.60E−09 |
| 163 | 9.80E−07 | 4.80E−07 | 2.38E−07 | 2.53E−06 | 6.33E−07 |
| 165 | 1.68E−08 | 2.79E−08 | 2.87E−08 | 1.47E−08 | 1.89E−08 |
| 167 | 4.83E−07 | 4.28E−07 | 1.01E−06 | 1.09E−07 | 2.77E−07 |
| 170 | 3.58E−07 | NT | NT | 3.29E−07 | 3.01E−07 |
| 171 | 8.37E−08 | 3.13E−08 | 1.37E−07 | 3.58E−08 | 2.70E−08 |
| 172 | 2.47E−07 | 7.52E−07 | 3.81E−07 | 8.53E−07 | 7.93E−07 |
| 173 | 4.03E−08 | 1.19E−07 | 4.98E−06 | 2.49E−06 | 7.09E−08 |
| 174 | 1.34E−08 | 2.76E−08 | 7.27E−08 | 9.80E−07 | 1.24E−08 |
| 175 | 3.87E−09 | 2.82E−09 | 1.59E−08 | 2.12E−07 | 2.84E−09 |
| 176 | 2.95E−08 | 1.98E−08 | 1.42E−08 | 2.41E−08 | 2.80E−09 |
| 182 | 3.98E−09 | 3.95E−08 | 3.19E−08 | 1.49E−08 | 1.26E−08 |
| 183 | 3.03E−08 | 3.72E−08 | 2.39E−08 | 2.67E−08 | 6.72E−03 |
| 212 | 8.68E−08 | 3.20E−08 | 8.58E−09 | 2.21E−08 | 3.34E−09 |
| 213 | 3.93E−08 | 1.82E−07 | 2.70E−08 | 1.72E−07 | 1.48E−08 |
| 217 | 1.07E−09 | TT | TT | 3.37E−12 | 2.66E−13 |

The invention claimed is:

1. A compound of the general formula Ia:

Ia

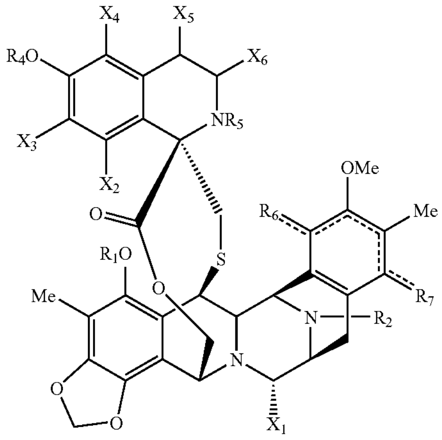

wherein $R_1$ is C(═O)R', C(═O)OR', P═O(OR')$_2$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, with the proviso that $R_1$ is not acetyl;

wherein $R_2$, $R_4$, $R_5$ are each independently selected from H, C(═O)R', C(═O)OR', P═O(OR')$_2$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl;

wherein $R_6$ and $R_7$ are both ═O and the dotted lines indicate a quinone ring, or $R_6$ is —$OR_3$, where $R_3$ is H, C(═O)R', C(═O)OR', substituted or unsubstituted $C_1$-$C_{18}$ alkyl, substituted or unsubstituted $C_2$-$C_{18}$ alkenyl, substituted or unsubstituted $C_2$-$C_{18}$ alkynyl, substituted or unsubstituted aryl, $R_7$ is H, and the dotted lines indicate a phenyl ring;

wherein $X_2$, $X_3$, $X_4$, $X_5$, $X_6$ are independently selected from H, OH, OR', SH, SR', SOR', $SO_2R'$, C(═O)R', C(═O)OR', $NO_2$, $NH_2$, NHR', $N(R')_2$, NHC(O)R', CN, halogen, unsubstituted $C_1$-$C_{24}$ alkyl, unsubstituted $C_2$-$C_{18}$ alkenyl, unsubstituted $C_2$-$C_{18}$ alkynyl, unsubstituted $C_6$-$C_{18}$ carbocyclic aryl, and unsubstituted heteroaromatic selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl tetrahyrdrofuranyl, tetrahydropyranyl, piperidinyl, morpholinyl and pyrolindinyl;

wherein $X_1$ is selected from hydrogen, hydroxy and cyano;

wherein when $R_1$, $R_2$, $R_3$, $R_4$, and $R_5$ are substituted, the substituents are each independently selected from the group consisting of OH, OR', SH, SR', SOR', $SO_2R'$, C(═O)R', C(═O)OR', $NO_2$, $NH_2$, NHR', $N(R')_2$, NHC (O)R', CN, halogen, ═O, unsubstituted $C_1$-$C_{18}$ alkyl, unsubstituted $C_2$-$C_{18}$ alkenyl, unsubstituted $C_2$-$C_{18}$ alkynyl, unsubstituted $C_6$-$C_{18}$ carbocyclic aryl, and unsubstituted heterocyclic selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholinyl and pyrolindinyl;

wherein each of the R' groups is independently selected from the group consisting of H, OH, $NO_2$, $NH_2$, SH, CN, halogen, C(═O)H, C(═O)$CH_3$, $CO_2H$, substituted or unsubstituted $C_1$-$C_{18}$ alkyl, substituted or unsubstituted $C_2$-$C_{18}$ alkenyl, substituted or unsubstituted $C_2$-$C_{18}$ alkynyl, and substituted or unsubstituted $C_6$-$C_{18}$ carbocylic aryl; and wherein when R' is substituted, the substituents are each independently selected from the group consisting of halogen, cyano, hydroxyl, nitro, azido, unsubstituted $C_1$-$C_6$ alkanoyl, carboxamido, unsubstituted $C_1$-$C_{12}$ alkyl, unsubstituted $C_2$-$C_{12}$ alkenyl, unsubstituted $C_2$-$C_{12}$ alkynyl, unsubstituted $C_1$-$C_{12}$ alkoxy, unsubstituted $C_6$-$C_{18}$ carbocyclic aryloxy, unsubstituted $C_1$-$C_{12}$ alkylthio, unsubstituted $C_1$-$C_{12}$ alkylsulfinyl, unsubstituted $C_1$-$C_{12}$ alkylsulfonyl, unsubstituted $C_1$-$C_{12}$ aminoalkyl, unsubstituted $C_6$-$C_{18}$ carbocyclic aryl, unsubstituted aralkyl and unsubstituted heterocyclic group which is selected from coumarinyl, quinolinyl, pyridyl, pyrazinyl,pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholinyl and pyrolindinyl.

2. A compound according to claim 1, wherein:

$R_3$ and $R_4$ are independently selected from hydrogen, $C_1$-$C_{18}$ alkyl, $C_2$-$C_{18}$ alkenyl, C═OR', and COOR', where R' is optionally substituted $C_1$-$C_{18}$ alkyl or optionally substituted $C_2$-$C_{18}$ alkenyl, the optional substituents being chosen from halo, amino, amino derived from amino acid, unsubstituted $C_6$-$C_{18}$ carbocyclic aryl or unsubstituted heterocyclic, which is selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahvdropyranyl, piperidinyl, morpholinyl and pyrolindinyl;

$R_2$ is hydrogen, $C_1$-$C_{18}$ alkyl or C(═O)OR', where R' is $C_1$-$C_{18}$ alkyl;

$R_5$ is hydrogen, $C_1$-$C_{18}$ alkyl or C(═O)OR', where R' is $C_2$-$C_{18}$ alkenyl;

$X_2$, $X_4$ and $X_5$ are hydrogen;

$X_3$ is OR', where R' is $C_1$-$C_{18}$ alkyl;

$X_6$ is hydrogen or unsubstituted $C_1$-$C_{24}$ alkyl;

$R_6$ is $OR_3$;

$R_7$ is hydrogen; and the dotted lines indicate a phenyl ring.

3. A compound according to claim 1, wherein $R_1$ is: $C_1$-$C_{18}$ alkyl;

C(═O)R', where R' is optionally substituted $C_1$-$C_{18}$ alkyl, the optional substituents being chosen from halogen, amino, unsubstituted $C_6$-$C_{18}$ carbocyclic aryl or unsusbtituted heterocyclic, which is selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholinyl and pyrolindinyl; optionally substituted $C_2$-$C_{18}$ alkenyl, the optional substituents being chosen from unsubstituted $C_6$-$C_{18}$ carbocyclic aryl; or C(═O)OR', where R'is $C_1$-$C_{18}$ alkyl or $C_2$-$C_{18}$ alkenyl.

4. A compound according to claim 1, wherein $R_2$ is hydrogen, methyl, or alkoxycarbonyl.

5. A compound according to claim 1, wherein $R_3$ is:

hydrogen;

$C_1$-$C_{18}$ alkyl;

(C═O)R', where R' is optionally substituted $C_1$-$C_{18}$ alkyl, the optional substituents being chosen from halogen, unsubstituted $C_6$-$C_{18}$ carbocyclic aryl or unsusbtituted heterocyclic, which is selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholinyl and pyrolindinyl; optionally substituted $C_2$-$C_{18}$ alkenyl, the optional substituents being chosen from unsubstituted $C_6$-$C_{18}$ carbocyclic aryl; or (C═O)OR', where R' is $C_1$-$C_{18}$ alkyl; optionally substituted $C_2$-$C_{18}$ alkenyl, the optional substituents being chosen from unsubstituted $C_6$-$C_{18}$ carbocyclic aryl.

6. A compound according to claim 1, wherein $R_4$ is:

C(═O)R', where R' is optionally substituted $C_1$-$C_{18}$ alkyl, the optional substituents being chosen from halogen, amino, unsubstituted $C_6$-$C_{18}$ carbocyclic aryl or unsusbtituted heterocyclic, which is selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholinyl and pyrolindinyl; optionally substituted $C_2$-$C_{18}$ alkenyl, the optional substituents being chosen from unsubstituted $C_6$-$C_{18}$ carbocyclic aryl; or C(═O)OR', where R' is optionally substituted $C_1$-$C_{18}$ alkyl or optionally substituted $C_2$-$C_{18}$ alkenyl, the optional substituents being chosen from unsubstituted $C_6$-$C_{18}$ carbocyclic aryl; or P═O$(OR')_2$, where R' is benzyl.

7. A compound according to claim 1, wherein $R_5$ is:

hydrogen;

$C_1$-$C_{18}$ alkyl; or (C═)OR' , where R' is $C_2$-$C_{18}$ alkenyl.

8. A compound according to claim 1, wherein $X_2$ is hydrogen.

9. A compound according to claim 1, wherein $X_3$ is OR', where R' is $C_1$-$C_{18}$ alkyl.

10. A compound according to claim 1, wherein $X_4$ is hydrogen.

11. A compound according to claim 1, wherein $X_5$ is hydrogen.

12. A compound according to claim 1, wherein $X_6$ is hydrogen or unsubstitited $C_1$-$C_{24}$ alkyl.

13. A compound according to claim 1, wherein $R_1$ is C(═O)R', where $R^1$ is optionally substituted $C_4$-$C_{18}$ alkyl or optionally substituted $C_2$-$C_{18}$ alkenyl.

14. A compound according to claim 13, wherein the optional substituent of $R_1$ is unsubstituted $C_6$-$C_{18}$ carbocyclic aryl or unsubstituted heterocyclic group which is selected from coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholinyl and pyrolindinyl; or R' is derived from an optionally protected amino acid.

15. A pharmaceutical composition comprising a compound according to claim 1, and a pharmaceutical carrier.

16. A compound according to claim 1, wherein $R_3$ is:
hydrogen;
$C_1$-$C_6$ alkyl;
cinnamoyl;
(C═O)R' where R' is $C_1$-$C_{18}$ alkyl, perfluoro $C_1$-$C_4$ alkyl, heterocyclicalkyl containing an alkyl of 1 to 6 carbon atoms with a ω-heterocyclic substituent; or
(C═O)OR' where R' is $C_1$-$C_6$ alkyl, vinyl, allyl or benzyl.

17. A compound according to claim 1, wherein $R_4$ is:
cinnamoyl;
(C═O)R' where R' is $C_1$-$C_{18}$ alkyl, ω-chloro- or perfluoro-$C_1$-$C_4$ alkyl, phenethyl, aminoacid, heterocyclicalkyl containing an alkyl of 1 to 6 carbon atoms with a ω-heterocyclic substituent;
(C═O)OR', where R' is $C_1$-$C_6$ alkyl, vinyl, allyl, benzyl; or P═O(OR')$_2$ where R' is benzyl.

18. A compound according to claim 1, wherein $R_1$ is:
$C_1$-$C_6$ alkyl;
cinnamoyl;
C(═O)R' where R' is $C_2$-$C_{18}$ alkyl, ω-chloro- or perfluoro-$C_1$-$C_4$ alkyl, heterocyclicalkyl containing an alkyl of 1 to 6 carbon atoms with a ω-heterocyclic substituent; aminoalkyl of 1 to 6 carbon atoms with a ω-amino group optionally protected, vinyl, allyl, benzyl; or C(═O)OR' where R' is $C_1$-$C_6$ alkyl, or allyl.

* * * * *